(12) United States Patent
Kim et al.

(10) Patent No.: US 11,679,129 B2
(45) Date of Patent: Jun. 20, 2023

(54) ENHANCED IMMUNE CELLS USING DUAL SHRNA AND COMPOSITION INCLUDING THE SAME

(71) Applicants: CUROCELL INC., Daejeon (KR); KOREA ADVANCED INSTITUTE OF SCIENCE AND TECHNOLOGY, Daejeon (KR)

(72) Inventors: Chan Hyuk Kim, Daejeon (KR); Young-Ho Lee, Daejeon (KR); Yujean Lee, Daejeon (KR); HyeongJi Lee, Daejeon (KR); Sang Hoon Lee, Daejeon (KR)

(73) Assignees: CUROCELL, INC., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/958,649

(22) PCT Filed: Jan. 10, 2019

(86) PCT No.: PCT/IB2019/050194
§ 371 (c)(1),
(2) Date: Jun. 26, 2020

(87) PCT Pub. No.: WO2019/138354
PCT Pub. Date: Jul. 18, 2019

(65) Prior Publication Data
US 2021/0060067 A1    Mar. 4, 2021

(30) Foreign Application Priority Data
Jan. 12, 2018  (KR) .................. 10-2018-0004238

(51) Int. Cl.
| | | |
|---|---|---|
| *C12N 15/113* | (2010.01) | |
| *A61K 35/17* | (2015.01) | |
| *A61P 35/00* | (2006.01) | |
| *A61K 31/7088* | (2006.01) | |
| *A61K 38/17* | (2006.01) | |
| *A61K 39/395* | (2006.01) | |
| *C07K 14/725* | (2006.01) | |
| *C07K 14/705* | (2006.01) | |
| *C07K 16/28* | (2006.01) | |
| *C07K 14/47* | (2006.01) | |
| *C12N 5/0783* | (2010.01) | |
| *A61K 39/00* | (2006.01) | |

(52) U.S. Cl.
CPC .......... *A61K 35/17* (2013.01); *A61K 31/7088* (2013.01); *A61K 38/177* (2013.01); *A61K 38/1774* (2013.01); *A61K 39/3955* (2013.01); *A61P 35/00* (2018.01); *C07K 14/4702* (2013.01); *C07K 14/7051* (2013.01); *C07K 14/70521* (2013.01); *C07K 14/70578* (2013.01); *C07K 16/2803* (2013.01); *C12N 5/0637* (2013.01); *C12N 15/1138* (2013.01); *A61K 2039/505* (2013.01); *A61K 2039/5154* (2013.01); *A61K 2039/5158* (2013.01); *C07K 2317/53* (2013.01); *C07K 2317/622* (2013.01); *C07K 2319/02* (2013.01); *C07K 2319/03* (2013.01); *C07K 2319/30* (2013.01); *C07K 2319/33* (2013.01); *C07K 2319/715* (2013.01); *C12N 2310/122* (2013.01); *C12N 2310/14* (2013.01); *C12N 2310/531* (2013.01); *C12N 2320/31* (2013.01); *C12N 2320/32* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |

(Continued)

FOREIGN PATENT DOCUMENTS

| | | |
|---|---|---|
| CN | 106967681 A | 7/2017 |
| RU | 2015139874 A | 3/2017 |

(Continued)

OTHER PUBLICATIONS

Travers et al 1974, Cell pp. 97-104 RNA Polymerase-Promoter Interactions: Review Some General Principles.*
Denti et al., 2004 Molecular Therapy pp. 191-199; A New Vector, Based on the PolII Promoter of the U1 snRNA Gene, for the Expression of siRNAs in Mammalian Cells.*
Moore et al ; 2010 RNA Therapeutics pp. 139-156 Short Hairpin RNA (shRNA): Design, Delivery, and Assessment of Gene Knockdown pp. 139-156.*
Josefsson et al., 2019, "TIGIT and PD-1 Mark Intratumoral T Cells With Reduced Effector Function in B-cell Non-Hodgkin Lymphoma," Cancer Immunol Res., 7(3):355-362.

(Continued)

*Primary Examiner* — Maria G Leavitt
(74) *Attorney, Agent, or Firm* — Perkins Cole LLP

(57) ABSTRACT

The present disclosure is broadly concerned with the field of cancer immunotherapy. For example, the present invention generally relates to an immune cell comprising a genetically engineered antigen receptor that specifically binds to a target antigen and a genetic disruption agent that reduces or is capable of reducing the expression in the immune cell of a gene that weakens the function of the immune cell.

6 Claims, 30 Drawing Sheets

Specification includes a Sequence Listing.

(56) References Cited

U.S. PATENT DOCUMENTS

| | | | |
|---|---|---|---|
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 9,169,483 | B2 | 10/2015 | Davidson et al. |
| 9,181,544 | B2 | 11/2015 | Davidson et al. |
| 10,640,569 | B2 * | 5/2020 | Beatty ............... A61P 13/10 |
| 2006/0121005 | A1 | 6/2006 | Berenson et al. |
| 2008/0293142 | A1 * | 11/2008 | Liu ................ C12N 15/113 |
| | | | 435/455 |
| 2014/0219975 | A1 | 8/2014 | June et al. |
| 2014/0227237 | A1 | 8/2014 | June et al. |
| 2016/0311917 | A1 | 10/2016 | Beatty et al. |
| 2020/0399655 | A1 * | 12/2020 | Slepushkin ........ C07K 14/7051 |
| 2021/0260119 | A1 | 8/2021 | Kim et al. |

FOREIGN PATENT DOCUMENTS

| | | |
|---|---|---|
| WO | 2014191128 A1 | 12/2014 |
| WO | WO 2015090230 A1 | 6/2015 |
| WO | WO 2015142675 A2 | 9/2015 |
| WO | WO 2015142675 A3 | 9/2015 |
| WO | WO 2015179525 A1 | 11/2015 |
| WO | WO 2016069282 A1 | 5/2016 |
| WO | WO 2016126608 A1 | 8/2016 |
| WO | WO 2017040945 A1 | 3/2017 |
| WO | 2017120996 A1 | 7/2017 |
| WO | 2017158019 A1 | 9/2017 |
| WO | WO 2018012895 A1 | 1/2018 |
| WO | 2018049471 A1 | 3/2018 |
| WO | WO 2020057486 A1 | 3/2020 |
| WO | WO 2021009701 A1 | 1/2021 |

OTHER PUBLICATIONS

Tang et al., 2020, "TGF-β Inhibition via CRISPR Promotes the Long-Term Efficacy of CAR T Cells Against Solid Tumors," JCI Insight, 5(4):e133977 (17 pages).
International Search Report and Written Opinion dated May 2, 2019 for International Patent Application No. PCT/IB2019/050194 (published as WO 2019138354), 16 pages.
International Search Report and Written Opinion for International Patent Application No. PCT/IB2020/056680 (published as WO 2021009701) dated Oct. 29, 2020 (16 pages).
Curran et al., 2010, "PD-1 and CTLA-4 combination blockade expands infiltrating T cells and reduces regulatory T and myeloid cells within B16 melanoma tumors," Proc. Natl. Acad. Sci. USA, 107(9):4275-4280.
Elbashir et al., 2001, "Elbashir SM et al., Nature, 2001, 411, 494-498," Nature, 411(6836):494-498.
Fewell et al., 2006, "Vector-based RNAi approaches for stable, inducible and genome-wide screens," Drug Discov. Today, 11(21-22):975-982.
Hung et al., 2018, "TIGIT and PD-1 dual checkpoint blockade enhances antitumor immunity and survival in GBM," Oncoimmunology, 7(8):e1466769 (13 pages).
Johnston et al., 2014, "The immunoreceptor TIGIT regulates antitumor and antiviral CD8(+) T cell effector function," Cancer Cell, 26(6):923-937.
Liddy et al., 2012, "Monoclonal TCR-redirected tumor cell killing" Nat. Med., 18(6):980-987.
Lu et al., 2005, "In vivo application of RNA interference: from functional genomics to therapeutics," Adv. Genet., 54:117-142.
Ma et al., 2016, "Versatile strategy for controlling the specificity and activity of engineered T cells," Proc. Natl. Acad. Sci. USA, 113(4):E450-E458.
Manieri et al., 2017, "TIGIT: A Key Inhibitor of the Cancer Immunity Cycle," Trends Immunol., 38(1):20-28 (Epub 2016).
Milone et al., 2009, "Chimeric receptors containing CD137 signal transduction domains mediate enhanced survival of T cells and increased antileukemic efficacy in vivo," Mol. Ther., 17(8):1453-1464.
Neelapu et al., 2018, "Chimeric antigen receptor T-cell therapy—assessment and management of toxicities," Nat. Rev. Clin Oncol., 15(1):47-62 (Epub 2017).
Rodriguez-Abreu et al., "Primary analysis of a randomized, double-blind, phase II study of the anti-TIGIT antibody tiragolumab (tira) plus atezolizumab (atezo) versus placebo plus atezo as first-line (1L) treatment in patients with PD-L1-selected NSCLC (Cityscape)," Journal of Clinical Oncology, 38(15 suppl):9503 (4 pages).
Sharma et al., 2015, "Immune checkpoint targeting in cancer therapy: toward combination strategies with curative potential," Cell, 161(2):205-214.
Stauss et al., 2007, "Monoclonal T-cell receptors: new reagents for cancer therapy," Mol. Ther., 15(10):1744-1750.
Topalian et al., 1987, "Therapy of cancer using the adoptive transfer of activated killer cells and interleukin-2" Acta. Haematol., 78 Suppl 1:75-76.
Wierz et al., 2018, "Dual PD1/LAG3 immune checkpoint blockade limits tumor development in a murine model of chronic lymphocytic leukemia" Blood, 131(14):1617-1621.
Zhang et al., 2012, "Genetic engineering with T cell receptors," Adv. Drug Deliv. Rev., 64(8):756-762 (Epub 2011).
Chauvin et al., 2015, "TIGIT and PD-1 impair tumor antigen-specific CD8+ T cells in melanoma patients," J. Clin Invest., 125(5):2046-2058.
Cherkassky et al., 2016, "Human CAR T cells with cell-intrinsic PD-1 checkpoint blockade resist tumor-mediated inhibition," J. Clin. Invest, 126(8):3130-3144.
Alberts, Molecular Biology of the Cell, 2002, Published by Garland Science, p. 121.
Anderson et al., Lag-3, tim-3, and TIGIT co-inhibitory receptors with specialized functions in immune regulation, 2017, Immunity, 44(5), 1-34.
Brunner et al., cytotoxic T Cells: Double-barreled shot guns, Nature Medicine, 1999, vol. 5, No. 1 p. 20.
He et al., 2017, CD155T/TIGIT signaling regulates CD8 T-cell metabolism and promotes tumor progression in human gastric cancer, Cancer Res, 77(22), 6375-7388.
Inozume et al., Melanoma cells control antimelanoma ctl responses via interaction between TIGIT and CD155 in the effector phase, 2016, Journal of Investigative Dermatology, 136, 255-263.
Moore et al., Short Hairpin RNA (sh RNA): Design, Delivery, and Assessment of Gene Knockdown, Methods Mol Biol. 2010, 629: 141-158.
Motegi et al., An effective gene-knockdown using multiple shRNA-expressing adenovirus vectors, 2011, Journal of Controlled Release, 153, 149-153.
Russia Office Action dated Aug. 26, 2022 in Application No. RU2020125399.
Russia Office Action dated Jan. 11, 2022 in Application No. RU2020125399.
Russia search report dated Jan. 11, 2022 in App. RU2020125399 with English translation.
Sasidharan et al., Immune checkpoint inhibitors in cancer therapy: a focus on t-regulatory cells, e-published 2017, Immunology & Cell Biology, 96, 21-33.
Sluijmer et al.,Benign Upper Extremity Tumors: Factors Associated with Operative Treatment. HAND. 2013,8 (3):274-281, abstract only, doi:10.1007/s11552-013-9518-5.
Song et al., Multiple shRNA expressing vector enhances efficiency of gene silencing, BMB Reports, 41(5), 258-362.
Ter Brake et al., Lentiviral vector design for multiple shRNA expression and durable HIV-1 inhibition, 2008, The American Society of Gene Therapy, 16(3), 557-564.
Final Office Action issued in related U.S. Appl. No. 17/205,951 dated Dec. 29, 2021 (24 pages).
EP Communication dated Jan. 26, 2023 in EP App. 21207719.2.
Russia Decision to Grant w/English translation dated Feb. 1, 2023 in App. RU2020125399.
Final Office Action dated Feb. 23, 2023 in U.S. Appl. No. 17/701,535.

(56) References Cited

OTHER PUBLICATIONS

Lambeth et al., A direct comparison of strategies for combinatorial RNA interference, BMC Molecular Biology, 2010, 11:77, URL: http://www.biomedcentral.com/1471-2199/11/77.

* cited by examiner

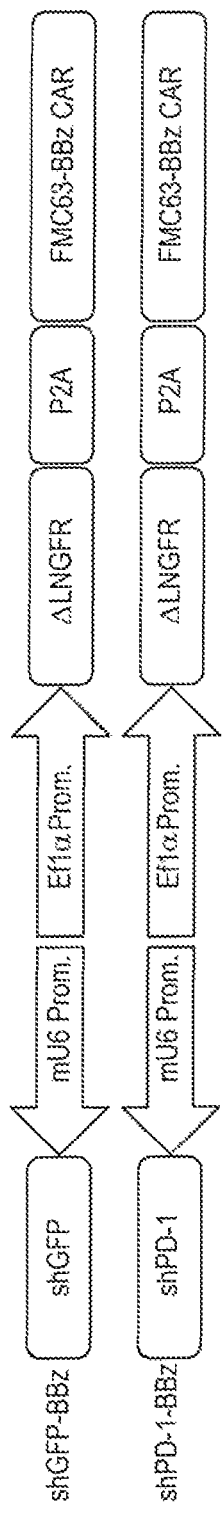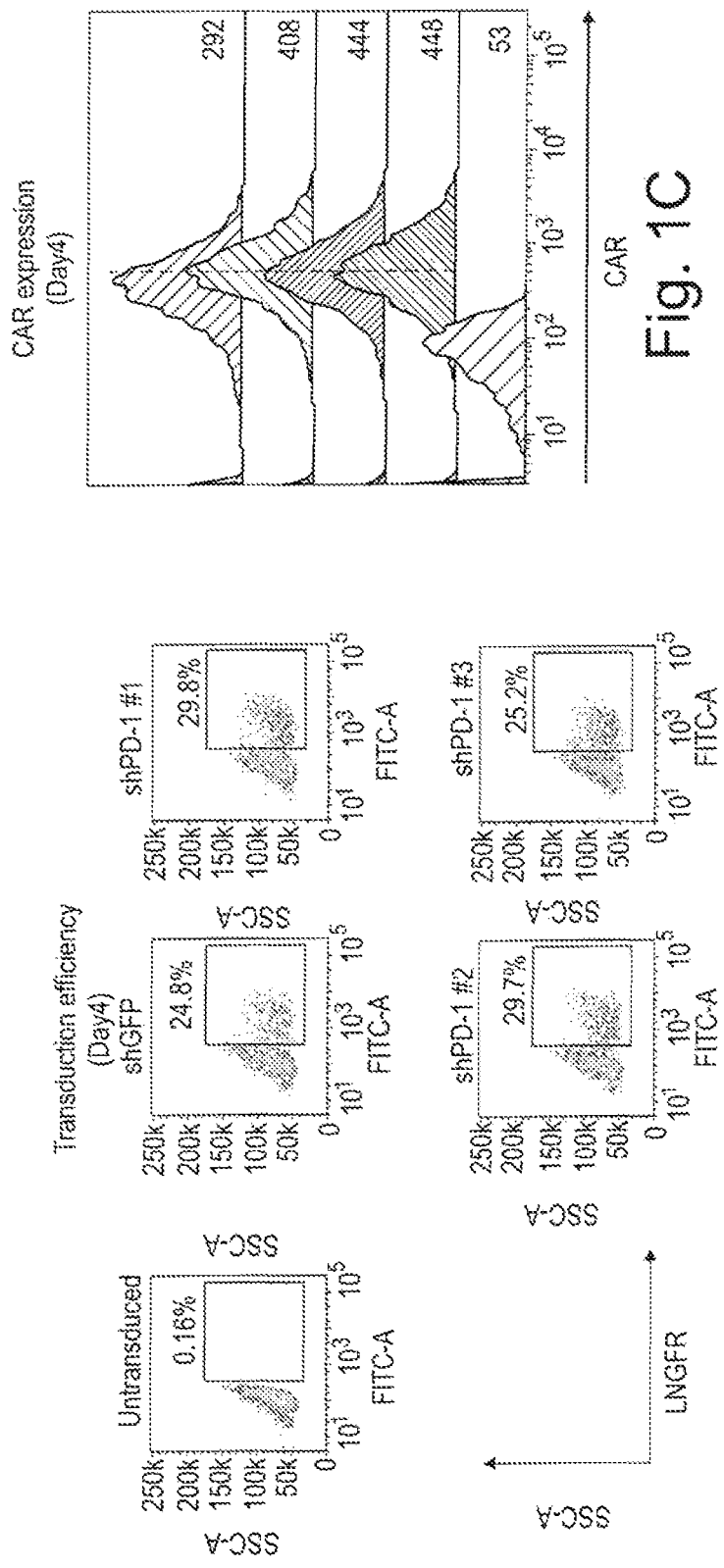

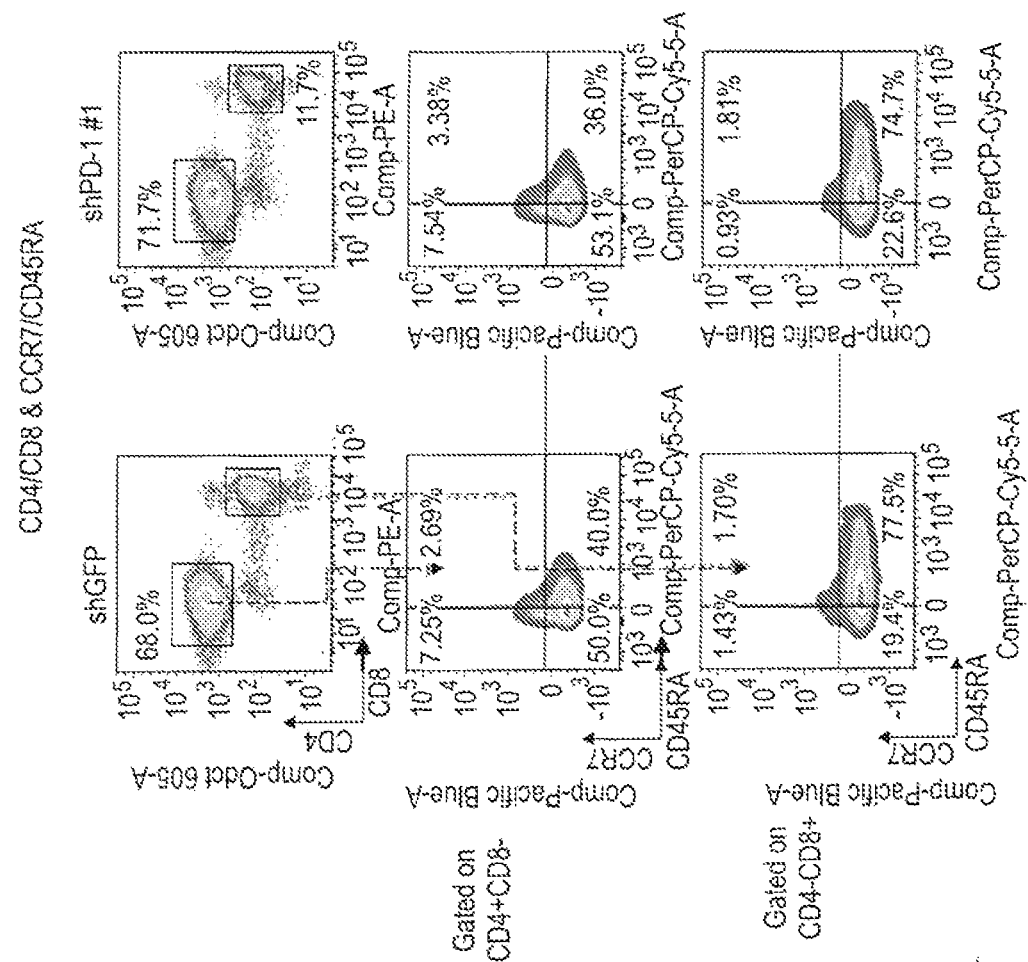
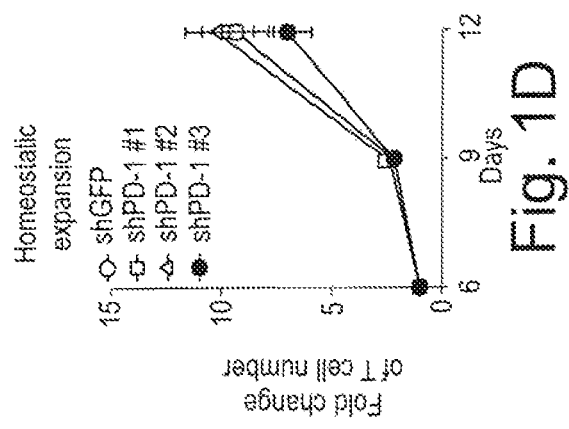
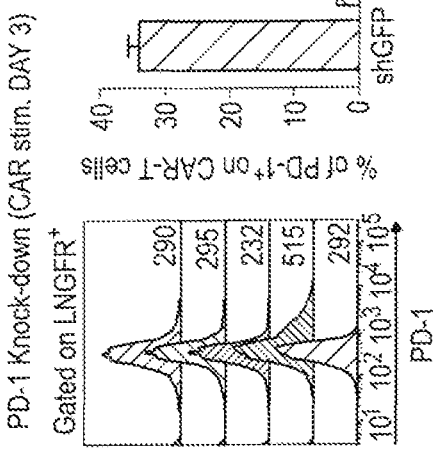

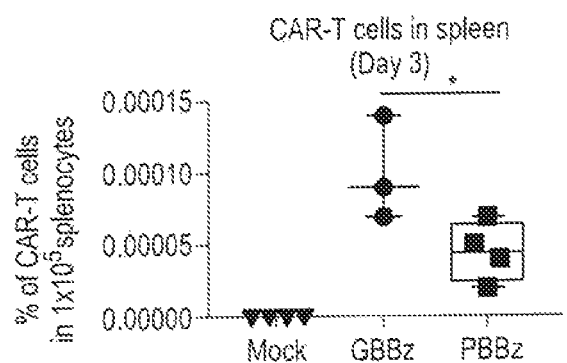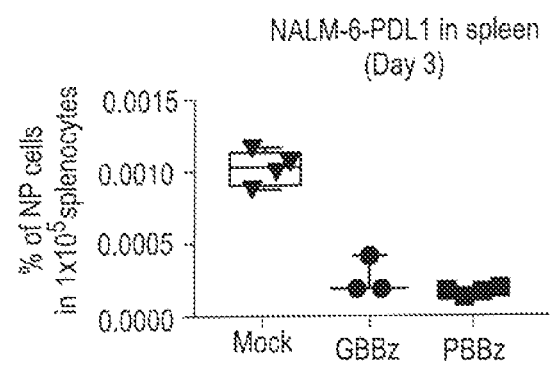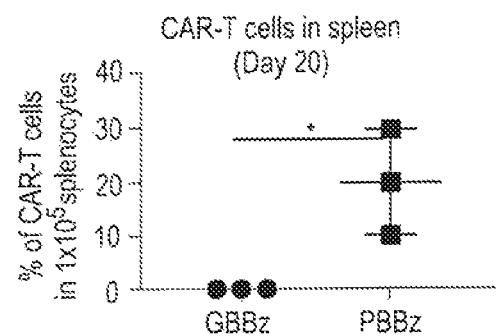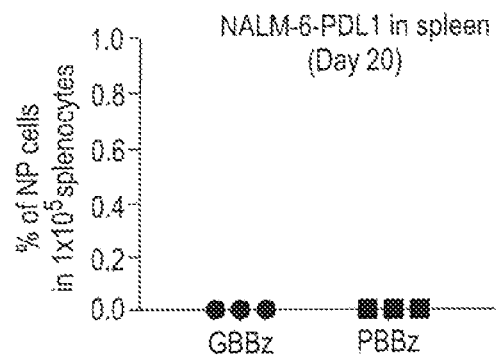
Fig. 5B

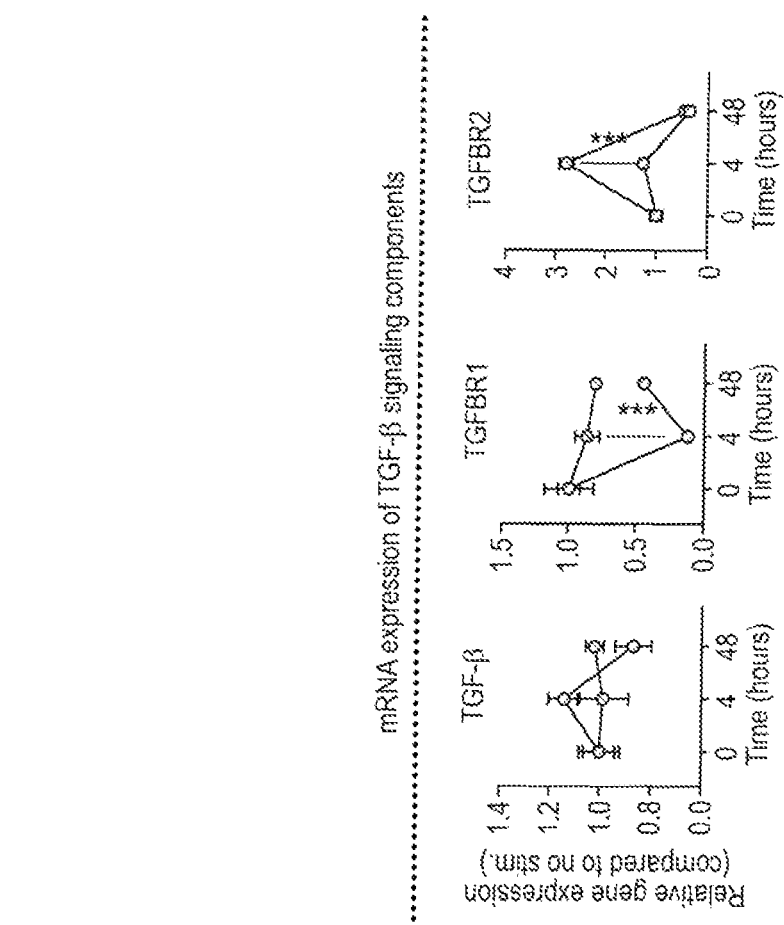
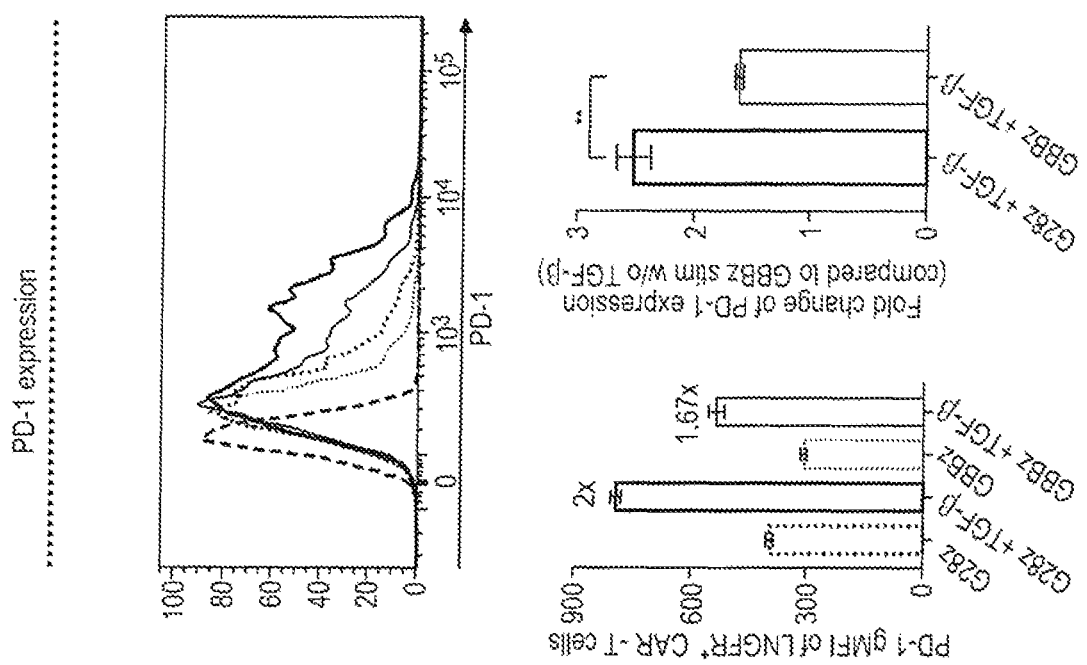
Fig. 11B
Fig. 11C

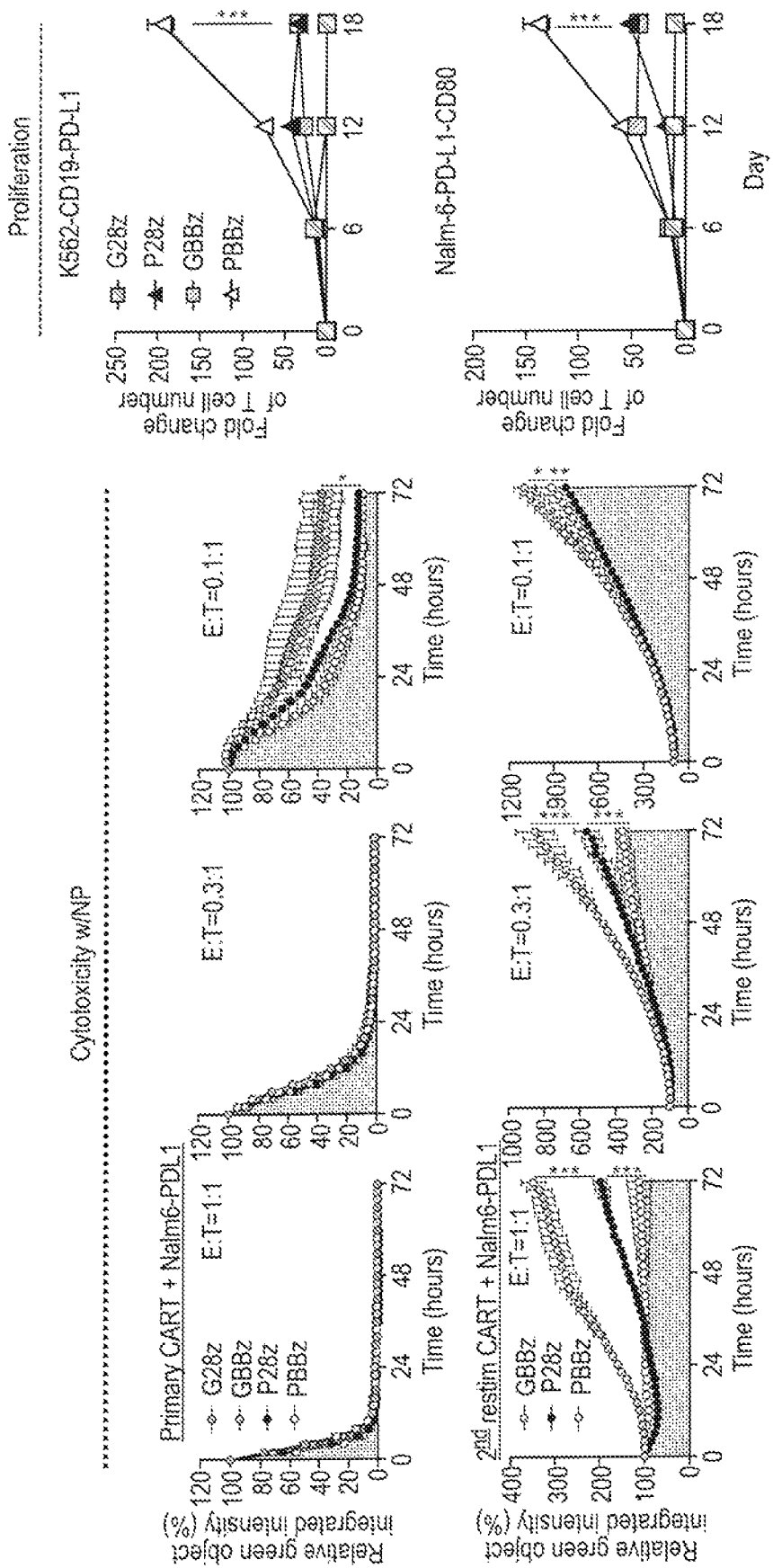

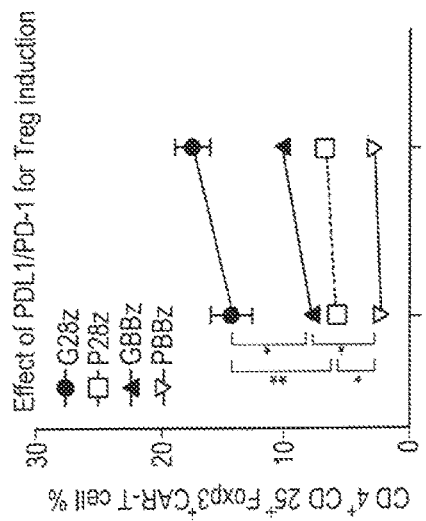
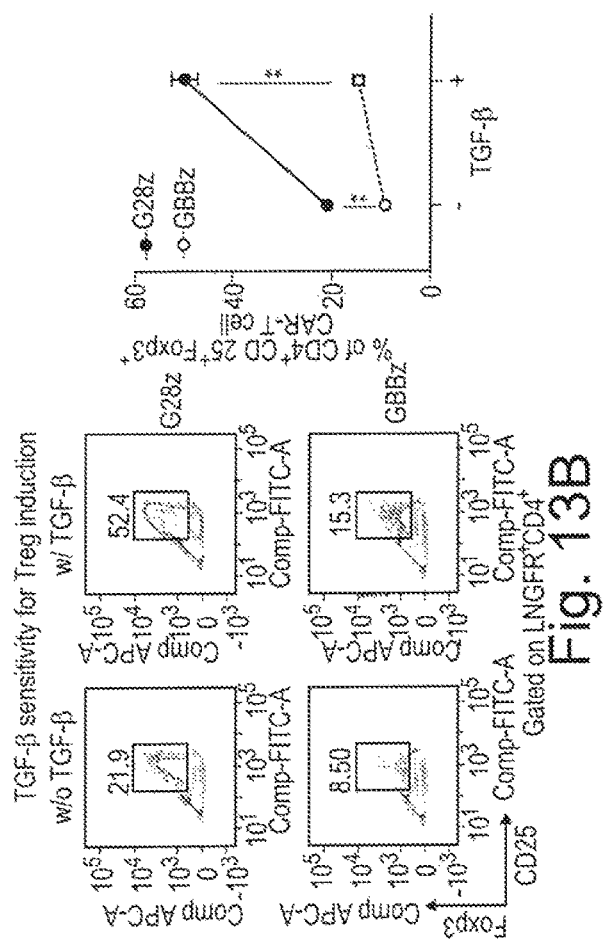
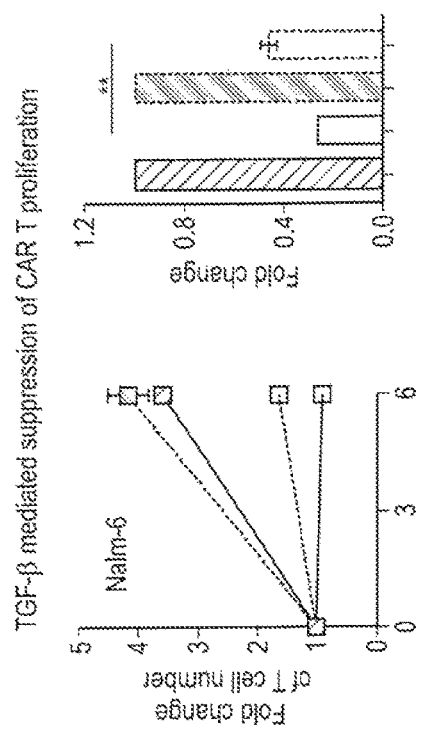
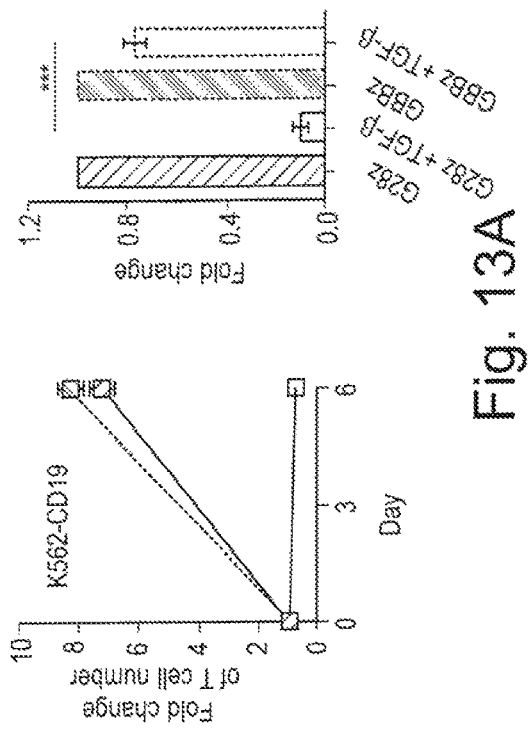
Fig. 13A  Fig. 13B  Fig. 13C

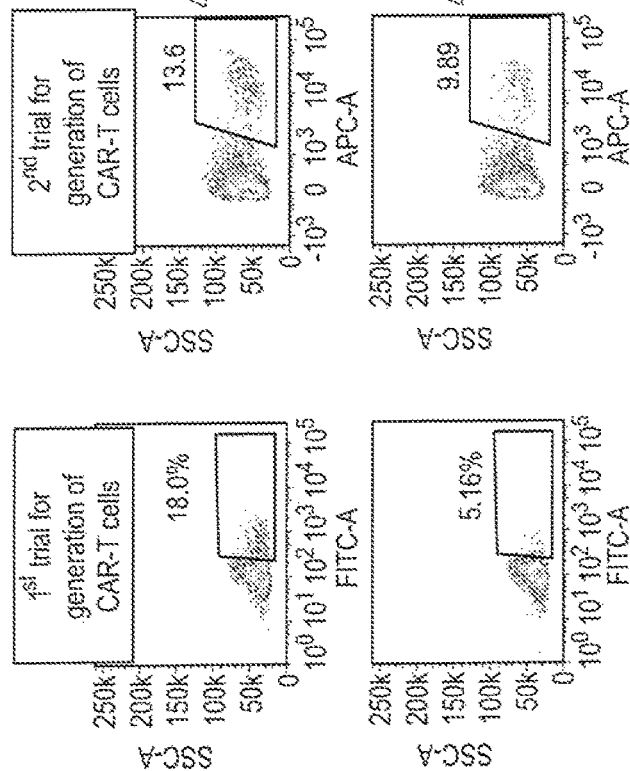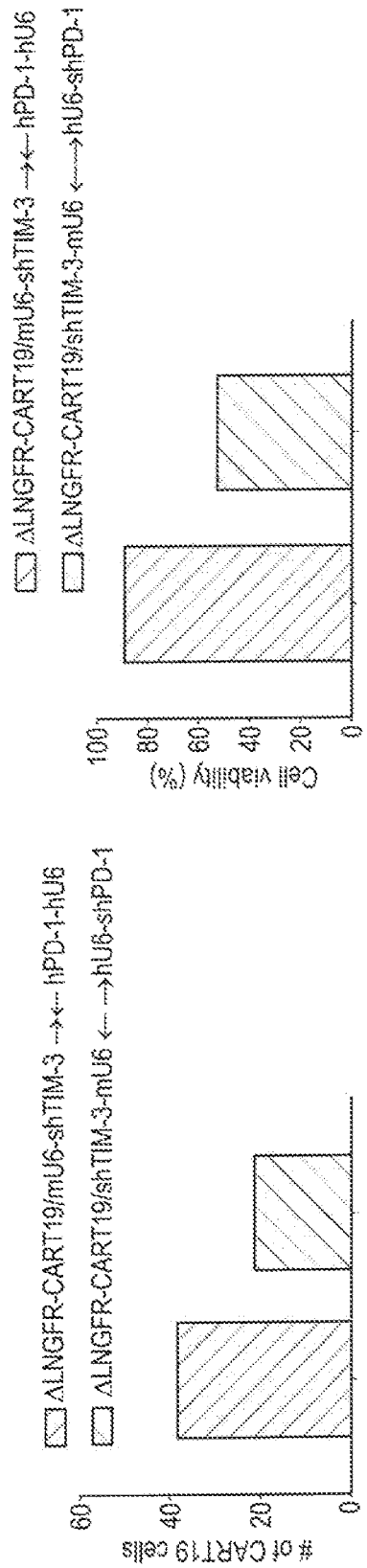
Fig. 20A
Fig. 20B
Fig. 20C

ENHANCED IMMUNE CELLS USING DUAL SHRNA AND COMPOSITION INCLUDING THE SAME

RELATED APPLICATION

This application is a national stage of International Patent Application No. PCT/IB2019/050194, filed Jan. 10, 2019, which claims priority to Korean Patent Application No. 10-2018-0004238, filed on Jan. 12, 2018. Each of the foregoing applications, in its entirety, is hereby incorporated herein by reference.

REFERENCE TO SEQUENCE LISTING SUBMITTED ELECTRONICALLY

This application incorporates by reference a Sequence Listing submitted with this application as a text file entitled 14570-001-228_SEQ_LISTING.txt, created on Jan. 5, 2019, and is 88,751 bytes in size.

FIELD OF THE INVENTION

The present disclosure is broadly concerned with the field of cancer immunotherapy. For example, the present invention generally relates to an immune cell comprising a genetically engineered antigen receptor that specifically binds to a target antigen and a genetic disruption agent that reduces or is capable of reducing the expression in the immune cell of a gene that weakens the function of the immune cell.

BACKGROUND

Anti-cancer therapies using immune cells by isolating T cells or NK cells (natural killer cells) from the body of a patient or a donor, culturing these cells in vitro, and then introducing them back into the body of a patient are currently receiving much attention as a new method of cancer therapy. In particular, immune cells having been subjected to a process of injecting new genetic information using viruses, etc. followed by culturing in an in vitro culturing process are reported to have greater anti-cancer effect over cells which have not. Here, the genetic information injected into the T cells is usually a Chimeric Antigen Receptor (hereinafter CAR) or a monoclonal T cell receptor (hereinafter mTCR) modified to have high affinity to the target antigen. These modified immune cells recognize and attack cancer cells which express the target antigen and induce cell death without being limited by their inherent antigen specificities. A method for genetically modifying T cells using CAR was first proposed by Eshhar et al. in 1989, and was called by the name of "T-body."

Provided herein are immune cell compositions and methods which address the problems with conventional concurrent immune cell therapies pointed out above, wherein said problems place a great economic burden on patients due to their high cost, act on T cells other than CAR-T, and pose a risk of autoimmune symptoms and cytokine release syndrome. Briefly, for example, disclosed herein are methods of preparation with high yield rates and low production costs. Moreover, by inhibiting molecules that suppress the function of immune cells with higher probability and effectiveness, the disclosure herein meets the need for technology to provide effective cell therapy. The technical problem the present disclosure aims to solve is not limited to the technical problem stated above, and other technical problems not mentioned shall be evident from the following to persons having ordinary skill in the art.

SUMMARY

Provided herein are vectors, immune cells, pharmaceutical compositions comprising the immune cells, and compositions comprising the immune cells. Also provided herein are methods of producing the immune cells, and methods of treatment and use of the immune cells.

In one aspect, provided herein are vectors. In some embodiments, provide is a vector comprising a base sequence encoding two types of short hairpin RNA (shRNA) which inhibit the expression of genes that weaken the function of immune cells, and a base sequence encoding a chimeric antigen receptor (CAR) or a T cell receptor (TCR), e.g., a monoclonal T cell receptor (mTCR). In some embodiments, the target of the CAR or TCR, e.g., mTCR, is a human tumor antigen selected from among increased antigens exhibiting increased expressed in cancer or from mutated forms of antigen found in cancer, for example, cancer cells, cancer tissue and/or tumor microenvironment.

In some embodiments, the expression of the two types of shRNA is characterized in that they are respectively regulated by two different promoters.

In some embodiments, the two promoters are RNA polymerase III promoters. In some embodiments, the two promoters are U6 promoters, for example, U6 promoters derived from different species. In some embodiments, the two promoters are oriented in the same direction relative to each other on the vector. In some embodiments, the two promoters are oriented in different directions from each other on the vector. For example, in a certain embodiment, the promoters are oriented in a head to head orientation. In another embodiment, the promoters are oriented in a tail to tail orientation.

In some embodiments, the gene weakening the function of immune cells is an immune checkpoint receptor or ligand.

In some embodiments, the immune checkpoint receptor or ligand is selected from a group consisting of PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK and 2B4.

In some embodiments, the gene weakening the function of immune cells is selected from a group consisting of FAS, CD45, PP2A, SHIP1, SHIP2, DGK alpha, DGK zeta, Cbl-b, CD147, LRR1, TGFBR1, IL10R alpha, KLGR1, DNMT3A and A2aR.

In some embodiments, two types of shRNA are utilized that target a gene or genes which weaken the function of immune cells. In some embodiments, the two types of shRNA either target a single gene which weakens the function of immune cells, or they target different genes which weaken the function of immune cells. In some embodiments, the two types of shRNA target PD-1. In some embodiments comprising two types of shRNA, one shRNA targets PD-1 and the second shRNA targets TIM-3. In some embodiments comprising two types of shRNA, one shRNA targets PD-1 and the second shRNA targets TIGIT.

shRNA forms a hairpin structure that comprises a sense shRNA sequence and an anti-sense shRNA sequence. In some embodiments, a base sequence encoding an shRNA described herein comprises a sequence selected from a group consisting of SEQ ID NOs: 2-219. In certain embodiments, a base sequence encoding an shRNA described herein comprises a sequence selected from a group consisting of SEQ ID NOs: 2-219, wherein said sequence encodes a sense shRNA sequence. In certain embodiments, a base sequence encoding an shRNA described herein comprises a sequence selected from a group consisting of SEQ ID NOs: 2-219, wherein said sequence encodes an anti-sense shRNA sequence.

In some embodiments, the vector comprises any one of the base sequences SEQ ID NO: 220 or 221. In some embodiments, the vector is a plasmid vector or a viral vector, for example a lentivirus vector, e.g., a retroviral vector, an adenovirus vector or an adeno-associated viral vector.

In another aspect, provided herein are immune cells comprising the vector expressing CAR or TCR, for example mTCR, and wherein expression of the target genes of the two types of shRNA is reduced to 40% or less than that of a control group which does not express shRNA for the target gene. In some embodiments, the immune cell is selected from between human-derived T cells and NK cells.

In another aspect, provided herein are pharmaceutical compositions for immune therapy of human patients comprising the immune cells described above. In some embodiments, the immune cell is originally derived from the patient. In some embodiments, the patient has a tumor or cancer in which an increase or variation in levels of cancer antigen targeted by the CAR or TCR, for example, mTCR expressed in the cell is detected.

In another aspect, provided herein are immune cells comprising a genetically engineered antigen receptor that specifically binds to a target antigen and a genetic disruption agent reducing or capable of reducing the expression in the immune cell of a gene that weakens the function of the immune cells.

In another aspect, provided herein is an immune cell comprising a genetically engineered antigen receptor that specifically binds to a target antigen and a genetic disruption agent reducing or capable of reducing the expression in the immune cell of a gene that weakens the function of the immune cell.

In some embodiments, the genetically engineered antigen receptor is a chimeric antigen receptor (CAR) or a T cell receptor (TCR).

In some embodiments, the genetically engineered antigen receptor is a CAR. In some embodiments, the CAR comprises an extracellular antigen recognition domain, a transmembrane domain, and an intracellular signal transduction domain. In some embodiments, the extracellular antigen recognition domain of the CAR specifically binds to the target antigen.

In some embodiments, the intracellular signal transduction domain of the CAR comprises an intracellular domain of a CD3 zeta (CD3ζ) chain. In some embodiments, the intracellular signal transduction domain of the CAR further comprises a costimulatory molecule. In some embodiments, the costimulatory molecule is selected from the group consisting of ICOS, 0X40, CD137 (4-1BB), CD27, and CD28. In some embodiments, the costimulatory molecule is CD137 (4-1BB). In some embodiments, the costimulatory molecule is CD28.

In some embodiments, the genetically engineered antigen receptor is a TCR. In some embodiments, the TCR is a monoclonal TCR (mTCR).

In some embodiments, the target antigen is expressed in or on the surface of a cancer cell, a cancer tissue, and/or a tumor microenvironment.

In some embodiments, the target antigen is selected from the group consisting of: 5T4 (Trophoblast glycoprotein), 707-AP, 9D7, AFP (α-fetoprotein), AlbZIP (androgen-induced bZIP), HPG1 (human prostate specific gene-1), α5β1-Integrin, σ5β6-Integrin, α-methylacyl-coenzyme A racemase, ART-4 (ADPribosyltransferase-4), B7H4 (v-set domain-containing T-cell activation inhibitor 1), BAGE-1 (B melanoma antigen-1), BCL-2 (B-cell CLL/lymphoma-2), BING-4 (WD repeat domain 46), CA 15-3/CA 27-29 (mucin 1), CA 19-9 (cancer antigen 19-9), CA 72-4 (cancer antigen 72-4), CA125 (cancer antigen 125), calreticulin, CAMEL (CTL-recognized antigen on melanoma), CASP-8 (caspase 8), cathepsin B, cathepsin L, CD19 (cluster of differentiation 19), CD20, CD22, CD25, CD30, CD33, CD4, CD52, CD55, CD56, CD80, CEA (carcinoembryonic antigen SG8), CLCA2 (chloride channel accessory 2), CML28 (chronic myelogenous leukemia tumor antigen 28), Coactosin-like protein, Collagen XXIII, COX-2 (cyclooxygenase-2), CT-9/BRD6 (cancer/testis antigen 9), Cten (c-terminal tensin-like protein), cyclin B1, cyclin D1, cyp-B, CYPB1 (cytochrome p450 family 1 subfamily b member 1), DAM-10/MAGE-B1 (melanoma-associated antigen B1), DAM-6/MAGE-B2, EGFR/Her1 (epidermal growth factor receptor), EMMPRIN (basigin), EpCam, EphA2 (EPH receptor A2), EphA3, ErbB3 (Erb-B2 receptor tyrosine kinase 3), EZH2 (enhancer of zeste 2 polycomb repressive complex 2 subunit), FGF-5 (fibroblast growth factor 5), FN (fibronectin), Fra-1 (Fosrelated antigen-1), G250/CAIX (carbonic anhydrase 9), GAGE-1 (G antigen-1), GAGE-2, GAGE-3, GAGE-4, GAGE-5, GAGE-6, GAGE-7b, GAGE-8, GDEP (gene differentially expressed in prostate), GnT-V (gluconate kinase), gp100 (melanocytes lineage-specific antigen GP100), GPC3 (glypican3), HAGE (helical antigen), HAST-2 (sulfotransferase family 1A member 1), hepsin, Her2/neu/ErbB2 (Erb-B2 receptor tyrosine kinase 2), HERV-K-MEL, HNE (medullasin), homeobox NKX 3.1, HOM-TES-14/SCP-1, HOM-TES-85, HPV-E6, HPVE7, HST-2 (sirtuin-2), hTERT, iCE (caspase 1), IGF-1R (insulin like growth factor-1 receptor), IL-13Ra2 (interleukin-13 receptor subunit a 2), IL-2R (interleukin-2 receptor), IL-5 (interleukin-5), immature laminin receptor, kallikrein 2, kallikrein 4, Ki67, KIAA0205 (lysophosphatidylglycerol acyltransferase 1), KK-LC-1 (kita-kyushu lung cancer antigen-1), KM-HN-1, LAGE-1 (L antigen family member-1), Livin, MAGE-A1, MAGE-A10, MAGE-A12, MAGEA2, MAGE-A3, MAGE-A4, MAGE-A6, MAGE-A9, MAGE-B1, MAGE-B10, MAGE-B16, MAGEB17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2 (melanoma antigen family L2), mammaglobin A, MART-1/Melan-A (melanoma antigen recognized by T-cells-1), MART-2, matrix protein 22, MC1R (melanocortin 1 receptor), M-CSF (macrophage colony-stimulating factor), Mesothelin, MG50/PXDN (peroxidasin), MMP 11 (matrix metalloprotease 11), MN/CA IX-antigen (carbonic anhydrase 9), MRP-3 (multidrug resistance-associated protein-3), MUC1 (mucin 1), MUC2, NA88-A (VENT-like homeobox 2 pseudogene 1), N-acetylglucos-aminyltransferase-V, Neo-PAP (Neo-poly (A) polymerase), NGEP (new gene expressed in prostate), NMP22 (nuclear matrix protein 22), NPM/ALK (nucleophosmin), NSE (neuron-specific enolase), NY-ESO-1, NY-ESO-B, OA1 (osteoarthritis QTL 1), OFA-iLRP (oncofetal antigen immature laminin receptor protein), OGT (O-GlcNAc transferase), OS-9 (endoplasmic reticulum lectin), osteocalcin, osteopontin, p15 (CDK inhibitor 2B), p53, PAGE-4 (P antigen family member-4), PAI-1 (plasminogen activator inhibitor-1), PAI-2, PAP (prostatic acid phosphatase), PART-1 (prostate androgen-regulated transcript 1), PATE (prostate and testis expressed 1), PDEF (prostate-derived Ets factor), Pim-1-Kinase (proviral integration site 1), Pin1 (Peptidyl-prolyl cis-trans isomerase NIMA-interacting 1), POTE (expressed in prostate, ovary, testis, and placenta), PRAME (preferentially expressed antigen in melanoma), prostein, proteinase-3, PSA(prostate-specific antigen), PSCA (prostate stem cell antigen), PSGR (prostate-specific G-protein coupled receptor), PSM, PSMA (prostate specific membrane antigen), RAGE-1 (renal tumor carcinoma antigen), RHAMM/CD168, RU1 (renal ubiquitous protein 1), RU2, SAGE(sarcoma antigen), SART-1 (squamous cell carcinoma antigen recognized by T-cells-1), SART-2, SART-3, Sp17 (sperm protein 17), SSX-1 (SSX family member 1), SSX-2/HOM-MEL-40, SSX-4, STAMP-1 (STEAP2 metalloreductase), STEAP, survivin, survivin-213, TA-90 (tumor associated antigen-90), TAG-72 (tumor associated glycoprotein-72), TARP(TCRγ alternate reading frame protein), TGFb (transforming growth factor β), TGFbR11 (transforming growth factor β receptor 11), TGM-4 (transglutaminase 4), TRAG-3(taxol resistance associated gene 3), TRG (T-cell receptor γ locus), TRP-1 (transient receptor potential-1), TRP-2/6b, TRP-2/INT2, Trp-p8, Tyrosinase, UPA (U-plasminogen activator), VEGF (vascular endothelial growth factor A), VEGFR-2/FLK-1, and WT1 (wilms tumor 1). In some embodiments, the target antigen is CD19 or CD22. In some embodiments, the target antigen is CD19.

In some embodiments, the target antigen is a cancer antigen whose expression is increased in or on the surface of a cancer cell, a cancer tissue, and/or a tumor microenvironment.

In some embodiments, the target antigen is selected from the group consisting of: α-actinin-4/m, ARTC1/m, bcr/abl, beta-Catenin/m, BRCA1/m, BRCA2/m, CASP-5/m, CASP-8/m, CDCl$_2$7/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYTSSX-1, SYT-SSX-2, TEL-AME1, TGFbRII, and TPI/m; and wherein the target antigen is a mutated form of a cancer antigen expressed in or on the surface of a cancer cell, a cancer tissue, and/or a tumor microenvironment.

In some embodiments, expression of the gene that weakens the function of the immune cell causes one or more of the following:
i) inhibition of proliferation of the immune cell;
ii) induction of cell death of the immune cell;
iii) inhibition of the ability of the immune cell to recognize the target antigen and/or to get activated;
iv) induction of differentiation of the immune cell into a cell that does not induce immune response to the target antigen;
v) decreased reactions of the immune cell to a molecule which promotes immune response of the immune cell; or
vi) increased reactions of the immune cell to a molecule which suppresses immune response of the immune cell.

In some embodiments, the gene that weakens the function of the immune cell is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, 2B4, FAS, CD45, PP2A, SHP1, SHP2, DGK alpha, DGK zeta, Cbl-b, Cbl-c, CD148, LRR1, TGFBR1, IL10RA, KLGR1, DNMT3A, and A2aR.

In some embodiments, the gene that weakens the function of the immune cell increases reactions of the immune cell to a molecule which suppresses immune response of the immune cell.

In some embodiments, the gene that increases reactions of the immune cell to a molecule which suppresses immune response of the immune cell encodes an immune checkpoint receptor or ligand.

In some embodiments, the immune checkpoint receptor or ligand is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, and 2B4.

In some embodiments, the genetic disruption agent reduces the expression of a gene in the immune cell that weakens the function of the immune cell by at least 30, 40, 50, 60, 70, 80, 90, or 95% as compared to the immune cell in the absence of the genetic disruption agent.

In some embodiments, the genetic disruption agent reduces the expression of a gene that increases reactions of the immune cell to a molecule which suppresses immune response of the immune cell.

In some embodiments, the genetic disruption agent reduces the expression of a gene that encodes an immune checkpoint receptor or ligand.

In some embodiments, the genetic disruption agent reduces the expression of a gene selected from the group consisting of: PD1, PD-L1, CTLA4, TIM3, CEACAM (CEACAM-1, CEACAM-3 or CEACAM-5), LAG3, VISTA, BTLA, TIGIT, LAIR1, CD160, CD96, MerTK, and 2B4.

In some embodiments, the genetic disruption agent reduces the expression of the gene that weakens the function of the immune cell by RNA interference (RNAi). In some embodiments, more than one genetic disruption agents reduce the expression of the gene that weakens the function of the immune cell in the immune cell by RNAi.

In some embodiments, the genetic disruption agents target a single gene which weakens the function of the immune cell, or target different genes which weaken the function of the immune cell wherein a first genetic disruption agent targets a first gene and a second genetic disruption agent targets a second gene, or in any combination thereof.

In some embodiments, the RNAi is mediated by a short hairpin RNA (shRNA).

In some embodiments, the RNAi is mediated by more than one shRNAs. In some embodiments, the RNAi is mediated by two shRNAs.

In some embodiments, two shRNAs target PD-1. In some embodiments, a first shRNA targets PD-1 and a second shRNA targets TIM-3. In some embodiments, a first shRNA targets PD-1 and a second shRNA targets CTLA-4. In some embodiments, a first shRNA targets PD-1 and a second shRNA targets LAG-3. In some embodiments, a first shRNA targets PD-1 and a second shRNA targets TIGIT.

In some embodiments, the immune cell comprises nucleotide sequences that encode a shRNA. In some embodiments, the immune cell comprises nucleotide sequences that encode more than one shRNAs. In some embodiments, the immune cell comprises nucleotide sequences that encode two shRNAs. Unless otherwise noted, as used herein the terms "base sequence" an nucleotide sequence" are interchangeable.

In some embodiments, the nucleotide sequences encoding the shRNA comprise sequences selected from the group consisting of SEQ ID NOs: 2-219 and 238-267.

In some embodiments, the nucleotide sequences encoding the shRNA is on a vector.

In some embodiments, the expression of different shRNA is respectively regulated by different promoters. In some embodiments, the expression of two different shRNA is respectively regulated by two different promoters. In some embodiments, the two different promoters are RNA polymerase III promoters. In some embodiments, the two promoters are U6 promoters. In some embodiments, the U6 promoters derive from different species. In some embodiments, the two promoters are oriented in different directions from each other. For example, in a certain embodiment, the promoters are oriented in a head to head orientation. In another embodiment, the promoters are oriented in a tail to tail orientation.

In some embodiments, the genetically engineered antigen receptor and the genetic disruption agent are each expressed from a vector. In some embodiments, the genetically engineered antigen receptor and the genetic disruption agent are expressed from the same vector.

In some embodiments, the vector is a plasmid vector or a viral vector. In some embodiments, the viral vector is a lentivirus vector or a adenovirus vector. In some embodiments, the lentivirus vector is a retrovirus vector.

In some embodiments, the immune cell is selected from the group consisting of a T cell and a natural killer (NK) cell. In some embodiments, the immune cell is a T cell. In some embodiments, the T cell is a CD4+ T cell or a CD8+ T cell.

In some embodiments, the immune cell comprises nucleotide sequences that encode two shRNAs and a CAR on the same vector. In some embodiments, the two shRNA are each regulated by two different RNA polymerase III promoters oriented in different directions from each other. For example, in a certain embodiment, the promoters are oriented in a head to head orientation. In another embodiment, the promoters are oriented in a tail to tail orientation. In some embodiments, the CAR targets CD19, the first shRNA targets PD-1, and the second shRNA targets TIGIT.

In another aspect, provided herein is a method of producing an immune cell comprising introducing into an immune cell, simultaneously or sequentially in any order:
(1) a gene encoding a genetically engineered antigen receptor that specifically binds to a target antigen; and
(2) a genetic disruption agent reducing or capable of reducing expression in the immune cell of a gene that weakens the function of the immune cell,
thereby producing an immune cell in which a genetically engineered antigen receptor is expressed and expression of the gene that weakens the function of the immune cell is reduced.

In some embodiments, the genetically engineered antigen receptor is a chimeric antigen receptor (CAR) or a T cell receptor (TCR).

In some embodiments, the genetically engineered antigen receptor is a CAR. In some embodiments, the CAR comprises an extracellular antigen recognition domain, a transmembrane domain, and an intracellular signal transduction domain. In some embodiments, the extracellular antigen recognition domain of the CAR specifically binds to the target antigen.

In some embodiments, the intracellular signal transduction domain of the CAR comprises an intracellular domain of a CD3 zeta (CD3ζ) chain. In some embodiments, the intracellular signal transduction domain of the CAR further comprises a costimulatory molecule. In some embodiments, the costimulatory molecule is selected from the group consisting of ICOS, 0X40, CD137 (4-1BB), CD27, and CD28.

In some embodiments, the costimulatory molecule is CD137 (4-1BB). In some embodiments, the costimulatory molecule is CD28.

In some embodiments, the genetically engineered antigen receptor is a TCR. In some embodiments, the TCR is a monoclonal TCR (mTCR).

In some embodiments, the target antigen is expressed in or on the surface of a cancer cell, a cancer tissue, and/or a tumor microenvironment.

In some embodiments, the target antigen is selected from the group consisting of: 5T4 (Trophoblast glycoprotein), 707-AP, 9D7, AFP (α-fetoprotein), AlbZIP (androgen-induced bZIP), HPG1 (human prostate specific gene-1), α5β1-Integrin, α5β6-Integrin, α-methylacyl-coenzyme A racemase, ART-4 (ADPribosyltransferase-4), B7H4 (v-set domain-containing T-cell activation inhibitor 1), BAGE-1 (B melanoma antigen-1), BCL-2 (B-cell CLL/lymphoma-2), BING-4 (WD repeat domain 46), CA 15-3/CA 27-29 (mucin 1), CA 19-9 (cancer antigen 19-9), CA 72-4 (cancer antigen 72-4), CA125 (cancer antigen 125), calreticulin, CAMEL (CTL-recognized antigen on melanoma), CASP-8 (caspase 8), cathepsin B, cathepsin L, CD19 (cluster of differentiation 19), CD20, CD22, CD25, CD30, CD33, CD4, CD52, CD55, CD56, CD80, CEA (carcinoembryonic antigen SG8), CLCA2 (chloride channel accessory 2), CML28 (chronic myelogenous leukemia tumor antigen 28), Coactosin-like protein, Collagen XXIII, COX-2 (cyclooxygenase-2), CT-9/BRD6 (cancer/testis antigen 9), Cten (c-terminal tensin-like protein), cyclin B1, cyclin D1, cyp-B, CYPB1 (cytochrome p450 family 1 subfamily b member 1), DAM-10/MAGE-B1 (melanoma-associated antigen B1), DAM-6/MAGE-B2, EGFR/Her1 (epidermal growth factor receptor), EMMPRIN (basigin), EpCam, EphA2 (EPH receptor A2), EphA3, ErbB3 (Erb-B2 receptor tyrosine kinase 3), EZH2 (enhancer of zeste 2 polycomb repressive complex 2 subunit), FGF-5 (fibroblast growth factor 5), FN (fibronectin), Fra-1 (Fosrelated antigen-1), G250/CAIX (carbonic anhydrase 9), GAGE-1 (G antigen-1), GAGE-2, GAGE-3, GAGE-4, GAGE-5, GAGE-6, GAGE-7b, GAGE-8, GDEP (gene differentially expressed in prostate), GnT-V (gluconate kinase), gp100 (melanocytes lineage-specific antigen GP100), GPC3 (glypican3), HAGE (helical antigen), HAST-2 (sulfotransferase family 1A member 1), hepsin, Her2/neu/ErbB2 (Erb-B2 receptor tyrosine kinase 2), HERV-K-MEL, HNE (medullasin), homeobox NKX 3.1, HOM-TES-14/SCP-1, HOM-TES-85, HPV-E6, HPVE7, HST-2 (sirtuin-2), hTERT, iCE (caspase 1), IGF-1R (insulin like growth factor-1 receptor), IL-13Ra2 (interleukin-13 receptor subunit a 2), IL-2R (interleukin-2 receptor), IL-5 (interleukin-5), immature laminin receptor, kallikrein 2, kallikrein 4, Ki67, KIAA0205 (lysophosphatidylglycerol acyltransferase 1), KK-LC-1 (kita-kyushu lung cancer antigen-1), KM-HN-1, LAGE-1 (L antigen family member-1), Livin, MAGE-A1, MAGE-A10, MAGE-A12, MAGEA2, MAGE-A3, MAGE-A4, MAGE-A6, MAGE-A9, MAGE-B1, MAGE-B10, MAGE-B16, MAGEB17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2 (melanoma antigen family L2), mammaglobin A, MART-1/Melan-A (melanoma antigen recognized by T-cells-1), MART-2, matrix protein 22, MC1R (melanocortin 1 receptor), M-CSF (macrophage colony-stimulating factor), Mesothelin, MG50/PXDN (peroxidasin), MMP 11 (matrix metalloprotease 11), MN/CA IX-antigen (carbonic anhydrase 9), MRP-3 (multidrug resistance-associated protein-3), MUC1 (mucin 1), MUC2, NA88-A (VENT-like homeobox 2 pseudogene 1), N-acetylglucos-aminyltransferase-V, Neo-PAP (Neo-poly (A) polymerase), NGEP (new gene expressed in prostate), NMP22 (nuclear matrix protein 22), NPM/ALK (nucleophosmin), NSE (neuron-specific enolase), NY-ESO-1, NY-ESO-B, OA1 (osteoarthritis QTL 1), OFA-iLRP (oncofetal antigen immature laminin receptor protein), OGT (O-GlcNAc transferase), OS-9 (endoplasmic reticulum lectin), osteocalcin, osteopontin, p15 (CDK inhibitor 2B), p53, PAGE-4 (P antigen family member-4), PAI-1 (plasminogen activator inhibitor-1), PAI-2, PAP (prostatic acid phosphatase), PART-1 (prostate androgen-regulated transcript 1), PATE (prostate and testis expressed 1), PDEF (prostate-derived Ets factor), Pim-1-Kinase (proviral integration site 1), Pin1 (Peptidyl-prolyl cis-trans isomerase NIMA-interacting 1), POTE (expressed in prostate, ovary, testis, and placenta), PRAME (preferentially expressed antigen in melanoma), prostein, proteinase-3, PSA(prostate-specific antigen), PSCA (prostate stem cell antigen), PSGR (prostate-specific G-protein coupled receptor), PSM, PSMA (prostate specific membrane antigen), RAGE-1 (renal tumor carcinoma antigen), RHAMM/CD168, RU1 (renal ubiquitous protein 1), RU2, SAGE(sarcoma antigen), SART-1 (squamous cell carcinoma antigen recognized by T-cells-1), SART-2, SART-3, Sp17(sperm protein 17), SSX-1 (SSX family member 1), SSX-2/HOM-MEL-40, SSX-4, STAMP-1 (STEAP2 metalloreductase), STEAP, survivin, survivin-213, TA-90 (tumor associated antigen-90), TAG-72 (tumor associated glycoprotein-72), TARP (TCRγ alternate reading frame protein), TGFb (transforming growth factor β), TGFbR11 (transforming growth factor β receptor 11), TGM-4 (transglutaminase 4), TRAG-3 (taxol resistance associated gene 3), TRG (T-cell receptor γ locus), TRP-1 (transient receptor potential-1), TRP-2/6b, TRP-2/INT2, Trp-p8, Tyrosinase, UPA (U-plasminogen activator), VEGF (vascular endothelial growth factor A), VEGFR-2/FLK-1, and WT1 (wilms tumor 1). In some embodiments, the target antigen is CD19 or CD22. In some embodiments, the target antigen is CD19.

In some embodiments, the target antigen is a cancer antigen whose expression is increased in or on the surface of a cancer cell, a cancer tissue, and/or a tumor microenvironment.

In some embodiments, the target antigen is selected from the group consisting of: α-actinin-4/m, ARTC1/m, bcr/abl, beta-Catenin/m, BRCA1/m, BRCA2/m, CASP-5/m, CASP-8/m, CDCl₂7/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYTSSX-1, SYT-SSX-2, TEL-AML1, TGFbRII, and TPI/m; and wherein the target antigen is a mutated form of a cancer antigen expressed in or on the surface of a cancer cell, a cancer tissue, and/or a tumor microenvironment.

In some embodiments, expression of the gene that weakens the function of the immune cell causes one or more of the following:
i) inhibition of proliferation of the immune cell;
ii) induction of cell death of the immune cell;
iii) inhibition of the ability of the immune cell to recognize the target antigen and/or to get activated;
iv) induction of differentiation of the immune cell into a cell that does not induce immune response to the target antigen;
v) decreased reactions of the immune cell to a molecule which promotes immune response of the immune cell; or
vi) increased reactions of the immune cell to a molecule which suppresses immune response of the immune cell.

In some embodiments, the gene that weakens the function of the immune cell is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, 2B4, FAS, CD45, PP2A, SHP1, SHP2, DGK alpha, DGK zeta, Cbl-b, Cbl-c, CD148, LRR1, TGFBR1, IL10RA, KLGR1, DNMT3A, and A2aR.

In some embodiments, the gene that weakens the function of the immune cell increases reactions of the immune cell to a molecule which suppresses immune response of the immune cell.

In some embodiments, the gene that increases reactions of the immune cell to a molecule which suppresses immune response of the immune cell encodes an immune checkpoint receptor or ligand.

In some embodiments, the immune checkpoint receptor or ligand is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, and 2B4.

In some embodiments, the genetic disruption agent reduces the expression of a gene in the immune cell that weakens the function of the immune cell by at least 30, 40, 50, 60, 70, 80, 90, or 95% as compared to the immune cell in the absence of the genetic disruption agent.

In some embodiments, the genetic disruption agent reduces the expression of a gene that increases reactions of the immune cell to a molecule which suppresses immune response of the immune cell.

In some embodiments, the genetic disruption agent reduces the expression of a gene that encodes an immune checkpoint receptor or ligand.

In some embodiments, the genetic disruption agent reduces the expression of a gene selected from the group consisting of: PD1, PD-L1, CTLA4, TIM3, CEACAM (CEACAM-1, CEACAM-3 or CEACAM-5), LAG3, VISTA, BTLA, TIGIT, LAIR1, CD160, CD96, MerTK, and 2B4.

In some embodiments, the genetic disruption agent reduces the expression of the gene that weakens the function of the immune cell by RNA interference (RNAi). In some embodiments, more than one genetic disruption agents reduce the expression of the gene that weakens the function of the immune cell in the immune cell by RNAi.

In some embodiments, the genetic disruption agents target a single gene which weakens the function of the immune cell, or target different genes which weaken the function of the immune cell wherein a first genetic disruption agent targets a first gene and a second genetic disruption agent targets a second gene, or in any combination thereof.

In some embodiments, the RNAi is mediated by a short hairpin RNA (shRNA). In some embodiments, the RNAi is mediated by more than one shRNAs. In some embodiments, the RNAi is mediated by two shRNAs.

In some embodiments, two shRNAs target PD-1. In some embodiments, a first shRNA targets PD-1 and a second shRNA targets TIM-3. In some embodiments, a first shRNA targets PD-1 and a second shRNA targets CTLA-4. In some embodiments, a first shRNA targets PD-1 and a second shRNA targets LAG-3. In some embodiments, a first shRNA targets PD-1 and a second shRNA targets TIGIT.

In some embodiments, the immune cell comprises nucleotide sequences that encode a shRNA. In some embodiments, the immune cell comprises nucleotide sequences that encode more than one shRNAs. In some embodiments, the immune cell comprises nucleotide sequences that encode two shRNAs.

In some embodiments, the nucleotide sequences encoding the shRNA comprise sequences selected from the group consisting of SEQ ID NOs: 2-219 and 238-267.

In some embodiments, the nucleotide sequences encoding the shRNA is on a vector.

In some embodiments, the expression of different shRNA is respectively regulated by different promoters. In some embodiments, the expression of two different shRNA is respectively regulated by two different promoters. In some embodiments, the two different promoters are RNA polymerase III promoters. In some embodiments, the two promoters are U6 promoters. In some embodiments, the U6 promoters derive from different species. In some embodiments, the two promoters are oriented in different directions from each other. For example, in a certain embodiment, the promoters are oriented in a head to head orientation. In another embodiment, the promoters are oriented in a tail to tail orientation.

In some embodiments, the genetically engineered antigen receptor and the genetic disruption agent are each expressed from a vector. In some embodiments, the genetically engineered antigen receptor and the genetic disruption agent are expressed from the same vector.

In some embodiments, the vector is a plasmid vector or a viral vector. In some embodiments, the viral vector is a lentivirus vector or a adenovirus vector. In some embodiments, the lentivirus vector is a retrovirus vector.

In some embodiments, the immune cell is selected from the group consisting of a T cell and a natural killer (NK) cell. In some embodiments, the immune cell is a T cell. In some embodiments, the T cell is a CD4+ T cell or a CD8+ T cell.

In some embodiments, the immune cell comprises nucleotide sequences that encode two shRNAs and a CAR on the same vector. In some embodiments, the two shRNA are each regulated by two different RNA polymerase III promoters oriented in different directions from each other. For example, in a certain embodiment, the promoters are oriented in a head to head orientation. In another embodiment, the promoters are oriented in a tail to tail orientation. In some embodiments, the CAR targets CD19, the first shRNA targets PD-1, and the second shRNA targets TIGIT.

In another aspect, provided herein is a composition comprising the engineered immune cell. In another aspect, provided herein is a pharmaceutical composition comprising the immune cell and a pharmaceutically acceptable carrier.

In another aspect, provided herein is a method of treatment comprising administering to a subject having a disease or a condition the immune cell or the composition. In some embodiments, the genetically engineered antigen receptor specifically binds to an antigen associated with the disease or the condition. In some embodiments, the disease or the condition is a cancer or a tumor.

In another aspect, provided herein is immune cell or composition for use in treating a disease or a condition. In another aspect, provided herein is use of an immune cell or the composition in the manufacture of a medicament for treating a disease or a condition. In some embodiments, the genetically engineered antigen receptor specifically binds to an antigen associated with the disease or the condition. In some embodiments, the disease or the condition is a cancer or a tumor.

Further non-limiting embodiments are presented below.

1. A vector, comprising:
a base sequence encoding two types of short hairpin RNA (shRNA) which inhibit the expression of at least one gene that weakens the function of immune cells, and
a base sequence encoding a chimeric antigen receptor (CAR) or a monoclonal T cell receptor (mTCR).

2. The vector according to Embodiment 1, wherein the expression of the two types of shRNA is characterized in that they are respectively regulated by two different promoters.

3. The vector according to Embodiment 2, wherein the two promoters are RNA polymerase III promoters.

4. The vector according to Embodiment 2, wherein the two promoters are U6 promoters derived from different species.

5. The vector according to Embodiment 2, wherein the two promoters are oriented in different directions from each other on the vector.

6. The vector according to Embodiment 1, wherein the gene weakening the function of immune cells is an immune checkpoint receptor or ligand.

7. The vector according to Embodiment 6, wherein the immune checkpoint receptor or ligand is selected from a group consisting of PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK and 2B4.

8. The vector according to Embodiment 1, wherein the gene weakening the function of immune cells is selected from a group consisting of FAS, CD45, PP2A, SHIP1, SHIP2, DGK alpha, DGK zeta, Cbl-b, CD147, LRR1, TGFBR1, IL10R alpha, KLGR1, DNMT3A and A2aR.

9. The vector according to Embodiment 1, wherein the two types of shRNA target a single gene which weakens the function of immune cells, or wherein the two types of shRNA target different genes which weaken the function of immune cells.

10. The vector according to Embodiment 1, wherein the two types of shRNA target PD-1.

11. The vector according to Embodiment 1, wherein, of the two types of shRNA, i) one shRNA targets PD-1 and the second shRNA targets TIM-3, or ii) one shRNA targets PD-1 and the second shRNA targets TIGIT.

12. The vector according to Embodiment 1, wherein, of the two types of shRNA, the base sequence encoding one shRNA comprises a sequence selected from a group consisting of SEQ ID NOs: 2-219, and the base sequence encoding the second shRNA comprises a different sequence selected from the group consisting of SEQ ID Nos: 2-219.

13. The vector according to Embodiment 1, wherein the target of the CAR or mTCR is a human tumor antigen that exhibits increased expression in a cancer cell, cancer tissue, and/or tumor microenvironment, or is a mutated form of antigen found in a cancer cell, cancer tissue and/or tumor microenvironment.

14. The vector according to Embodiment 1, whether the vector comprises the base sequence of SEQ ID NO: 220 or 221.

15. The vector according to Embodiment 1, wherein the vector is a plasmid vector, a lentivirus vector, an adenovirus vector, an adeno-associated vector or a retrovirus vector.

16. An immune cell comprising the vector according to Embodiment 1, wherein expression of the one or more genes is reduced to 40% or less than that of expression in the absence of the shRNAs.
17. The immune cell according to Embodiment 16, wherein the immune cell is a human-derived T cell or natural killer (NK) cell.
18. A pharmaceutical composition comprising the immune cell according to any one of Embodiment 1-17.
19. The pharmaceutical composition according to Embodiment 18, for treatment of a patient in need of immune therapy, wherein the immune cell is originally obtained from the patient.
20. The pharmaceutical composition according to Embodiment 19, wherein the patient has a tumor or cancer in which the target, and/or an increase or variation in levels of the target, of the CAR or mTCR expressed in the immune cell is detected.
21. An immune cell comprising a genetically engineered antigen receptor that specifically binds to a target antigen and a genetic disruption agent reducing or capable of reducing the expression in the immune cell of a gene that weakens the function of the immune cell.
22. The immune cell of embodiment 21, wherein the genetically engineered antigen receptor is a chimeric antigen receptor (CAR) or a T cell receptor (TCR).
23. The immune cell of embodiment 22, wherein the genetically engineered antigen receptor is a CAR.
24. The immune cell of embodiment 23, wherein the CAR comprises an extracellular antigen recognition domain, a transmembrane domain, and an intracellular signal transduction domain.
25. The immune cell of embodiment 24, wherein the extracellular antigen recognition domain of the CAR specifically binds to the target antigen.
26. The immune cell of embodiment 24, wherein the intracellular signal transduction domain of the CAR comprises an intracellular domain of a CD3 zeta (CD3ζ) chain.
27. The immune cell of embodiment 26, wherein the intracellular signal transduction domain of the CAR further comprises a costimulatory molecule.
28. The immune cell of embodiment 27, wherein the costimulatory molecule is selected from the group consisting of ICOS, 0X40, CD137 (4-1BB), CD27, and CD28.
29. The immune cell of embodiment 28, wherein the costimulatory molecule is CD137 (4-1BB).
30. The immune cell of embodiment 28, wherein the costimulatory molecule is CD28.
31. The immune cell of embodiment 22, wherein the genetically engineered antigen receptor is a TCR.
32. The immune cell of embodiment 31, wherein the TCR is a monoclonal TCR (mTCR).
33. The immune cell of embodiment 31 or 32, wherein the target antigen is expressed in or on the surface of a cancer cell, a cancer tissue, and/or a tumor microenvironment.
34. The immune cell of embodiment 33, wherein the target antigen is selected from the group consisting of:
5T4 (Trophoblast glycoprotein), 707-AP, 9D7, AFP (α-fetoprotein), AlbZIP (androgen-induced bZIP), HPG1 (human prostate specific gene-1), α5β1-Integrin, α5β6-Integrin, α-methylacyl-coenzyme A racemase, ART-4 (ADPribosyltransferase-4), B7H4 (v-set domain-containing T-cell activation inhibitor 1), BAGE-1 (B melanoma antigen-1), BCL-2 (B-cell CLL/lymphoma-2), BING-4 (WD repeat domain 46), CA 15-3/CA 27-29 (mucin 1), CA 19-9 (cancer antigen 19-9), CA 72-4 (cancer antigen 72-4), CA125 (cancer antigen 125), calreticulin, CAMEL (CTL-recognized antigen on melanoma), CASP-8 (caspase 8), cathepsin B, cathepsin L, CD19 (cluster of differentiation 19), CD20, CD22, CD25, CD30, CD33, CD4, CD52, CD55, CD56, CD80, CEA (carcinoembryonic antigen SG8), CLCA2 (chloride channel accessory 2), CML28 (chronic myelogenous leukemia tumor antigen 28), Coactosin-like protein, Collagen XXIII, COX-2 (cyclooxygenase-2), CT-9/BRD6 (cancer/testis antigen 9), Cten (c-terminal tensin-like protein), cyclin B1, cyclin D1, cyp-B, CYPB1 (cytochrome p450 family 1 subfamily b member 1), DAM-10/MAGE-B1 (melanoma-associated antigen B1), DAM-6/MAGE-B2, EGFR/Her1 (epidermal growth factor receptor), EMMPRIN (basigin), EpCam, EphA2 (EPH receptor A2), EphA3, ErbB3 (Erb-B2 receptor tyrosine kinase 3), EZH2 (enhancer of zeste 2 polycomb repressive complex 2 subunit), FGF-5 (fibroblast growth factor 5), FN (fibronectin), Fra-1 (Fosrelated antigen-1), G250/CAIX (carbonic anhydrase 9), GAGE-1 (G antigen-1), GAGE-2, GAGE-3, GAGE-4, GAGE-5, GAGE-6, GAGE-7b, GAGE-8, GDEP (gene differentially expressed in prostate), GnT-V (gluconate kinase), gp100 (melanocytes lineage-specific antigen GP100), GPC3 (glypican3), HAGE (helical antigen), HAST-2 (sulfotransferase family 1A member 1), hepsin, Her2/neu/ErbB2 (Erb-B2 receptor tyrosine kinase 2), HERV-K-MEL, HNE (medullasin), homeobox NKX 3.1, HOM-TES-14/SCP-1, HOM-TES-85, HPV-E6, HPVE7, HST-2 (sirtuin-2), hTERT, iCE (caspase 1), IGF-1R (insulin like growth factor-1 receptor), IL-13Ra2 (interleukin-13 receptor subunit a 2), IL-2R (interleukin-2 receptor), IL-5 (interleukin-5), immature laminin receptor, kallikrein 2, kallikrein 4, Ki67, KIAA0205 (lysophosphatidylglycerol acyltransferase 1), KK-LC-1 (kita-kyushu lung cancer antigen-1), KM-HN-1, LAGE-1 (L antigen family member-1), Livin, MAGE-A1, MAGE-A10, MAGE-A12, MAGEA2, MAGE-A3, MAGE-A4, MAGE-A6, MAGE-A9, MAGE-B1, MAGE-B10, MAGE-B16, MAGEB17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2 (melanoma antigen family L2), mammaglobin A, MART-1/Melan-A (melanoma antigen recognized by T-cells-1), MART-2, matrix protein 22, MC1R (melanocortin 1 receptor), M-CSF (macrophage colony-stimulating factor), Mesothelin, MG50/PXDN (peroxidasin), MMP 11 (matrix metalloprotease 11), MN/CA IX-antigen (carbonic anhydrase 9), MRP-3 (multidrug resistance-associated protein-3), MUC1 (mucin 1), MUC2, NA88-A (VENT-like homeobox 2 pseudogene 1), N-acetylglucos-aminyltransferase-V, Neo-PAP (Neo-poly (A) polymerase), NGEP (new gene expressed in prostate), NMP22 (nuclear matrix protein 22), NPM/ALK (nucleophosmin), NSE (neuron-specific enolase), NY-ESO-1, NY-ESO-B, OA1 (osteoarthritis QTL 1), OFA-iLRP (oncofetal antigen immature laminin receptor protein), OGT (O-GlcNAc transferase), OS-9 (endoplasmic reticulum lectin), osteocalcin, osteopontin, p15 (CDK inhibitor 2B), p53, PAGE-4 (P antigen family member-4), PAI-1 (plasminogen activator inhibitor-1), PAI-2, PAP (prostatic acid phosphatase), PART-1 (prostate androgen-regulated transcript 1), PATE (prostate and testis expressed 1), PDEF (prostate-derived Ets factor), Pim-1-Kinase (proviral integration site 1), Pin1 (Peptidyl-prolyl cis-trans isomerase NIMA-interacting 1), POTE (expressed in prostate, ovary, testis, and placenta), PRAME (preferentially expressed antigen in melanoma), protein, proteinase-3, PSA (prostate-specific antigen), PSCA (prostate stem cell antigen), PSGR (prostate-specific G-protein coupled receptor), PSM, PSMA (prostate specific membrane antigen), RAGE-1 (renal tumor carcinoma antigen), RHAMM/CD168, RU1 (renal ubiquitous protein 1), RU2, SAGE (sarcoma antigen), SART-1 (squamous cell carcinoma antigen recognized by T-cells-1), SART-2, SART-3, Sp17 (sperm protein 17), SSX-1 (SSX family member 1), SSX-2/HOM-MEL-40, SSX-4, STAMP-1 (STEAP2 metalloreductase), STEAP, survivin, survivin-213, TA-90 (tumor associated antigen-90), TAG-72(tumor associated glycoprotein-72), TARP (TCRγ alternate reading frame protein), TGFb (transforming growth factor β), TGFbR11 (transforming growth factor β receptor 11), TGM-4 (transglutaminase 4), TRAG-3 (taxol resistance associated gene 3), TRG (T-cell receptor γ locus), TRP-1 (transient receptor potential-1), TRP-2/6b, TRP-2/INT2, Trp-p8, Tyrosinase, UPA(U-plasminogen activator), VEGF (vascular endothelial growth factor A), VEGFR-2/FLK-1, and WT1 (wilms tumor 1).

35. The immune cell of embodiment 35, wherein the target antigen is CD19 or CD22.
36. The immune cell of embodiment 36, wherein the target antigen is CD19.
37. The immune cell of any of embodiments 34-36, wherein the target antigen is a cancer antigen whose expression is increased in or on the surface of a cancer cell, a cancer tissue, and/or a tumor microenvironment.
38. The immune cell of embodiment 33, wherein the target antigen is selected from the group consisting of: α-actinin-4/m, ARTC1/m, bcr/abl, beta-Catenin/m, BRCA1/m, BRCA2/m, CASP-5/m, CASP-8/m, CDCl$_2$7/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYTSSX-1, SYT-SSX-2, TEL-AML1, TGFbRII, and TPI/m; and
wherein the target antigen is a cancer antigen that is a mutated form of antigen expressed in or on the surface of a cancer cell, a cancer tissue, and/or a tumor microenvironment.
39. The immune cell of any of embodiments 21-38, wherein expression of the gene that weakens the function of the immune cell causes one or more of the following:
i) inhibition of proliferation of the immune cell;
ii) induction of cell death of the immune cell;
iii) inhibition of the ability of the immune cell to recognize the target antigen and/or undergo activation;
iv) induction of differentiation of the immune cell into a cell that does not induce immune response to the target antigen;
v) decreased reactions of the immune cell to a molecule which promotes immune response of the immune cell; or
vi) increased reaction of the immune cell to a molecule which suppresses immune response of the immune cell.
40. The immune cell of embodiment 39, wherein the gene that weakens the function of the immune cell is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, 2B4, FAS, CD45, PP2A, SHP1, SHP2, DGK alpha, DGK zeta, Cbl-b, Cbl-c, CD148, LRR1, TGFBR1, IL10RA, KLGR1, DNMT3A, and A2aR.
41. The immune cell of embodiment 39, wherein the gene that weakens the function of the immune cell increases reaction of the immune cell to a molecule which suppresses immune response of the immune cell.
42. The immune cell of embodiment 41, wherein the gene that increases reaction of the immune cell to a molecule which suppresses immune response of the immune cell encodes an immune checkpoint receptor or ligand.
43. The immune cell of embodiment 42, wherein the immune checkpoint receptor or ligand is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, and 2B4.
44. The immune cell of any of embodiments 21-43, wherein the genetic disruption agent reduces the expression of a gene in the immune cell that weakens the function of the immune cell by at least 30, 40, 50, 60, 70, 80, 90, or 95% as compared to the immune cell in the absence of the genetic disruption agent.
45. The immune cell of embodiment 44, wherein the genetic disruption agent reduces the expression of a gene that increases reaction of the immune cell to a molecule which suppresses immune response of the immune cell.
46. The immune cell of embodiment 45, wherein the genetic disruption agent reduces the expression of a gene that encodes an immune checkpoint receptor or ligand.
47. The immune cell of embodiment 46, wherein the genetic disruption agent reduces the expression of a gene selected from the group consisting of: PD1, PD-L1, CTLA4, TIM3, CEACAM (CEACAM-1, CEACAM-3 or CEACAM-5), LAG3, VISTA, BTLA, TIGIT, LAIR1, CD160, CD96, MerTK, and 2B4.
48. The immune cell of any of embodiments 45-47, wherein the genetic disruption agent reduces the expression of the gene that weakens the function of the immune cell by RNA interference (RNAi).
49. The immune cell of embodiment 48, wherein more than one genetic disruption agents reduce the expression of the gene that weakens the function of the immune cell in the immune cell by RNAi.
50. The immune cell of embodiment 49, wherein the genetic disruption agents target a single gene which weakens the function of the immune cell, or wherein different genetic disruption agents target different genes which weaken the function of the immune cell, for example, wherein a first genetic disruption agent targets a first gene and a second genetic disruption agent targets a second gene.
51. The immune cell of any of embodiments 48-50, wherein the RNAi is mediated by a short hairpin RNA (shRNA).
52. The immune cell of embodiment 51, wherein the RNAi is mediated by more than one shRNA.
53. The immune cell of embodiment 52, wherein the RNAi is mediated by two shRNAs.
54. The immune cell of any of embodiments 52-53, wherein two shRNAs target PD-1.
55. The immune cell of any of embodiments 52-53, wherein a first shRNA targets PD-1 and a second shRNA targets TIM-3.
56. The immune cell of any of embodiments 52-53, wherein a first shRNA targets PD-1 and a second shRNA targets CTLA-4.
57. The immune cell of any of embodiments 52-53, wherein a first shRNA targets PD-1 and a second shRNA targets LAG-3.
58. The immune cell of any of embodiments 52-53, wherein a first shRNA targets PD-1 and a second shRNA targets TIGIT.

59. The immune cell of any of embodiments 51-58, wherein the immune cell comprises nucleotide sequences that encode a shRNA.
60. The immune cell of embodiment 59, wherein the immune cell comprises nucleotide sequences that encode more than one shRNA.
61. The immune cell of embodiment 59, wherein the immune cell comprises nucleotide sequences that encode two shRNAs.
62. The immune cell of any of embodiments 59-61, wherein the nucleotide sequence encoding the shRNA(s) comprises a nucleotide sequence selected from the group consisting of SEQ ID NOs: 2-219 and 238-267.
63. The immune cell of any of embodiments 59-62, wherein the nucleotide sequence encoding the shRNA(s) is present on a vector.
64. The immune cell of any of embodiment 63, wherein the expression of different shRNAs is regulated by different promoters.
65. The immune cell of embodiment 64, wherein the expression of two different shRNA is regulated by two different promoters.
66. The immune cell of embodiment 65, wherein the two different promoters are RNA polymerase III promoters.
67. The immune cell of embodiment 66, wherein the two promoters are U6 promoters.
68. The immune cell of embodiment 67, wherein the U6 promoters derived from different species.
69. The immune cell of any of embodiments 65-68, wherein the two promoters are oriented in different directions from each other.
70. The immune cell of any of embodiments 21-69, wherein the genetically engineered antigen receptor and the genetic disruption agent(s) are each expressed from a vector.
71. The immune cell of embodiment 70, wherein the genetically engineered antigen receptor and the genetic disruption agent(s) are expressed from the same vector.
72. The immune cell of any of embodiments 70-71, wherein the vector is a plasmid vector or a viral vector.
73. The immune cell of embodiment 72, wherein the viral vector is a lentivirus vector, adenovirus vector or adeno-associated viral vector.
74. The immune cell of embodiment 73, wherein the lentivirus vector is a retrovirus vector.
75. The immune cell of any of embodiments 21-74, wherein the immune cell is selected from the group consisting of a T cell and a natural killer (NK) cell.
76. The immune cell of embodiment 75, wherein the immune cell is a T cell.
77. The immune cell of embodiment 76, wherein the T cell is a CD4+ T cell or a CD8+ T cell.
78. The immune cell of any of embodiment 76 or 77, wherein the immune cell comprises nucleotide sequences that encode two shRNAs and a CAR or mTCR on the same vector.
79. The immune cell of embodiment 78, wherein the two shRNA are each regulated by two different RNA polymerase III promoters oriented in different directions from each other.
80. The immune cell of embodiment 79, wherein the CAR targets CD19, the first shRNA targets PD-1, and the second shRNA targets TIGIT.
81. A method of producing an immune cell comprising introducing into an immune cell, simultaneously or sequentially in any order:

(1) a gene encoding a genetically engineered antigen receptor that specifically binds to a target antigen; and
(2) a genetic disruption agent, wherein the genetic disruption agent, or expression thereof, reduces or is capable of reducing expression in the immune cell of a gene that weakens the function of the immune cell, thereby producing an immune cell in which a genetically engineered antigen receptor is expressed and expression of a gene that weakens the function of the immune cell is reduced.
82. The method of embodiment 81, wherein the genetically engineered antigen receptor is a chimeric antigen receptor (CAR) or a T cell receptor (TCR).
83. The method of embodiment 82, wherein the genetically engineered antigen receptor is a CAR
84. The method of embodiment 83, wherein the CAR comprises an extracellular antigen recognition domain, a transmembrane domain, and an intracellular signal transduction domain.
85. The method of embodiment 84, wherein the extracellular antigen recognition domain of the CAR specifically binds to the target antigen.
86. The method of embodiment 84, wherein the intracellular signal transduction domain of the CAR comprises an intracellular domain of a CD3 zeta (CD3ζ) chain.
87. The method of embodiment 86, wherein the intracellular signal transduction domain of the CAR further comprises a costimulatory molecule.
88. The method of embodiment 87, wherein the costimulatory molecule is selected from the group consisting of ICOS, OX40, CD137 (4-1BB), CD27, and CD28.
89. The method of embodiment 88, wherein the costimulatory molecule is CD137 (4-1BB).
90. The method of embodiment 88, wherein the costimulatory molecule is CD28.
91. The method of embodiment 82, wherein the genetically engineered antigen receptor is a TCR.
92. The method of embodiment 91, wherein the TCR is a monoclonal TCR (mTCR).
93. The method of any of embodiments 81-92, wherein the target antigen is expressed in or on the surface of a cancer cell, a cancer tissue, and/or a tumor microenvironment.
94. The method of embodiment 93, wherein the target antigen is selected from the group consisting of:
5T4 (Trophoblast glycoprotein), 707-AP, 9D7, AFP (α-fetoprotein), AlbZIP (androgen-induced bZIP), HPG1 (human prostate specific gene-1), α5β1-Integrin, α5β6-Integrin, α-methylacyl-coenzyme A racemase, ART-4 (ADPribosyltransferase-4), B7H4 (v-set domain-containing T-cell activation inhibitor 1), BAGE-1 (B melanoma antigen-1), BCL-2 (B-cell CLL/lymphoma-2), BING-4 (WD repeat domain 46), CA 15-3/CA 27-29 (mucin 1), CA 19-9 (cancer antigen 19-9), CA 72-4 (cancer antigen 72-4), CA125 (cancer antigen 125), calreticulin, CAMEL (CTL-recognized antigen on melanoma), CASP-8 (caspase 8), cathepsin B, cathepsin L, CD19 (cluster of differentiation 19), CD20, CD22, CD25, CD30, CD33, CD4, CD52, CD55, CD56, CD80, CEA (carcinoembryonic antigen SG8), CLCA2 (chloride channel accessory 2), CML28 (chronic myelogenous leukemia tumor antigen 28), Coactosin-like protein, Collagen XXIII, COX-2 (cyclooxygenase-2), CT-9/BRD6 (cancer/testis antigen 9), Cten (c-terminal tensin-like protein), cyclin B1, cyclin D1, cyp-B, CYPB1 (cytochrome p450 family 1 subfamily b member 1), DAM-10/MAGE-B1 (melanoma-associated antigen B1), DAM-6/MAGE-B2, EGFR/Her1 (epidermal growth factor receptor), EMMPRIN (basigin), EpCam, EphA2 (EPH receptor A2), EphA3, ErbB3 (Erb-B2 receptor tyrosine kinase 3), EZH2 (enhancer of zeste 2 polycomb repressive complex 2 subunit), FGF-5 (fibroblast growth factor 5), FN (fibronectin), Fra-1 (Fosrelated antigen-1), G250/CAIX (carbonic anhydrase 9), GAGE-1 (G antigen-1), GAGE-2, GAGE-3, GAGE-4, GAGE-5, GAGE-6, GAGE-7b, GAGE-8, GDEP (gene differentially expressed in prostate), GnT-V (gluconate kinase), gp100 (melanocytes lineage-specific antigen GP100), GPC3 (glypican3), HAGE (helical antigen), HAST-2 (sulfotransferase family 1A member 1), hepsin, Her2/neu/ErbB2 (Erb-B2 receptor tyrosine kinase 2), HERV-K-MEL, HNE (medullasin), homeobox NKX 3.1, HOM-TES-14/SCP-1, HOM-TES-85, HPV-E6, HPVE7, HST-2 (sirtuin-2), hTERT, iCE (caspase 1), IGF-1R (insulin like growth factor-1 receptor), IL-13Ra2 (interleukin-13 receptor subunit a 2), IL-2R (interleukin-2 receptor), IL-5 (interleukin-5), immature laminin receptor, kallikrein 2, kallikrein 4, Ki67, KIAA0205 (lysophosphatidylglycerol acyltransferase 1), KK-LC-1 (kita-kyushu lung cancer antigen-1), KM-HN-1, LAGE-1 (L antigen family member-1), Livin, MAGE-A1, MAGE-A10, MAGE-A12, MAGEA2, MAGE-A3, MAGE-A4, MAGE-A6, MAGE-A9, MAGE-B1, MAGE-B10, MAGE-B16, MAGEB17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2 (melanoma antigen family L2), mammaglobin A, MART-1/Melan-A (melanoma antigen recognized by T-cells-1), MART-2, matrix protein 22, MC1R (melanocortin 1 receptor), M-CSF (macrophage colony-stimulating factor), Mesothelin, MG50/PXDN (peroxidasin), MMP 11 (matrix metalloprotease 11), MN/CA IX-antigen (carbonic anhydrase 9), MRP-3 (multidrug resistance-associated protein-3), MUC1 (mucin 1), MUC2, NA88-A (VENT-like homeobox 2 pseudogene 1), N-acetylglucos-aminyltransferase-V, Neo-PAP (Neo-poly (A) polymerase), NGEP (new gene expressed in prostate), NMP22 (nuclear matrix protein 22), NPM/ALK (nucleophosmin), NSE (neuron-specific enolase), NY-ESO-1, NY-ESO-B, OA1 (osteoarthritis QTL 1), OFA-iLRP (oncofetal antigen immature laminin receptor protein), OGT (O-GlcNAc transferase), OS-9 (endoplasmic reticulum lectin), osteocalcin, osteopontin, p15 (CDK inhibitor 2B), p53, PAGE-4 (P antigen family member-4), PAI-1 (plasminogen activator inhibitor-1), PAI-2, PAP (prostatic acid phosphatase), PART-1 (prostate androgen-regulated transcript 1), PATE (prostate and testis expressed 1), PDEF (prostate-derived Ets factor), Pim-1-Kinase (proviral integration site 1), Pin1 (Peptidyl-prolyl cis-trans isomerase NIMA-interacting 1), POTE (expressed in prostate, ovary, testis, and placenta), PRAME (preferentially expressed antigen in melanoma), prostein, proteinase-3, PSA (prostate-specific antigen), PSCA (prostate stem cell antigen), PSGR (prostate-specific G-protein coupled receptor), PSM, PSMA (prostate specific membrane antigen), RAGE-1 (renal tumor carcinoma antigen), RHAMM/CD168, RU1 (renal ubiquitous protein 1), RU2, SAGE (sarcoma antigen), SART-1 (squamous cell carcinoma antigen recognized by T-cells-1), SART-2, SART-3, Sp17 (sperm protein 17), SSX-1 (SSX family member 1), SSX-2/HOM-MEL-40, SSX-4, STAMP-1 (STEAP2 metalloreductase), STEAP, survivin, survivin-213, TA-90 (tumor associated antigen-90), TAG-72 (tumor associated glycoprotein-72), TARP (TCRγ alternate reading frame protein), TGFb (transforming growth factor β), TGFbR11 (transforming growth factor (3 receptor 11), TGM-4 (transglutaminase 4), TRAG-3 (taxol resistance associated gene 3), TRG (T-cell receptor γ locus), TRP-1 (transient receptor potential-1), TRP-2/6b, TRP-2/INT2, Trp-p8, Tyrosinase, UPA (U-plasminogen activator), VEGF (vascular endothelial growth factor A), VEGFR-2/FLK-1, and WT1 (wilms tumor 1).

95. The method of embodiment 95, wherein the target antigen is CD19 or CD22.

96. The method of embodiment 96, wherein the target antigen is CD19.

97. The method of any of embodiments 94-96, wherein the target antigen is a cancer antigen, wherein the cancer antigen is an antigen whose expression is increased in or on the surface of a cancer cell, a cancer tissue, and/or a tumor microenvironment.

98. The method of embodiment 93, wherein the target antigen is selected from the group consisting of:
α-actinin-4/m, ARTC1/m, bcr/abl, beta-Catenin/m, BRCA1/m, BRCA2/m, CASP-5/m, CASP-8/m, CDC1$_2$7/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYTSSX-1, SYT-SSX-2, TEL-AML1, TGFbRII, and TPI/m; and
wherein the target antigen is a cancer antigen, wherein the cancer antigen is a mutated form of antigen expressed in or on the surface of a cancer cell, a cancer tissue, and/or a tumor microenvironment.

99. The method of any of embodiments 81-98, wherein expression of the gene that weakens the function of the immune cell causes one or more of the following:
i) inhibition of proliferation of the immune cell;
ii) induction of cell death of the immune cell;
iii) inhibition of the ability of the immune cell to recognize the target antigen and/or to get activated;
iv) induction of differentiation of the immune cell into a cell that does not induce immune response to the target antigen;
v) decreased reaction of the immune cell to a molecule which promotes immune response of the immune cell; or
vi) increased reaction of the immune cell to a molecule which suppresses immune response of the immune cell.

100. The method of embodiment 99, wherein the gene that weakens the function of the immune cell is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, 2B4, FAS, CD45, PP2A, SHP1, SHP2, DGK alpha, DGK zeta, Cbl-b, Cbl-c, CD148, LRR1, TGFBR1, IL10RA, KLGR1, DNMT3A, and A2aR.

101. The method of embodiment 99, wherein the gene that weakens the function of the immune cell increases reaction of the immune cell to a molecule which suppresses immune response of the immune cell.

102. The method of embodiment 101, wherein the gene that increases reaction of the immune cell to a molecule which suppresses immune response of the immune cell encodes an immune checkpoint receptor or ligand.

103. The method of embodiment 102, wherein the immune checkpoint receptor or ligand is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, and 2B4.

104. The method of any of embodiments 81-103, wherein the genetic disruption agent reduces the expression of a gene in the immune cell that weakens the function of the immune cell by at least 30, 40, 50, 60, 70, 80, 90, or 95% as compared to the immune cell in the absence of the genetic disruption agent(s).

105. The method of embodiment 104, wherein the genetic disruption agent reduces the expression of a gene that increases reaction of the immune cell to a molecule which suppresses immune response of the immune cell.

106. The method of embodiment 105, wherein the genetic disruption agent reduces the expression of a gene that encodes an immune checkpoint receptor or ligand.

107. The method of embodiment 106, wherein the genetic disruption agent reduces the expression of a gene selected from the group consisting of: PD1, PD-L1, CTLA4, TIM3, CEACAM (CEACAM-1, CEACAM-3 or CEACAM-5), LAG3, VISTA, BTLA, TIGIT, LAIR1, CD160, CD96, MerTK, and 2B4.

108. The method of any of embodiments 105-107, wherein the genetic disruption agent reduces the expression of the gene that weakens the function of the immune cell by RNA interference (RNAi).

109. The method of embodiment 108, wherein more than one genetic disruption agents reduce the expression of the gene that weakens the function of the immune cell in the immune cell by RNAi.

110. The method of embodiment 109, wherein the genetic disruption agents target a single gene which weakens the function of the immune cell, or target different genes which weaken the function of the immune cell wherein a first genetic disruption agent targets a first gene and a second genetic disruption agent targets a second gene, or in any combination thereof.

111. The method of any of embodiments 108-110, wherein the RNAi is mediated by a short hairpin RNA (shRNA).

112. The method of embodiment 111, wherein the RNAi is mediated by more than one shRNA.

113. The method of embodiment 112, wherein the RNAi is mediated by two shRNAs.

114. The method of embodiment 112 or 113, wherein two shRNAs target PD-1.

115. The method of embodiment 112 or 113, wherein a first shRNA targets PD-1 and a second shRNA targets TIM-3.

116. The method of embodiment 112 or 113, wherein a first shRNA targets PD-1 and a second shRNA targets CTLA-4.

117. The method of embodiment 112 or 113, wherein a first shRNA targets PD-1 and a second shRNA targets LAG-3.

118. The method of embodiment 112 or 113, wherein a first shRNA targets PD-1 and a second shRNA targets TIGIT.

119. The method of any of embodiments 111-118, wherein the immune cell comprises nucleotide sequences that encode a shRNA.

120. The method of embodiment 119, wherein the immune cell comprises nucleotide sequences that encode more than one shRNA.

121. The method of embodiment 119, wherein the immune cell comprises nucleotide sequences that encode two shRNAs.

122. The method of any of embodiments 119-121, wherein the nucleotide sequences encoding the shRNA(s) comprise sequences selected from the group consisting of SEQ ID NOs: 2-219 and 238-267.

123. The method of any of embodiments 119-122, wherein the nucleotide sequences encoding the shRNA is present on a vector.

124. The method of any of embodiment 123, wherein the expression of different shRNAs is respectively regulated by different promoters.

125. The method of embodiment 124, wherein the expression of two different shRNAs is respectively regulated by two different promoters.

126. The method of embodiment 125, wherein the two different promoters are RNA polymerase III promoters.

127. The method of embodiment 126, wherein the two promoters are U6 promoters.

128. The method of embodiment 127, wherein the U6 promoters derive from different species.

129. The method of any of embodiments 125-128, wherein the two promoters are oriented in different directions from each other.

130. The method of any of embodiments 81-129, wherein the genetically engineered antigen receptor and the genetic disruption agent(s) are each expressed from a vector.

131. The method of embodiment 130, wherein the genetically engineered antigen receptor and the genetic disruption agent(s) are expressed from the same vector.

132. The method of any of embodiments 130-131, wherein the vector is a plasmid vector or a viral vector.

133. The method of embodiment 132, wherein the viral vector is a lentivirus vector, adenovirus vector of adeno-associated viral vector.

134. The method of embodiment 133, wherein the lentivirus vector is a retrovirus vector.

135. The method of any of embodiments 81-134, wherein the immune cell is selected from the group consisting of a T cell and a natural killer (NK) cell.

136. The method of embodiment 135, wherein the immune cell is a T cell.

137. The method of embodiment 136, wherein the T cell is a CD4+ T cell or a CD8+ T cell.

138. The method of embodiment 136 or 137, wherein the immune cell comprises nucleotide sequences that encode two shRNAs and a CAR on the same vector.

139. The method of embodiment 138, wherein the two shRNAs are each regulated by two different RNA polymerase III promoters oriented in different directions from each other.

140. The method of embodiment 139, wherein the CAR targets CD19, the first shRNA targets PD-1, and the second shRNA targets TIGIT.

141. A composition comprising the immune cell of any of embodiments 21-80.

142. A pharmaceutical composition comprising the immune cell of any of embodiments 21-80 and a pharmaceutically acceptable carrier.

143. A method of treatment comprising administering to a subject having a disease or condition in need of immune therapy the immune cell of any of embodiments 21-80 or the composition of embodiment 141 or 142.

144. The method of embodiment 143, wherein the genetically engineered antigen receptor specifically binds to an antigen associated with the disease or the condition.

145. The method of embodiment 143 or 144, wherein the disease or the condition is a cancer, e.g., a tumor.

146. The immune cell of any of embodiments 21-80 or the composition of embodiments 141-142 for use in treating a disease or a condition.

147. Use of the immune cell of any of embodiments 21-80 or the composition of embodiments 121-122 in the manufacture of a medicament for treating a disease or a condition.

148. The immune cells or the composition of embodiment 146 or the use of embodiment 147, wherein the genetically engineered antigen receptor specifically binds to an antigen associated with the disease or the condition.

149. The use, composition, or immune cell of embodiment 147 or embodiment 148, wherein the disease or the condition is a cancer, e.g. a tumor.

BRIEF DESCRIPTION OF THE DRAWINGS

FIGS. 1A-1F. Generation of cell intrinsic PD-1 blockade CAR-T cells. (FIG. 1A) Schematic representation of two-in-one CAR vectors. (FIGS. 1B-C) LNGFR and CAR expression were analyzed at 4 day after transduction. (FIG. 1D) CAR-T cells were sorted by using LNGFR magnetic beads and seeded at 2×10$^5$/ml. Cumulative CAR T cell counts were assessed by trypan blue staining. (FIG. 1E) LNGFR+CAR T cells were mixed with γ-irradiated NALM-6 without exogenous cytokines. (FIG. 1F) Differentiation status and CD4/CD8 composition of the cell intrinsic PD-1 blockade (shPD-1 #1) CAR-T cells versus control CAR-T cells were determined.

(FIG. 3A) LNGFR+CAR T cells are mixed with live NALM-6 or NALM-6-PDL1 at a E:T ratio of 1:1, 0.3:1, 0.1:1. (FIG. 3B) LNGFR+CAR T cells were mixed with γ-irradiated NALM-6-PDL1, NALM-6-PDL1-CD80 or K562-CD19-PDL1 at an E:T ratio of 1:1 without exogenous cytokines. (FIG. 3C) Expression of CD80, a representative costimulatory signal, was determined in the K562-CD19 cells versus the Nalm-6 cells.

FIG. 5B shows delayed in vivo expansion of CAR-T cells with cell-intrinsic PD-1 disruption.

(FIG. 6A) Schematic representation of G28z, GBBz, P28z and PBBz vectors. (FIG. 6B) Flow cytometric analysis showing LNGFR expression of transduced T cells at 4 day after transduction.

(FIG. 7A) LNGFR+ CAR T cells were incubated with γ-irradiated NALM-6 or K562-CD19 without exogenous cytokines. PD-1 expression of LNGFR+ CAR T cells were analyzed at 3 day after incubation. (FIG. 7B) Quantitative Real-Time PCR results performed with PD-1 primers.

(FIG. 8A) Schematic representation of NFAT-RE 3x-eGFP and NF-κB-RE 5x-eGFP reporter vectors. (FIG. 8B) Fold change of reporter activity calculated using eGFP gMFI of LNGFR+ CAR T cells.

(FIG. 9A) Reporter transduced T cells were re-stimulated and transduced using G28z or GBBz. (FIG. 9B) mRNA level of NFAT target genes in CAR T cells was assessed by qPCR.

FIGS. 11A-11C. TGF-β signaling intensity of G28z CART is slightly higher BBz CART. (FIG. 11A) Phosphorylated SMAD2/3 in the CAR-T cells was analyzed by intracellular flow cytometry following incubation with NALM-6 at an E:T cell at a ratio of 1:1 for 4 hr or 24 hr. (FIG. 11B) Flow cytometric analysis showing PD-1 expression in G28z and GBBz CAR T cells with 10 ng/ml recombinant human TGF-β1. (FIG. 11C) mRNA level of TGF-β1, TGFBR1 and TGFBR2 in CAR T cells was evaluated by qPCR.

FIGS. 12A-12B. Retained cytotoxicity and proliferative capacity in vitro of PBBz CAR T cells under repeat CD19 and PD-L1 stimulation. (FIG. 12A) Cytotoxicity. Top, After LNGFR magnatic soting, 12 day primary LNGFR+ CAR T cells were mixed with NALM-6-PDL1 at a E:T ratio of 1:1, 0.3:1, 0.1:1. Bottom, LNGFR+ CAR T cells were stimulated with γ-irradiated K562-CD19-PDL1 at an E:T ratio of 1:1. (FIG. 12B) LNGFR+ CAR T cells were repeatedly stimulated mixed with γ-irradiated NALM-6-PDL1-CD80 or K562-CD19-PDL1 at an E:T ratio of 1:1 without exogenous cytokines.

FIGS. 13A-13C. Less sensitive to TGF-beta mediated dysfunction and lowly generated in vitro CAR-derived regulatory T cells in PBBz CAR T cells. (FIG. 13A) TGF-beta mediated suppression of CAR-T proliferation. (FIG. 13B) TGF-beta sensitivity for Treg induction. (FIG. 13C) Effect of PDL1/PD-1 for Treg induction.

FIG. 18A. Flow cytometry data for ΔLNGFR-CART19/mU6-shTIM-3→←shPD-1-hU6 cells and ΔLNGFR-CART19/shTIM-3-mU6→←hU6-shPD-1 cells produced using methods in Example 8. FIG. 18B. Expression of PD-1 and TIM-3 in the CAR-T cells.

FIGS. 20A-20C. Evaluation of CAR-T cells produced using the methods in Example 8. FIG. 20A: Transduction efficiency. FIG. 20B: Proliferation ability. FIG. 20C: Viability.

FIG. 21A: 2 day CD3/CD28 stimulated T cells are electroporated with CTLA-4, LAG-3, TIGIT and TIM-3 targeting 21-mer siRNAs. siRNA-mediated knock-down efficiencies was confirmed at 2 day after transfection. Shading: Based on sequence of selected siRNAs, Two-in-One vectors expressing CAR and shRNA were constructed. Shading indicates initially selected siRNAs. FIG. 21B: T cells were transduced with Two-in-One vectors containing CTLA-4, LAG-3, TIGIT or TIM-3 shRNAs and sorted with LNGFR magnetic beads. LNGFR+ CAR T cell counts was measured every 3 days after seeded at 2×10$^5$/ml. FIG. 21C: Tim3 expression (%).

(FIG. 22A) Schematic representation of Dual Two-in-One vectors. FIG. 22B: LNGFR+ T cells % were analyzed at 4 day after Dual Two-in-One transduction.

(FIG. 22C) Dual KD (knock down) CAR-T cells were sorted and seeded at $2 \times 10^5$/ml. Cumulative CAR T cell counts were measured by trypan blue staining. (FIGS. 22D-22E) LAG-4, PD-1, TIGIT or TIM-3 expression of LNGFR+ CAR T cells were analyzed at 3 day after γ-irradiated NALM-6 or K562-CD19 co-culture. CTLA-4 expression was analyzed by intracellular flow cytometry.

DETAILED DESCRIPTION

Figure 2:
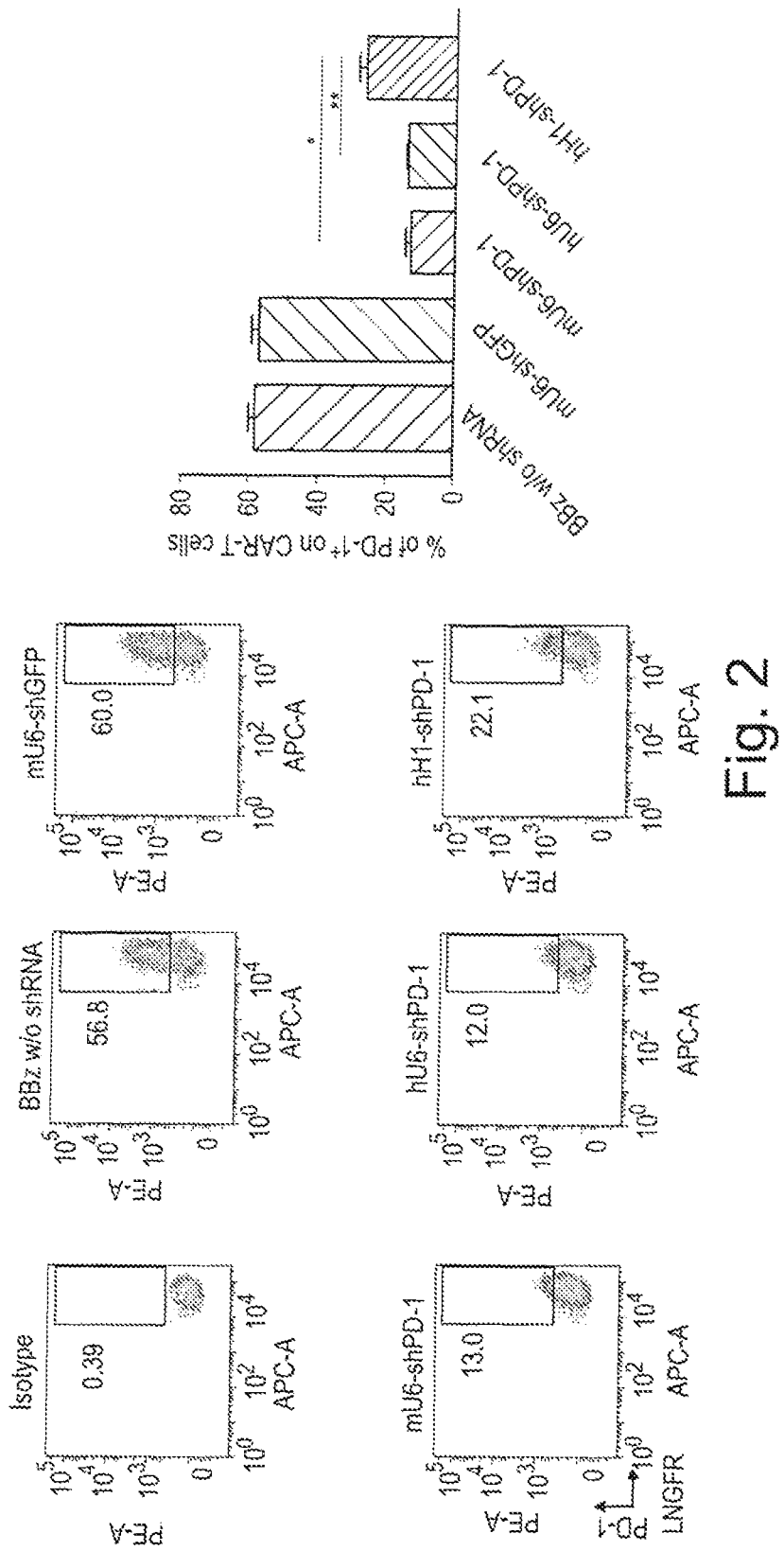
FIG. 2. Effect of Pol III promoter types on cell intrinsic PD-1 blockade.

The features of the present disclosure are set forth specifically in the appended claims. A better understanding of the features and benefits of the present disclosure will be obtained by reference to the following detailed description that sets forth illustrative embodiments, in which the principles of the disclosure are utilized. To facilitate a full understanding of the disclosure set forth herein, a number of terms are defined below.

Briefly, in one aspect, disclosed herein are vectors comprising: a base sequence encoding two types of short hairpin RNA (shRNA) which inhibit the expression of one or more genes that weaken the function of immune cells, including immune checkpoint receptors and ligands, and a base sequence encoding an antigen receptor such as a chimeric antigen receptor (CAR) or a T cell receptor (TCR), for example, a monoclonal T cell receptor (mTCR); an immune cell comprising a genetically engineered antigen receptor that specifically binds to a target antigen and one or more genetic disruption agents that reduce or are capable of reducing the expression in the immune cell of a gene or genes that weakens the function of the immune cell; methods of producing the immune cell; a composition or pharmaceutical composition comprising the immune cell, e.g., for immune therapy of human patients; and a method of treatment comprising administering the immune cell to a subject having a disease or a condition. As the immune cell, composition, or pharmaceutical composition comprises one or more genetic disruption agents, e.g., encodes two shRNAs that reduce the expression of two immune checkpoint molecule genes which may be activated by cancer cells to weaken the function of immune cells, it is possible to eliminate severe and systemic adverse reactions such as cytokine release syndrome or autoimmune symptoms which can result from use of a separate inhibitor for these genes, as well as reducing the burden due to the increased cost of treatment resulting from expensive concurrent therapies, while providing cell therapy more effective than cases where only one shRNA is expressed.

1. General Techniques

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (4th ed. 2012); *Current Protocols in Molecular Biology* (Ausubel et al. eds., 2003); *Therapeutic Monoclonal Antibodies: From Bench to Clinic* (An ed. 2009); *Monoclonal Antibodies: Methods and Protocols* (Albitar ed. 2010); and *Antibody Engineering* Vols 1 and 2 (Kontermann and Dübel eds., 2nd ed. 2010). *Molecular Biology of the Cell* (6th Ed., 2014).

2. Definitions

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

The terms used in the present disclosure are used only to explain specific embodiments, and are not intended to limit the scope of the present invention. Singular expressions, unless clearly indicated otherwise by context, include plural expressions. It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Reference throughout this specification to "one embodiment," "an embodiment," "a particular embodiment," "a related embodiment," "a certain embodiment," "an additional embodiment," or "a further embodiment" or combinations thereof or the like means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

A "construct" refers to a macromolecule or complex of molecules comprising a polynucleotide to be delivered to a target cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vector, viral vectors, cosmids, and artificial chromosomes. Viral vectors include, but are not limited to, adenovirus vector, adeno-associated virus vector, retrovirus vector, lentivirus vector, Sendai virus vector, and the like.

A "two-in-one vector," as described herein is a vector that comprises a base sequence encoding one or more short hairpin RNAs (shRNAs) which inhibit the expression of a gene or genes that weaken the function of immune cells, and a base sequence encoding a chimeric antigen receptor (CAR) or a T cell receptor, e.g., a monoclonal T cell receptor (mTCR). A "dual two-in-one vector" as described herein is a vector that comprises a base sequence encoding two types of short hairpin RNA (shRNA) which inhibit the expression of genes that weaken the function of immune cells, and a base sequence encoding any one of a chimeric antigen receptor (CAR) and T cell receptor, e.g., monoclonal T cell receptor (mTCR). Dual two-in-one vectors described herein are a form of two-in-one vector.

"RNAi" (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells. DNA expression plasmids can be used to stably express the siRNA duplexes or dsRNA of the present disclosure in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

The term "shRNA" refers an RNA molecule wherein some self-complementary sequences create a tight hairpin structure with its stem. The RNA molecule can have a length of approximately 80 bp. When shRNA is expressed in a cell, it is processed through a series of steps to become small interfering RNA (siRNA) which acts as a guide for gene silencing. Simply put, when shRNA is expressed, it is processed by Drosha complexes in the cell to become pre-shRNA, which is then transported outside the nucleus where it undergoes further processing by a Dicer to become siRNA, and then is single stranded and loaded by an RISC (RNA-induced silencing complex) complex. Here, the antisense strand of siRNA acts as a guide for the RISC complex to attach to the mRNA of the target gene, and gene silencing occurs when the RISC complex, which has attached in this manner, cuts the mRNA. As shRNA in a target gene allows for gene silencing which is lasting and specific to a certain gene, it is included in the vector for the purpose of inhibiting the target gene.

The term "promoter" refers to the upstream region of a gene involved in the beginning of transcription of a gene. The two types of shRNA described above also cause the promoter to regulate expression. Here, the expression of the two types of shRNA may be characterized in that they are regulated by two different promoters, respectively. If cloning occurs with identical base sequences using repeated inserts, it is judged highly likely that proper cloning will not occur due to binding between these identical base sequences, resulting in recombination or deletion. The promoters may be RNA polymerase I promoter, RNA polymerase II promoter or RNA polymerase III promoter depending on which RNA polymerase attaches to the promoter and begins transcription. The two promoters above may be characterized in that they are RNA polymerase III promoters (hereinafter pol III promoter). Pol III promoters may be made to transcribe accurately from the 5' terminal to the 3' terminal without attaching the cap at the 5' terminal or the poly (A) tail at the 3' terminal of the RNA which is transcribed with regulation by the promoter. Types of pol III promoter include, but are not limited to, U6 promoter, H1 promoter and 7SK promoter, etc.

Figure 6A:
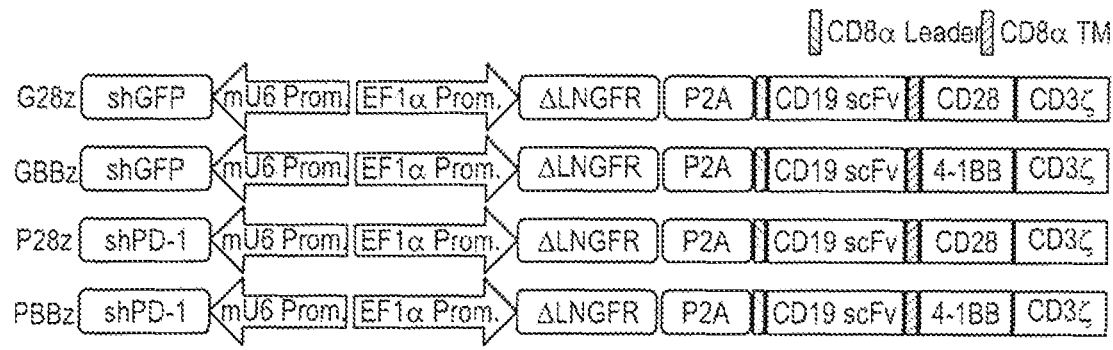
FIGS. 6A-6B. Function of CD28/CD3ζ or 4-1BB/CD3ζ CAR-T cells in cell-intrinsic PD-1 disruption.

The term "G28z" used herein refers a construct that includes an shGFP expression cassette, a CD28 costimulation domain and a CD3ζ domain (FIG. 6A). More specifically, in the term "G28z", the "G" represents shGFP; the "28" represents CD28; the "z" represents CD3. Following the same pattern, the term "P28z" used herein refers to a construct that includes an shPD-1 expression cassette, a CD28 costimulation domain, and a CD3ζ domain (FIG. 6A), wherein "P" represents shPD-1, "28" represents "CD28", and "z" represents CD3. The term "GBBz" used herein refers to a construct that includes an shGFP expression cassette, a 4-1BB costimulation domain, and a CD3ζ domain (FIG. 6A), wherein the "G" represents shGFP; the "BB" represents 4-1BB; the "z" represents CD3. The term "PBBz" used herein refers to a construct that includes an shPD-1 expression cassette, 4-1BB costimulation domain, and a CD3ζ domain (FIG. 6A), wherein the "P" represents shPD-1; the "BB" represents 4-1BB; the "z" represents CD3.

"CAR" is generally a set of polypeptides which, when existing on an immune cell, causes the immune cell to have specificity to a target cell (normally a cancer cell) while causing signal transduction in the cell. CAR at minimum comprises an extracellular antigen recognition domain which recognizes the target antigen to be described below, a transmembrane domain, and an intracellular signal transduction domain, wherein the intracellular signal transduction domain is derived from the promoting molecules or costimulatory molecules to be described below. The set comprising polypeptides may be attached, or may be in a form where they attach through a switch which is dimerized through stimulation. The promoting molecule may be the zeta chain of the TCR described in the above. "CD19 CAR" is a CAR which targets the CD19 cancer antigen.

The term "T-cell receptor (TCR)" as used herein refers to a protein receptor on T cells that is composed of a heterodimer of an alpha (α) and beta (β) chain, although in some cells the TCR consists of gamma and delta (γ/δ) chains. In certain embodiments, the TCR may be modified on any cell comprising a TCR, including a helper T cell, a cytotoxic T cell, a memory T cell, regulatory T cell, natural killer T cell, and gamma delta T cell, for example.

The term "monoclonal T cell receptor (mTCR)" used herein refers to a T-cell receptor (TCR) that is genetically modified to specifically target a particular antigen. It is can also be referred to as an antigen-specific TCR. T cells having mTCR are reported to be used in immunotherapy, such as adoptive T-cell therapy, for viral infection and cancer. In some aspect, retroviral transfer of chimeric single chain antibody constructs (scFv) has been used as a strategy to produce T cells with defined antigen-specificity. For the most part, chimeric scFv constructs were linked to the intracellular signaling domains of FcR-gamma or CD3 zeta to trigger T-cell effector function. The CD3 zeta domain has been combined with the signaling domains of co-stimulatory molecules such as CD28, 4-1BB or OX40. Monoclonal T cell receptors (mTCRs) and their applications in cancer therapy are described in Stauss et al., 2007, Molecular Therapy, 15(10):1744-50, Zhang and Morgan, 2012, Advanced Drug Delivery Reviews, 64(8): 756-762, and Liddy et al., 2012, Nature Medicine, 18(6):980-7, the content of each of which is herein incorporated by reference in its entirety.

The term "ΔLNGFR" used herein refers to a LNGFR (low-affinity nerve growth factor receptor) without a cytoplasmic domain used for purification of cells wherein the insertion described above has taken place.

An "immune cell" may be characterized herein as selected from, but not limited to, lymphocytes, such as killer T cells, helper T cells, gamma delta T cells and B cells, natural killer cells, mast cells, eosinophils, basophils; and the phagocytic cells include macrophages, neutrophils, and dendritic cells. The T cells include CD4+ T cells and CD8+ T cells.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γ6 T cells), and the like. Additional types of helper T cells include cells such as Th3 (Treg), Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

"CD4+ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL2, IL4 and IL10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"CD8+ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3- and CD56+, expressing at least one of NKG2C and CD57, and optionally, CD16, but lack expression of one or more of the following: PLZF, SYK, FceRγ, and EAT-2. In some embodiments, isolated subpopulations of CD56+NK cells comprise expression of CD16, NKG2C, CD57, NKG2D, NCR ligands, NKp30, NKp40, NKp46, activating and inhibitory KIRs, NKG2A and/or DNAM-1. CD56+ can be dim or bright expression.

As used herein, the term "immune checkpoints" refer to molecules that exist in the immune system, and are able to turn immune response on or off. Originally, they are safety devices to regulate excessive activation of immune cells, which causes cell death or autoimmune response. These immune checkpoint molecules can be broadly categorized into stimulatory immune checkpoint molecules which increase immune response, and inhibitory immune checkpoint molecules which inhibit immune response. For example, the immune checkpoint receptor and ligands may be selected from a group consisting of PD1 (Programmed cell death protein 1), PD-L1 (Programmed death-ligand 1), CTLA4 (Cytotoxic T-lymphocyte associated protein 4), TIM-3 (T-cell immunoglobulin and mucin-domain containing-3), CEACAM (Carcinoembryonic antigen-related cell adhesion molecule, including the three subtypes CEACAM-1, CEACAM-3 or CEACAM-5), LAG3 (Lymphocyte-activation gene 3), VISTA (V-domain Ig suppressor of T cell activation), BTLA (B- and T-lymphocyte attenuator), TIGIT (T cell immunoreceptor with Ig and ITIM domains), LAIR1 (Leukocyte-associated immunoglobulin-like receptor 1), CD160 (Cluster of differentiation 160), CD96 (Cluster of differentiation 96), MerTK (Proto-oncogene tyrosine-protein kinase MER) and 2B4 (NK cell activation-inducing ligand), and may, for example, be selected between PD1 and TIM3.

The term "culture" or "cell culture refers to the maintenance, growth and/or differentiation of cells in an in vitro environment. "Cell culture media," "culture media" (singular "medium" in each case), "supplement" and "media supplement" refer to nutritive compositions that cultivate cell cultures. The term "cultivate" or "maintain" refers to the sustaining, propagating (growing) and/or differentiating of cells outside of tissue or the body, for example in a sterile plastic (or coated plastic) cell culture dish or flask. "Cultivation" or "maintaining" may utilize a culture medium as a source of nutrients, hormones and/or other factors helpful to propagate and/or sustain the cells.

A "pharmaceutical composition" for immune therapy in human patients described herein comprises the immune cells. As it is self-evident that, in addition to the cells, other pharmaceutically acceptable salts, carriers, excipients, vehicles and other additives, etc. which may further improve immune response may be added to the pharmaceutical composition, a detailed explanation thereof shall be omitted.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "treating" or "to treat" refer to suppressing, eliminating, reducing, and/or ameliorating a symptom, the severity of the symptom, and/or the frequency of the symptom of the disease being treated. As used herein, the terms "treat," "treatment" and "treating" also refer to the reduction or amelioration of the progression, severity, and/or duration of a disease or condition resulting from the administration of one or more therapies.

"Effective amount" or "therapeutically effective amount" are used interchangeably herein, and refer to an amount of a compound, formulation, material, or composition, such as T cells, as described herein effective to achieve a particular biological result. Such results may include, but are not limited to, the inhibition of cancer as determined by any means suitable in the art.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

3. Two-in-One Vectors Targeting One or More Immune Checkpoints

Tumor cells express various immune checkpoints, e.g.i, checkpoint ligands. Therefore, even if one immune checkpoint is inhibited, it might be difficult to expect sustained effect of CAR-T through activation of other immune checkpoints. Combination of monoclonal antibodies has been mainly used to inhibit multiple immune checkpoints and its antitumor effect is been reported continuously (J Clin Invest., 2015, Chauvin J M; PNAS, 2010, Curran M A; Blood, 2018, Wierz M; Cancer cell. 2014, Johnston R J). However, it was known that therapeutic antibodies could induce systemically excessive immune response. In addition, CAR-T cell therapy is also associated with life-threatening cytokine-release syndrome (CRS) and neurotoxicity (Nat Rev Clin Oncol, 2017, Neelapu S S), suggesting that the combination of CAR-T and antibody therapy could maximize the potential of side effects. Furthermore, the conventional concurrent immune cell therapies place an even greater economic burden on patients due to their high cost and that they also act on T cells other than CAR-T and pose a risk of autoimmune symptoms and cytokine release syndrome. The present invention has been devised to address the above problems.

In one embodiment, provided herein is a Two-in-One vector, the vector comprising: a base sequence encoding one or more types of short hairpin RNA (shRNA) which inhibit the expression of genes that weaken the function of immune cells, and a base sequence encoding a chimeric antigen receptor (CAR) a T cell receptor, such as a monoclonal T cell receptor (mTCR).

The vector may be selected from among DNA, RNA, plasmid, lentivirus vector, adenovirus vector and retrovirus vector. For example, lentivirus vector and retrovirus vectors can insert genes into the genomic DNA of cells allowing for stable expression of the genes. In some embodiments, for example, a Two-in-One lentivirus vector, for example, a dual Two-in-one vector, can be used to genes on the vector into the genome of cells.

In some embodiments, provide is a vector comprising a base sequence encoding two types of short hairpin RNA (shRNA) which inhibit the expression of genes that weaken the function of immune cells, and a base sequence encoding any one of a chimeric antigen receptor (CAR) and a T cell receptor, for example a monoclonal T cell receptor (mTCR).

In some embodiments, the expression of the two types of shRNA is characterized in that they are respectively regulated by two different promoters. In some embodiments, the two promoters are RNA polymerase III promoters. In some embodiments, the two promoters are U6 promoters derived from different species. In some embodiments, the two promoters are oriented in different directions from each other on the vector. For example, in a certain embodiment, the promoters are oriented in a head to head orientation. In another embodiment, the promoters are oriented in a tail to tail orientation. In some embodiments, the gene weakening the function of immune cells is an immune checkpoint receptor or ligand.

In some embodiments, the immune checkpoint receptor or ligand is selected from a group consisting of PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK and 2B4. In some embodiments, the gene weakening the function of immune cells is selected from a group consisting of FAS, CD45, PP2A, SHIP1, SHIP2, DGK alpha, DGK zeta, Cbl-b, CD147, LRR1, TGFBR1, IL10R alpha, KLGR1, DNMT3A and A2aR.

In some embodiments, the two types of shRNA either target different parts of a single gene which weakens the function of immune cells, or they target different genes which weaken the function of immune cells. In some embodiments, the two types of shRNA target different parts of PD-1. In some embodiments, the two types of shRNA target PD-1 and TIM-3, respectively. In some embodiments, the base sequences encoding the two types of shRNA comprise different sequences selected from a group consisting of SEQ ID NOs: 2-219.

In some embodiments, the target of the CAR or TCR, for example, mTCR, is a human tumor antigen selected from among increased cancer antigens in cancer or from mutated forms of cancer antigen found in cancer.

In some embodiments, the vector comprises any one of the base sequences SEQ ID NO: 220 or 221. In some embodiments, the vector is selected from among DNA, RNA, plasmid, lentivirus vector, adenovirus vector and retrovirus vector.

3.1 RNA Interference and Short Hairpin RNA

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells. DNA expression plasmids can be used to stably express the siRNA duplexes or dsRNA described herein in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

Short hairpin RNA (shRNA) as used herein is an RNA molecule wherein some self-complementary sequences create a tight hairpin structure with its stem. The shRNA molecules described herein may be about 40 to 120 nucleotides long, e.g.i, about 70 to 90 nucleotides long. In an exemplary embodiment, the shRNA can be 80 nucleotides long. The shRNA is modeled on micro interfering RNA (miRNA), an endogenous trigger of the RNAi pathway (Lu et al., 2005, Advances in Genetics 54: 117-142, Fewell et al., 2006, Drug Discovery Today 11: 975-982). When shRNA is expressed in a cell, it is processed through a series of steps to become small interfering RNA (siRNA) which acts as a guide for gene silencing. Simply put, when shRNA is expressed, it is processed by Drosha complexes in the cell to become pre-shRNA, which is then transported outside the nucleus where it undergoes further processing by a Dicer to become siRNA, and then is single stranded and loaded by an RISC (RNA-induced silencing complex). Here, the antisense strand of siRNA acts as a guide for the RISC complex to attach to the mRNA of the target gene, and gene silencing occurs when the RISC complex, which has attached in this manner, cuts the mRNA. As shRNA in a target gene allows for gene silencing which is lasting and specific to a certain gene, it is included in the vector for the purpose of inhibiting the target gene.

Naturally expressed small RNA molecules, named microRNAs (miRNAs), elicit gene silencing by regulating the expression of mRNAs. The miRNAs containing RISC targets mRNAs presenting a perfect sequence complementarity with nucleotides 2-7 in the 5' region of the miRNA which is called the seed region, and other base pairs with its 3' region. miRNA mediated down regulation of gene expression may be caused by cleavage of the target mRNAs, translational inhibition of the target mRNAs, or mRNA decay. miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., *Nature*, 2001, 411, 494-498). Since this initial report, post-transcriptional gene silencing by siRNAs quickly emerged as a powerful tool for genetic analysis in mammalian cells and has the potential to produce novel therapeutics.

RNAi molecules which were designed to target against a nucleic acid sequence that encodes poly-glutamine repeat proteins which cause poly-glutamine expansion diseases such as Huntington's Disease, are described in U.S. Pat. Nos. 9,169,483 and 9,181,544 and International Patent Publication No. WO2015179525, the content of each of which is herein incorporated by reference in their entirety. U.S. Pat. Nos. 9,169,483 and 9,181,544 and International Patent Publication No. WO2015179525 each provide isolated RNA duplexes comprising a first strand of RNA (e.g., 15 contiguous nucleotides) and second strand of RNA (e.g., complementary to at least 12 contiguous nucleotides of the first strand) where the RNA duplex is about 15 to 30 base pairs in length. The first strand of RNA and second strand of RNA may be operably linked by an RNA loop (~4 to 50 nucleotides) to form a hairpin structure which may be inserted into an expression cassette. Non-limiting examples of loop portions include SEQ ID NOs: 9-14 of U.S. Pat. No. 9,169,483, the content of which is herein incorporated by reference in its entirety. Non-limiting examples of strands of RNA which may be used, either full sequence or part of the sequence, to form RNA duplexes include SEQ ID NOs: 1-8 of U.S. Pat. No. 9,169,483 and SEQ ID NOs: 1-11, 33-59, 208-210, 213-215 and 218-221 of U.S. Pat. No. 9,181,544, the contents of each of which is herein incorporated by reference in its entirety. Non-limiting examples of RNAi molecules include SEQ ID NOs: 1-8 of U.S. Pat. No. 9,169,483, SEQ ID NOs: 1-11, 33-59, 208-210, 213-215 and 218-221 of U.S. Pat. No. 9,181,544 and SEQ ID NOs: 1, 6, 7, and 35-38 of International Patent Publication No. WO2015179525, the contents of each of which is herein incorporated by reference in their entirety.

In vitro synthetized siRNA molecules may be introduced into cells in order to activate RNAi. An exogenous siRNA duplex, when it is introduced into cells, similar to the endogenous dsRNAs, can be assembled to form the RNA induced silencing complex (RISC), a multiunit complex that interacts with RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complexes are mRNAs presenting a perfect sequence complementarity. Then, siRNA mediated gene silencing occurs by cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases, it requires higher concentration of the ss-siRNA to achieve the effective gene silencing potency of the corresponding duplex.

Guidelines for designing siRNAs exist in the art. These guidelines generally recommend generating a 19-nucleotide duplexed region, symmetric 2-3 nucleotide 3' overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing mammalian target gene expression may be readily designed.

As provided herein, a Two-in-One vector includes a base sequence encoding one or more types of short hairpin RNA (shRNA) which inhibit the expression of one or more genes that weaken the function of immune cells, and a base sequence encoding any one of a chimeric antigen receptor (CAR) or a T cell receptor, for example, a monoclonal T cell receptor (mTCR).

In some embodiments, the base sequence encodes one type of shRNA, which inhibits the expression of a gene that weaken the function of immune cells. In some embodiments, the base sequence encodes two types of shRNA, which inhibits the expression of two genes that weaken the function of immune cells, wherein the vector can be referred to as a "dual Two-in-One vector." In other embodiments, the base sequence encodes more than two types of shRNA, which inhibit the expression of more than two genes that weaken the function of immune cells.

In some embodiments, the two or more types of shRNA may be characterized in that they target a single gene, for example different parts of a single gene, which weakens the function of immune cells. For example, the two or more types of shRNA can target PD-1, for example, different parts of PD-1. In other embodiments, the two or more types of shRNA may be characterized in that they target different genes which weaken the function of immune cells, for example targeting PD-1 and TIM-3.

In exemplary embodiments, the base sequences encoding the two or more types of shRNA may be characterized in that they comprise different sequences selected from a group consisting of SEQ ID NOs 2 through 219 and 238 through 267, for example, they may comprise different sequences selected from a group consisting of SEQ ID NOs 2 through 117 and 238 through 267, e.g., they may comprise different sequences selected from a group consisting of SEQ ID NOs 2 through 12, 70 through 75, and 266 through 267.

In some embodiments, the expression of the two types of shRNA may be characterized in that they are regulated by two different promoters, respectively, to minimize recombination or deletion artifacts during cloning.

In some embodiments, the promoters may be RNA polymerase I promoter, RNA polymerase II promoter or RNA polymerase III promoter depending on which RNA polymerase attaches to the promoter and begins transcription. The two promoters above may be characterized in that they are RNA polymerase III promoters (hereinafter pol III promoters). Pol III promoters may be made to transcribe accurately from the 5' terminal to the 3' terminal without attaching the cap at the 5' terminal or the poly (A) tail at the 3' terminal of the RNA which is transcribed with regulation by the promoter. Types of pol III promoter include, but are not limited to, U6 promoter, H1 promoter and 7SK promoter, etc. The two promoters included in the vector may be different, selected from among pol III promoters including the three types stated above, and if the same type of promoters are selected, they may be derived from different species. For example, the two promoters may be U6 promoters, e.g., U6 promoters derived from different species, such as U6 promoters derived from humans and mice. As the transcript created by a U6 promoter remains within the nucleus, it is judged that this will be able to cause the Drosha complex that exists in the nucleus to promote the process wherein shRNA is processed into pre-shRNA.

Figure 15:
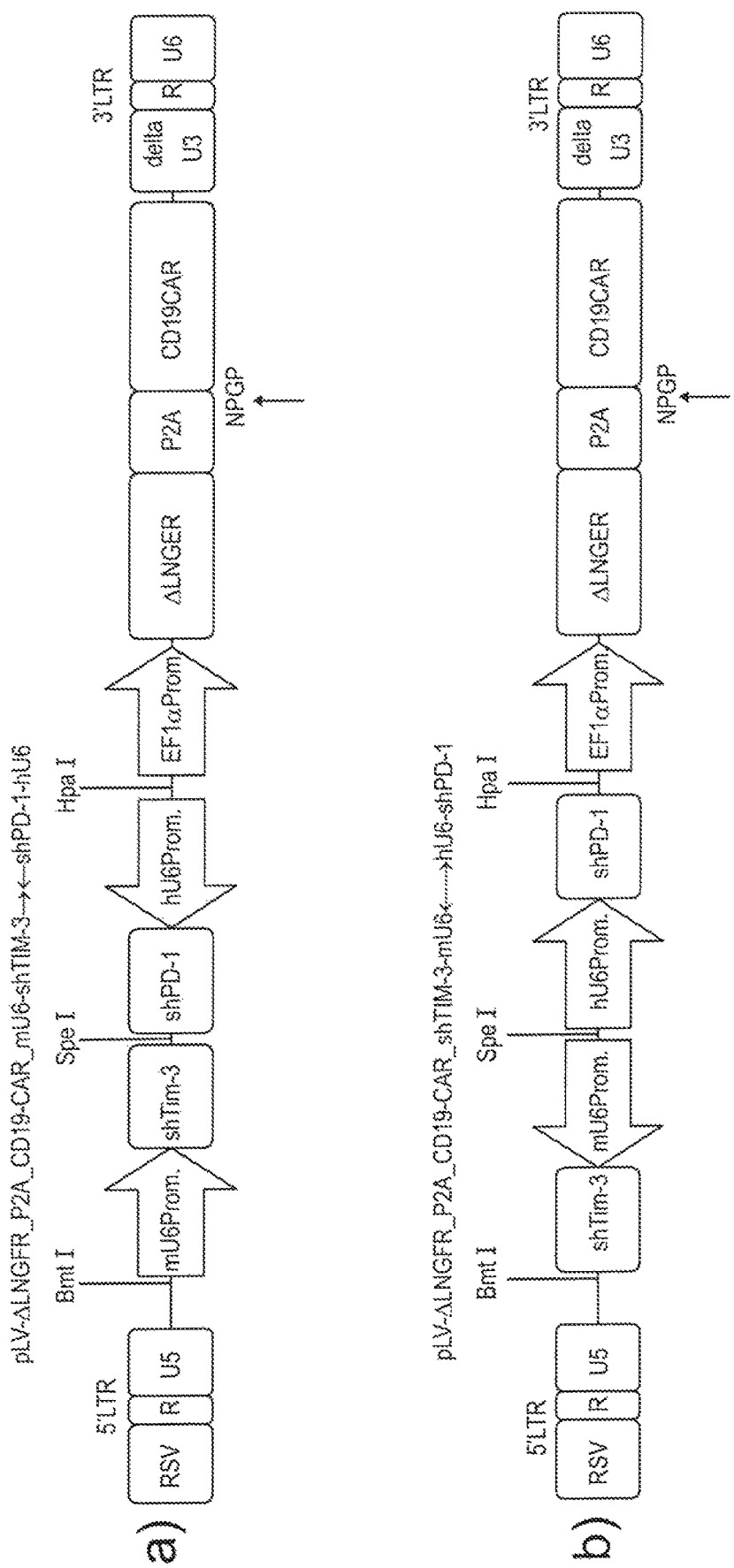
FIG. 15. Diagram of the composition of two types of vectors encoding two types of shRNA one of which inhibits the expression of PD-1 and the second of which inhibits the expression of TIM-3, and a CD19 CAR expression cassette.

In some embodiments, the two or more promoters may be characterized in that they are oriented in different directions from others on the vector. For example, in a certain embodiment, the promoters are oriented in a head to head (→←) orientation. In another embodiment, the promoters are oriented in a tail to tail (←→) orientation. In a dual Two-in-One vector, to be oriented in different directions on a vector means that when the respective shRNAs whose expression is regulated by the two promoters are transcribed, the directions in which the RNA polymerases move are oriented in different directions on a single nucleic acid molecule. In an exemplary embodiment, the two promoters can be in →← directions (FIG. 15 panel a). In another exemplary embodiment, the two promoters can be in ←→ directions (FIG. 15 panel b). For example, the two promoters may assume the →← directions on the vector.

In some embodiments the expression of the target genes of the one of more types of shRNA is reduced to about 90% or less of that of a control group, for example the expression of the target genes is reduced to about 80% or less, about 70% or less, about 60% or less, about 50% or less, about 40% or less, about 30% or less, about 20% or less, and about 10% or less of that of a control group.

Ordinarily, shRNA is designed to have a sequence having high homology with part of the mRNA sequence of its target gene (hereinafter the sense shRNA base sequence), a sequence able to produce a sharp hairpin, and a sequence complementary to the sequence having high homology (hereinafter the antisense shRNA base sequence). Non-covalent bonds between the self-complementary portions form a stem structure, and when the shRNA is expressed and processed in the cell, the anti-sense shRNA base sequence acts as a guide for the mRNA of the target gene in the gene silencing process. For example, the base sequences of a cassette used in herein for the expression of shRNA can comprise a NNNNNNNNNNNNNNNNNNNNN (21 base)-loop sequence-NNNNNNNNNNNNNNNNNNN (19 base) structure. In one embodiment, the 21 base stretch encodes the sense shRNA base sequences and the 19 base stretch is complementary or substantially complementary to the 21 base stretch and encodes the anti-sense shRNA base sequences. In another embodiment, the 19 base stretch encodes the sense shRNA base sequences and the 21 base stretch is complementary or substantially complementary to the 19 base stretch and encodes the anti-sense shRNA base sequences. When expressed, therefore, the resulting RNA forms a stem and loop structure. In certain embodiments, such sense or anti-sense shRNA base sequences for a target gene (human derived) which may be included in the cassette are selected from a group consisting of SEQ ID NOs: 1-219. In specific embodiments, the base sequences of the cassette used in herein for the expression of shRNA can be selected from a group consisting of SEQ ID NOs: 220-224.

In some embodiments, the entire shRNA base sequence can be positioned at the 3' terminal of a mouse or human U6 promoter, and the TTTTT necessary for terminating transcription by the U6 promoter can be positioned at the 3' terminals of all of the shRNA base sequences.

In some embodiments, the nucleic acid sequences of the respective shRNAs may, in addition to the sequences described herein, comprise nucleic acid sequences exhibiting at least 50%, specifically at least 70%, more specifically at least 80%, even more specifically at least 90%, and most specifically at least 95% sequence homology with these sequences. This is because, in the case of siRNA (small interfering RNA) and shRNA which is processed intracellularly to become siRNA in particular, it has been reported that some degree of mutation, especially mutation at the 5' terminal is tolerable, causing normal knockdown of the target gene, and that mutations of siRNA and shRNA made to have a structure similar to that of miRNA that plays a role in gene silencing more effectively induce knockdown of the target gene. Further, in the use of vectors, self-evident to those skilled in the art are variations within the vector, that is, the addition, modification or deletion of base sequences which may occur in the cloning process for introducing a certain sequence into the vector, or changes to or introduction of components to improve the ease of use of the vector of the degree to which the intended gene is expressed.

Various modes of action exist for genes which weaken the function of immune cells. Examples include inhibiting proliferation of immune cells or causing cell death, reducing reactions with molecules with which immune cells need to react with in order to become activated, inhibiting the expression of genes necessary for immune cells to recognize reaction targets, and causing differentiation into different types of immune cell to play a different function instead of causing immune response to a particular target. Representative examples include, but are not limited to, molecules associated with the immune checkpoints to be explained below.

In some embodiments, the gene weakening the function of immune cells may be characterized in that it is an immune checkpoint receptor or ligand. Immune checkpoints are molecules that exist in the immune system, and are able to turn immune response on or off. They can be considered as safety devices to regulate excessive activation of immune cells, which causes cell death or autoimmune response. These immune checkpoint molecules can be broadly categorized into stimulatory immune checkpoint molecules which increase immune response, and inhibitory immune checkpoint molecules which inhibit immune response. It is reported that many cancer cells escape the immune system by activating inhibitory immune checkpoint signals, especially inhibitory immune checkpoint receptors and ligands on immune cells. Accordingly, immune cell therapy targeting a particular cancer may be made effective by rendering this evasive action of cancers ineffective, and this may be achieved by inhibiting the activation of inhibitory immune checkpoint receptors and their ligands, or by reducing their expression. For example, the immune checkpoint receptor and ligands may be selected from a group consisting of PD1 (Programmed cell death protein 1), PD-L1 (Programmed death-ligand 1), CTLA4 (Cytotoxic T-lymphocyte associated protein 4), TIM-3 (T-cell immunoglobulin and mucin-domain containing-3), CEACAM (Carcinoembryonic antigen-related cell adhesion molecule, including the three subtypes CEACAM-1, CEACAM-3 or CEACAM-5), LAG3 (Lymphocyte-activation gene 3), VISTA (V-domain Ig suppressor of T cell activation), BTLA (B- and T-lymphocyte attenuator), TIGIT (T cell immunoreceptor with Ig and ITIM domains), LAIR1 (Leukocyte-associated immunoglobulin-like receptor 1), CD160 (Cluster of differentiation 160), CD96 (Cluster of differentiation 96), MerTK (Proto-oncogene tyrosine-protein kinase MER) and 2B4 (NK cell activation-inducing ligand), and may, for example, be selected among PD1, TIM3 and TIGIT.

In other embodiments, the gene weakening the function of immune cells may be characterized in that it encodes a receptor which can promote AICD (activation-induced cell death), acting as a negative regulator for T lymphocytes which have been activated by repeated stimulation by TCR, for example FAS (also referred to as CD95, APO-1 or apoptosis antigen-1). In some embodiments, the gene weakening the function of immune cells may be characterized in that it encodes factors that suppress signal activation of TCR, for example the factors can be selected from CD45, PP2A, SHP1, SHP2, DGK alpha, DGK zeta, Cbl-b, Cbl-c and CD148. In some embodiments, the gene weakening the function of immune cells may be characterized in that it encodes a protein that suppress the efficacy of CAR and/or TCR, for example, mTCR through signal suppression of 4-1BB, wherein 4-1BB is a costimulatory molecule described herein of TCR, for example a LRR1 (Leucine rich repeat protein 1). In some embodiments, the gene weakening the function of immune cells may be characterized in that it encodes a receptor, whose ligand is a cytokine, that suppress T cells, for example TGFBR1 (Transforming growth factor beta receptor 1) and IL10R alpha (IL-10R subunit alpha). In some embodiments, the gene weakening the function of immune cells may be characterized in that it encodes a receptor that inhibit the proliferation ability and cytotoxicity of T cells and NK cells, for example KLGR1 (Killer cell lectin like receptor G1). In some embodiments, the gene weakening the function of immune cells may be characterized in that it encodes a regulator associated with methylation of new DNA which is reported to suppress exhaustion of T cell exhaustion when knocked out (KO), for example TNMT3a (DNA methyltransferase 3 alpha). In some embodiments, the gene weakening the function of immune cells may be characterized in that it encodes a receptor of adenosine which is present in excess in tumor microenvironments, which when activated can inhibit the cell toxicity and cytokine production ability of T cells, for example A2aR (Adenosine receptor subtype A2a).

In some embodiments, the gene weakening the function of immune cells may be characterized in that it are selected from a group consisting of FAS, CD45, PP2A, SHP1, SHP2, DGK alpha, DGK zeta, Cbl-b, Cbl-c, CD148, LRR1, TGFBR1, IL10RA, KLGR1, DNMT3A and A2aR.

3.2 Chimeric Antigen Receptor (CAR) and T Cell Receptor, for Example, Monoclonal T Cell Receptor (mTCR).

As provided herein, a Two-in-One vector includes a base sequence encoding one or more types of short hairpin RNA (shRNA) which inhibit the expression of one or more genes that weaken the function of immune cells, and a base sequence encoding any one of a chimeric antigen receptor (CAR) or a T cell receptor, for example, a monoclonal T cell receptor (mTCR).

CAR is generally a set of polypeptides which, when existing on an immune cell, causes the immune cell to have specificity to a target cell (normally a cancer cell) while causing signal transduction in the cell. CAR at minimum comprises an extracellular antigen recognition domain which recognizes the target antigen to be described below, a transmembrane domain, and an intracellular signal transduction domain, wherein the intracellular signal transduction domain is derived from the promoting molecules or costimulatory molecules.

The structure of CARs commonly used today for clinical applications comprises a single chain variable fragment domain (hereinafter scFv) which gives specificity to an antigen, a spacer domain to regulate the distance between the scFv and the cell membrane, a transmembrane domain, and an intracellular signaling domain (hereinafter ISD). The ISD in turn comprises a costimulatory domain (CD28, CD137 or OX40) which contributes to in vivo proliferation and long life of one or multiple T cells, and a TCR signaling domain (CD3 zeta, CD3) which contributes to T cell activation. T-cells modified to express CAR that have been prepared in this manner can be activated by recognizing cancer cells which express the target antigen with high specificity, effectively induce the death of such cancer cells, simultaneously proliferate exponentially in the body, and remain alive for a long time. For example, when CAR-T cells (CART-19) prepared to target CD19, a B cell-specific antigen, were administered to a B-cell leukemia patient, it was reported that the cells proliferated to 1,000 to 10,000 times and remained alive in the body for several years. As a result, CART-19 exhibited 90% complete response in a clinical trial carried out on terminal acute lymphoblastic leukemia (B-ALL) patients on whom conventional chemotherapy, etc., had not been effective, leading to a rare case of licensing to a global pharmaceuticals company in the early investigator-initiated clinical trial phase. It became the first CAR-T cell therapy agent to receive U.S. FDA approval in 2017, and thereafter, a second CAR-T was also approved.

On the surface of immune cells, for example T cells, exist immune checkpoint receptors such as CTLA-4 (cytotoxic T-lymphocyte associated protein-4) or PD-1 (programmed cell death protein-1). These receptors are originally safety devices to regulate excessive activation and cell death of T cells, or the triggering of autoimmune responses. However, cancer cells, especially solid cancers, are reported to use this to avoid immunosurveillance by T cells. For example, if a cancer cell expresses PD-L1 (programmed death-ligand 1) on the surface, a T cell which expresses PD-1, the receptor therefor, recognizes the cancer cell and is activated, but will soon become exhausted by an activation inhibition signal from the PD-1. To prevent inhibition of T cell activity by signals from these immune checkpoint receptors, monoclonal antibodies to CTLA4 or PD-1, etc. that inhibit signal transmittance by target immune checkpoint receptors were developed. Therapies which improve the overall immune function of T cells through the blocking of immune checkpoints by using these immune checkpoint receptor inhibitors are exhibiting efficacy against various solid cancers as well.

As CAR-T cells are also ultimately a therapy that relies on the cytotoxicity of activated T cells, the existence of an immunosuppressive environment around CAR-T cells acts as a major hindrance to their therapeutic effect. In fact, unlike their therapeutic effects exhibited in B-cell leukemia, CAR-Ts prepared to target solid tumors have rarely exhibited hopeful therapeutic effects. This is thought to be because solid tumors, unlike blood cancers, create immune-suppressive tumor microenvironments to suppress the activity and proliferation of CAR-T cells. Further, even among B cell blood cancers, it has been reported that unlike acute lymphoblastic leukemia (ALL) patients of whom almost 90% were responsive to therapy using CART-19, the therapeutic effects were relatively less in lymphoma patients (20 to 50% response) or chronic lymphoblastic leukemia patients (CLL, around 20% response).

Further, it was reported that PD-L1 and other immunosuppressive ligands are expressed in the tumor microenvironments formed by lymphoma, according to which the function of T cells within cancerous tissue is exhausted. Further, it has been reported that the T cells obtained from CLL patients had already been substantially exhausted, with high degrees of expression of immune checkpoint receptors such as PD-1, CD160 and CD244.

Pre-clinical trial results showing that simultaneous use of anti-CTLA or anti-PD-1 inhibitory antibodies with CAR-T cells to recover this lowered activity of CAR-T cells improves the anti-cancer effect were reported, and clinical trials using these combinations are currently underway. However, a problem with such concurrent therapies of antibody and CAR-T cells is that the antibodies spread out throughout the body impact not just the CAR-T cells but all other T cells that exist in the body, potentially resulting in severe and systemic adverse reactions such as cytokine release syndrome, as well as autoimmune symptoms. Another problem which has been pointed out is the increased cost of treatment resulting from concurrent use of expensive antibody therapies with cell therapy.

Accordingly, there have recently been attempts to regulate gene expression within cells to allow for suppression of the immune checkpoints of CAR-T cells. International patent application publication WO2016/069282 discloses compositions and methods for generating a modified T cell with a nucleic acid capable of downregulating endogenous gene expression selected from the group consisting of TCR α chain, TCR β chain, β-2 microglobulin and FAS further comprising a nucleic acid encoding a modified T cell receptor (TCR) comprising affinity for a surface antigen on a target cell or an electroporated nucleic acid encoding a chimeric antigen receptor (CAR). The publication states that gene scissors such as CRISPR/Cas9 can be used to knockout the expression of endogenous genes, but the method of preparation of the CAR-T cells disclosed in the patent publication is rather complicated, and has the problems of low production yield and high production cost.

Meanwhile, international patent publication WO2015/090230 discloses that one single type of short hairpin RNA (shRNA) inhibiting a molecule that additionally suppresses the function of T cells, may be used on cells expressing CAR. As the cost burden of cell therapy is high, a patient faces various burdens in the event of failure. A single type of shRNA, however, may not be able to effectively inhibit the activity of such target molecules. In some embodiments, the set comprising polypeptides may be attached. In some embodiments, the set comprising polypeptide may be in a form where they attach through a switch which is dimerized through stimulation. In some embodiments, the CAR may be a fusion protein which comprises the extracellular antigen recognition domain, the transmembrane domain and the intracellular signal transduction domain. In further embodiments, the CAR fusion protein may additionally comprise a leader sequence at the N terminal, and the leader sequence may be cut away in the process of the CAR being expressed and becoming anchored in the cell membrane.

The TCR, for example, mTCR, described herein may comprise a chain selected from among α, β, γ and δ chains. In some embodiments, the chains are able to recognize the target antigen to be described below, CD3, and a zeta chain, and additionally a costimulatory molecule, where the costimulatory molecule may be selected from among ICOS, OX40, CD137 (4-1BB), CD27 or CD28.

In some embodiments, retroviral transfer of chimeric single chain antibody constructs (scFv) can be used to produce TCR, for example mTCR with defined antigen-specificity. In further embodiments, chimeric scFv constructs can be linked to the intracellular signaling domains of FcR-gamma or CD3ζ to trigger T-cell effector function. In the CD3 ζ domain can be combined with the signaling domains of costimulatory molecules, wherein antibody engagement can trigger effector T-cell function and also deliver co-stimulatory signals. In further embodiments, the the costimulatory molecules can be selected from CD28, 4-1BB and OX40.

In some embodiments, the Two-in-One vectors can comprise a CD3ζ domain, wherein the chains of the TCR, for example, mTCR can form a complex through noncovalent bonds with CD3 and a zeta (ζ) chain. When an antigen is recognized through the antigen recognition sites of the chains, the CD3 and zeta chains send signals into the cytoplasm of immune cells on which such TCR complex is expressed, inducing functional activation.

In some embodiments, the intracellular signal transduction domain may additionally comprise one or more functional signal transduction domains derived from the costimulatory molecules. In some embodiments, the promoting molecule may be the zeta chain of the TCR described in the above.

CAR and TCR, for example, mTCR are cell surface receptors. In some embodiments, the target of the CAR or TCR, for example, mTCR may be characterized in that it is a cancer antigen whose expression is specifically increased in cancer. In some embodiments, the target of the CAR or TCR, for example, mTCR may be characterized in that it is a cancer antigen that exists in mutated forms in cancer.

In some embodiments, the target of the CAR or TCR, for example, mTCR may be a human tumor antigen whose expression is increased in a cancer which is to be treated. For example, the target can be selected from 5T4 (trophoblast glycoprotein), 707-AP, 9D7, AFP (α-fetoprotein), AlbZIP (androgen-induced bZIP), HPG1 (human prostate specific gene-1), α5β1-Integrin, α5β6-Integrin, α-methylacyl-coenzyme A racemase, ART-4 (ADPribosyltransferase-4), B7H4 (v-set domain-containing T-cell activation inhibitor 1), BAGE-1 (B melanoma antigen-1), BCL-2 (B-cell CLL/lymphoma-2), BING-4 (WD repeat domain 46), CA 15-3/CA 27-29 (mucin 1), CA 19-9 (cancer antigen 19-9), CA 72-4 (cancer antigen 72-4), CA125 (cancer antigen 125), calreticulin, CAMEL (CTL-recognized antigen on melanoma), CASP-8 (caspase 8), cathepsin B, cathepsin L, CD19 (cluster of differentiation 19), CD20, CD22, CD25, CD30, CD33, CD4, CD52, CD55, CD56, CD80, CEA (carcinoembryonic antigen SG8), CLCA2 (chloride channel accessory 2), CML28 (chronic myelogenous leukemia tumor antigen 28), Coactosin-like protein, Collagen XXIII, COX-2 (cyclooxygenase-2), CT-9/BRD6 (cancer/testis antigen 9), Cten (c-terminal tensin-like protein), cyclin B1, cyclin D1, cyp-B, CYPB1 (cytochrome p450 family 1 subfamily b member 1), DAM-10/MAGE-B1 (melanoma-associated antigen B1), DAM-6/MAGE-B2, EGFR/Her1 (epidermal growth factor receptor), EMMPRIN (basigin), EpCam, EphA2 (EPH receptor A2), EphA3, ErbB3 (Erb-B2 receptor tyrosine kinase 3), EZH2 (enhancer of zeste 2 polycomb repressive complex 2 subunit), FGF-5 (fibroblast growth factor 5), FN (fibronectin), Fra-1 (Fosrelated antigen-1), G250/CAIX (carbonic anhydrase 9), GAGE-1 (G antigen-1), GAGE-2, GAGE-3, GAGE-4, GAGE-5, GAGE-6, GAGE-7b, GAGE-8, GDEP (gene differentially expressed in prostate), GnT-V (gluconate kinase), gp100 (melanocytes lineage-specific antigen GP100), GPC3 (glypican3), HAGE (helical antigen), HAST-2 (sulfotransferase family 1A member 1), hepsin, Her2/neu/ErbB2 (Erb-B2 receptor tyrosine kinase 2), HERV-K-MEL, HNE (medullasin), homeobox NKX 3.1, HOM-TES-14/SCP-1, HOM-TES-85, HPV-E6, HPVE7, HST-2 (sirtuin-2), hTERT, iCE (caspase 1), IGF-1R (insulin like growth factor-1 receptor), IL-13Ra2 (interleukin-13 receptor subunit a 2), IL-2R (interleukin-2 receptor), IL-5 (interleukin-5), immature laminin receptor, kallikrein 2, kallikrein 4, Ki67, KIAA0205 (lysophosphatidylglycerol acyltransferase 1), KK-LC-1 (kita-kyushu lung cancer antigen-1), KM-HN-1, LAGE-1 (L antigen family member-1), Livin, MAGE-A1, MAGE-A10, MAGE-A12, MAGEA2, MAGE-A3, MAGE-A4, MAGE-A6, MAGE-A9, MAGE-B1, MAGE-B10, MAGE-B16, MAGEB17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2 (melanoma antigen family L2), mammaglobin A, MART-1/Melan-A (melanoma antigen recognized by T-cells-1), MART-2, matrix protein 22, MC1R (melanocortin 1 receptor), M-CSF (macrophage colony-stimulating factor), Mesothelin, MG50/PXDN (peroxidasin), MMP 11 (matrix metalloprotease 11), MN/CA IX-antigen (carbonic anhydrase 9), MRP-3 (multidrug resistance-associated protein-3), MUC1 (mucin 1), MUC2, NA88-A (VENT-like homeobox 2 pseudogene 1), N-acetylglucos-aminyltransferase-V, Neo-PAP (Neo-poly (A) polymerase), NGEP (new gene expressed in prostate), NMP22 (nuclear matrix protein 22), NPM/ALK (nucleophosmin), NSE (neuron-specific enolase), NY-ESO-1, NY-ESO-B, OA1 (osteoarthritis QTL 1), OFA-iLRP (oncofetal antigen immature laminin receptor protein), OGT (O-GlcNAc transferase), OS-9 (endoplasmic reticulum lectin), osteocalcin, osteopontin, p15 (CDK inhibitor 2B), p53, PAGE-4 (P antigen family member-4), PAI-1 (plasminogen activator inhibitor-1), PAI-2, PAP (prostatic acid phosphatase), PART-1 (prostate androgen-regulated transcript 1), PATE (prostate and testis expressed 1), PDEF (prostate-derived Ets factor), Pim-1-Kinase (proviral integration site 1), Pin1 (Peptidyl-prolyl cis-trans isomerase NIMA-interacting 1), POTE (expressed in prostate, ovary, testis, and placenta), PRAME (preferentially expressed antigen in melanoma), prostein, proteinase-3, PSA (prostate-specific antigen), PSCA (prostate stem cell antigen), PSGR (prostate-specific G-protein coupled receptor), PSM, PSMA (prostate specific membrane antigen), RAGE-1 (renal tumor carcinoma antigen), RHAMM/CD168, RU1 (renal ubiquitous protein 1), RU2, SAGE (sarcoma antigen), SART-1 (squamous cell carcinoma antigen recognized by T-cells-1), SART-2, SART-3, Sp17 (sperm protein 17), SSX-1 (SSX family member 1), SSX-2/HOM-MEL-40, SSX-4, STAMP-1 (STEAP2 metalloreductase), STEAP, survivin, survivin-213, TA-90 (tumor associated antigen-90), TAG-72 (tumor associated glycoprotein-72), TARP (TCRγ alternate reading frame protein), TGFb (transforming growth factor β), TGFbR11 (transforming growth factor (3 receptor 11), TGM-4 (transglutaminase 4), TRAG-3 (taxol resistance associated gene 3), TRG (T-cell receptor γ locus), TRP-1 (transient receptor potential-1), TRP-2/6b, TRP-2/INT2, Trp-p8, Tyrosinase, UPA (U-plasminogen activator), VEGF (vascular endothelial growth factor A), VEGFR-2/FLK-1 and WT1 (wilms tumor 1), or may be a mutated form of human tumor antigen discovered in the cancer to be treated, selected from among α-actinin-4/m, ARTC1/m, bcr/abl, beta-Catenin/m, BRCA1/m, BRCA2/m, CASP-5/m, CASP-8/m, $CDCl_2$7/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYTSSX-1, SYT-SSX-2, TEL-AML1, TGFbRII and TPI/m. For example, the target antigen may be selected between CD19 or CD22.

3.3 Components of the Two-in-One Vectors

As provided herein, a Two-in-One vector includes a base sequence encoding one or more types of short hairpin RNA (shRNA) which inhibit the expression of one or more genes that weaken the function of immune cells, and a base sequence encoding a chimeric antigen receptor (CAR) or a T cell receptor (TCR), for example, monoclonal T cell receptor (mTCR).

In some embodiments, the Two-in-One vectors can comprise sequences encoding factors that promote the insertion of the sequences into the host cell genome. In some embodiments, the sequences are located at either or both end(s) of the vector gene. In some embodiments, the sequences are LTRs (long terminal sequence).

In some embodiments, the Two-in-One vectors can comprise a domain encodes proteins that is used for purification of cells wherein the insertion described above has taken place. In some embodiments, the domain is a ΔLNGFR domain, wherein ΔLNGFR is a LNGFR (low-affinity nerve growth factor receptor) without a cytoplasmic domain used for purification of cells wherein the insertion described above has taken place.

Figure 22A:
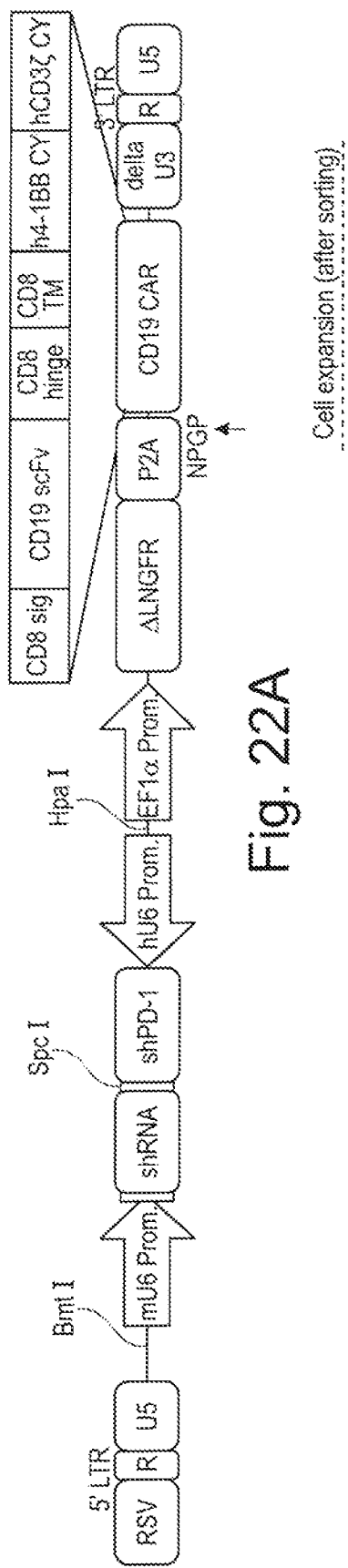
FIGS. 22A-22E. Generation of dual immune checkpoint-disrupted CAR T cells.

In some embodiments, the Two-in-One vectors can comprise promoters that induce the expression of both ΔLNGFR and CAR characterized by sustained expression, for example an EF1α promoter inducing expression of both ΔLNGFR and CD19 CAR as shown in FIG. 22A. In further embodiments, ΔLNGFR and CD19 CAR are first transcribed in a form wherein they exist on a single mRNA. In such embodiments where two or more cistrons exist on the same mRNA, an IRES (internal ribosome entry site) may be inserted there between to cause expression of both cistrons. However, IRES is excessively long, and it has been reported that the expression efficiency of the downstream cistron is reduced. In some embodiments, components other than IRES can be used to overcome such disadvantages, for example a P2A (2a peptide), wherein, during translation, the ribosome passes without forming a peptide bond at the C terminal of P2A, allowing for the downstream gene to be expressed later.

Some exemplary Two-in-One vectors are the Two-in-One vector shown in FIGS. 1A, 6A, 14 and 22A, the vector comprising any one of the base sequences SEQ ID 220 or 221. Exemplary vectors, which comprise the base sequences of SEQ ID 220 and 221, can have the structure shown in FIGS. 1A and 1B. Some exemplary plasmids are listed in Table 1.

TABLE 1

Exemplary plasmids.

| No. | Exemplary Plasmid |
|---|---|
| 1 | pLV (lentivirus)-ΔLNGFR_P2A_CD19-CAR_mU6-shGFP |
| 2 | pLV-ΔLNGFR_P2A_CD19-CAR_mU6-shPD-1 |
| 3 | pLV-ΔLNGFR_P2A_CD19-CAR_mU6-shTIM-3 |
| 4 | pLV-ΔLNGFR_P2A_CD19-CAR_mU6-shPD-1_MCS |
| 5 | pLV-ΔLNGFR_P2A_CD19-CAR_hU6-shPD-1_MCS |
| 6 | pLV-ΔLNGFR_P2A_CD19-CAR_mU6-shTIM-3→←shPD-1-hU6 |
| 7 | pLV-ΔLNGFR_P2A_CD19-CAR_shPD-1-hU6_MCS |
| 8 | pLV-ΔLNGFR_P2A_CD19-CAR_shTIM-3-mU6→←hU6-shPD-1 |

In some embodiments, the base sequences included in the vector described above, and the nucleic acid sequences of the respective shRNAs may, in addition to the sequences described herein, comprise nucleic acid sequences exhibiting at least 50%, specifically at least 70%, more specifically at least 80%, even more specifically at least 90%, and most specifically at least 95% sequence homology with these sequences. This is because, in the case of siRNA (small interfering RNA) and shRNA which is processed intracellularly to become siRNA in particular, it has been reported that some degree of mutation, especially mutation at the 5' terminal is tolerable, causing normal knockdown of the target gene, and that mutations of siRNA and shRNA made to have a structure similar to that of miRNA that plays a role in gene silencing more effectively induce knockdown of the target gene. Further, in the use of vectors, self-evident to those skilled in the art are variations within the vector, that is, the addition, modification or deletion of base sequences which may occur in the cloning process for introducing a certain sequence into the vector, or changes to or introduction of components to improve the ease of use of the vector of the degree to which the intended gene is expressed.

4. Production and Evaluation of CAR-T Cells that Targeting One or More Immune Checkpoints As provided herein, a Two-in-One vector includes a base sequence encoding one or more types of short hairpin RNA (shRNA) which inhibit the expression of genes that weaken the function of immune cells, and a base sequence encoding any one of a chimeric antigen receptor (CAR) and a T cell receptor (TCR), for example, monoclonal T cell receptor (mTCR). The vector can be used for the production of immune cells having inhibited expression of genes that weaken the function of immune cell. In some embodiments, the vector is selected from the group consisting of DNA, RNA, plasmid, lentivirus vector, adenovirus vector, and retrovirus vector.

In one aspect, the immune cell described herein is characterized in that it comprises the above vector and expresses CAR or a TCR, for example, mTCR, and in that expression of the target genes of the one or more types of shRNA is reduced. In some embodiments the expression of the target genes of the one of more types of shRNA is reduced to about 90% or less of that of a control group, for example the expression of the target genes is reduced to about 80% or less, about 70% or less, about 60% or less, about 50% or less, about 40% or less, about 30% or less, about 20% or less, and about 10% or less of that of a control group. In some embodiments, the immune cell is selected from between human-derived T cells and NK cells.

In another aspect, provided herein are methods. In some embodiments, provided is a method of producing an immune cell comprising introducing into an immune cell, simultaneously or sequentially in any order: (1) a gene encoding a genetically engineered antigen receptor that specifically binds to a target antigen; and (2) a genetic disruption agent reducing or capable of reducing expression in the immune cell of a gene that weakens the function of the immune cell, thereby producing an immune cell in which a genetically engineered antigen receptor is expressed and expression of the gene that weakens the function of the immune cell is reduced.

In some embodiments, the genetically engineered antigen receptor is a chimeric antigen receptor (CAR) or a T cell receptor (TCR). In some embodiments, the genetically engineered antigen receptor is a CAR. In some embodiments, the CAR comprises an extracellular antigen recognition domain, a transmembrane domain, and an intracellular signal transduction domain.

In some embodiments, the extracellular antigen recognition domain of the CAR specifically binds to the target antigen.

In some embodiments, the intracellular signal transduction domain of the CAR comprises an intracellular domain of a CD3 zeta (CD3ζ) chain. In some embodiments, the intracellular signal transduction domain of the CAR further comprises a costimulatory molecule.

In some embodiments, the costimulatory molecule is selected from the group consisting of ICOS, OX40, CD137 (4-1BB), CD27, and CD28. In some embodiments, the costimulatory molecule is CD137 (4-1BB). In some embodiments, the costimulatory molecule is CD28.

In some embodiments, the target antigen is expressed on the cell surface of a cancer cell, a cancer tissue, and/or a tumor microenvironment. In some embodiments, the target antigen is either a cancer antigen whose expression is increased, or a mutated form of a cancer antigen, in the cancer cell, the cancer tissue, and/or the tumor microenvironment.

In some embodiments, the cancer antigen whose expression is increased in the cancer cell, the cancer tissue, and/or the tumor microenvironment is selected from the group consisting of: 5T4 (trophoblast glycoprotein), 707-AP, 9D7, AFP (α-fetoprotein), AlbZIP (androgen-induced bZIP), HPG1 (human prostate specific gene-1), α5β1-Integrin, α5β6-Integrin, α-methylacyl-coenzyme A racemase, ART-4 (ADPribosyltransferase-4), B7H4 (v-set domain-containing T-cell activation inhibitor 1), BAGE-1 (B melanoma antigen-1), BCL-2 (B-cell CLL/lymphoma-2), BING-4 (WD repeat domain 46), CA 15-3/CA 27-29 (mucin 1), CA 19-9 (cancer antigen 19-9), CA 72-4 (cancer antigen 72-4), CA125 (cancer antigen 125), calreticulin, CAMEL (CTL-recognized antigen on melanoma), CASP-8 (caspase 8), cathepsin B, cathepsin L, CD19 (cluster of differentiation 19), CD20, CD22, CD25, CD30, CD33, CD4, CD52, CD55, CD56, CD80, CEA (carcinoembryonic antigen SG8), CLCA2 (chloride channel accessory 2), CML28 (chronic myelogenous leukemia tumor antigen 28), Coactosin-like protein, Collagen XXIII, COX-2 (cyclooxygenase-2), CT-9/BRD6 (cancer/testis antigen 9), Cten (c-terminal tensin-like protein), cyclin B1, cyclin D1, cyp-B, CYPB1 (cytochrome p450 family 1 subfamily b member 1), DAM-10/MAGE-B1 (melanoma-associated antigen B1), DAM-6/MAGE-B2, EGFR/Her1 (epidermal growth factor receptor), EMMPRIN (basigin), EpCam, EphA2 (EPH receptor A2), EphA3, ErbB3 (Erb-B2 receptor tyrosine kinase 3), EZH2 (enhancer of zeste 2 polycomb repressive complex 2 subunit), FGF-5 (fibroblast growth factor 5), FN (fibronectin), Fra-1 (Fosrelated antigen-1), G250/CAIX (carbonic anhydrase 9), GAGE-1 (G antigen-1), GAGE-2, GAGE-3, GAGE-4, GAGE-5, GAGE-6, GAGE-7b, GAGE-8, GDEP (gene differentially expressed in prostate), GnT-V (gluconate kinase), gp100 (melanocytes lineage-specific antigen GP100), GPC3 (glypican3), HAGE (helical antigen), HAST-2 (sulfotransferase family 1A member 1), hepsin, Her2/neu/ErbB2 (Erb-B2 receptor tyrosine kinase 2), HERV-K-MEL, HNE (medullasin), homeobox NKX 3.1, HOM-TES-14/SCP-1, HOM-TES-85, HPV-E6, HPVE7, HST-2 (sirtuin-2), hTERT, iCE (caspase 1), IGF-1R (insulin like growth factor-1 receptor), IL-13Ra2 (interleukin-13 receptor subunit a 2), IL-2R (interleukin-2 receptor), IL-5 (interleukin-5), immature laminin receptor, kallikrein 2, kallikrein 4, Ki67, KIAA0205 (lysophosphatidylglycerol acyltransferase 1), KK-LC-1 (kita-kyushu lung cancer antigen-1), KM-HN-1, LAGE-1 (L antigen family member-1), Livin, MAGE-A1, MAGE-A10, MAGE-A12, MAGEA2, MAGE-A3, MAGE-A4, MAGE-A6, MAGE-A9, MAGE-B1, MAGE-B10, MAGE-B16, MAGEB17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2 (melanoma antigen family L2), mammaglobin A, MART-1/Melan-A (melanoma antigen recognized by T-cells-1), MART-2, matrix protein 22, MC1R (melanocortin 1 receptor), M-CSF (macrophage colony-stimulating factor), Mesothelin, MG50/PXDN (peroxidasin), MMP 11 (matrix metalloprotease 11), MN/CA IX-antigen (carbonic anhydrase 9), MRP-3 (multidrug resistance-associated protein-3), MUC1 (mucin 1), MUC2, NA88-A (VENT-like homeobox 2 pseudogene 1), N-acetylglucos-aminyltransferase-V, Neo-PAP (Neo-poly (A) polymerase), NGEP (new gene expressed in prostate), NMP22 (nuclear matrix protein 22), NPM/ALK (nucleophosmin), NSE (neuron-specific enolase), NY-ESO-1, NY-ESO-B, OA1 (osteoarthritis QTL 1), OFA-iLRP (oncofetal antigen immature laminin receptor protein), OGT (O-GlcNAc transferase), OS-9 (endoplasmic reticulum lectin), osteocalcin, osteopontin, p15 (CDK inhibitor 2B), p53, PAGE-4 (P antigen family member-4), PAI-1 (plasminogen activator inhibitor-1), PAI-2, PAP (prostatic acid phosphatase), PART-1 (prostate androgen-regulated transcript 1), PATE (prostate and testis expressed 1), PDEF (prostate-derived Ets factor), Pim-1-Kinase (proviral integration site 1), Pin1 (Peptidyl-prolyl cis-trans isomerase NIMA-interacting 1), POTE (expressed in prostate, ovary, testis, and placenta), PRAME (preferentially expressed antigen in melanoma), prostein, proteinase-3, PSA(prostate-specific antigen), PSCA (prostate stem cell antigen), PSGR (prostate-specific G-protein coupled receptor), PSM, PSMA (prostate specific membrane antigen), RAGE-1 (renal tumor carcinoma antigen), RHAMM/CD168, RU1 (renal ubiquitous protein 1), RU2, SAGE (sarcoma antigen), SART-1 (squamous cell carcinoma antigen recognized by T-cells-1), SART-2, SART-3, Sp17 (sperm protein 17), SSX-1 (SSX family member 1), SSX-2/HOM-MEL-40, SSX-4, STAMP-1 (STEAP2 metalloreductase), STEAP, survivin, survivin-213, TA-90 (tumor associated antigen-90), TAG-72 (tumor associated glycoprotein-72), TARP (TCRγ alternate reading frame protein), TGFb (transforming growth factor β), TGFbR11 (transforming growth factor β receptor 11), TGM-4 (transglutaminase 4), TRAG-3 (taxol resistance associated gene 3), TRG (T-cell receptor γ locus), TRP-1 (transient receptor potential-1), TRP-2/6b, TRP-2/INT2, Trp-p8, Tyrosinase, UPA (U-plasminogen activator), VEGF (vascular endothelial growth factor A), VEGFR-2/FLK-1, and WT1 (wilms tumor 1).

In some embodiments, the target antigen is CD19 or CD22. In some embodiments, the target antigen is CD19.

In some embodiments, the mutated form of a tumor antigen is selected from the group consisting of: α-actinin-4/m, ARTC1/m, bcr/abl, beta-Catenin/m, BRCA1/m, BRCA2/m, CASP-5/m, CASP-8/m, $CDCl_2$7/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYTSSX-1, SYT-SSX-2, TEL-AML1, TGFbRII, and TPI/m.

In some embodiments, expression of the gene that weakens the function of the immune cell causes one or more of the following: i) inhibits proliferation of the immune cell; ii) induces cell death of the immune cell; iii) inhibits the function of a molecule necessary for the immune cell to recognize the target antigen and/or to get activated; iv) induces differentiation of the immune cell into a different type that plays a different function instead of causing immune response to the target antigen; v) decreases reactions of the immune cell with a molecule which promotes immune response of the immune cell; or vi) increases reactions of the immune cell with a molecule which suppresses immune response of the immune cell.

In some embodiments, the gene that weakens the function of the immune cell is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, 2B4, FAS, CD45, PP2A, SHP1, SHP2, DGK alpha, DGK zeta, Cbl-b, Cbl-c, CD148, LRR1, TGFBR1, IL10RA, KLGR1, DNMT3A, and A2aR. In some embodiments, the gene that weakens the function of the immune cell increases reactions of the immune cell with a molecule which suppresses immune response of the immune cell. In some embodiments, the gene that increases reactions of the immune cell with a molecule which suppresses immune response of the immune cell encodes an immune checkpoint receptor or ligand.

In some embodiments, the immune checkpoint receptor or ligand is selected from the group consisting of: PD1, PD-L1, CTLA4, TIM3, CEACAM (CEACAM-1, CEACAM-3 or CEACAM-5), LAG 3, VISTA, BTLA, TIGIT, LAIR1, CD160, CD96, MerTK, and 2B4.

In some embodiments, the genetic disruption agent reduces the expression of a gene in the immune cell that weakens the function of the immune cell by at least 30, 40, 50, 60, 70, 80, 90, or 95% as compared to the immune cell in the absence of the genetic disruption agent. In some embodiments, the genetic disruption agent reduces the expression of a gene that increases reactions of the immune cell with a molecule which suppresses immune response of the immune cell. In some embodiments, the genetic disruption agent reduces the expression of a gene that encodes an immune checkpoint receptor or ligand. In some embodiments, the genetic disruption agent reduces the expression of a gene selected from the group consisting of: PD1, PD-L1, CTLA4, TIM3, CEACAM (CEACAM-1, CEACAM-3 or CEACAM-5), LAG3, VISTA, BTLA, TIGIT, LAIR1, CD160, CD96, MerTK, and 2B4.

In some embodiments, the genetic disruption agent reduces the expression of the gene that weakens the function of the immune cell by RNA interference (RNAi). In some embodiments, more than one genetic disruption agents reduce the expression of a gene that weakens the function of the immune cell in the immune cell by RNAi. In some embodiments, the genetic disruption agents target different parts of a single gene which weakens the function of the immune cell, target different genes which weaken the function of the immune cell, or in any combination thereof. In some embodiments, the RNAi is mediated by a short hairpin RNA (shRNA). In some embodiments, the RNAi is mediated by more than one shRNAs.

In some embodiments, the RNAi is mediated by two shRNAs. In some embodiments, two shRNAs target different parts of PD-1. In some embodiments, two shRNAs target PD-1 and TIM-3, respectively. In some embodiments, two shRNAs target PD-1 and CTLA-4, respectively. In some embodiments, two shRNAs target PD-1 and LAG-3, respectively. In some embodiments, two shRNAs target PD-1 and TIGIT, respectively.

In some embodiments, base sequences encoding the shRNAs comprise sequences selected from the group consisting of SEQ ID NOs: 1-219 and 238-267.

In some embodiments, the expression of different shRNA is respectively regulated by different promoters. In some embodiments, the expression of two different shRNA is respectively regulated by two different promoters. In some embodiments, the two different promoters are RNA polymerase III promoters. In some embodiments, the two promoters are U6 promoters derived from different species. In some embodiments, the two promoters are oriented in different directions from each other.

In some embodiments, the genetically engineered antigen receptor and the genetic disruption agent are each expressed from a vector. In some embodiments, the genetically engineered antigen receptor and the genetic disruption agent are expressed from the same vector. In some embodiments, the vector is selected from the group consisting of DNA, RNA, plasmid, lentivirus vector, adenovirus vector, and retrovirus vector. In some embodiments, the vector is lentivirus vector.

The immune cell may be characterized in that it is selected from lymphocytes, such as killer T cells, helper T cells, gamma delta T cells and B cells, natural killer cells, mast cells, eosinophils, basophils; and the phagocytic cells include macrophages, neutrophils, and dendritic cells. The T cells include CD4+ T cells and CD8+ T cells. In some embodiments, the B-cell lymphoma is diffuse large B cell lymphoma (DLBCL), primary mediastinal B-cell lymphoma (PMBL), Hodgkin lymphoma (HL), non-Hodgkin lymphoma, mediastinal gray zone lymphoma, or nodular sclerosis HL. In some embodiments, the T-cell lymphoma is anaplastic large cell lymphoma (ALCL), peripheral T cell lymphoma not otherwise specified (PTCL-NOS), or angio-immunoblastic T cell lymphoma (AITL). In a preferred embodiment, the immune cell may be selected from human-derived T cells or T lymphocytes and natural killer (NK) cells. In some embodiments, the immune cell is a T cell. In some embodiments, the T cell is a CD4+ T cell or a CD8+ T cell.

In some embodiments, the immune cells are produced from cells originally derived from a subject. In some embodiments, the subject can be a human being. In some embodiments, the human being can be a healthy donor. In other embodiments, the subject may be characterized as having a tumor or cancer, wherein an increase or variation in levels of cancer antigen targeted by the CAR or the TCR, for example, mTCR expressed in the cell is detected. In some embodiments, cells may be produced and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In some embodiments, CAR-T cells are produced. In further embodiments, the production of CAR-T cells comprises a step of providing peripheral blood monoclonal cells. In further embodiments, the peripheral blood monoclonal cells can be separated from whole blood samples. In some embodiment, the production of CAR-T cells described herein comprises a step of stimulation of the peripheral blood monoclonal cells using antibodies. By way of example, the agent providing the primary stimulation signal is an anti-CD3 antibody or an antigen-binding fragment thereof and the agent providing the costimulatory signal is an anti-CD28 antibody or antigen-binding fragment thereof. In some embodiments, the production of CAR-T cells described herein comprises a step of transduction of CAR, wherein the CAR can target any target described herein and any other known targets of CAR, for example the CAR can be a CD19 CAR that targets CD19. In further embodiments, CAR-T cells produced are isolated.

Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-I 0, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). Several cycles of stimulation may also be desired such that culture time of T cells can be 60 days or more.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree. Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Various assays can be used to evaluate the CAR-T cells, such as but not limited to, the ability to expand following antigen stimulation, sustain T cell expansion in the absence of re-stimulation, and anti-cancer activities in appropriate in vitro and animal models. Assays are described in further detail below.

In some embodiments, western blot analysis of CAR expression in primary T cells can be used to detect the presence of monomers and dimers. See, e.g., Milone et al., Molecular Therapy 17(8): 1453-1464 (2009).

In some embodiments, in vitro expansion of CAR+ T cells following antigen stimulation can be measured by flow cytometry. For example, a mixture of CD4+ and CD8+ T cells are stimulated with αCD3/αCD28 aAPCs followed by transduction with lentiviral vectors expressing GFP under the control of the promoters to be analyzed. Exemplary promoters include the CMV IE gene, EF-1 a, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17(8): 1453-1464 (2009). Alternatively, a mixture of CD4+ and CD8+ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated, e.g., with K562 cells expressing hCD32 and 4-1BBL in the presence of anti-CD3 and anti-CD28 antibody (K562-BBL-3/28) following washing. Exogenous IL-2 is added to the cultures every other day at 100 IU/ml. GFP+ T cells are enumerated by flow cytometry using bead-based counting. See, e.g., Milone et al., Molecular Therapy 17(8): 1453-1464 (2009). Sustained CAR+ T cell expansion in the absence of re-stimulation can also be measured.

Assessment of cell proliferation and cytokine production has been previously described, e.g., at Milone et al., Molecular Therapy 17(8): 1453-1464 (2009). Briefly, assessment of CAR-mediated proliferation are performed in microtiter plates by mixing washed T cells with target cells, such as K562-Meso, Ovcar3, Ovcar8, SW1990, Panc02.03 cells or CD32 and CD137 (KT32-BBL) for a final T-cell:target cell ratio of 1:1. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T cell expansion ex vivo. T cells are enumerated in cultures using CountBright™ fluorescent beads (Invitrogen, Carlsbad, Calif.) and flow cytometry as described by the manufacturer. CAR+ T cells are identified by GFP expression using T cells that are engineered with eGFP-2A linked CAR-expressing lentiviral vectors. CD4+ and CD8+ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by methods described herein, e.g., in the examples, or by a standard $^{51}$Cr-release assay (Milone et al., Molecular Therapy 17(8): 1453-1464 (2009)). Briefly, target cells (e.g., BHK or CHO cells) are loaded with 51 Cr (as NaCr04, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell: target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}$Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average $^{51}$Cr released for each experimental condition. Alternative cytotoxicity assays may also be used, such as flow based cytotoxicity assays.

Other assays, including those described in the Example section herein as well as those that are known in the art can also be used to evaluate the CAR-T cells produced herein.

In some embodiments, the immune cells produced herein can be involved in immune response to diseases wherein the antigens targeted by the two types of shRNA and the CAR or the TCR, for example, mTCR are expressed. In further embodiments, the immune cells can be used to provide a pharmaceutical composition for immune therapy of human patients. In some embodiments, the pharmaceutical composition can show therapeutic effect on the target illness without the need for immune checkpoint inhibitors, which may cause severe adverse reactions and burden the patient additionally with high costs.

In some embodiments, the immune cells can be used as immune cell therapeutic agents; such immune cells are normally used for the treatment of cancers but are not limited thereto. In further embodiments, to make these immune cells recognize cancers, they are modified to express cell surface receptors which target cancer antigens.

In another aspect, provided herein are compositions comprising the engineered immune cells described above.

5. Treatment Using CAR-T Cells that Targeting One or More Immune Checkpoints As provided herein, a Two-in-One vector includes a base sequence encoding one or more types of short hairpin RNA (shRNA) which inhibit the expression of genes that weaken the function of immune cells, and a base sequence encoding any one of a chimeric antigen receptor (CAR) and a T cell receptor (TCR) for example, a monoclonal T cell receptor (mTCR). Using the vector according to one embodiment, immune cells can be produced, wherein the immune cells have reduced immune checkpoint receptor expression and which express CAR or TCR, for example, mTCR specific to target molecules. Said immune cells can be used to provide a pharmaceutical composition for immune therapy.

A variety of diseases may be ameliorated by introducing immune cells as described herein to a subject suitable for adoptive immune therapy. In some embodiments, the produced CAR-T cells as provided is for allogeneic adoptive cell therapies. Additionally provided herein are therapeutic use of the compositions described herein, comprising introducing the composition to a subject suitable for adoptive cell therapy, wherein the subject has an autoimmune disorder; a hematological malignancy; a solid tumor; or an infection associated with HIV, RSV, EBV, CMV, adenovirus, or BK polyomavirus.

Examples of hematological malignancies include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes. Examples of solid cancers include, but are not limited to, cancer of the brain, prostate, breast, lung, colon, uterus, skin, liver, bone, pancreas, ovary, testes, bladder, kidney, head, neck, stomach, cervix, rectum, larynx, and esophagus. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV—(human immunodeficiency virus), HSV—(herpes simplex virus), KSHV—(Kaposi's sarcoma-associated herpesvirus), RSV—(Respiratory Syncytial Virus), EBV—(Epstein-Barr virus), CMV—(cytomegalovirus), VZV (Varicella zoster virus), adenovirus-, a lentivirus-, a BK polyomavirus-associated disorders.

Acute leukemia is characterized by the rapid proliferation of immature blood cells. This crowding makes the bone marrow unable to produce healthy blood cells. Acute forms of leukemia can occur in children and young adults. In fact, it is a more common cause of death for children in the U.S. than any other type of malignant disease. Immediate treatment is required in acute leukemia due to the rapid progression and accumulation of the malignant cells, which then spill over into the bloodstream and spread to other organs of the body. Central nervous system (CNS) involvement is uncommon, although the disease can occasionally cause cranial nerve palsies. Chronic leukemia is distinguished by the excessive build up of relatively mature, but still abnormal, blood cells. Typically taking months to years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy. Furthermore, the diseases are classified into lymphocytic or lymphoblastic, which indicate that the cancerous change took place in a type of marrow cell that normally goes on to form lymphocytes, and myelogenous or myeloid, which indicate that the cancerous change took place in a type of marrow cell that normally goes on to form red cells, some types of white cells, and platelets (see lymphoid cells vs. myeloid cells).

Acute lymphocytic leukemia (also known as acute lymphoblastic leukemia, or ALL) is the most common type of leukemia in young children. This disease also affects adults, especially those aged 65 and older. Chronic lymphocytic leukemia (CLL) most often affects adults over the age of 55. It sometimes occurs in younger adults, but it almost never affects children. Acute myelogenous leukemia (also known as acute myeloid leukemia, or AML) occurs more commonly in adults than in children. This type of leukemia was previously called "acute nonlymphocytic leukemia." Chronic myelogenous leukemia (CML) occurs mainly in adults. A very small number of children also develop this disease.

Lymphoma is a type of cancer that originates in lymphocytes (a type of white blood cell in the vertebrate immune system). There are many types of lymphoma. According to the U.S. National Institutes of Health, lymphomas account for about five percent of all cases of cancer in the United States, and Hodgkin's lymphoma in particular accounts for less than one percent of all cases of cancer in the United States. Because the lymphatic system is part of the body's immune system, patients with a weakened immune system, such as from HIV infection or from certain drugs or medication, also have a higher incidence of lymphoma.

In the 19th and 20th centuries the affliction was called Hodgkin's Disease, as it was discovered by Thomas Hodgkin in 1832. Colloquially, lymphoma is broadly categorized as Hodgkin's lymphoma and non-Hodgkin lymphoma (all other types of lymphoma). Scientific classification of the types of lymphoma is more detailed. Although older classifications referred to histiocytic lymphomas, these are recognized in newer classifications as of B, T, or NK cell lineage.

When the pharmaceutical composition are administered to a patient having a cancer wherein the target molecule of the CAR or TCR, for example, mTCR, is expressed, the pharmaceutical composition can recognize the cancer and have immune activity without the activation of genes which weaken the function of immune cells with regard to cancer cells, and without problems such as exhaustion due to activation-inhibiting signaling caused thereby.

In some embodiment, the above pharmaceutical composition comprising immune cells is able to more effectively suppress the expression of immune checkpoint receptors while simultaneously maximizing the effectiveness of anti-cancer immune cell therapy wherein chimeric antigen receptors can function. In further embodiments, as cells wherein expression of immune checkpoint receptors is suppressed as described in the above are used in the pharmaceutical composition, it is possible to eliminate the severe and systemic adverse reactions such as cytokine release syndrome or autoimmune symptoms which may result from using a separate inhibitor for immune checkpoint receptor, as well the burden due to the increased cost of treatment resulting from the concurrent use of expensive antibody therapies with cell therapy.

As it is self-evident that, in addition to the cells, other pharmaceutically acceptable salts, carriers, excipients, vehicles and other additives, etc. which may further improve immune response may be added to the pharmaceutical composition, a detailed explanation thereof shall be omitted.

In some embodiments, the pharmaceutical composition comprises dual CAR-T cells targeting two immune checkpoints as describe herein. For example dual immune checkpoints can be selected from a group consisting of PD1 (Programmed cell death protein 1), PD-L1 (Programmed death-ligand 1), CTLA4 (Cytotoxic T-lymphocyte associated protein 4), TIM-3 (T-cell immunoglobulin and mucin-domain containing-3), CEACAM (Carcinoembryonic antigen-related cell adhesion molecule, including the three subtypes CEACAM-1, CEACAM-3 or CEACAM-5), LAG3 (Lymphocyte-activation gene 3), VISTA (V-domain Ig suppressor of T cell activation), BTLA (B- and T-lymphocyte attenuator), TIGIT (T cell immunoreceptor with Ig and ITIM domains), LAIR1 (Leukocyte-associated immunoglobulin-like receptor 1), CD160 (Cluster of differentiation 160), CD96 (Cluster of differentiation 96), MerTK (Proto-oncogene tyrosine-protein kinase MER) and 2B4 (NK cell activation-inducing ligand), and may, for example, be selected between PD1 and TIM3.

In some embodiments, the types of targeted immune checks affect the anti-tumor effect of the pharmaceutical composition. For example, a pharmaceutical composition targeting PD-1 and TIM3 can show different level of anti-tumor effect from that of a pharmaceutical composition targeting PD-1 and TIGIT. In further embodiments, said difference in the anti-tumor effect is unpredictable from known knowledge on anti-tumor effects of other drugs targeting the same immune checkpoint, for example the other drugs can include an antibody targeting the immune checkpoint. In some embodiments, targeting certain two immune checkpoints can produce surprisingly high anti-tumor effect. In an exemplary embodiment (example 10), the CAR-T cells targeting PD-1 and TIGIT shows surprisingly superior antitumor effect compared to other dual KD CAR-T cells targeting combinations of PD-1 and CTLA-4, PD-1 and LAG-3, and PD-1 and TIM-3.

In one aspect, a composition described herein can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of a composition described herein, alone or in combination with other active agents, calculated in an amount sufficient to produce the desired effect, in association with a pharmaceutically acceptable diluent, carrier, or vehicle, where appropriate. The specifications for the novel unit dosage forms of cells or compositions described herein depend on the particular pharmacodynamics associated with the pharmaceutical composition in the particular subject.

In some embodiments, the preferred pharmaceutical dosage form for the cells or compositions described herein may be determined based on the content of the present disclosure and general knowledge of formulation techniques and according to the intended administration pathway, method of delivery and the target dose. The method of administration notwithstanding, the effective dose may be calculated in according to the patient's body weight, surface area or organ size. Calculations to determine the appropriate administration doses for therapy using the respective dosage forms stated in the present specification, as well as additional purification, are carried out on a daily basis in the art, and are included within the scope of work carried out on a daily basis in the art. The appropriate administration doses may be identified through use of appropriate dose-response data.

Pharmaceutical compositions described herein can be used alone or in combination with other known agents useful for treating cancer. Whether delivered alone or in combination with other agents, pharmaceutical compositions described herein can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration. Exemplary route of administration to a subject includes intravenous (IV) injection, and regional (intratumoral, intraperitoneal) administration. In some embodiment, the pharmaceutical composition can be administered via infusion into a solid tumor.

In some embodiments, in addition to the genomically engineered immune cells as provided herein, additional therapeutic agent comprising an antibody, or an antibody fragment that targets an antigen associated with a condition, a disease, or an indication may be used with these effector cells in a combinational therapy. In some embodiments, the antibody is a monoclonal antibody. In some embodiments, the antibody is a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the antibodies suitable for combinational treatment as an additional therapeutic agent to the administered genomically engineered immune cells include, but are not limited to, anti-CD20 (rituximab, veltuzumab, ofatumumab, ublituximab, ocaratuzumab, obinutuzumab), anti-HER2 (trastuzumab, pertuzumab), anti-CD52 (alemtuzumab), anti-EGFR (certuximab), anti-GD2 (dinutuximab), anti-PDL1 (avelumab), anti-CD38 (daratumumab, isatuximab, MOR202), anti-CD123 (7G3, CSL362), anti-SLAMF7 (elotuzumab); and their humanized or Fc modified variants or fragments, or their functional equivalents and biosimilars.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of transduced T cells to be utilized by the practitioner upon optimizing the methods described herein. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

Any of the compositions described herein may be comprised in a kit. In some embodiments, the CAR T-cells are provided in the kit, which also may include reagents suitable for expanding the cells, such as media, aAPCs, growth factors, antibodies (e.g., for sorting or characterizing CAR T-cells) and/or plasmids encoding CARs or transposase.

In a non-limiting example, a chimeric receptor expression construct, one or more reagents to generate a chimeric receptor expression construct, cells for transfection of the expression construct, and/or one or more instruments to obtain allogeneic cells for transfection of the expression construct (such an instrument may be a syringe, pipette, forceps, and/or any such medically approved apparatus).

In some embodiments, an expression construct for eliminating endogenous TCR α/β expression, one or more reagents to generate the construct, and/or CAR' T cells are provided in the kit. In some embodiments, there includes expression constructs that encode zinc finger nuclease(s). In some aspects, the kit comprises reagents or apparatuses for electroporation of cells.

The kits may comprise one or more suitably aliquoted compositions described herein or reagents for generating compositions as described herein. The components of the kits may be packaged either in aqueous media or in lyophilized form. The container means of the kits may include at least one vial, test tube, flask, bottle, syringe, or other container means, into which a component may be placed, and in certain embodiments, suitably aliquoted. Where there is more than one component in the kit, the kit also will generally contain a second, third, or other additional container into which the additional components may be separately placed. However, various combinations of components may be comprised in a vial. The kits described herein also will typically include a means for containing the chimeric receptor construct and any other reagent containers in close confinement for commercial sale. Such containers may include injection or blow molded plastic containers into which the desired vials are retained, for example.

In one aspect, provided herein are pharmaceutical compositions comprising the immune cell described above and a pharmaceutically acceptable carrier. In another aspect, provided herein are pharmaceutical compositions for immune therapy of human patients comprising the immune cells described above. In some embodiments, the immune cell is originally derived from the patient. In some embodiments, the patient has a tumor or cancer in which an increase or variation in levels of cancer antigen targeted by the CAR or TCR, for example, mTCR, expressed in the cell is detected.

In another aspect, provided herein are methods. In some embodiment, provided are methods of treatment comprising administering to a subject having a disease or a condition the immune cell described above or the composition described above. In some embodiments, the genetically engineered antigen receptor specifically binds to an antigen associated with the disease or the condition. In some embodiments, the disease or the condition is a cancer or a tumor.

In another aspect, provided herein are immune cells and compositions. In some embodiments, provided are immune cells and compositions described above for use in treating a disease or a condition.

In another aspect, provided herein is use of the immune cells or compositions. In some embodiments, provided is use of the immune cells or compositions described above in the manufacture of a medicament for use in a method for treating a disease or a condition. In some embodiments, the genetically engineered antigen receptor specifically binds to an antigen associated with the disease or the condition. In some embodiments, the disease or the condition is a cancer or a tumor.

The above description of the present invention is intended to be exemplary, and persons with ordinary skill in the art shall understand that the present invention may be easily modified into certain other forms without changing the technical idea or essential characteristics of the present invention. Accordingly, the embodiments described in the above shall be understood ad being exemplary and not limiting in all aspects. For example, respective component elements which are described as being integrated may be carried out separately, and likewise, component elements which are described as being carried out separately may be carried out in an integrated manner.

The scope of the present invention is represented by the appended claims, and all modified or changed forms derived from the meaning and scope of the claims and concepts equivalent thereto shall be interpreted as being included within the scope of the present invention.

SEQUENCE LISTING

| SEQ ID NO. | Sequence |
|---|---|
| 1. | tctcggcatggacgagctgta |
| 2. | tggaacccattcctgaaatta |
| 3. | ggaacccattcctgaaattat |
| 4. | gaacccattcctgaaattatt |
| 5. | acccattcctgaaattattta |
| 6. | cccattcctgaaattatttaa |
| 7. | ccttccctgtggttctattat |
| 8. | cttccctgtggttctattata |
| 9. | ttccctgtggttctattatat |
| 10. | tccctgtggttctattatatt |
| 11. | ccctgtggttctattatatta |
| 12. | cctgtggttctattatattat |
| 13. | gatgaaagggatgtgaattat |
| 14. | gggagcctccctgatataaat |
| 15. | ggaattcgctcagaagaaa |
| 16. | ggaccaaactgaagctatatt |
| 17. | agaactttggtttcctttaat |
| 18. | atgaaagggatgtgaattatt |
| 19. | tcttatcttcggcgctttaat |
| 20. | cttatcttcggcgctttaatt |
| 21. | ttatcttcggcgctttaattt |
| 22. | gaggagcccaatgagtattat |
| 23. | aggagcccaatgagtattatt |
| 24. | atagatccaaccaccttattt |
| 25. | atgtcattgcctctgtattta |
| 26. | tgtcattgcctctgtatttaa |
| 27. | accaccatgcccagctaattt |
| 28. | tgttgagatttaggcttattt |
| 29. | gaccaaactgaagctatattt |
| 30. | aggccttcagcaatctatatt |
| 31. | ggccttcagcaatctatatta |
| 32. | gagtggtccctaaacttaaat |
| 33. | agtggtccctaaacttaaatt |
| 34. | gtggtccctaaacttaaattt |
| 35. | ctaacacaaatatccacat |
| 36. | tcagcagcccagtccaaataa |
| 37. | cagcagcccagtccaaataaa |
| 38. | tcaacgtctccatcatgtata |

SEQUENCE LISTING

| SEQ ID NO. | Sequence |
|---|---|
| 39. | caacgtctccatcatgtataa |
| 40. | ctggagacaatggcgacttta |
| 41. | ctcagcagcccagtccaaata |
| 42. | agcagcccagtccaaataaac |
| 43. | gggatcaaagctatctatata |
| 44. | ggatcaaagctatctatataa |
| 45. | ggcaacggaacccagatttat |
| 46. | tgaagaagagagtccatattt |
| 47. | ttggatgcggaacccaaatta |
| 48. | agcatcacttgggattaatat |
| 49. | tgatgtgggtcaaggaattaa |
| 50. | agcgagggagaagactatatt |
| 51. | tttacgtatgagacgtttata |
| 52. | gctcctgtatagtttacttcc |
| 53. | ggaaattaacctggttgatgc |
| 54. | gcaccaacagaatatgcatcc |
| 55. | gctcaacaggatgtcaaataa |
| 56. | gcatcttgctgttcttcttac |
| 57. | gcatttgtggacaacttatgt |
| 58. | ggaacgcgactaaacttaatc |
| 59. | gatgttcaccataagccaagt |
| 60. | gcaagatgagtctgactatgg |
| 61. | ggcacagagaagaatgcaaca |
| 62. | gggaagagatgctaaatatac |
| 63. | gcaaatcagtgtaatccttga |
| 64. | gcaacttctccatcaccatgc |
| 65. | gcaaagatgcaccatccaact |
| 66. | gcggatggacagcaacattca |
| 67. | ggacacttctgagtatgaagc |
| 68. | gggaaccacaatgcacgaaag |
| 69. | ggtgctttccaacacactttc |
| 70. | gcttctggccatttgtaatgc |
| 71. | gggagtacttctgcatctatc |
| 72. | gctgcatgactacttcaatgt |
| 73. | taacgtggatcttgatcataa |
| 74. | ggagacatacacaggccttca |

SEQUENCE LISTING

| SEQ ID NO. | Sequence |
|---|---|
| 75. | gcatttgggccttgatctacc |
| 76. | gacaggttgcaaggcagttct |
| 77. | gggagtgcctcttcagttaca |
| 78. | ggacgaggaggttgacattaa |
| 79. | gaggagaaagaggaaggagaa |
| 80. | gcccttccttcaatagcacta |
| 81. | ggttgactgcatttctagact |
| 82. | gcatttgctgaacgcatttac |
| 83. | gctgcactaattgtctattgg |
| 84. | ggatccagtcacctctgaaca |
| 85. | gcacatcctccaaatgaaagg |
| 86. | ggattctcaacctgtggttta |
| 87. | ggtgcttggtctcctctataa |
| 88. | gcacagtactcctggcttatc |
| 89. | gcaacaggaccacagtcaaga |
| 90. | gcaacaccaccctcagcataa |
| 91. | gcctgttcagagcactcattc |
| 92. | gcagtaatgccttctcctatt |
| 93. | gcaccttggtgcttagctaga |
| 94. | gcttccatctatgaggaattg |
| 95. | gccagagaaccagctataagt |
| 96. | gggtccctgatgaatatctgg |
| 97. | ggcttgcagggaaagtgaatg |
| 98. | gcttgcagggaaagtgaatgg |
| 99. | agcttccatctatgaggaatt |
| 100. | ggaatccagaacgaattaagt |
| 101. | ggctgattgatgggaacatcc |
| 102. | ggactacagtcaagacaatca |
| 103. | ggaccctcactctattcaatg |
| 104. | gctactggccgcaataattcc |
| 105. | gctctttgtatgacagaatac |
| 106. | ggtccaaggtcaccaataaga |
| 107. | gcaaccatacgatagaaatag |
| 108. | ggttctgaaatttcctcaaca |
| 109. | gcaagatatccagctacatct |
| 110. | gcaactcaccctcttccatct |
| 111. | gctgcattccctaagataatt |

SEQUENCE LISTING

| SEQ ID NO. | Sequence |
|---|---|
| 112. | gggacagtagatccacataca |
| 113. | ggacaacagtcacaatgagca |
| 114. | ggctgttgatgttctagagag |
| 115. | gcagacaaggccacagtcaat |
| 116. | ggaggtttctaaccagcatcc |
| 117. | gccttgagactgtgctataca |
| 118. | ccaagcccagaatgactatgg |
| 119. | gccttcttgttcttgccttgt |
| 120. | gcttctgactgcagttcttct |
| 121. | gctggatgaaatatggtaacc |
| 122. | ggaaatgagcctgctccaagt |
| 123. | ggattggtctgaggaacaatt |
| 124. | gccaagaagggaaggagtaca |
| 125. | gccaattccactaattgtttg |
| 126. | ggttctcatgaatctccaact |
| 127. | gctggagtcatgacactaagt |
| 128. | gcctggtttggagatactaac |
| 129. | ggaaccacctaaagaacttcc |
| 130. | ccgcgttgatttaaagaaaga |
| 131. | gcctgatacatatcagcattt |
| 132. | gcggaattggaatttcttagc |
| 133. | gcacgactacagaaatatagc |
| 134. | tttccggttaagttgcactcg |
| 135. | gcctggatctaattcagaaag |
| 136. | gaaagccactgttcggttaaa |
| 137. | tcctgtggatatctgtctaag |
| 138. | ggctcatagaggctgtaatgt |
| 139. | gggcttgtccgagttgatatg |
| 140. | aagatttggataccgcaaaaa |
| 141. | gtggtactgaagcacctatta |
| 142. | gcttgttcagagaacaattgc |
| 143. | ggagattgttggtacccaagg |
| 144. | gcagctaggcttacagcattg |
| 145. | ggtcctttctgtgcactatga |
| 146. | ggtggtagctaaagaacattc |
| 147. | ggacctgtctacaggtgatct |

SEQUENCE LISTING

| SEQ ID NO. | Sequence |
|---|---|
| 148. | gccaaggtcattgcaggaatg |
| 149. | gcagaacaagcccatgattga |
| 150. | cccaaggtcaaggagattatt |
| 151. | gcagaagtgccggaacattga |
| 152. | gcgtcacacagaagcatatcc |
| 153. | ccggctcttctttgagttcta |
| 154. | cagaacgtcaccaactacttt |
| 155. | ccatgctaggttggaacaact |
| 156. | ccaagtggcctgtctctttga |
| 157. | ggtgtctatttgcggatcttc |
| 158. | agaccttccgcaagatcattc |
| 159. | tccttagccatgagctcaagg |
| 160. | gaaagtactgtggacacatgt |
| 161. | gcacgtgtccatcttcgagtt |
| 162. | ggccaacactcctcaagaact |
| 163. | ggcttctacctctacccagat |
| 164. | ggccatggactccacatttga |
| 165. | ggccgtgagtatctaccagtt |
| 166. | gccagaagacaagttagaatt |
| 167. | gctctggaagttccagtatat |
| 168. | ggaaatgatctggctcgatgc |
| 169. | gcaaagatcctcaaggattta |
| 170. | ggatgcctctattgctcatcg |
| 171. | gctatggtacttcgaatttgc |
| 172. | ggaagggattccagcagaagt |
| 173. | gcaaggagattgtggccatca |
| 174. | gggcatccttcaagaggaagt |
| 175. | gcaaagatcatccagtctttc |
| 176. | gctggagatgtaccgcaaagt |
| 177. | gcacaggatgagatttatatc |
| 178. | ggaagaccacatacaggaaac |
| 179. | gcattggtgtttcctgcatga |
| 180. | gcacacggttgggtagattat |
| 181. | gggtctgtaatggaaggaaat |
| 182. | gcatgttgcgagatgacatga |
| 183. | gcagaccgagtctacacaagt |
| 184. | gcaccatcatccacctcaagt |

SEQUENCE LISTING

| SEQ ID NO. | Sequence |
|---|---|
| 185. | ggtcacccacatcaaggtcat |
| 186. | gggcaagaaccgctacaagaa |
| 187. | ggaacaaatgcgtcccatact |
| 188. | gcctggactgtgacattgaca |
| 189. | gaacctgcacactaagaacaa |
| 190. | gcagatcctacctctgaaagg |
| 191. | gcaatgacggcaagtctaaag |
| 192. | ggaactgaaatacgacgttgg |
| 193. | gcgtgttaggaacgtcaaaga |
| 194. | gctcatgactatacgctaaga |
| 195. | ggagagaacggtctggcaata |
| 196. | gcagctgaacgagaaccaagt |
| 197. | ggagactgtgactcttcttgt |
| 198. | ggaatgccaacgtttggaaat |
| 199. | ggatcgtttacaggaagttcc |
| 200. | gcctttgtatgtggaagtata |
| 201. | gcctgctgtatttatagtaac |
| 202. | gctgcacatcaaggagtaatt |
| 203. | gctggaaatactctggttaga |
| 204. | ggagcttgttgaaagggatga |
| 205. | gcagaatactggccgtcaatg |
| 206. | ggttatgttgtcaagctaagg |
| 207. | gcagaacccaaggaattaatc |
| 208. | ggtgtaacatcacaggcttac |
| 209. | gccatagagttcaggacaaat |
| 210. | gcaattctcgggtagaaataa |
| 211. | gctggcttcaccaacattacc |
| 212. | gggagcaaatcatctgcattc |
| 213. | gcgactcaaatatcaccttga |
| 214. | gctcctgaggtatggaataga |
| 215. | gcaaatgacacatatgaaagc |
| 216. | ggtctaaagaggagtgcatct |
| 217. | gggctatttgaaacaggatcc |
| 218. | gctgtaggaatggaagcttca |
| 219. | gcttgtgtttgctgctaatgt |
| 220. | gttaacaaggtcgggcaggaagagggcctatttcccatgattccttcatatttgcatatacgatacaaggctgttaga gagataattagaattaatttgactgtaaacacaaagatattagtacaaaatacgtgacgtagaaagtaataatttctt |

SEQUENCE LISTING

| SEQ ID NO. | Sequence |
|---|---|
| | gggtagtttgcagttttaaaattatgttttaaaatggactatcatatgcttaccgtaacttgaaagtatttcgatttc<br>ttggctttatatatcttgtggaaaggacgaaacaccgcctgtggttctattatattatttcaagagaataatataata<br>gaaccacaggttttgactagtcaaaaaggaattcgctcagaagaaatctcttgaatttcttctgagcgaattccaaa<br>caaggcttttctccaaggagtatttatagtctcaaaacacacaattacttttacagttagggtgagtttccttttgtgc<br>tgtttttaaaataataatttagtatttgtatctcttatagaaatccaagcctatcatgtaaaatgtagctagtatta<br>aaaagaacagattatctgtctttatcgcacattaagcctctatagttactaggaaatattatatgcaaattaaccgg<br>ggcaggggagtagccgagcttctcccacaagtctgtgcgagggggccggcgcgggcctagagatggcggcgtcggatc<br>gctagccatatgtctagagtatac |
| 221. | gttaaccaaaaacctgtggttctattatattattctcttgaaataatataatagaaccacaggcggtgtttcgtcctt<br>tccacaagatatataaagccaagaaatcgaaatacttcaagttacggtaagcatatgatagtccattttaaaacata<br>attttaaaactgcaaactacccaagaaattattactttctacgtcacgtattttgtactaatatctttgtgtttacag<br>tcaaattaattctaattatctctaacagccttgtatcgtatatgcaaatatgaaggaatcatgggaaataggccct<br>cttcctgcccgaccttactagtgatccgacgccgccatctctaggcccgcgccggccccctcgcacagacttgtggga<br>gaagctcggctactccctgccccggttaatttgcatataatatttcctagtaactatagaggcttaatgtgcgataa<br>aagacagataatctgttcttttaatactagctacattttacatgataggcttggatttctataagagatacaaatac<br>taaattattatttttaaaaaacagcacaaaaggaaactcaccctaactgtaaagtaattgtgtgttttgagactataaa<br>tatcccttggagaaaagccttgtttggaattcgctcagaagaaattcaagagatttcttctgagcgaattcctttttg<br>gctagccatatgtctagagtatac |
| 222. | gttaacgatccgacgccgccatctctaggcccgcgccggccccctcgcacagacttgtgggagaagctcggctactcc<br>cctgccccggttaatttgcatataatatttcctagtaactatagaggcttaatgtgcgataaaagacagataatctgt<br>tcttttaatactagctacattttacatgataggcttggatttctataagagatacaaatactaaattattattttaa<br>aaaacagcacaaaaggaaactcaccctaactgtaaagtaattgtgtgttttgagactataaatatcccttggagaaaa<br>gccttgtttgnnnnnnnnnnnnnnnnnnnnnnnttcaagagannnnnnnnnnnnnnnnnnnnnttttttggttaac |
| 223. | gttaacgatccgacgccgccatctctaggcccgcgccggccccctcgcacagacttgtgggagaagctcggcta<br>ctcccctgccccggttaatttgcatataatatttcctagtaactatagaggcttaatgtgcgataaaagacagataat<br>ctgttcttttaatactagctacattttacatgataggcttggatttctataagagatacaaatactaaattattatt<br>ttaaaaaacagcacaaaaggaaactcaccctaactgtaaagtaattgtgtgttttgagactataaatatcccttggag<br>aaaagccttgtttgcctgtggttctattatattatttcaagagaataatataatagaaccacaggttttgactagtg<br>ctagccatatgtctagagtatac |
| 224. | gttaacaaggtcgggcaggaagagggcctatttcccatgattccttcatatttgcatatacgatacaaggctgttaga<br>gagataattagaattaatttgactgtaaacacaaagatattagtacaaaatacgtgacgtagaaagtaataatttctt<br>gggtagtttgcagttttaaaattatgttttaaaatggactatcatatgcttaccgtaacttgaaagtatttcgatttc<br>ttggctttatatatcttgtggaaaggacgaaacaccgcctgtggttctattatattatttcaagagaataatataata<br>gaaccacaggttttg |
| 225. | QVQLQQSGPGLVKPSQTLSLTCAISGDSVSSNSAAWNWIRQSPSRGLEW<br>LGRTYYRSKWYNDYAVSVKSRITINPDTSKNQFSLQLNSVTPEDTAVY<br>YCAREVTGDLEDAFDIWGQGTMVTVSSGGGGSGGGGSGGGGSDIQMT<br>QSPSSLSASVGDRVTITCRASQTIWSYLNWYQQRPGKAPNLLIYAASSL<br>QSGVPSRFSGRGSGTDFTLTISSLQAEDFATYYCQQSYSIPQTFGQGTKL<br>EITTTPAPRPPTPAPTIASQPLSLRPEACRPAAGGAVHTRGLDFACDIYIW<br>APLAGTCGVLLLSLVITLYCKRGRKKLLYIFKQPFMRPVQTTQEEDGCS<br>CRFPEEEEGGCELRVKFSRSADAPAYKQGQNQLYNELNLGRREEYDVL<br>DKRRGRDPEMGGKPRRKNPQEGLYNELQKDKMAEAYSEIGMKGERRR<br>GKGHDGLYQGLSTATKDTYDALHMQALPPR |
| 226. | MALPVTALLLPLALLLHAARPDIQMTQTTSSLSASLGDRVTISCRASQDI<br>SKYLNWYQQKPDGTVKLLIYHTSRLHSGVPSRFSGSGSGTDYSLTISNL<br>EQEDIATYFCQQGNTLPYTFGGGTKLEITGGGGSGGGGSGGGGSEVKL<br>QESGPGLVAPSQSLSVTCTVSGVSLPDYGVSWIRQPPRKGLEWLGVIW<br>GSETTYYNSALKSRLTIIKDNSKSQVFLKMNSLQTDDTAIYYCAKHYYY<br>GGSYAMDYWGQGTSVTVSSTTTPAPRPPTPAPTIASQPLSLRPEACRPA<br>AGGAVHTRGLDFACDIYIWAPLAGTCGVLLLSLVITLYCKRGRKKLLYI<br>FKQPFMRPVQTTQEEDGCSCRFPEEEEGGCELRVKFSRSADAPAYKQG<br>QNQLYNELNLGRREEYDVLDKRRGRDPEMGGKPRRKNPQEGLYNELQ<br>KDKMAEAYSEIGMKGERRRGKGHDGLYQGLSTATKDTYDALHMQAL<br>PPR |
| 227. | MGAGATGRAMDGPRLLLLLLLGVSLGGAKEACPTGLYTHSGECCKAC<br>NLGEGVAQPCGANQTVCEPCLDSVTFSDVVSATEPCKPCTECVGLQSM<br>SAPCVEADDAVCRCAYGYYQDETTGRCEACRVCEAGSGLVFSCQDKQ<br>NTVCEECPDGTYSDEANHVDPCLPCTVCEDTERQLRECTRWADAECEE<br>IPGRWITRSTPPEGSDSTAPSTQEPEAPPEQDLIASTVAGVVTTVMGSSQ<br>PVVTRGTTDNLIPVYCSILAAVVVGLVAYIAFKRWGSGATNFSLLKQA<br>GDVEENPGPALPVTALLLPLALLLHAARPDIQMTQTTSSLSASLGDRVTI<br>SCRASQDISKYLNWYQQKPDGTVKLLIYHTSRLHSGVPSRFSGSGSGTD<br>YSLTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRKGLE<br>WLGVIWGSETTYYNSALKSRLTIIKDNSKSQVFLKMNSLQTDDTAIYYC |

SEQUENCE LISTING

| SEQ ID NO. | Sequence |
|---|---|
| | AKHYYGGSYAMDYWGQGTSVTVSSTTTPAPRPPTPAPTIASQPLSLRP EACRPAAGGAVHTRGLDFACDIYIWAPLAGTCGVLLLSLVITLYCKRG RKKLLYIFKQPFMRPVQTTQEEDGCSCRFPEEEEGGCELRVKFSRADA PAYKQGQNQLYNELNLGRREEYDVLDKRRGRDPEMGGKPRRKNPQEG LYNELQKDKMAEAYSEIGMKGERRRGKGHDGLYQGLSTATKDTYDAL HMQALPPR |
| 228. | ggtatactctagacatatggctagcactagtcaaaaacctgtggttc |
| 229. | ttgtaccgttaacgatccgacgccgc |
| 230. | tgactagtcaaaaacctgtggttctattatattattctcttgaaataatataatagaaccacaggcggtgtttcgtcctttccacaagatatataaagccaa |
| 231. | gtaccgttaacaaggtcgggcaggaagagggcctatttcccatgattcct |
| 232. | aggactagtcaaaaaggaattcgctcagaagaaatctct |
| 233. | ctagctagcgatccgacgccgccatct |
| 234. | atgttaaccaaaaacctgtggttctattatattattctcttg |
| 235. | tcactagtaaggtcgggcaggaagagggcctatt |
| 236. | taggccctcactagtgatccgacgccgcc |
| 237. | ctagctagccaaaaaggaattcgctcagaagaaatctc |
| 238. | gcttctggccatttgtaatgc |
| 239. | gggagtacttctgcatctatc |
| 240. | gctgcatgactacttcaatgt |
| 241. | taacgtggatcttgatcataa |
| 242. | ggagacatacacaggccttca |
| 243. | gcatttgggccttgatctacc |
| 244. | ccagctttccagctttcctct |
| 245. | gatctcagccttctgcgaaga |
| 246. | gcttcaacgtctccatcatgt |
| 247. | ggtctttcctcactgccaagt |
| 248. | ctggagacaatggcgacttta |
| 249. | gccactgtcacattggcaatc |
| 250. | tccagtatctggacaagaacg |
| 251. | gcagcagtgtacttcacagag |
| 252. | gctgtttctcatccttggtgt |
| 253. | gcctttggcttccacctttgg |
| 254. | tcagcagcccagtccaaataa |
| 255. | ggtggagctcatgtacccacc |
| 256. | cccaaattacgtgtactacaa |
| 257. | gcatcacttgggattaatatg |
| 258. | gcgagggagaagactatattg |
| 259. | gccagtgatgctaaaggttgt |
| 260. | ggtggtatctgagttgacttg |

SEQUENCE LISTING

| SEQ ID NO. | Sequence |
|---|---|
| 261. | gatgaaagggatgtgaattat |
| 262. | gggagcctccctgatataaat |
| 263. | ggaattcgctcagaagaaa |
| 264. | ggaccaaactgaagctatatt |
| 265. | cctgtggttctattatattat |
| 266. | gcctagagaagtttcagggaa |
| 267. | cattgtctttcctagcggaat |
| 268. | gattaagtccctgccctttg |
| 269. | gttcacctacggaaaccttg |
| 270. | cctccacctttacacatgcc |
| 271. | cttactgcctcagcttccct |
| 272. | ccaagaaggccacagaactga |
| 273. | gttgtttcagatccctttagttccag |
| 274. | actttgaacagcctcacagag |
| 275. | ccgagttgaccgtaacagacat |
| 276. | caaccgatccacctcacctt |
| 277. | ggcactttgcctcccagat |
| 278. | cacaagctctgccactcggaa |
| 279. | tgcagtgacctggaaggctc |
| 280. | ctacctgggcataggcaacg |
| 281. | ccccgaactaactgctgcaa |
| 282. | gaaacagcacattcccagagttc |
| 283. | atggcccagcggatgag |
| 284. | cccagcatctgcaaagctc |
| 285. | gtccttgcggaagtcaatgt |
| 286. | acatgattcagccacagatacc |
| 287. | gcatagatgtcagcacgtttg |
| 288. | acgtgttgagagatcgagg |
| 289. | cccagcactcagtcaacgtc |

Examples

Examples related to the present invention are described below. In most cases, alternative techniques can be used. The examples are intended to be illustrative and are not limiting or restrictive to the scope of the invention.

General Methods

Cell lines and culture. Nalm-6, Nalm-6GL (expressing GFP and firefly luciferase), K562, K562-CD19, IM-9, Raji, Daudi cell lines were cultured in RPMI-1640 supplemented with 10% heat-inactivated fetal bovine serum and 2 mM L-glutamine and 1% penicillin/streptomycin in a humidified incubator with 5% $CO_2$ at 37° C. Lenti-X™ 293T Cell Line was purchased from Takara, and was maintained in DMEM supplemented with 10% heat-inactivated fetal bovine serum (FBS), 2 mM L-glutamine, 0.1 mM nonessential amino acids, 1 mM sodium pyruvate, and 1% penicillin/streptomycin. To generate the CD19+ PD-L1+ cell lines, K562-CD19 or NALM-6-GL cells were transduced with lentivirus encoding human PD-L1 (NM 014143.3). Nalm-6-PDL1-

CD80 cell line was generated by transduction of Nalm-6-PDL1 cells with lentivirus encoding human CD80 (NM 005191.3).

Plasmid construction. Construction of the pLV-CD19-BBz vector containing the anti-CD19 scFv (FMC63), CD8a hinge and transmembrane region, and the cytoplasmic domains of 4-1BB(CD137) and CD3, has been previously described (PNAS, 2016, Ma JSY). To generate pLV-CD19-28z, the cytoplasmic domain of 4-1BB was replaced with the sequence of human CD28 costimulatory domain. For the detection and purification of transduced CAR-T cells, ΔLNGFR (cytoplasmic domain truncated CD271) sequence was amplified from pMACS-ΔLNGFR (Milteny Biotec) vector, and was inserted in front of the CAR-Transgene via P2A sequence, to yield pLV-ΔLNGFR-CD19-28z or pLV-ΔLNGFR-CD19-BBz.

To generate Two-in-One LV vectors that encode both CAR and shRNA expression cassettes, shRNA expressing cassette containing shRNA (link sequence; TTCAAGAGA, termination sequence; TTTTT) and PolIII promoters (mU6, hU6 or hH1) were synthesized and subcloned into CAR-encoding LV vectors upstream of central polypurine tract (cPPT). For generation of Dual Two-in-One vectors expressing two shRNAs by different promoters (mU6 and hU6), BstZ17I-Xba1-Nde1-Bmt1-Spe1 MCS sequence was inserted into pLV-hU6-shPD-1 ΔLNGFR-CD19-BBz vector downstream of hU6 promoter. The second mU6-shRNA cassette fragments were subcloned into the MCS.

For establishment of reporter vectors, NFAT RE x3 sequence derived from pGL2 NFAT-Luc reporter (addgene #10959) are amplified by PCR. NF-kB-RE 5× (5'-GGGAATTCC-3') and miniP sequence were synthesized (IDT Technologies). EF-1a promoter of pLV-eGFP vector were replaced with these reporter fragments, to yield pLV-NFAT-RE 3x-eGFP or pLV-NF-kB-RE 5x-eGFP reporter vectors.

Selection the siRNA or shRNA sequences. The candidate sequences of 21-mer siRNAs that are specific for inhibitory immune checkpoints (CTLA-4, LAG-3, TIGIT, and TIM-3) were designed by using BLOCK-iT™ RNAi Designer or Sfold programs before synthesizing. RNA oligomers. siRNAs targeting CTLA-4 were selected from the group consisting of SEQ ID NOs. 255-260. siRNAs targeting LAG-3 were selected from the group consisting of SEQ ID NOs. 244-254. siRNAs targeting TIGIT were selected from the group consisting of SEQ ID NOs. 238-243. siRNAs targeting TIM-3 were selected from the group consisting of SEQ ID NOs. 261-264.) (IDT Technologies). To analyze the expression kinetics of immune checkpoints, PBMCs were stimulated with Dynabeads Human T-Activator CD3/CD28 (Thermofisher) or 4 μg/ml anti-CD3 antibody and 2 μg/ml anti-CD28 antibody in the presence of human recombinant IL-2. The expression levels of immune checkpoints were analyzed for 12 days (day 3, day 6, and day 12). For the selection of optimal siRNA sequences, 2 days after stimulation, PBMCs were electroporated with siRNA oligomers using Neon® Transfection System (Thermofisher). The knock-down efficiencies of siRNAs were measured 2 day after transfection by flow cytometry. 2-3 siRNA sequences were selected for each immune checkpoint based on their efficiency, and were converted into shRNA format to generate the dual Two-in-One lentiviral vectors. To validate shRNA-mediated knock-down efficacies, the lentivirus-transduced T cells were stimulated with γ-irradiated K562-CD19 cells at a 1:1 ratio for 3 days, and were analyzed for their expression levels of immune checkpoints by flow cytometry.

Flow cytometry. The expression level of anti-CD19 CAR was analyzed by AF647-conjugated anti-mouse F(ab')$_2$ antibody (115-606-072, Jackson ImmunoResearch) or biotin-conjugated rhCD19-Fc (CD9-H5259, ACRO Biosystems) coupled with AF647-cojugated streptavidin (405237, Biolegend). ΔLNGFR expression was analyzed by APC- or FITC-conjugated anti-CD271 antibody (ME20.4-1.H4; Mitenyi Biotec). Expression of immune checkpoints in CAR-T cells was measured by conventional flow cytometry using following antibodies: PD-1 (PE, clone J105; Thermofisher), TIM-3 (PE, clone 344823; R & D systems), LAG-3 (PE, clone 7H2C65; Biolgend), TIGIT (PE, clone MBSA43; Thermofisher).

CTLA-4 expression on CAR-T cells was analyzed by intracellular flow cytometry following incubation with irradiated NALM-6 or K562-CD19 cells at an E:T ratio of 1:1 for 3 days. The cells were fixed/permeabilized with Cytofix/Cytoperm™ solution (BD Bioscience), followed by staining with anti-human CD152 (CTLA-4) antibody (PE, clone BNI3; Biolegend).

The expression of stimulatory or inhibitory immune checkpoint ligands on tumor cells was analyzed using the following antibodies: CD80 (PE, clone 2D10; Biolgend), CD86 (BV421, clone 2331(FUN-1); BD Bioscience), PD-L1 (APC, clone 29E.2A3; Biolgend), HLA-DR (PE, clone L243; Biolgend), CD112 (PE, clone TX31; Biolgend), CD155 (PE, clone SKII.4; Biolgend).

For the analysis of the effect of TGF-β on the expression of PD-1, CAR-T cells were stimulated with irradiated NALM-6 cells for 3 days in the presence of 10 ng/ml recombinant human TGF-β1 (R & D systems) before measuring PD-1 expression by flow cytometry.

Analysis of the phosphorylation status of SMAD2/3 by intracellular flow cytometry. To determine phosphorylation status of SMAD2/3, CAR-T cells were incubated with NALM-6 cells at an E:T cell ratio of 1:1 for 4 hr or 24 hr. The cells were fixed with Lyse/Fix Buffer (BD Bioscience), followed by permeabilization with Perm Buffer III (BD Bioscience). The phosphorylation status on LNGFR$^+$ CAR-T cells was determined with anti-human Smad2 (pS465/pS467)/Smad3 (pS423/pS425) antibody (PE, clone 072-670; BD Bioscience).

Detection of induced regulatory T cells. Induction of regulatory T cells (CD4$^+$ CD25$^+$ FOXP3$^+$), generated from CAR-T cells, was analyzed by intracellular staining after co-culture with NALM-6 cells for 3 days. The cells that were fixed and permeabilzed with Foxp3/Transcription Factor Staining Buffer (Thermofisher) were stained with following antibodies: anti-CD4 (BV605, clone OKT4; Biolgend), anti-CD25 (FITC, clone VT-072; Biolgend), and anti-FOXP3 (APC, clone 236A/E7; Thermofisher).

CAR-T proliferation assay. CAR-T cells expressing ΔLNGFR surface marker were sorted by magnetic beads (Miltenyi Biotec). LNGFR$^+$ CAR-T cells ($1\times10^6$; >95% purity) were stimulated with γ-irradiated K562-CD19-PDL1 cells ($1\times10^6$) every 6 day in absence of cytokines. Fold-expansion of CAR-T cells was calculated by cell counting at day 6, 12, and 18 using trypan blue exclusion.

In vitro cytotoxicity of CAR-T cells. The cytotoxicity of CAR-T cells was determined by using Incucyte S3 live cell analysis system. NALM-6 or NALM-6-PDL1 target cells that constitutively express GFP were plated into a 96-well plate at a density of $1\times10^5$ cells per well in triplicate. LNGFR$^+$ CAR-T cells were added into each well at an E:T ratio of 1:1, 0.3:1, 0.1:1. The real-time change of GFP intensity of each wells was recorded every 2 hour as green object integrated intensity (Avg. mean GFP intensity×μm$^2$/ wells). The percentage of relative green object integrated intensity was calculated by the following formula: (total integrated GFP intensity of at each time point/total integrated GFP intensity of at the start time point)*100.

NFAT and NF-κB reporter assay. To determine the specific activity of NFAT transcription factor in CAR-T cells, PBMCs that were stimulated with 4 μg/ml anti-CD3 and 2 μg/ml anti-CD28 antibodies in the presence of human recombinant IL-2 (300 IU/mL) for 2 days were first transduced with the lentivirus encoding the NFAT-RE x3-eGFP reporter gene. Eight days after transduction, the total cells were re-stimulated with anti-CD3 and anti-CD28 antibody in the presence of human recombinant IL-2 (300 IU/mL) for 2 days. The activated cells were splitted into two separated wells and transduced with different CAR-encoding lentivirus (CD19-28z or CD19-BBz). After 6 days, the total cells in each well were co-incubated with NALM-6 cells at a 1:1 ratio. The reporter activity of NFAT in CAR-T cells was determined by the gMFI value of the eGFP signal within the LNGFR+ CAR-T populations (20~25% in total CD3+ cells) at 24-and 48-hour time point. The specific activity of NF-κB transcription factor in CAR-T cells was measured following a similar procedure but using the lentivirus encoding NF-κB-RE x5-eGFP reporter gene.

Quantitative real-time PCR. $3 \times 10^6$ LNGFR+ G28z or GBBz CAR-T cells were co-cultured with CD19+ NALM-6 target cells at a 1:1 ratio. After 4 and 48 hours of co-culture, LNGFR+ CAR-T cells were sorted using a MoFlo Astrios sorter (Beckman Coulter). The mRNA from LNGFR+ CAR-T cells was extracted by RNeasy mini kit (Qiagen) and reverse transcribed into cDNA using QuantiTect Reverse Transcription Kit (Qiagen). Quantitative Real-Time PCR was performed with the SYBR protocol using CFX96 Real-Time PCR Detection System (Biorad) and SYBR Green Realtime PCR Master Mix (TOYOBO). The primer sequences for detection of 18s rRNA comprise SEQ ID NOs. 268 and 269. The primer sequences for detection of PDCD1 comprise SEQ ID NOs. 270 and 271. The primer sequences for detection of IL2 comprise SEQ ID NOs. 272 and 273. The primer sequences for detection of IL4 comprise SEQ ID NOs. 274 and 275. The primer sequences for detection of IL17A comprise SEQ ID NOs. 276 and 277. The primer sequences for detection of CD25 comprise SEQ ID NOs. 278 and 279. The primer sequences for detection of CTLA4 comprise SEQ ID NOs. 280 and 281. The primer sequences for detection of FOXP3 comprise SEQ ID NOs. 282 and 283. The primer sequences for detection of TGF-beta1 comprise SEQ ID NOs. 284 and 285. The primer sequences for detection of TGFBR1 comprise SEQ ID NOs. 286 and 287. The primer sequences for detection of TGFBR2 comprise SEQ ID NOs. 288 and 289.

The amount of target mRNA was normalized to the endogenous reference 18s rRNA: ΔCt (sample)=Ct (gene of target)−Ct (18s rRNA). Comparative Ct method was applied to analyze the relative fold change of the target mRNA compared with the unstimulated condition based on the following equation: $2^{-\Delta\Delta Ct} = 2^{\wedge}-(\Delta Ct[\text{stimulated}]-\Delta Ct[\text{unstimulated}])$.

Animal experiments. All procedures described herein were approved by the Institutional Animal Care and Use Committee at KAIST. To establish CD19+ blood cancer model, NSG mice (4 to 6 weeks of age) were intravenously injected with $1 \times 10^6$ CD19+ NALM-6 leukemia cells that are engineered to express EGFP-fused firefly luciferase as well as human PDL1 (NALM6-GL-PDL1 cells). CAR-T cells were prepared from the whole blood samples of healthy donors following the procedures described above. At day 4 after transduction, CAR− T cells were sorted and further expanded for 6 day prior to the injection into mice. Five days after NALM6-GL-PDL1 cell injection, 2.5 or $1 \times 10^6$ CAR-T cells were intravenously infused to the mice. Bioluminescence imaging of NALM6-GL-PDL1 within mice was monitored with Xenogen IVIS Spectrum and the signals were quantified as radiance in the region of interest (photon/sec) using Living Image software (Perkin Elmer). For the solid tumor model, NSG mice were subcutaneously injected with $5 \times 10^6$ IM-9 cells (CD19+ PD-L1+ CD155+). LNGFR+ CAR-T cells intravenously infused to the mice 14 days after the injection of tumor cells (approximately 150-300 mm³ tumor volume). Tumors were monitored every week by caliper measurement and the volume was estimated by (length×width)/2.

Example 1: Methods of Production and Evaluation of Two-in-One Vectors Expressing CART19 and shRNA Targeting PD-1

This example describes the methods of production and evaluation of Two-in-One vectors expressing CART19 and shRNA inhibiting PD-1 expression.

To generate Two-in-One lentiviral vectors that encode both CAR and shRNA expression cassettes, shRNA expressing cassettes containing shRNA (link sequence; TTCAAGAGA, termination sequence; TTTTT) and PolIII promoters (mU6, hU6 or hH1) were synthesized and subcloned into CAR-encoding LV vectors upstream of central polypurine tract (cPPT). A lentiviral vector was constructed that spontaneously express 4-1BB-based CART19 by EF-1α promoter and PD-1 targeting shRNA by mU6 promoter (FIGS. 1A and 1B).

To select PD-1-targeting shRNA, three shRNA candidates were used. shPD-1 #1 showed surprisingly effective inhibitory effect on the expression of PD-1 (FIG. 1E) without affecting CAR expression (FIG. 1C), homeostatic expansion (FIG. 1D), differentiation status, and CD4/CD8 composition. (FIG. 1F). It has been reported that a shRNA expression level can be different depending on the types of Pol III promoter (Mol Ther., 2006, Irvin S. Y. Chen). Therefore, the effect of mU6, hU6, or hH1 promoters on PD-1 expression was evaluated. mU6 and hu6 had similar KD efficacy, but hH1 was less (FIG. 2).

The Two-in-One lentiviral vectors produced herein showed surprisingly effective inhibition on the expression of PD-1, thus can be used in the production of PD-1 KD modified CAR-T cells in the following example.

Example 2: Methods of Production and In Vitro Evaluation of PD-1 KD CAR-T Cells This example describes the methods of production and in vitro evaluation of PD-1 KD modified CAR-T cells.

Peripheral blood mononuclear cells were separated from whole blood samples of healthy donors by Ficoll-Paque Plus (GE Healthcare) density gradient centrifugation method. These cells were stimulated with 4 μg/ml of plate-bound anti-CD3 antibody (clone OKT3; Bio X cell) and 2 μg/ml of soluble anti-CD28 antibody (clone CD28.2; Bio X cell) in the presence of 300 IU/ml human recombinant IL-2 (BMIKOREA). For recombinant lentivirus production, $6 \times 10^5$ 293 T cells in 2.5 mL of growth medium (DMEM supplemented with 10% FBS, 2 mM L-glutamine, 0.1 mM nonessential amino acids, and 1 mM sodium pyruvate) were seeded in a 6-well plate 24 hours prior to transfection. The cells were transfected with the mixture of the packaging vectors (pMDL, pRev, pMDG.1) and a transfer vector using 10 µl of Lipofectamine2000 (Thermofisher). Two days after transfection, the culture supernatant containing lentivirus was collected and centrifuged at 1800 rpm for 5 minutes. The activated T cells were mixed with the viral supernatant in the presence of protamine sulfate (1 µg/ml), centrifuged at 1000×g for 90 minutes, and incubated overnight at 37° C. The next day, the culture supernatant was aspirated and replaced with fresh PRMI-1640 supplemented with 10% FBS, 2 mM L-glutamine, 0.1 mM nonessential amino acids, 1 mM sodium pyruvate and 55 µM β-mercaptoethanol. The transduced T cells were cultured at a density below $1 \times 10^6$ cells/mL in the RPMI-1640 supplemented with 10% heat-inactivated FBS and 2 mM L-glutamine and 1% penicillin/streptomycin T cell media containing human recombinant IL-2 (300 IU/mL), which were replenished every 2-3 days.

Figure 3A:
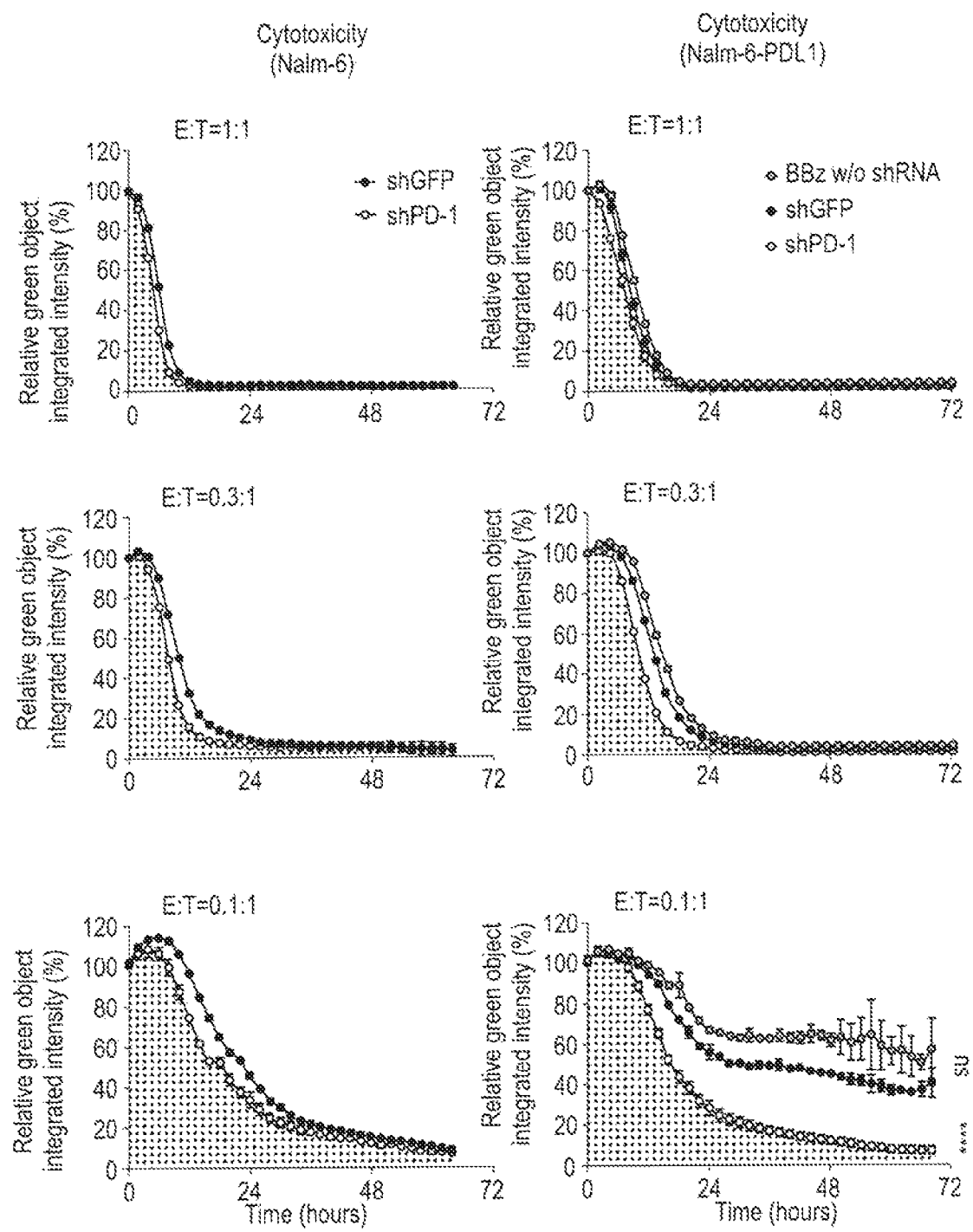
FIGS. 3A-3C. In vitro cytotoxicity and proliferation under CD19 and PD-L1 stimulation with PD-1 blockade.

The in vitro lytic and proliferative activity of shPD-1 CAR-T cells was investigated. Nalm-6-PDL1 or K562-CD19-PDL1 was used as $CD19^+$ $PDL1^+$ target cells. First, long-term lytic activity using IncuCyte real-time imaging system was examined. When CAR-T cells were mixed with NALM-6 cells, WT (shGFP) CART and PD-1 KD (shPD-1) CAR-T cells had similar lytic activity. However, shPD-1 CAR-T cells showed surprisingly more effective lytic activity than that of shGFP CAR, when CAR-T cells were cultured with NALM-6-PDL1 cell (FIG. 3A). It was also found that unexpectedly BBz w/o shRNA cassette CAR-T cells and shGFP CAR-T cells retained similar cytotoxicity, suggesting that shRNA expression itself has little effect on activity of CAR-T cells.

Figures 3B, 3C:
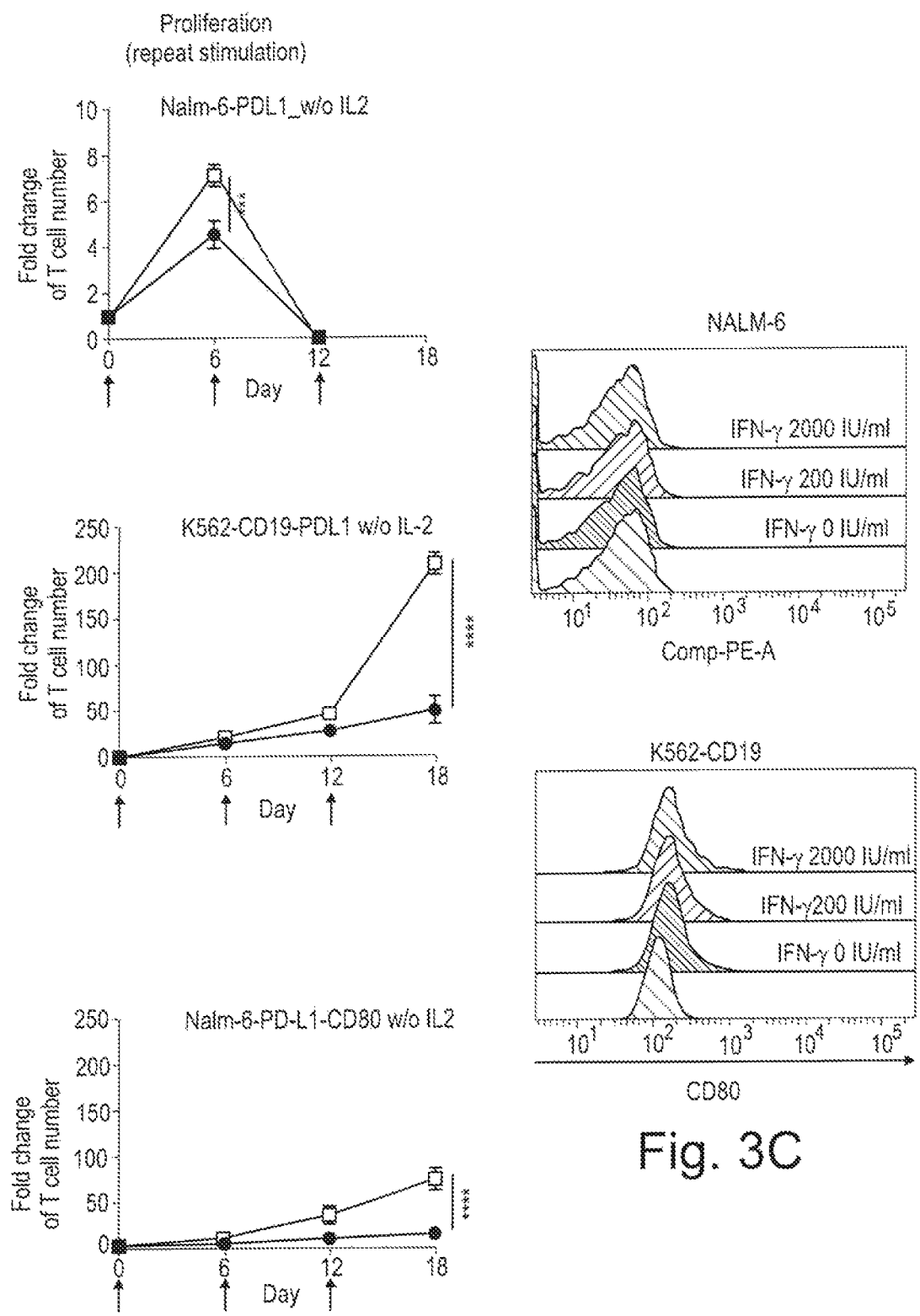

Next, the proliferative activity of CAR-T cells repeatedly exposed to CD19 antigen and PD-L1 was evaluated. The shPD-1 CAR-T cells achieved 4- to 5-fold greater T cell proliferative activity against K562-CD19-PDL1 target rather than shGFP CAR-T cells in the absence of exogenous IL-2 (FIG. 3B). It is known that the costimulatory ligands facilitates optimal T cell expansion and are not infrequently expressed in tumor cells. To examine whether the expression of costimulatory ligand in the target cells affects the cell proliferation upon repeat stimulation, it was examined whether CD80, a representative costimulatory ligand, is expressed in the target cells. K562-CD19 expressed CD80 but not Nalm-6 (FIG. 3C). It was found that CD80-overexpressing NALM-6-PDL1 (NALM-6-PDL1-CD80) enables CAR-T cells to proliferate under repeat stimulation. CD80 might facilitate CART proliferation under repeated in vitro stimulation (FIG. 3B). Collectively, it was corroborated that cell-intrinsic PD-1 disruption surprisingly effectively contribute to in vitro functional improvement of CD19 specific CAR-T cells upon repeat CAR & PDL1 stimulation.

In this example, the PD-1 KD modified CAR-T cells generated using the Two-in-One vectors described in example 1 showed surprising level of enhancement in in vitro lytic and proliferative activity when compared to WT CAR-T cells, thus their therapeutic potential was further evaluated in in vivo models in mice model bearing $CD19^+$ $PDL1^+$ blood tumor in the example below.

Example 3: Methods of Treatment of CD19+ Blood Cancer In Vivo Using PD-1 KD CAR-T Cells This example describes the methods to treat $CD19^+$ blood cancer in vivo using PD-1 KD CAR-T cells.

Figure 4:
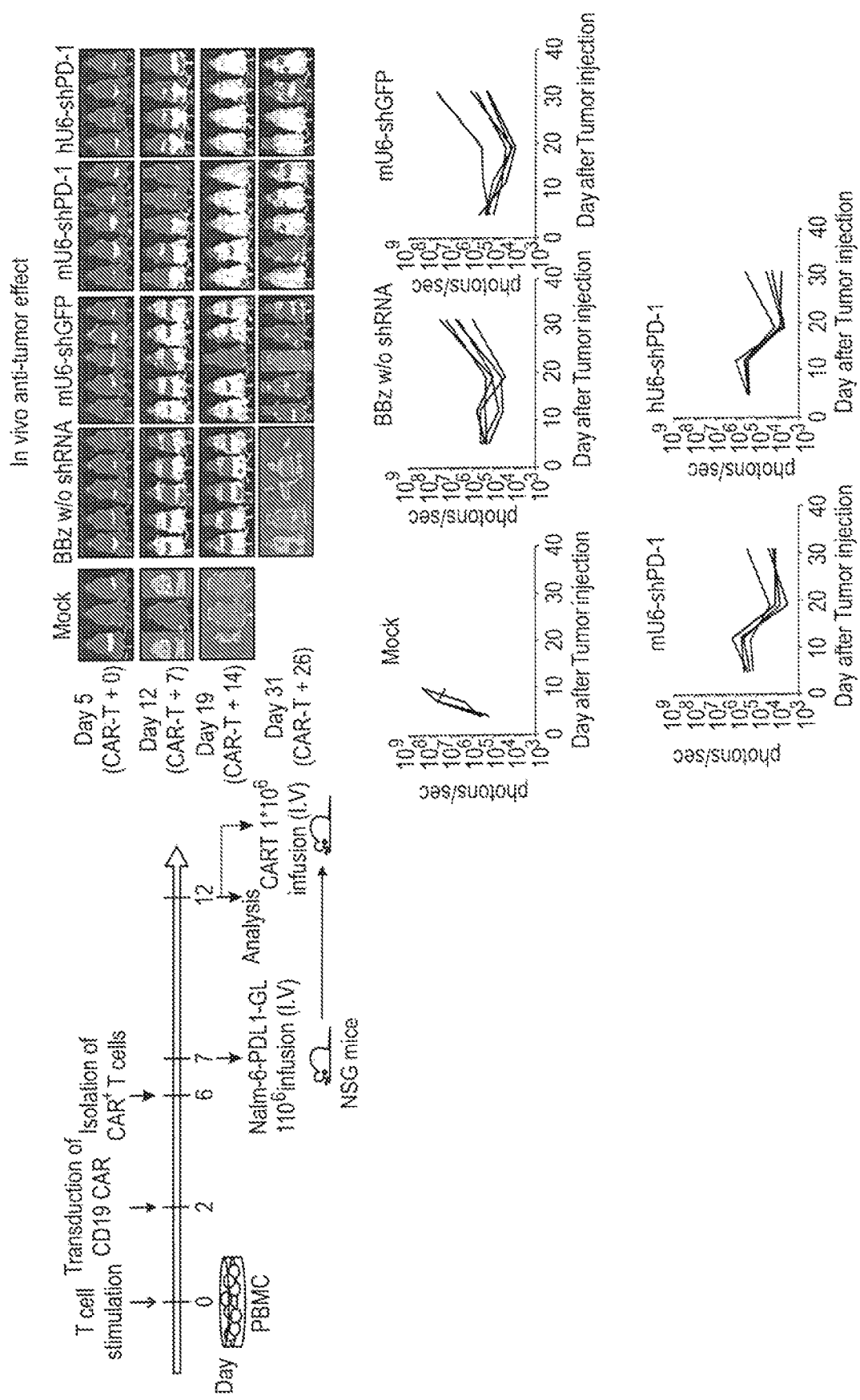
FIG. 4. Anti-tumor function of CAR-T cells in vivo with cell-intrinsic PD-1 blockade.

To establish $CD19^+$ blood cancer model, NSG mice (4 to 6 weeks of age) were intravenously injected with $1 \times 10^6$ $CD19^+$ NALM-6 leukemia cells that are engineered to express EGFP-fused firefly luciferase as well as human PDL1 (NALM6-GL-PDL1 cells). CAR-T cells were prepared from the whole blood samples of healthy donors following the procedures described above. At day 4 after transduction, $CAR^-$ T cells were sorted and further expanded for 6 day prior to the injection into mice. Five days after NALM6-GL-PDL1 cell injection, $1 \times 10^6$ CAR-T cells were intravenously infused to the mice. Bioluminescence imaging of NALM6-GL-PDL1 within mice was monitored with Xenogen IVIS Spectrum and the signals were quantified as radiance in the region of interest (photon/sec) using Living Image software (Perkin Elmer). Mice treated with shPD-1 CAR-T cells had a surprisingly uniform reduction in tumor burden compared to shGFP CAR-T cells (FIG. 4). In addition, it was found that two types of shRNA expressing promoter have similar anti-tumor effect and shRNA expression itself surprisingly do not affect the antitumor effect.

Figure 5A:
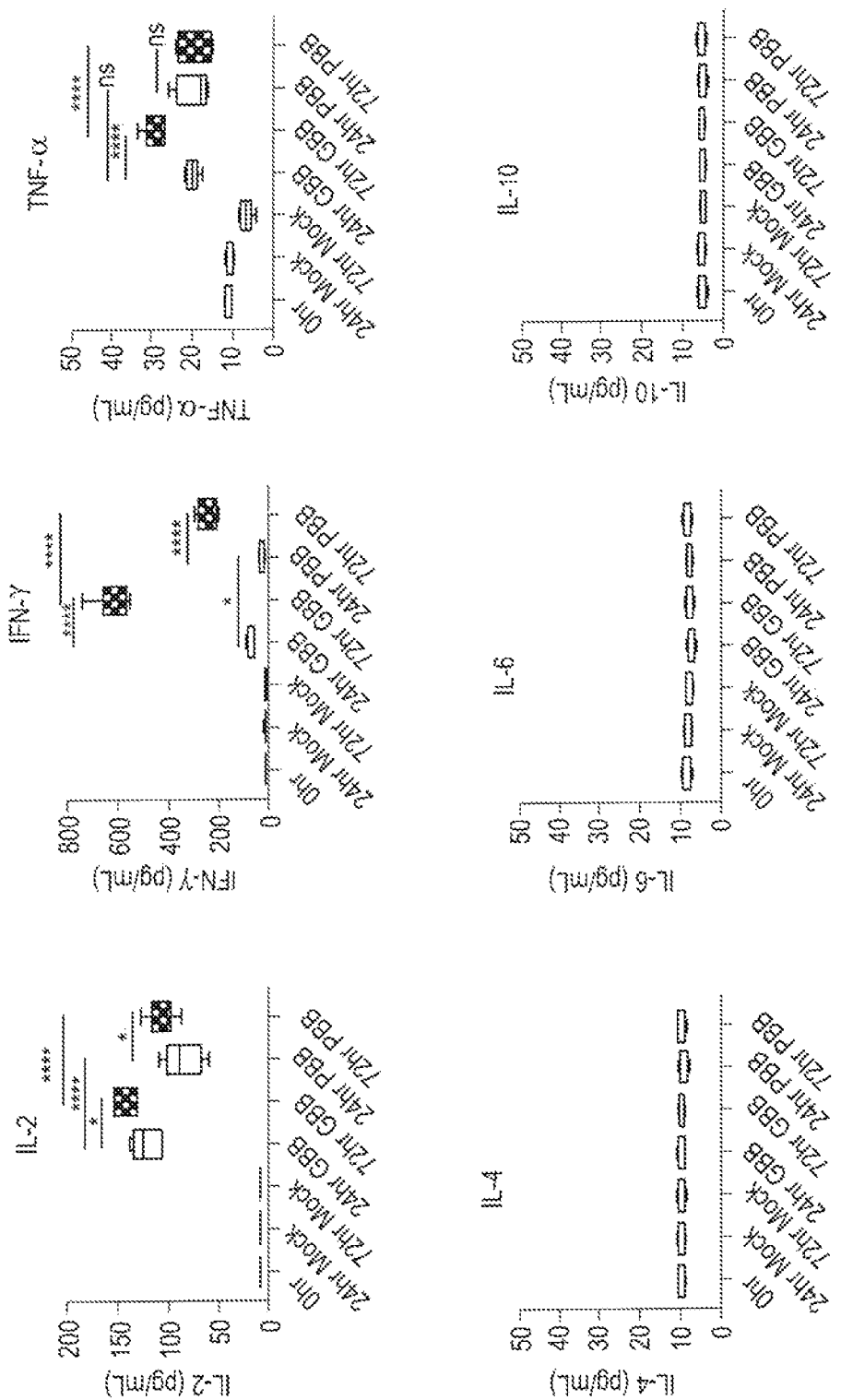
FIG. 5A. Reduced in vivo cytokine production in cell-intrinsic PD-1 disruption of CAR-T cells.

To examine the effect of cell-intrinsic PD-1 disruption of CAR-T cells on in vivo cytokine production. The peripheral blood of individual mice was obtained at 24 and 72 hours after CAR-T injection. Plasma was harvested from the peripheral blood by centrifugation for 5 minutes at 300×g at room temperature. In vivo cytokine level are analyzed with Human Th1/Th2 Cytokine Kit (BD Bioscience) following the manufacturer's instructions. Cell-intrinsic PD-1 disruption of CAR-T cells unexpectedly reduced in vivo cytokine production (FIG. 5A).

To examine the effect of cell-intrinsic PD-1 disruption of CAR-T cells on in vivo expansion of CAR-T cells, the spleen of individual mice was obtained at 3 or 20 days after CAR-T injection. The percentage of CAR-T cells (Live/Dead$^-$ $CD3^+$) or NALM-6-PDL1(Live/Dead$^-$ $GFP^+$) was evaluated with flow cytometry. Cell-intrinsic PD-1 disruption unexpectedly delayed in vivo expansion of CAR-T cells (FIG. 5B).

CAR-T cell-intrinsic PD-1 disruption, acquired by Two-in-One vector system described herein, showed unexpectedly high level of increase in the in vivo anti-tumor effect of CD19 specific CAR-T cells against CD19+ PDL1+ tumor. Thus, the PD-1 KD CAR-T cells were further used in the methods in the following examples.

Example 4: Evaluation of Environment of Constimulatory Molecules in PD-1 Signaling This example describes the evaluation of environment of constimulatory molecules, including CD28 and 4-1BB, in PD-1 signaling.

Figure 6B:
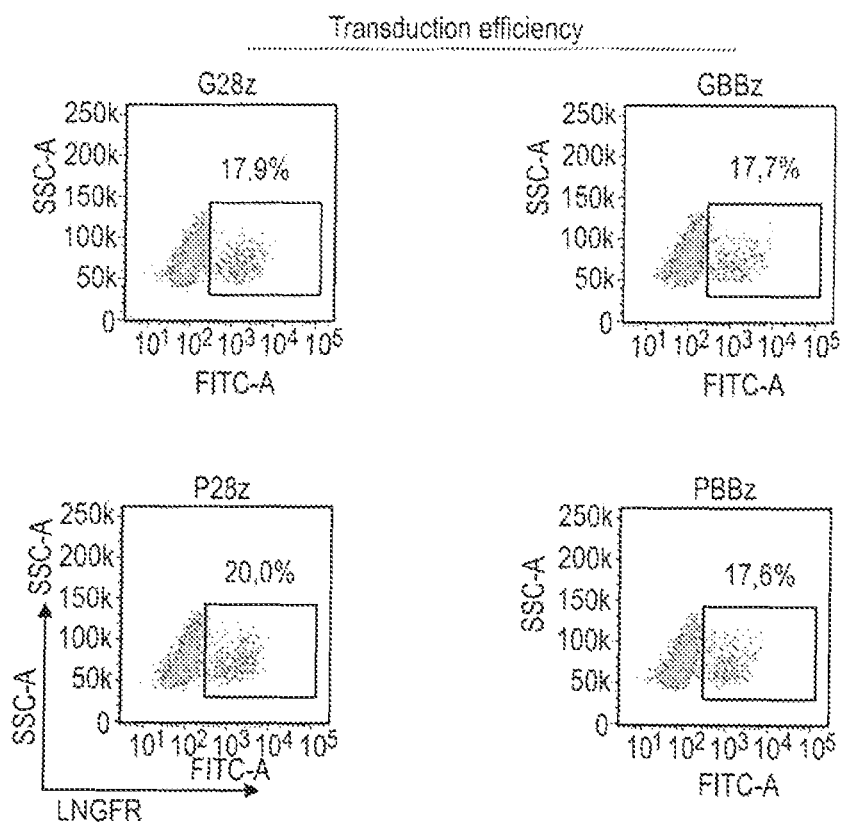
Figures 7A, 7B:
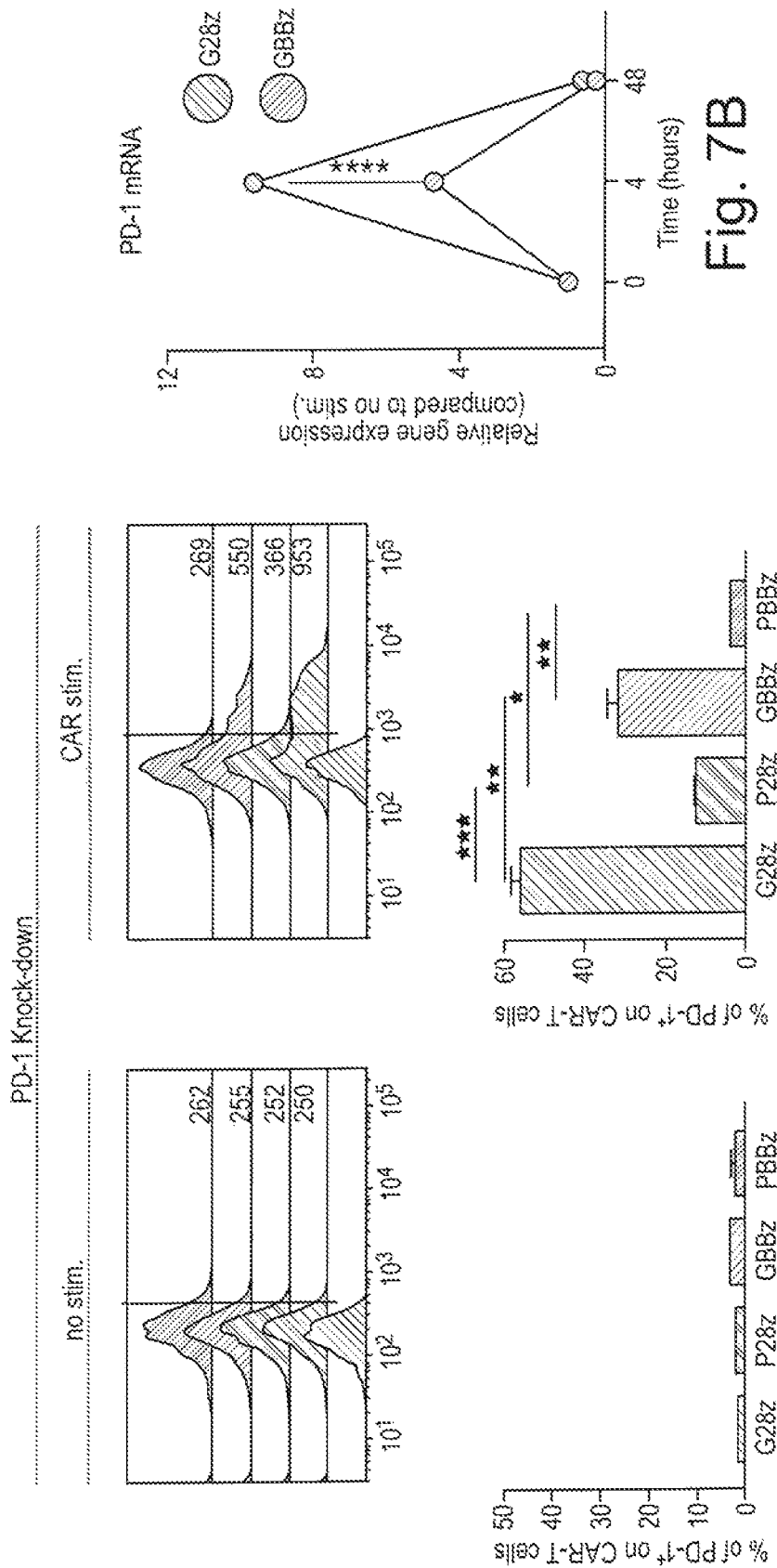
FIGS. 7A-7B. PD-1 expression level when costimulation with CD28 or 4-1BB.
Figure 8A:
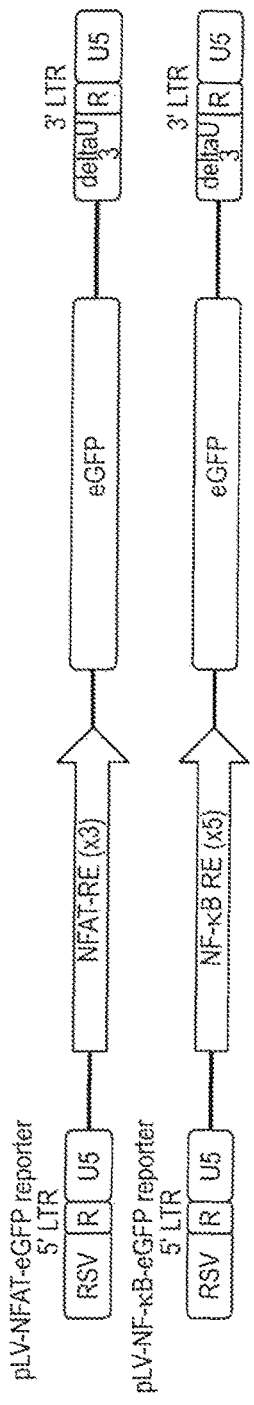
FIGS. 8A-8B. Establishment of NFAT or NF-κB reporter system.
Figure 8B:
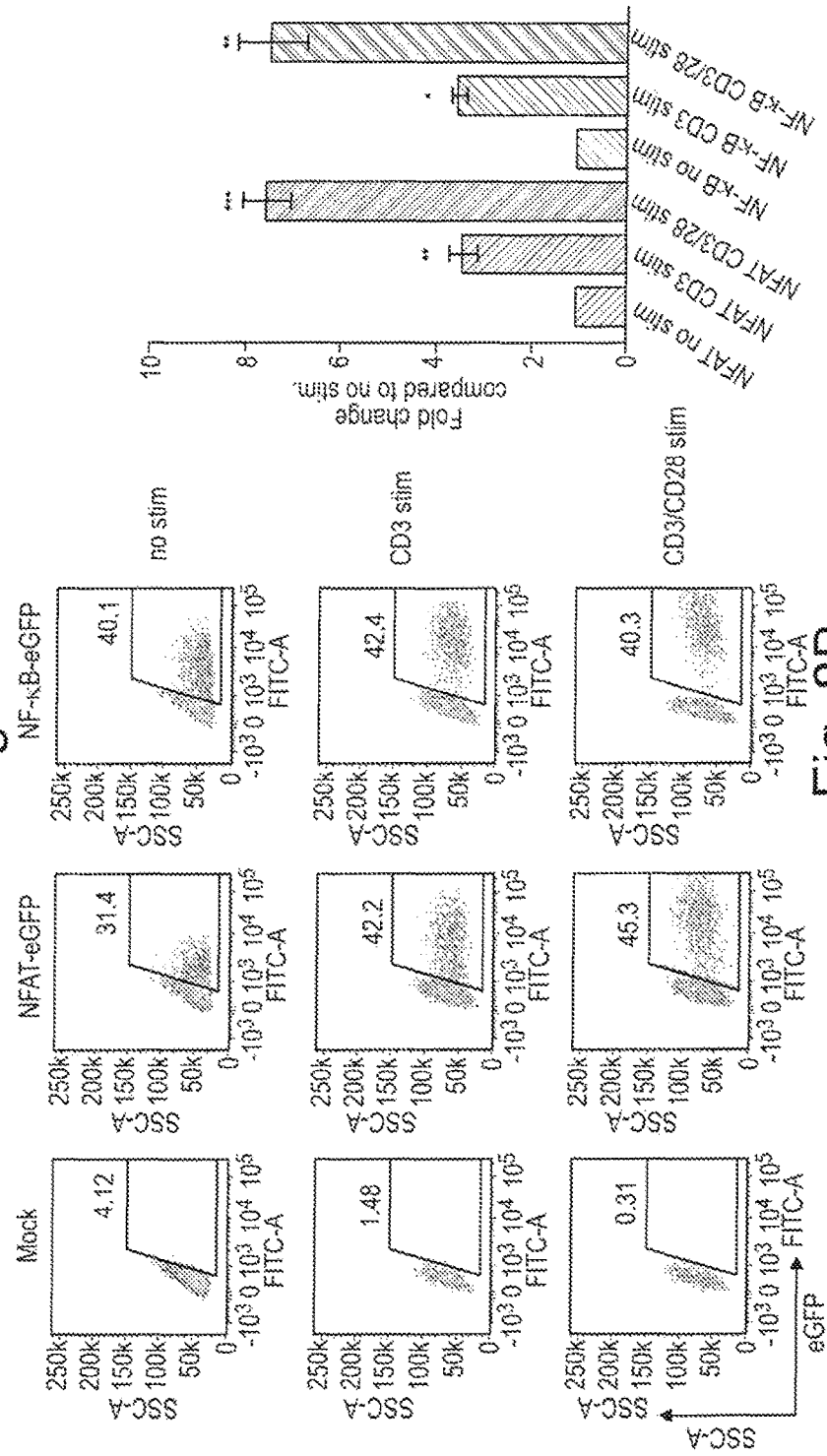
Figure 9A:
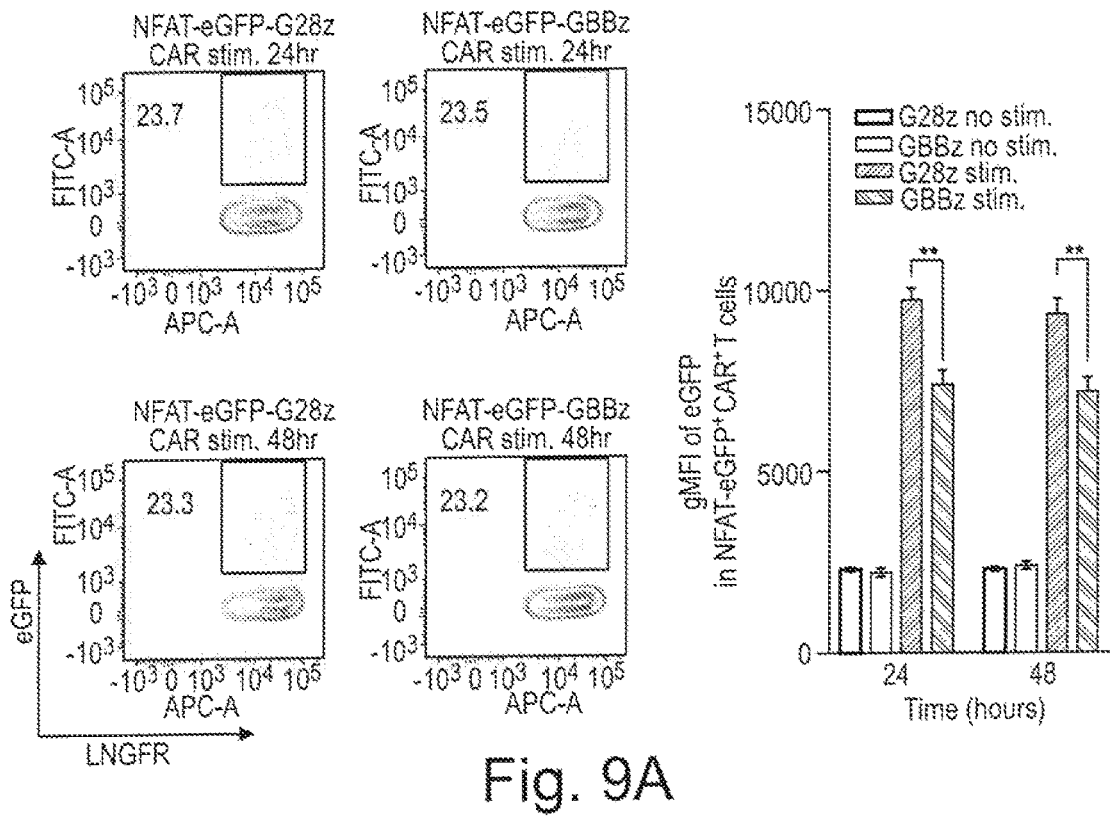
FIGS. 9A-9B. Activated NFAT signaling in CD28 costimulation but not in 4-1BB costimulation.
Figure 9B:
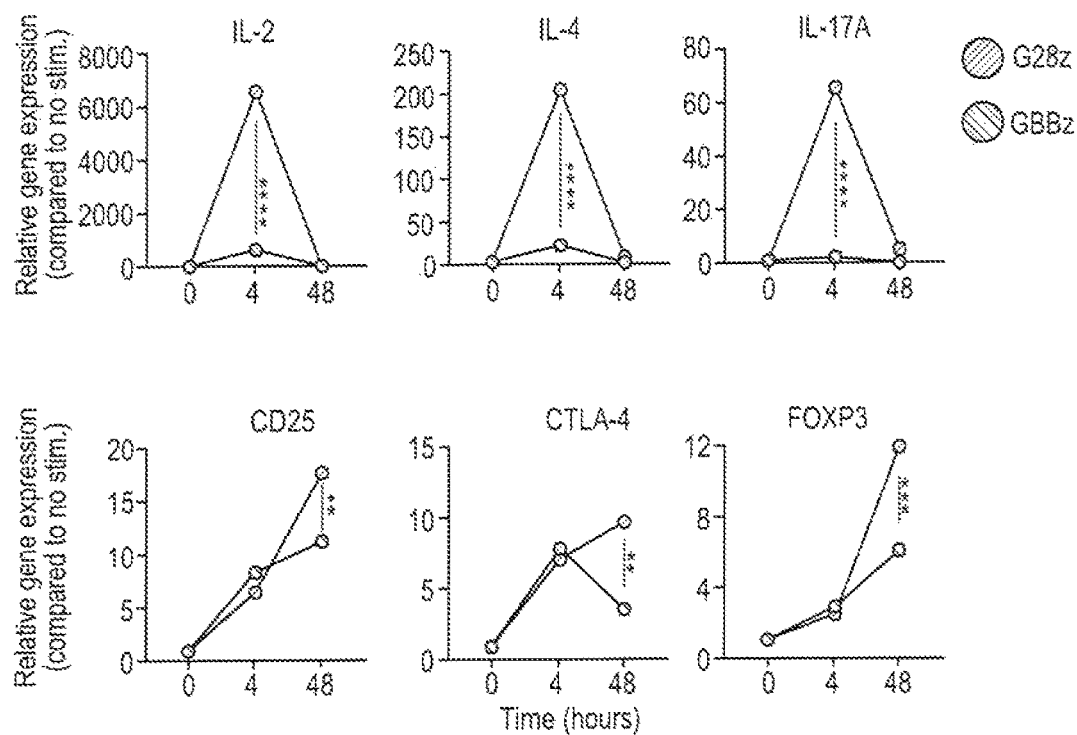
Figure 10:
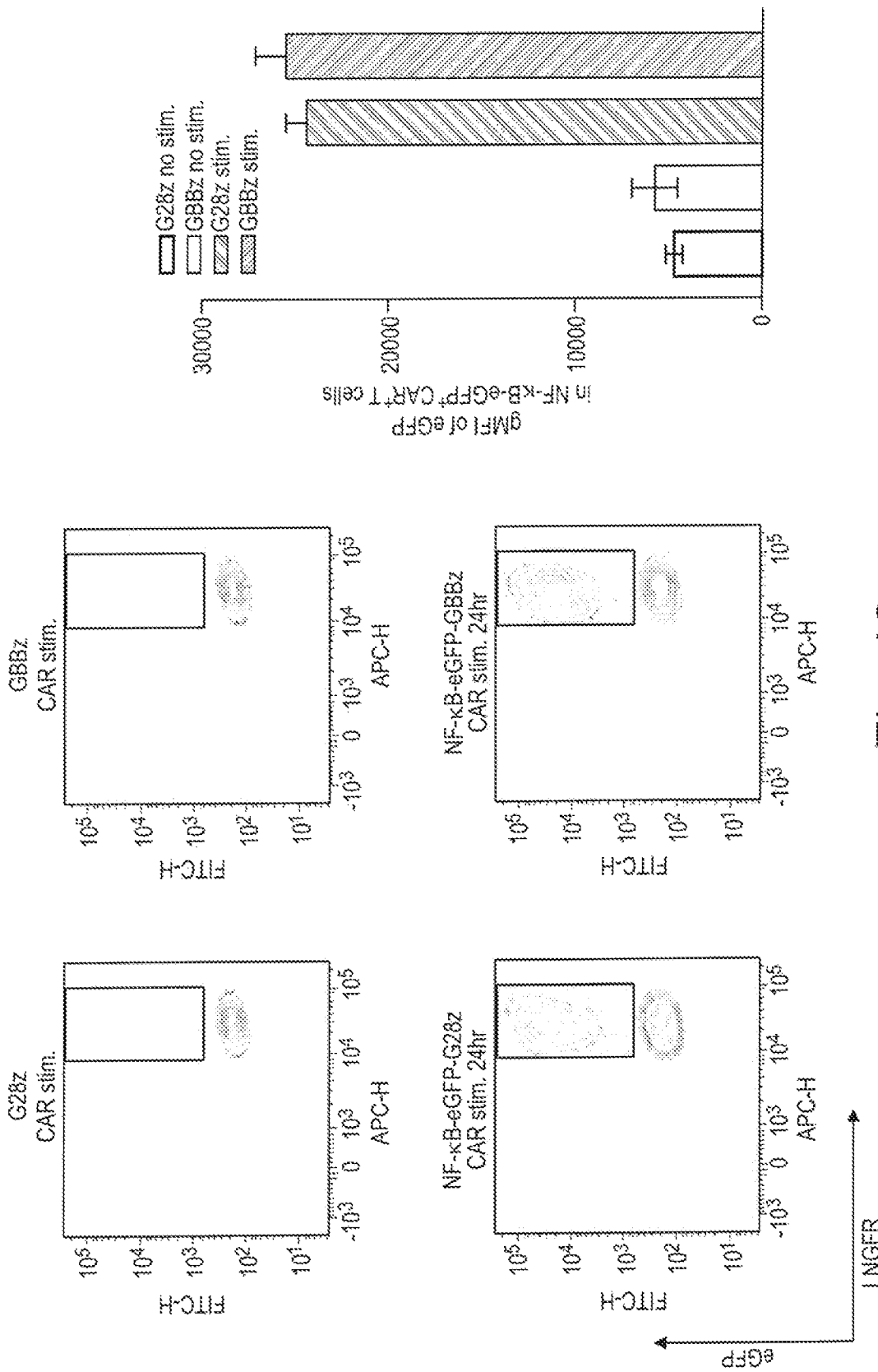
FIG. 10. Activated NF-κB signaling in both CD28 and 4-1BB costimulation.
Figure 11A:
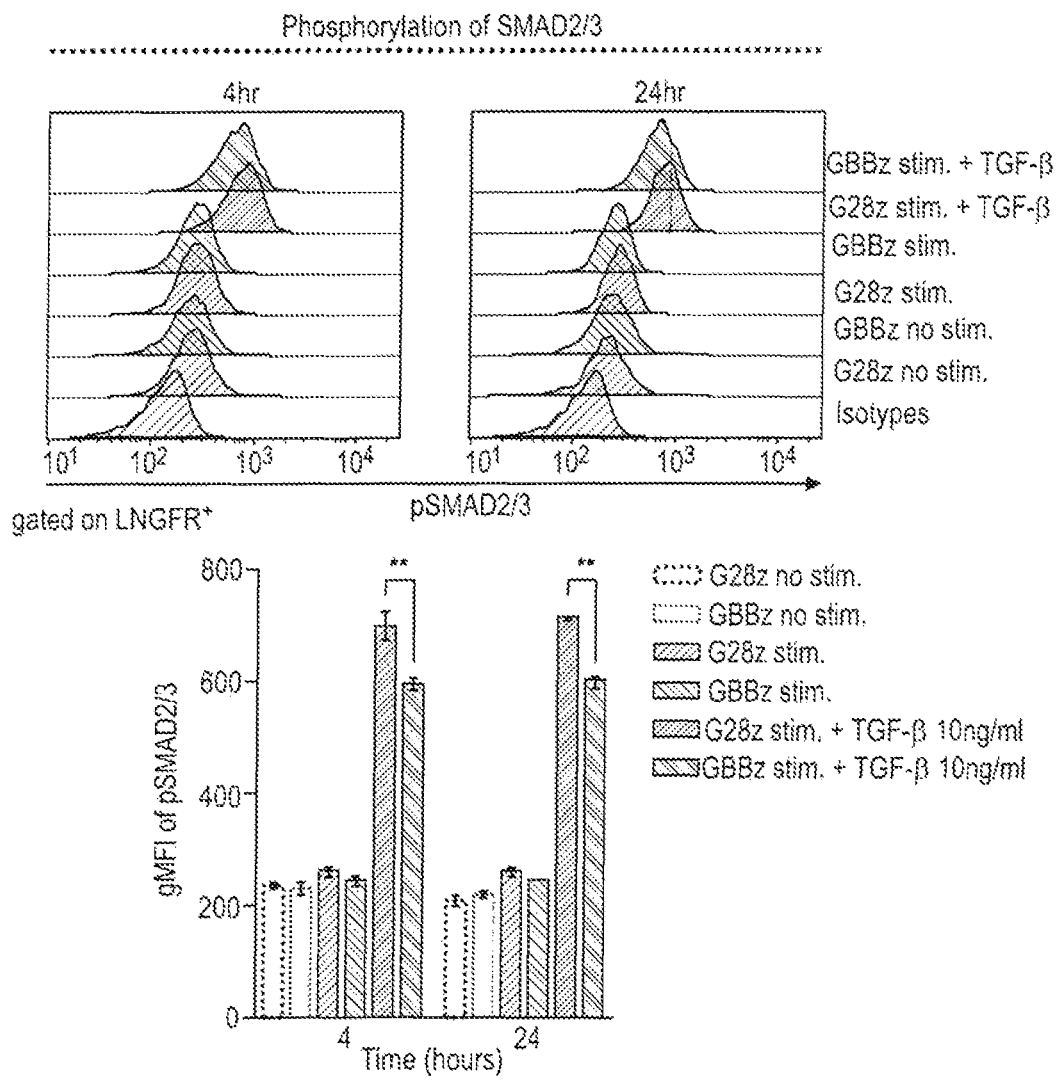

How cell-intrinsic PD-1 disruption affects a function of CD28/CD3ζ or 4-1BB/CD3ζ CAR-T cells was investigated (FIG. 6A). G28z GBBz, P28z and PBBz CAR-T cells were first generated. These CAR-T cells similarly transduced (FIG. 6B). The PD-1 expression level was higher in G28z CAR-T cells than GBBz CAR-T cells, and PD-1 level of P28z was higher than that of PBBz (FIG. 7A). It was also found that this different PD-1 protein level resulted from transcriptional level (FIG. 7B). It was hypothesized that each costimulatory domain represent a different intensity on the activation of the factors involved in PD-1 transcription. Among the transcription factors involved in PD-1 transcription, NFAT and NF-κB were significantly involved PD-1 transcription, and SMAD2/3 were involved in PD-1 transcription in the presence of exogenous TGF-β that is major immunosuppressive factor of tumor microenvironment (*Cancer Discov.*, 2016, Benjamine V Park). NFAT or NF-kB activity was investigated during CAR stimulation. NFAT response element(NFAT-RE x3)-eGFP or Classic NF-κB response element(NF-κB RE x5)-eGFP reporter lentiviral vector was constructed. It was showed that NFAT or NF-kB RE-mediated eGFP induction (FIGS. 8A and 8B). Reporter-transduced T cells are re-stimulated and additionally transduced with G28z or GBBz. It was found that G28z transduced NFAT reporter CAR-T cells (G28z-NFAT) had slightly high level of NFAT activity compared to GBBz-NFAT (FIG. 9A) and mRNA level of NFAT target genes was also higher in G28z (FIG. 9B). However, G28z transduced NF-κB reporter CAR-T cells (G28z-NF-κB) are similar in NFAT activity compared to GBB-NF-κB (FIG. 10). To investigate the activity of SMAD2/3 of each CAR-T cells, TGF-β was treated to G28z or GBBz CAR-T cells during CAR stimulation. It was found that SMAD2/3 phosphorylation of G28z CART is slightly higher BBz CART (FIG. 11A) and the degree of increase in PD-1 expression by TGF-β treatment is greater for G28z than GBBz (fold change of G28z 2.39±0.031, GBBz 1.61+0.034) (FIG. 11B). Whether this difference was due to differences in the expression levels of the TGF-β signaling elements was investigated. It was found that TGF-β and TGF-β receptor 1 (TGFBR1) was not significantly different between the two CARTs, but TGF-β receptor 2 (TGFBR2) was expressed at higher level in CD28z (FIG. 11C).

In this example, the environment of constimulatory molecules, including CD28 and 4-1BB, in PD-1 signaling, was evaluated. CD28 costimulation strongly induced signaling associated with PD-1 transcription, and the induction could be related to activation of NFAT and TGF-β signaling. The induction of CD28 costimulation was stronger than that of 4-1BB costimulation.

Example 5: Methods of Engineering and Evaluation of PD-1 KD CAR-T Cells

This example describes methods of engineering and evaluation of PD-1 KD CAR-T cells.

To mimic the in vivo conditions of CAR-T cells with multiple sequential antigen and immune checkpoint ligand encounters, CAR-T cells were co-cultured with CD19+ PDL1+ target cells without exogenous cytokines. In primary CAR-T cells, PD-1 KD CAR-T groups showed surprisingly higher lytic activity than WT CAR-T groups, but there was no difference in lytic activity between CD28-based and 4-1BB-based CAR-T groups (FIG. 12A). After $2^{nd}$ restim CAR-T cells, G28z CAR-T cells lost the ability to expand following the second stimulation, lytic activity of 3 CAR-T cells was thus analyzed. PBBz and P28z CAR-T cells had surprisingly higher lytic activity upon repeated antigen and PD-L1 exposure than GBBz CAR-T cells. PBBz CAR-T cells showed unexpectedly higher capacity in retaining lytic function than P28z CAR-T cells (FIG. 12A). This tendency was also observed in the cell proliferation assay (FIG. 12B). Collectively, Application of 4-1BB costimulatory domain to PD-1 KD CART contributes the retained cytotoxicity and proliferative capacity in vitro compared to CD28 costimulatory domain. PBBz CAR-T cells show delayed exhaustion upon repeated CD19 and PD-L1 exposure.

The possible effect of immunosuppressive mechanism on BBz CAR-T cells was examined. CD28 CAR-T cells was more sensitive to TGF-β than BBz CART (FIG. 11B), therefore GBBz CAR-T cells were compared to G28z CAR-T cells on how much their antigen specific proliferation would be suppressed by TGF-β. While a significant difference in proliferation was not observed between two CAR-T cells during CAR stimulation without TGF-β, proliferation of G28z CAR-T cells were meaningfully reduced rather than GBBz CAR-T cells (FIG. 13A).

It has been reported that TGF-β not only inhibits proliferation but is also deeply involved in the induction of regulatory T cells (JEM, 2003, WanJun Chen; Science, 2003, Shohei Hori; Blood, 2007, Dat Q. Tran). To examine whether Treg induction is different between G28z and BBz CAR-T cells in absence of exogenous TGF-β, G28z and BBz CAR-T cells were cultured with NALM-6 target cells during 3 day. G28z CAR-T cells had two to three times of in vitro CD4+ CD25+ FOXP3+ Tregs % compared to GBBz CAR-T cells (FIG. 13B). This result is consistent with the increase in expression of Treg-related genes such as CD25 and FOXP3 (FIG. 9B). Next, changes in Treg % after TGF-β treatment was observed and compared. It was shown that TGF-β significantly improved the Treg % in 28z CAR-T cells, but did not affect the Treg % in BBz CAR-T cells (FIG. 13B). It was concluded that CD28 costimulation has a greater potential to induce Treg than 4-1BB costimulation, and if TGF-β existed, its potential is further exploded. Whether cell intrinsic PD-1 disruption affects to induction of Treg was also investigated. P28z and PBBz CAR-T cells had two to three time lower % of Treg compared to G28z and GBBz respectively. Especially, PBBz had the lowest Treg % (FIG. 13C). Finally, the percentage of Treg in the condition that the PD-1/PD-L1 signaling was activated was examined. Treg % change after NALM-6 or NALM-6-PDL1 co-culture was examined. It was found that PD-1/PDL1 signaling did not significantly affect the induction of CAR-T-derived Tregs (FIG. 13C), suggesting that intracellular PD-1 expression levels is related to the formation of Tregs. It was concluded that PBBz CAR-T cells could be surprisingly insensitive to immunosuppressive mechanism.

In this example, PBBz CAR-T cells were produced and showed delayed exhaustion upon repeated CD19 and PD-L1 exposure. PBBz CAR-T cells also unexpectedly avoid immunosuppressive mechanism. Thus, these cells were further evaluated for their in vivo antitumor effect.

Example 6: Methods of Treatment of CD19+ Blood Cancer In Vivo Using PBBz CAR-T Cells This example describes the methods of treatment of CD19+ blood cancer in vivo using PBBz CAR-T cells.

Figure 14:
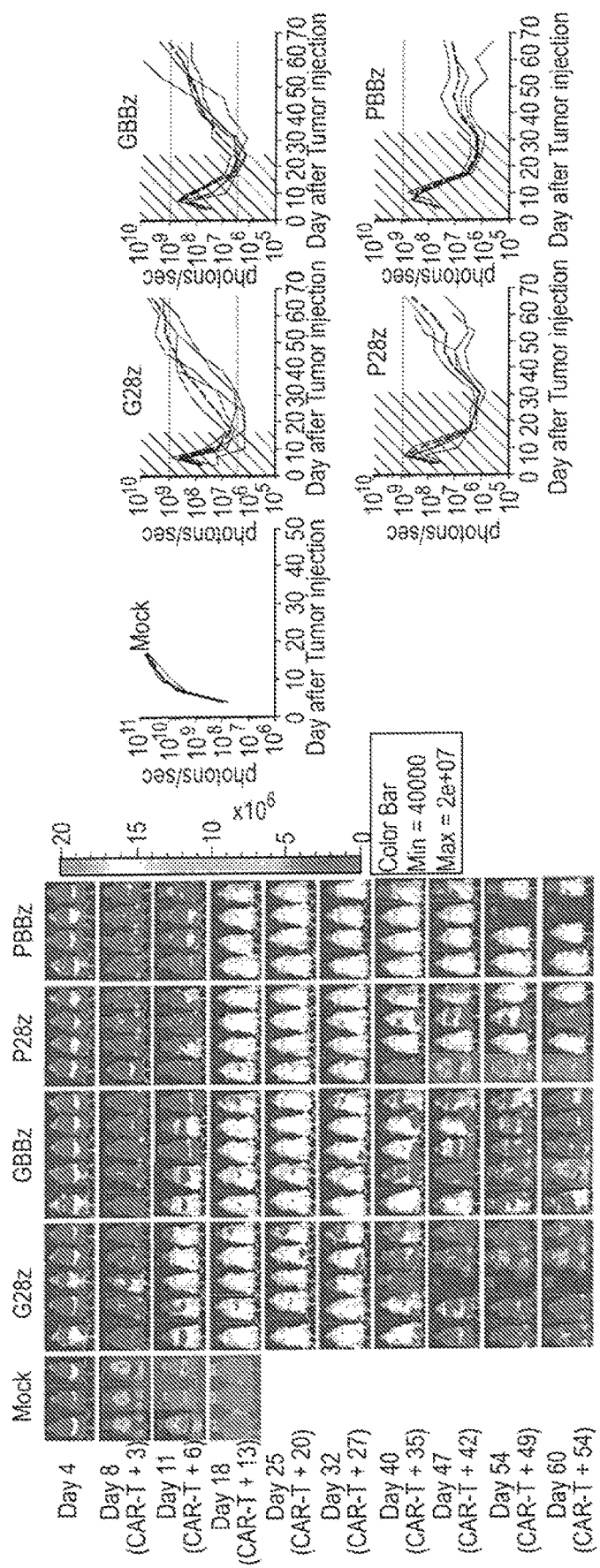
FIG. 14. Continuous inhibition of leukemia progression by PBBz CAR T cells.

The CD19+ blood tumor model was established as described in example 3. The antitumor effect of the G28z, GBBz, P28z and PBBz CAR-T cells against CD19+ B-ALL cells in vivo were compared. CAR-T cells administered at a single dose of 2.5×10⁶ day 4 after target cells infusion. In vivo imaging of NALM6-GL-PDL1 bearing mice was acquired with Xenogen IVIS Spectrum and quantified as radiance in the region of interest (photon/sec). As shown in FIG. 14, PD-1 KD CART cells (PBBz or P28z) shows superior antitumor effect to WT CAR-T cells (GBBz or G28z). Especially, PBBz CAR-T cells inhibited leukemia progression for longer periods than the other three CAR-T cells. WT CAR-T cells had a strong antitumor response, but did not have a sustained antitumor response. On the other hand, PD-1 KD CAR-T showed a weak response to the initial periods, but a persistent antitumor response, suggesting that PD-1 disruption in CAR-T cells might potentially reduce the risk for CRS. PBBz CAR-T cells conferred unexpectedly superior in vivo antitumor effect than that of P28z.

Example 7: Methods of Production of Dual Two-in-One Vectors Having 2 Types of shRNA Cassette Enter in The →← or the ←→ Directions This example describes the methods of producing dual Two-in-One vectors, wherein 2 types of shRNA cassette enter in the ←→ directions (shTIM-3-mU64←→hU6-shPD-1) or the →← directions (mU6-shTIM-3→←shPD-1-hU6) and express shPD-1, shTIM-3 and CD19-CAR simultaneously.

To construct a lentivirus wherein the expression of the shRNA for PD-1 (hereinafter shPD-1), the shRNA for TIM-3 (hereinafter shTIM-3) and CD19-CAR are regulated by human U6 promoter (hereinafter hU6), mouse U6 promoter (hereinafter mU6), and EF1-α promoter, respectively. The plasmid wherein both types of shRNA are expressed simultaneously was prepared so that the respective shRNA cassettes were disposed in the →← direction (mU6-shTIM-3→←shPD-1-hU6) and the ←→ direction (shTIM-3-mU64←→hU6-shPD-1) (FIG. 15 panel a and FIG. 15 panel b, respectively). To this end, (1) insertion of a multiple cloning site (MCS), (2) conversion of the mouse U6 promoter of shPD-1 into human U6 promoter, (3) insertion of shTIM-3 and (4) cloning such as switching positions of shTIM-3 and shPD-1 were performed.

To insert MCS into the mU6-shPD-1 the 3' part of pLV-ΔLNGFR_P2A_CD19-CAR_mU6-shPD-1 (plasmid ID #2), and primers comprising SEQ ID NOs.228 and 229. were used to make a PCR product (416 bp) wherein the Hpa1 restriction enzyme recognition site of mU6-shPD-1 3' is modified into a BsgZ171-Xba1-Nde-1-Bmt1-Spe1 multiple cloning site. Thereafter, the PCR product was treated with BstZ17y and Hpa1 restriction enzymes and plasmid ID #2 was treated with Hpa1 restriction enzyme and CIP, after which blunt end ligation was used to prepare a pLV-ΔLNGFR-P2A-CD19-CAR-mU6-shPD-1_MCS (plasmid ID #4) including the shPD-1-mU6-MCS base sequence (shRNA cassette SEQ ID NO.223).

Thereafter, a plasmid was constructed so that shPD-1 was expressed by human U6 promoter instead of mouse U6 promoter. LentiCRISPR V2 plasmid was used with primers comprising SEQ ID NOs. 230 and 231 to obtain a PCR product including human U6 promoter. The PCR product was treated with Hpa1 and Spe1 restriction enzyme, and then ligated to plasmid ID #4 treated with Hpa1 and Spe1 restriction enzyme to prepare a pLV-ΔLNGFR_P2A_CD19-CAR hU6-shPD-1 MSC (plasmid ID #5) comprising the hU6-shPD-1 base sequence (SEQ ID NO. 224). It was intended to insert the mU6-shTIM-3 cassette into plasmid ID #5 to construct a plasmid which expresses shTIM-3 and shPd-1 simultaneously.

The PCR product including the mU6-shTIM-3 cassette was obtained using plasmid ID #3 and primers comprising SEQ ID NOs. 232 and 233. After treating the PCR product with Bmt1 and Spe1 restriction enzymes, it was ligated to plasmid ID #5 treated with Bmt1 and Spe1 restriction enzymes to prepare a pLV-ΔLNGFR_P2A_CD19-CAR mU6-shTIM-3→←shPD-1-hU6 (plasmid ID #6) comprising a →← direction (mU6-shTIM-3→←shPD-1-hU6) base sequence (SEQ ID NO. 220).

To build a plasmid wherein two types of shRNa cassettes are arranged in the ←→ directions (shTIM-3-mU64←→hU6-shPD-1), plasmid ID #6 and primers comprising SEQ ID NOs. 234 and 235 were used to obtain a PCR product. After treating with Spe1 and Hpa1 restriction enzyme, it was inserted into plasmid ID #4 treated with the same restriction enzymes to produce pLV-ΔLNGFR-P2A-CD19-CAR-shPD-1-hU6-MCS (plasmid ID #7). Thereafter, plasmid ID #6 and primers comprising SEQ ID NOs. 236 and 237 were used to obtain a PCR product. After treating with Bmt1 and Spe1 restriction enzyme, it was ligated to plasmid ID #7 treated with the same restriction enzyme to ultimately prepare a pLV-ΔLNGFR-P2A-CD19-CAR_sh-TIM-3-mU6←→hU6-shPD-1 (plasmid ID #8) comprising a ←→ direction (shTIM-3-mU64←→hU6-shPD-1) base sequence (SEQ ID NO. 221).

The Two-in-One lentiviral vectors wherein 2 types of shRNA cassette enter in the ←→ or the →← directions produced herein can be used in the production of PD-1 KD modified CAR-T cells in the following examples.

Example 8: Methods of Production and In Vitro Evaluation of PD-1 KD CAR-T Cells

This example describes the methods of producing and in vitro evaluating dual KD CAR-T cells wherein shPD-1, shTIM-3 and CD19-CAR are expressed simultaneously.

Figure 16:
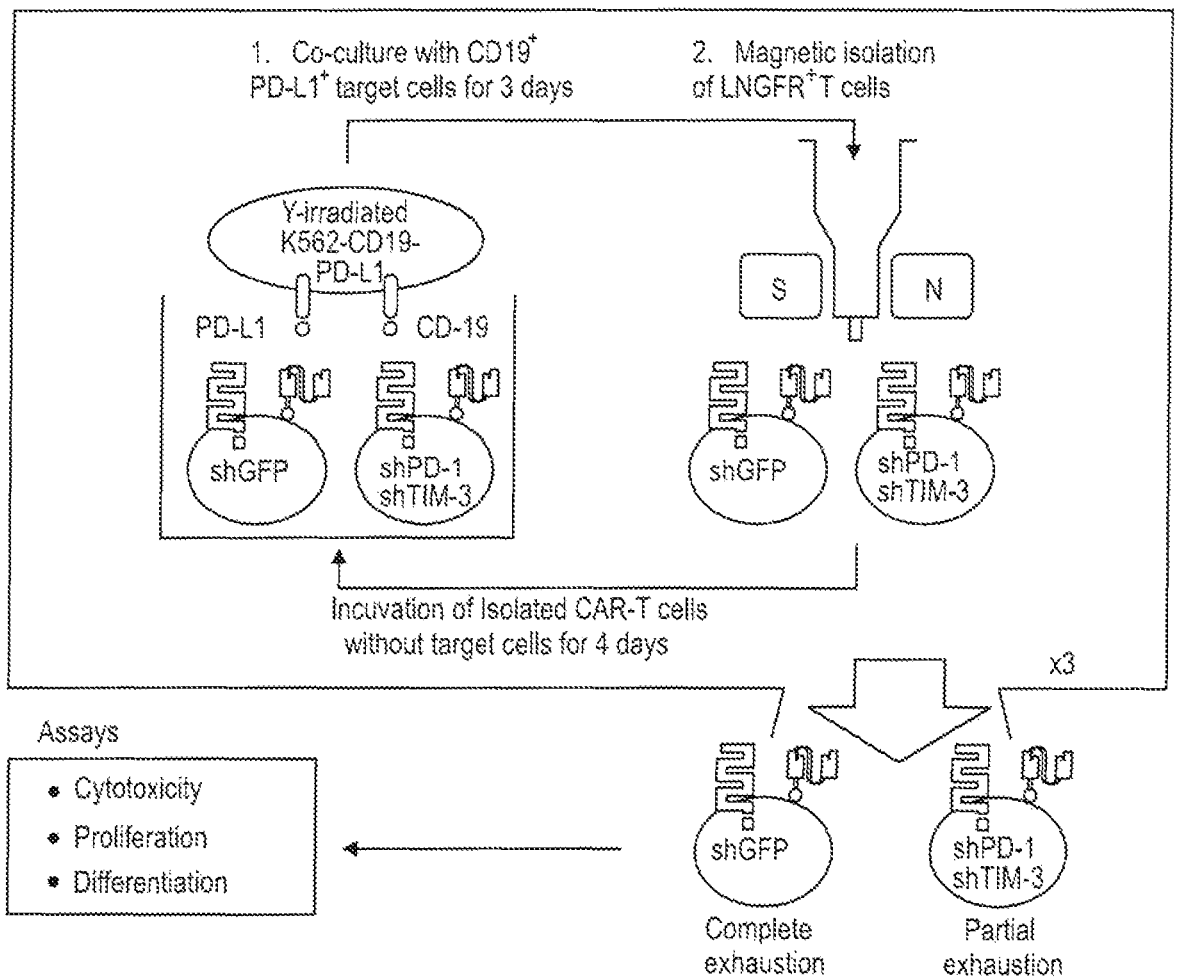
FIG. 16. Diagram of the CAR-T cell preparation process, wherein ΔLNGFR-CART19/mU6-shTIM-3→←shPD-1-hU6 cells and ΔLNGFR-CART19/shTIM-3-mU6→←hU6-shPD-1 cells were prepared and isolated as described herein.

Plasmid ID #1 (pLV-ΔLNGFR_P2A_CD19-CAR mU6-shGFP), #6 (pLV-ΔLNGFR_P2A_CD19-CAR_mU6-shTIM-3→←shPD-1-hU6), and #8 (pLV-ΔLNGFR_P2A_CD19-CAR_shTIM-3-mU6→←hU6-shPD-1) in Table 1, and packaging plasmids pMDL g/p, pRSVrev and pMDG.1 were transfected into HEK293 T cells using lipofectamine, and after 48 hours had passed, a cell culture fluid including lentivirus was obtained. Using ficoll-paque solution, peripheral blood mononuclear cells (PBMC) were isolated from human blood, and human CD3 and CD28 target antibodies were used to specifically activate the T cells. After one to two days following initial activation of the T cells, they were transduced using the virus obtained previously. The CAR-T cells prepared were thereafter cultured using AIM-V culture fluid including 5% human plasma and human IL-2. On the sixth day after transduction, the MACSelect LNGFR System (miltenyibiotec, Germany) was used to obtain pure CAR-T cells, and LNGFR target antibody was used to isolate LNGFR+ CAR-T Cells with a flow cytometer. In the following, the cells prepared using plasmid ID #1, #6 and #8 are indicated as ΔLNGFRCART19/shGFP (or shGFP/CART19), ΔLNGFR-CART19/mU6-shTIM-3→←shPD-1-hU6 (or shPD-1 shTIM-3/CART19) and ΔLNGFR-CART19/shTIM-3-mU6→←hU6-shPD-1, respectively (FIG. 16). To prepare control CAR-T cells comprising the mU6-shPD-1, mU6-TIM-3 and shPD-1-hU6 cassettes, respectively, plasmid ID #2 (pLV-ΔLNGFR_P2A_CD19-CAR_mU6-shPD-1), #3 (pLV-ΔLNGFR_P2A_CD19-CAR_mU6-shTIM-3), and #7 (pLV-ΔLNGFR_P2A_CD19-CAR_shPD-1-hU6_MCS) in Table 1, and packaging plasmids pMDL g/p, pRSVrev and pMDG.1 were transfected into HEK293 T cells using lipofectamine. After 48 hours had passed, a cell culture fluid including lentivirus was obtained. Using ficoll-paque solution, peripheral blood mononuclear cells (PBMC) were isolated from human blood, and human CD3 and CD28 target antibodies were used to specifically activate the T cells. After one to two days following initial activation of the T cells, they were transduced using the virus obtained previously. The CAR-T cells prepared were thereafter cultured using AIM-V culture fluid including 5% human plasma and human IL-2. On the sixth day after transduction, the MACSelect LNGFR System (miltenyibiotec, Germany) was used to obtain pure CAR-T cells, and LNGFR target antibody was used to isolate LNGFR+ CAR-T Cells with a flow cytometer. In the following, the cells prepared using plasmid ID #2, #3 and #7 are indicated as ΔLNGFR-CART19/shPD-1(or shPD-1/CART19), ΔLNGFR-CART19/shTIM-3 (or shTIM-3/CART19) and ΔLNGFRCART19/shPD-1-hU6, respectively.

Figure 17:
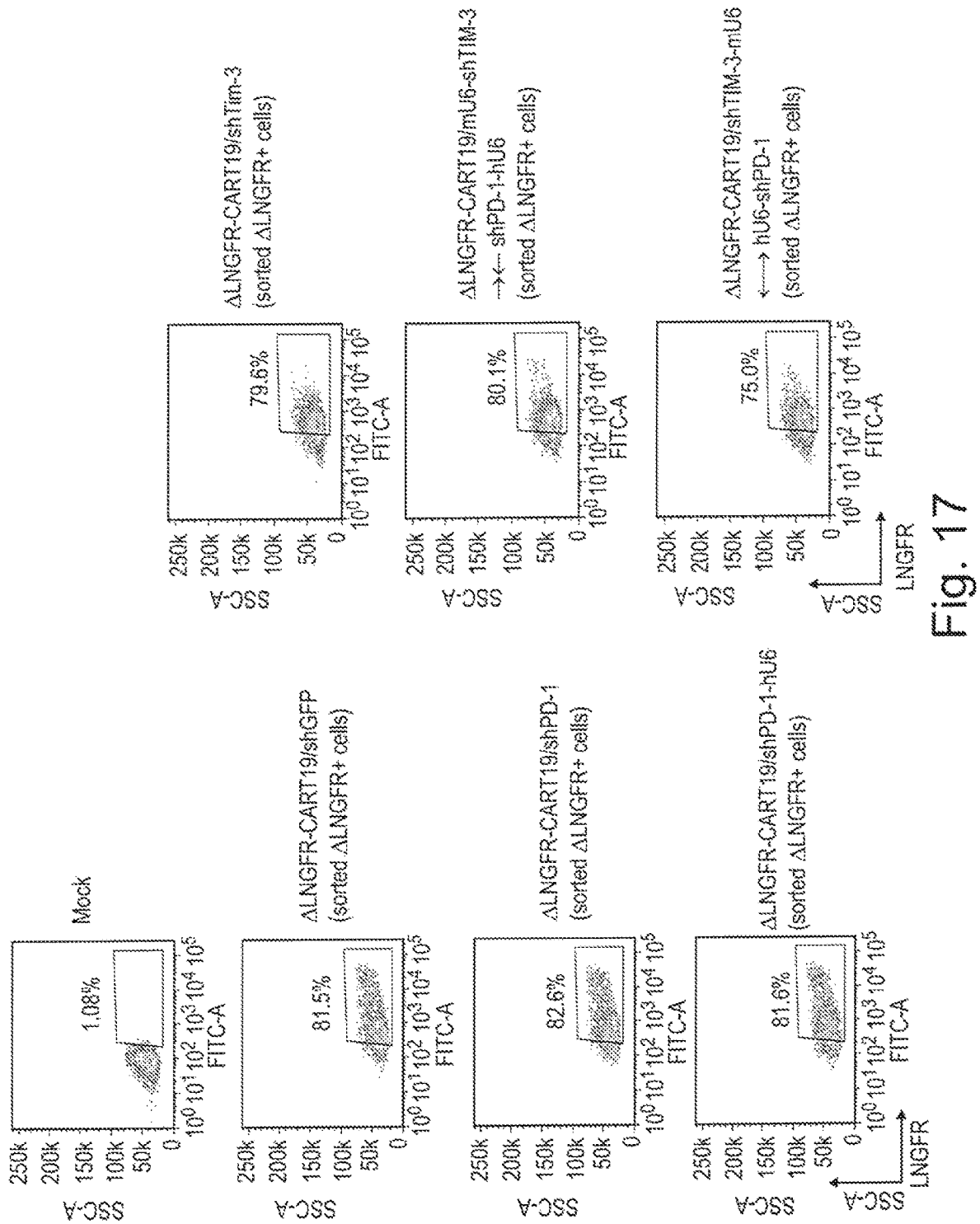
FIG. 17. Flow cytometry data from CAR-T cells comprising the vectors illustrated in FIG. 15 (ΔLNGFR-CART19/mU6-shTIM-3→←shPD-1-hU6 cells and ΔLNGFR-CART19/shTIM-3-mU6→hU6-shPD-1 cells).

To measure the purity of the dual KD CAR-T cells produced herein, flow cytometry was performed using the LNGFR target antibodies for the cells prepared above. As shown in FIG. 17, around 80% of LNGFR+ CAR-T cells were obtained.

Figure 18A:
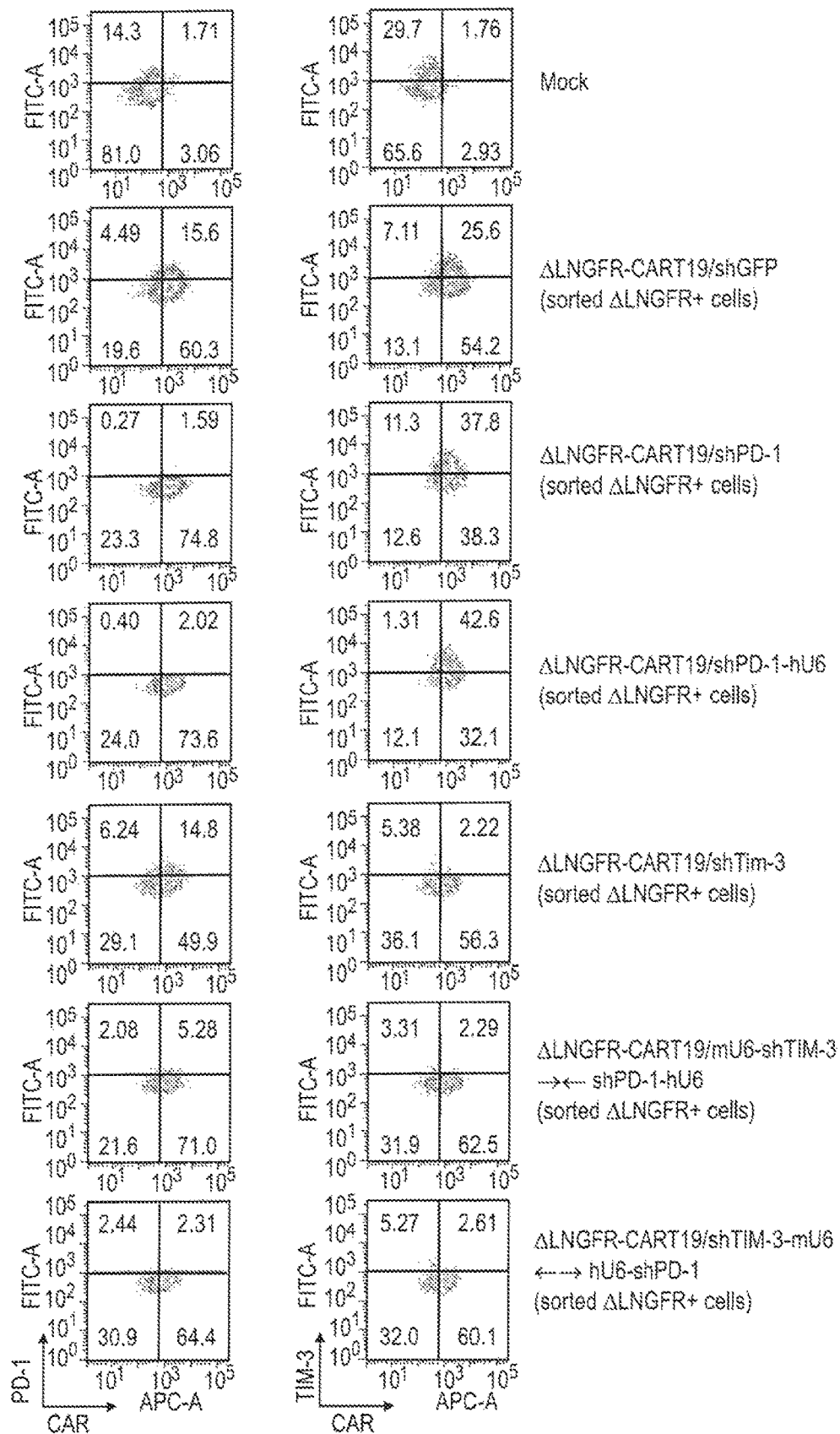
FIG. 18A-18B.
Figure 18B:
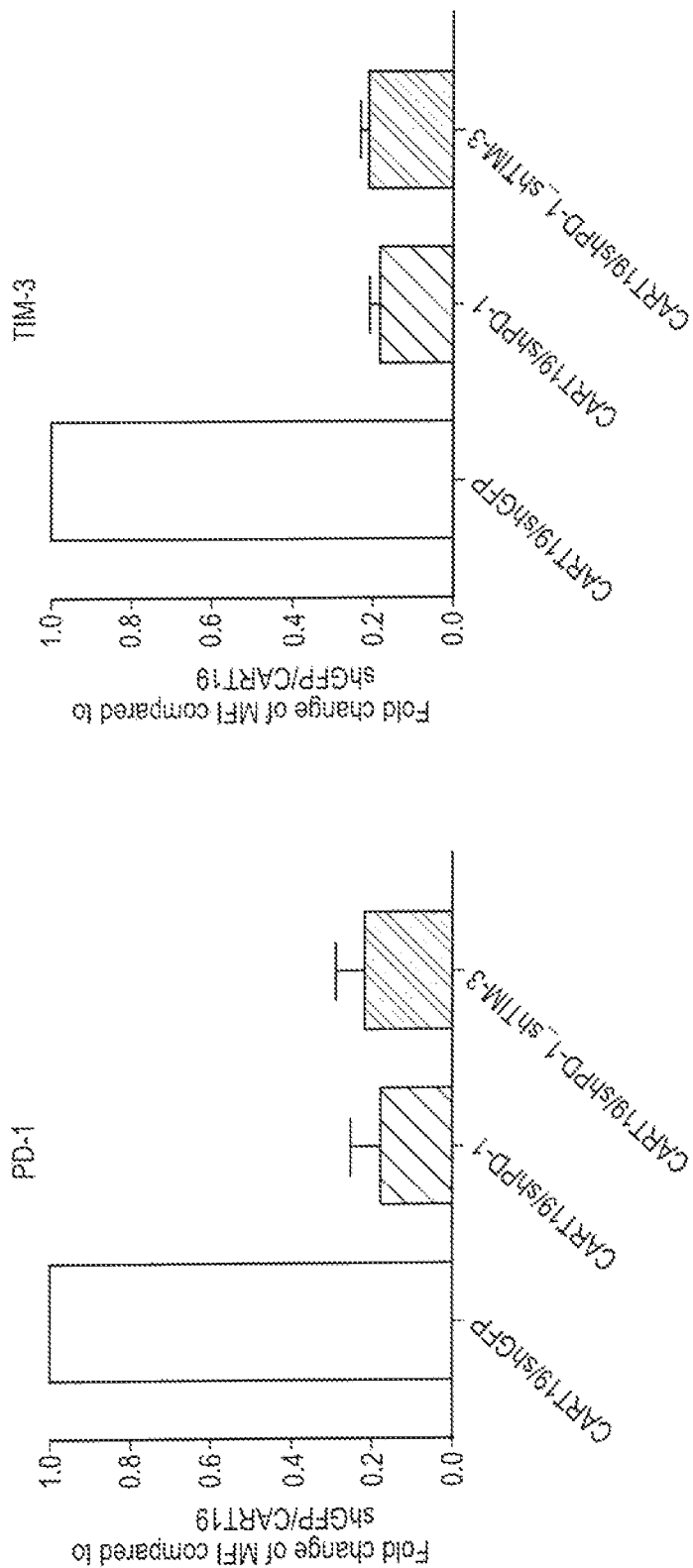

The reduced expression of PD-1 and TIM-3 in the dual KD CAR-T cells produced herein was measured, and sustained reduction in expression thereof. The dual KD CAR-T cells were stimulated for three days with human CD3 and CD28 target antibody to induce expression of PD-1 and TIM-3. Thereafter, the PD-1 and TIM-3 expression of the dual KD CAR-T cells was analyzed through flow cytometry using CAR, PD-1 and TIM-3 target antibodies. As shown in FIGS. 18A and 18B, analysis of the effect of the two simultaneously expressed shRNA types on the reduction in expression of PD-1 and TIM-3 showed that the degree of reduction of PD-1 and TIM-3 expression observed in a CD19-CAR T cell expressing shPD-1 and shTIM-3 simultaneously was similar to the degree of reduction in a CD19-CAR T cell wherein only shPD-1 or shTIM-3 is expressed.

Figure 19:
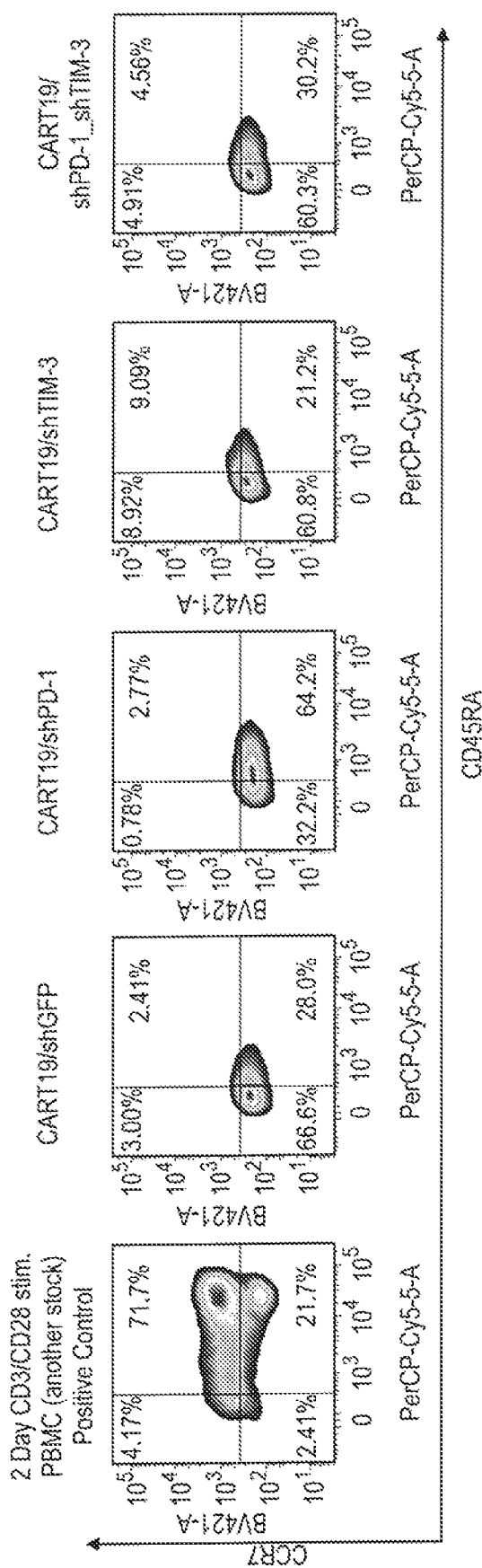
FIG. 19. Flow cytometry data wherein CAR-T cells were repeatedly stimulated using the target cells, after which the degree of cell differentiation was confirmed using CD45RA and CCR7 antibodies.

The impact of dual KD CAR-T cells produced herein on differentiation was measured. To observe the degree of PD-1 and TIM-3 differentiation of dual KD CAR-T cells, flow cytometry was carried out using CD45RA and CCR7 target antibodies. As shown in FIG. 19, in ΔLNGFR-CART19/shPD-1 cells subjected to repeated antigen stimulation, there is an increase in terminally differentiated TEMRA (CCR7-CD45RA+) T cells compared to ΔLNGFR-CART19/shGFP. On the other hand, ΔLNGFR-CART19/mU6-shTIM-3→←shPD-1-hU6 to which shTIM-3 has been added comprises more TN (CCR7+CD45RA+) T cells, TCM (CCR7+CD45RA−) T cells and TEM (CCR7-CD45RA−) T cell subtypes than ΔLNGFR-CART19/shPD-1. As similar results are observed with ΔLNGFR-CART19/shTIM-3 cells as well, it can be said that the reduced differentiation ability of ΔLNGFR-CART19/mU6-shTIM-3→←shPD-1-hU6 cells arises due to suppression of TIM-3 expression, and accordingly, it can be said that the effect of shTIM-3 has priority over the effect of shPD-1 in terms of the influence had on cell differentiation. As it is known that less differentiated T cell subtypes can promote improved cancer therapeutic ability of T cells, it is expected that the ΔLNGFR-CART19/mU6-shTIM-3→←shPD-1-hU6 cells will exhibit better in vivo anti-cancer efficiency than ΔLNGFR-CART19/shPD-1 cells.

The transduction efficiency, proliferation ability, and viability of dual KD CAR-T cells into which CD19-CAR vectors comprising shRNA cassettes with different orientations have been introduced was compared. Of the CAR-T cells produced herein, flow cytometry was performed using LNTFR antibody for the cells using plasmids comprising →← direction (mU6-shTIM-3→←shPD-1-hU6) and ←→ direction (shTIM-3-mU6→←hU6-shPD-1) cassettes. For cell viability analysis, trypan blue dyeing was performed, and the ratio of cells not dyed was found. As shown in FIGS. 20A-20C, compared to the cells using the →← direction cassettes, (ΔLNGFR-CART19/mU6-shTIM-3→←shPD-1-hU6) the cells using the ←→ direction cassettes (ΔLNGFR-CART19/shTIM-3-mU6←→hU6-shPD-1) had unexpected trouble forming transduced cells, and the transduced T cells had low proliferation ability and viability.

This example describes the methods of producing dual KD CAR-T cells wherein shPD-1, shTIM-3 and CD19-CAR are expressed simultaneously. The dual KD CAR-T cells were produced using Two-in-One lentiviral vectors produced herein having 2 types of shRNA cassette enter in the →← or ←→ directions. When compared to the cells using the ←→ directions cassettes, the cells using the →← direction cassettes (ΔLNGFR-CART19/mU6-shTIM-3→←shPD-1-hU6) showed surprisingly higher proliferation ability and viability and were thus used in the following examples.

Example 9: Methods of Production of Dual Two-in-One Vectors and Dual KD CAR-T Cells This example describes the methods of producing dual Two-in-One vectors and dual KD CAR-T cells.

Figure 21A:
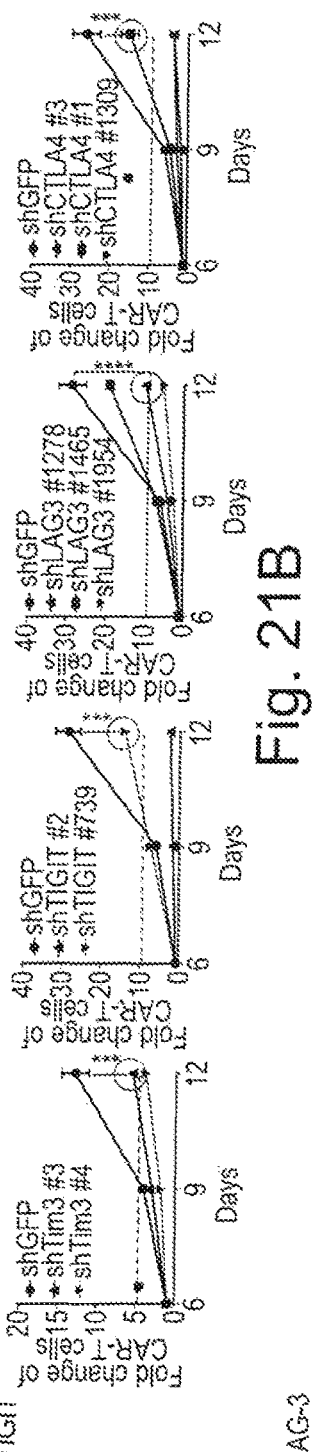
FIGS. 21A-21C. Selection of CTLA-4, LAG-3, TIGIT, and TIM-3 targeting shRNAs.
Figure 21B:
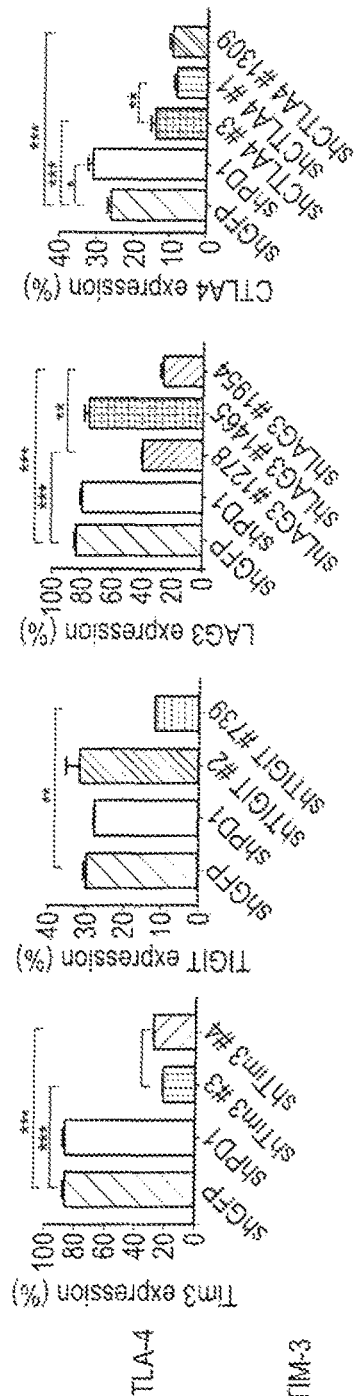
Figure 21C:
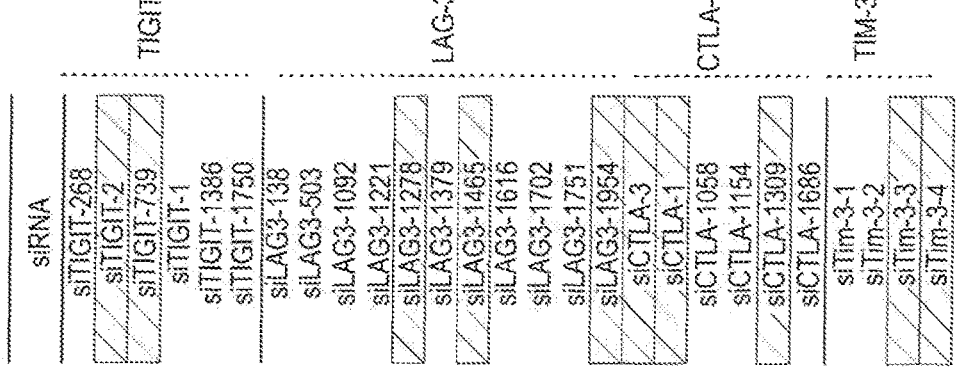
Figure 22C:
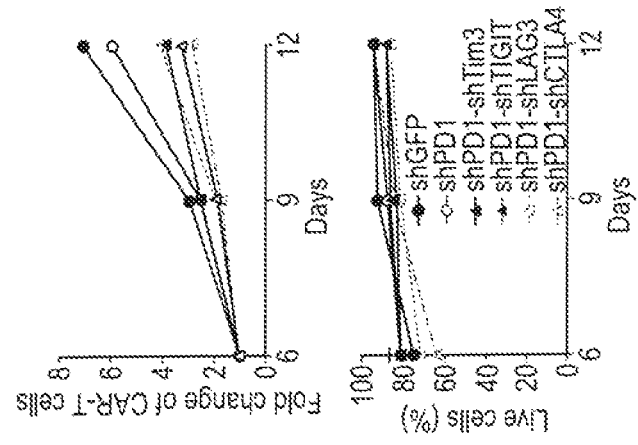
Figure 22B:
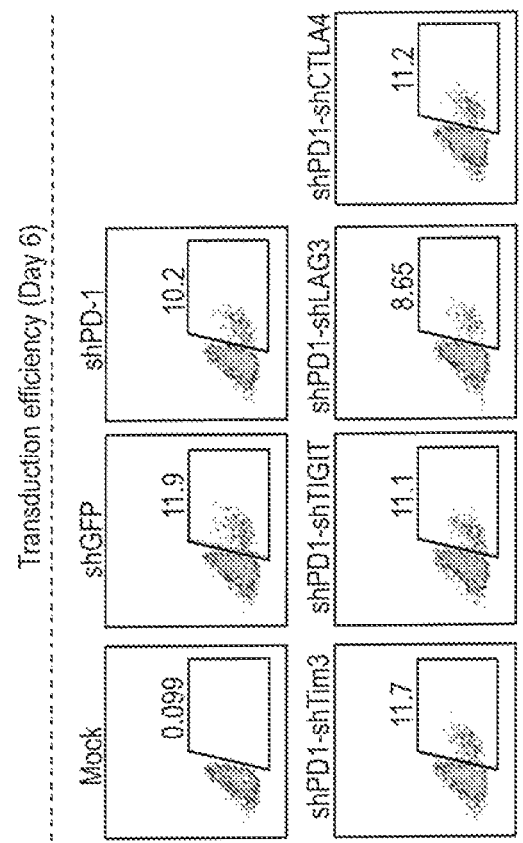
Figure 22D:
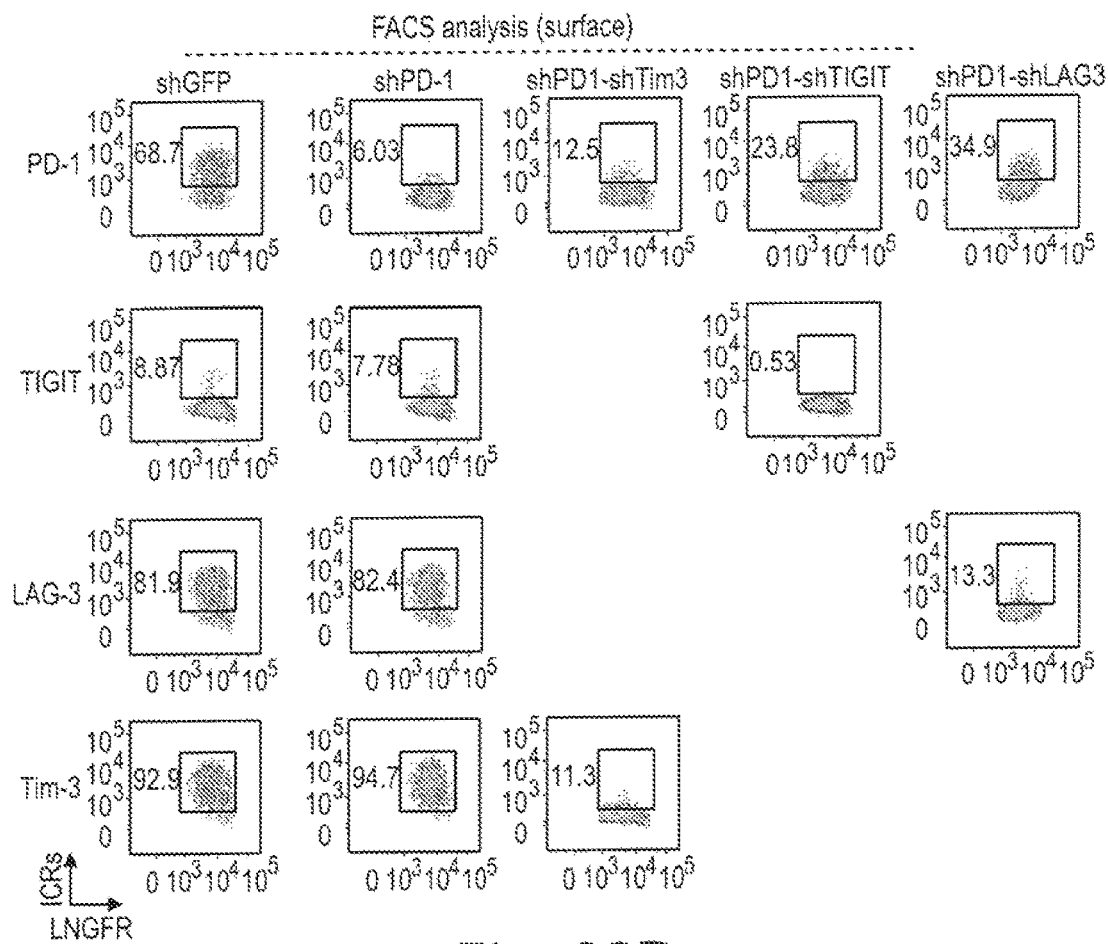
Figure 22E:
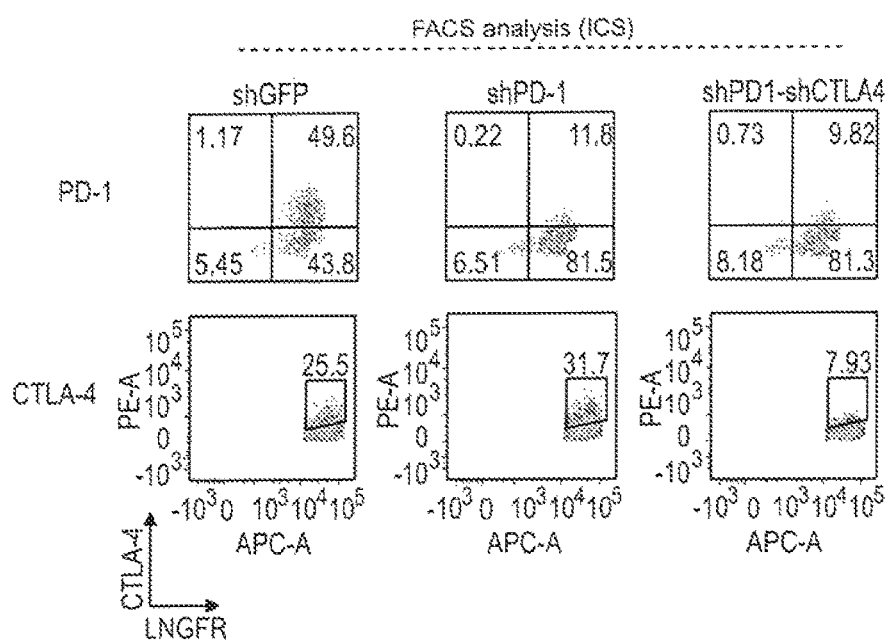

For generation of dual Two-in-One vectors expressing two shRNAs by different promoters (mU6 and hU6), a BstZ17I-XbaI-NdeI-BmtI-SpeI multiple cloning site (MCS) was inserted into the pLV-hU6-shPD-1 ΔLNGFR-CD19-BBz vector downstream of hU6 promoter. The second mU6-shRNA cassette fragments were subcloned into the MCS. To limit the blockade of multiple immune checkpoints to CAR-T cells only, a Dual Two-in-One vector was devised to express two shRNAs by mU6 and hU6 Pol III promoters to repress expression of two immune checkpoints of CAR-T cells. To find effective CTLA-4, LAG-3, TIGIT or TIM-3 targeting siRNAs, siRNAs were electroporated to CD3/CD28-stimulated T cells. Two or more effective siRNAs were selected (FIG. 21A). A Two-in-One vector for CTLA-4, LAG-3, TIGIT or TIM-3 KD CAR-T cells were constructed through transformation of 21-mer siRNAs to shRNA format and finally selected each immune checkpoints targeting shRNAs (shCTLA-4: #1; shLAG-3: #1278; shTIGIT: #739; #3), which significantly repress the expression and are less affected to CAR-T expansion (FIGS. 21B-21C). Finally, PD-1 CTLA-4, PD-1 LAG-3, PD-1 TIGIT, or PD-1 TIM-3 CAR-T cells were constructed by dual Two-in-One vector (FIGS. 22A-22E). All of dual KD CAR-T cells was less expanded compared to single PD-1 KD CAR-T cells (FIG. 22C). These results were also observed in single KD CAR-T cells (FIG. 21B).

In this example, dual Two-in-One vectors were produced. Dual KD CAR-T cells were produced using the dual Two-in-One vectors, and their therapeutic potential was further evaluated in in vivo mice model bearing CD19$^+$ PDL1$^+$ blood tumor and in a solid tumor model in the example below.

Example 10: Methods of Treatment of CD19+ Blood Cancer In Vivo Using Dual KD CAR-T Cells Targeting PD-1 and TIGIT This example describes the methods of treatment of CD19+ blood cancer in vivo using dual KD CAR-T cells targeting two immune checkpoints, including the following combinations, PD-1 and CTLA-4, PD-1 and LAG-3, PD-1 and TIGIT, and PD-1 and TIM-3.

Figure 23:
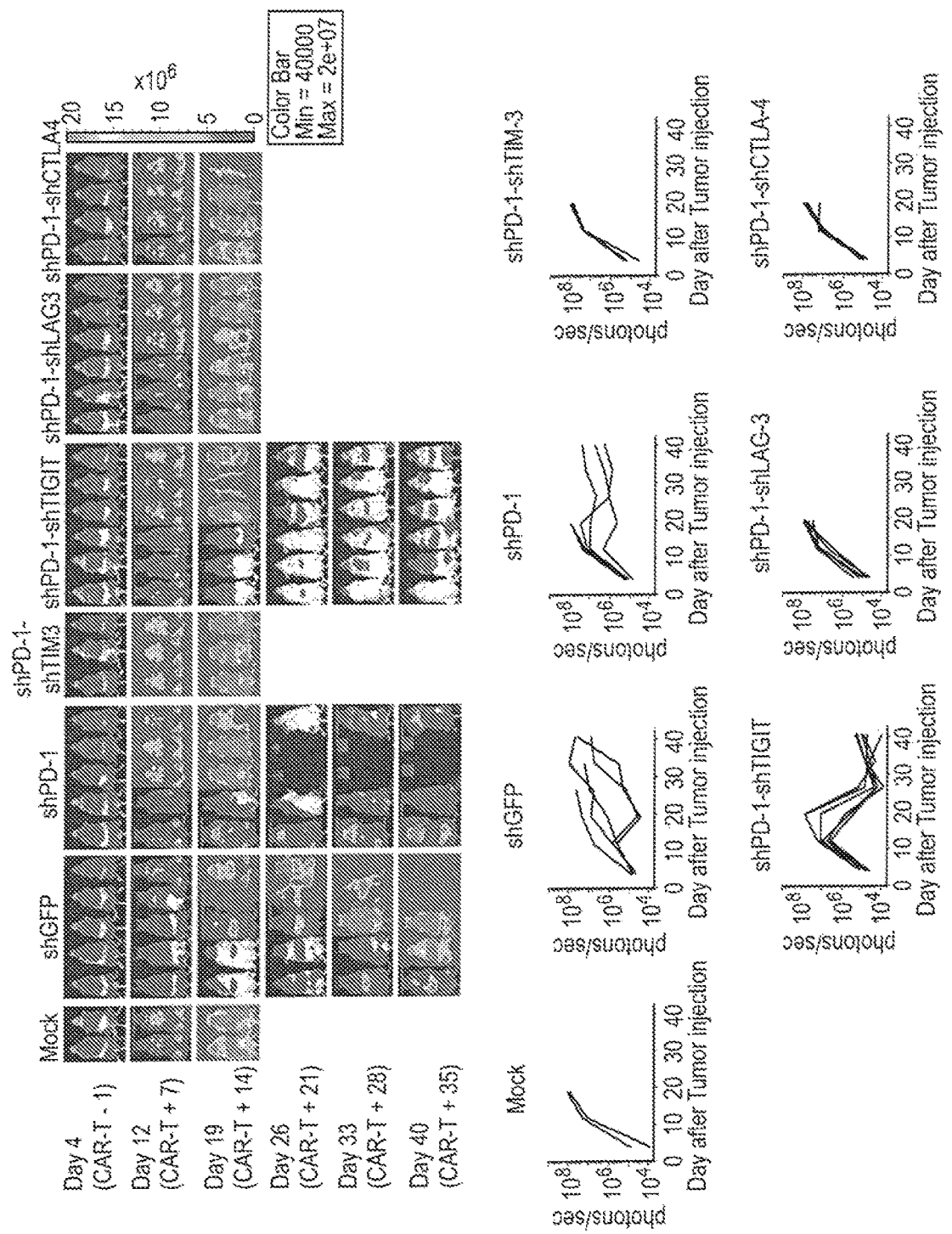
FIG. 23. Treatment of CD19+ blood cancer in vivo using dual KD CAR-T cells targeting two immune checkpoints.

The CD19$^+$ blood tumor model was established as described in example 3. The antitumor effect of the PD-1 CTLA-4, PD-1 LAG-3, PD-1 TIGIT, or PD-1 TIM-3 KD CAR-T cells against blood CD19$^+$ B-ALL model were evaluated. Each CAR-T cells injected at a single dose of $1 \times 10^6$ day 5 after target cells infusion. It was found that PD-1_TIGIT KD CAR-T cells shows surprisingly superior antitumor effect compared to other dual KD CAR-T cells (FIG. 23). Thus, the PD-1_TIGIT KD CAR-T cells in a solid tumor model were further evaluated in the following example.

Example 11: Methods of Treatment in a Solid Tumor Model Using Dual KD CAR-T Cells Targeting PD-1 and TIGIT This example describes the methods of treatment of cancer in a solid tumor model using dual KD CAR-T cells targeting PD-1 and TIGIT.

Figure 24:
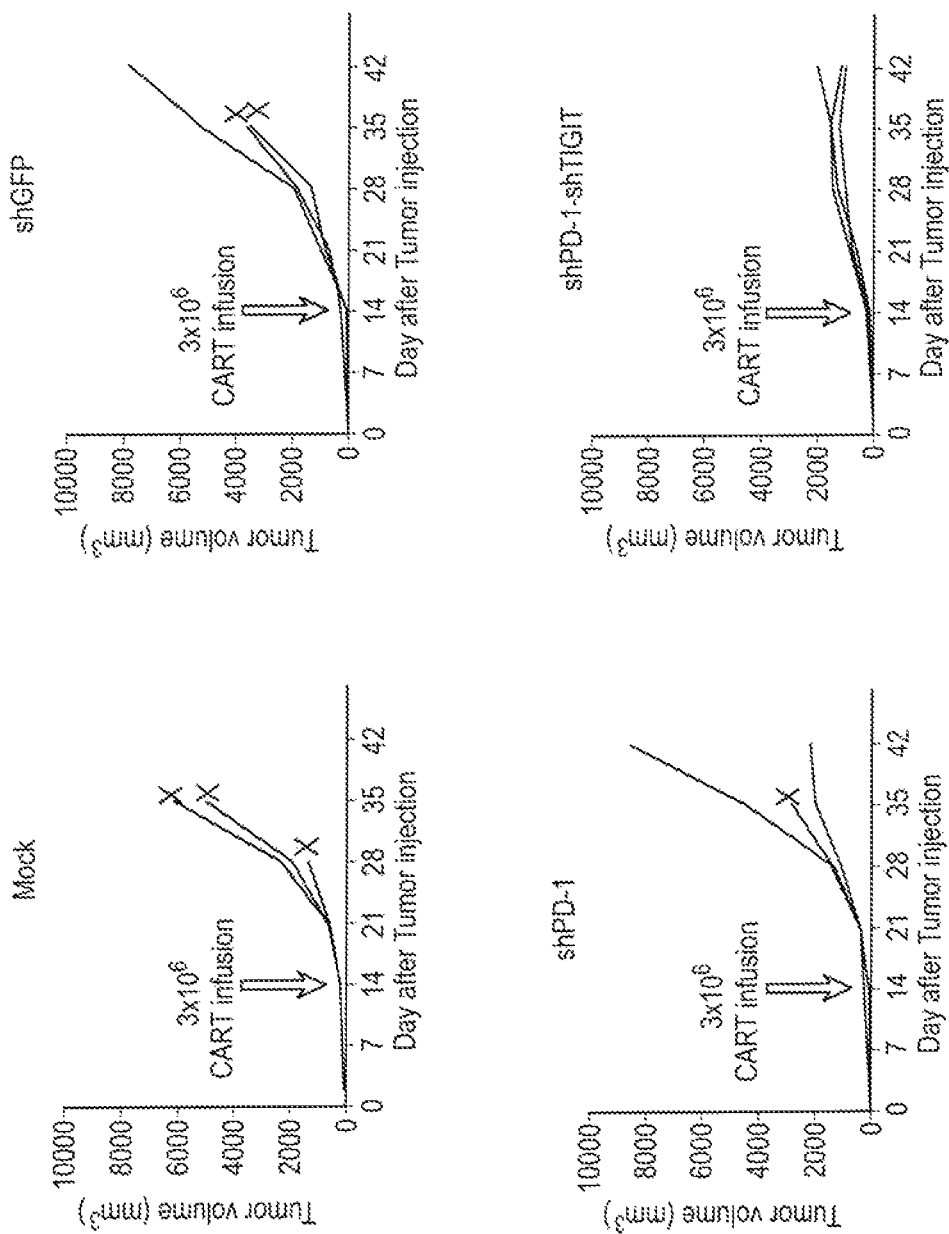
FIG. 24. Treatment of cancer in a solid tumor model using dual KD CAR-T cells targeting PD-1 and TIGIT.

To establish the solid tumor model, 4 to 6 week-aged NSG mice were subcutaneously injected with $5 \times 10^6$ IM-9 cells (CD19+ PD-L1+ CD155+). Once the tumors reached at a volume of 150~250 mm³, CAR-T cells are intravenously injected at a single dose of $3 \times 10^6$. Tumors were monitored every week by caliper measurement and the volume was estimated by (length×width)/2. As shown in the blood tumor model (Nalm-6-PDL1), PD-1_TIGIT KD CAR-T cells were also most surprisingly effective against solid tumor model (IM-9) (FIG. 24). Cell intrinsic PD-1_TIGIT blockade has unexpectedly higher level of antitumor effect than of PD-1 blockade.

The invention claimed is:

1. A method of treating cancer, comprising administering a T cell to a human subject having cancer, said T cell comprising a dual two-in-one vector that comprises
  (i) a first nucleotide sequence that encodes and expresses in the T cell:
    (a) a short hairpin RNA (shRNA) that inhibits expression of programmed cell death protein 1 (PD-1 shRNA), wherein the nucleotide sequence encoding the PD-1 shRNA consisting of SEQ ID NO:265 is regulated by a U6 Pol III promoter, and
    (b) an shRNA that inhibits expression of T cell immunoreceptor with Ig and ITIM domains (TIGIT shRNA), wherein the nucleotide sequence encoding the TIGIT shRNA consisting of SEQ ID NO: 240 is regulated by a U6 Pol III promoter,
    wherein the two U6 Pol III promoters are oriented in different orientations from each other; and
  (ii) a second nucleotide sequence that encodes and expresses in the T cell a chimeric antigen receptor (CAR), wherein the CAR comprises an extracellular antigen recognition domain that binds a target antigen associated with the cancer, a transmembrane domain, and an intracellular signal transduction domain;
  wherein the first nucleotide sequence and the second nucleotide sequence are present on a single vector.

2. The method of claim 1, wherein the target antigen is a cancer antigen whose expression is increased in or on the surface of a cancer cell, a cancer tissue, and/or a tumor microenvironment.

3. The method of claim 1, wherein the target antigen is CD19 or CD22.

4. The method of claim 1, wherein the intracellular signal transduction domain of the CAR further comprises a costimulatory molecule selected from the group consisting of ICOS, 0X40, CD137 (4-1BB), CD27, and CD28.

5. The method of claim 1, wherein the two U6 Pol III promoters are oriented in a head to head orientation.

6. The method of claim 1, wherein the two U6 Pol III promoters are oriented in a tail to tail orientation.

* * * * *

UNITED STATES PATENT AND TRADEMARK OFFICE
CERTIFICATE OF CORRECTION

PATENT NO. : 11,679,129 B2
APPLICATION NO. : 16/958649
DATED : June 20, 2023
INVENTOR(S) : Chan Hyuk Kim et al.

Page 1 of 1

It is certified that error appears in the above-identified patent and that said Letters Patent is hereby corrected as shown below:

On the Title Page

Item (73) First Assignee name should read CUROCELL INC.

Signed and Sealed this
First Day of August, 2023

Katherine Kelly Vidal
*Director of the United States Patent and Trademark Office*

SEQUENCE LISTING

```
<160> NUMBER OF SEQ ID NOS: 289

<210> SEQ ID NO 1
<211> LENGTH: 21
<212> TYPE: DNA
<213> ORGANISM: Artificial Sequence
<220> FEATURE:
<223> OTHER INFORMATION: partial shRNA sequence, included in shRNA to
      target GFP for RNA interference

<400> SEQUENCE: 1
tctcggcatg gacgagctgt a                                                   21

<210> SEQ ID NO 2
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 2
tggaacccat tcctgaaatt a                                                   21

<210> SEQ ID NO 3
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 3
ggaacccatt cctgaaatta t                                                   21

<210> SEQ ID NO 4
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 4
gaacccattc ctgaaattat t                                                   21

<210> SEQ ID NO 5
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 5
acccattcct gaaattattt a                                                   21

<210> SEQ ID NO 6
<211> LENGTH: 21
<212> TYPE: DNA
```

```
<213> ORGANISM: Artificial Sequence
<220> FEATURE:
<223> OTHER INFORMATION: partial shRNA sequence, included in shRNA to
      target PD-1 for RNA interference

<400> SEQUENCE: 6
cccattcctg aaattattta a                                              21

<210> SEQ ID NO 7
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 7
ccttccctgt ggttctatta t                                              21

<210> SEQ ID NO 8
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 8
cttccctgtg gttctattat a                                              21

<210> SEQ ID NO 9
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 9
ttccctgtgg ttctattata t                                              21

<210> SEQ ID NO 10
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 10
tccctgtggt tctattatat t                                              21

<210> SEQ ID NO 11
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-1 for RNA interference

<400> SEQUENCE: 11
ccctgtggtt ctattatatt a                                              21

<210> SEQ ID NO 12
<211> LENGTH: 21
<212> TYPE: DNA
<213> ORGANISM: Artificial Sequence
```

```
<220> FEATURE:
<223> OTHER INFORMATION: partial shRNA sequence, included in shRNA to
      target PD-1 for RNA interference

<400> SEQUENCE: 12
cctgtggttc tattatatta t                                              21

<210> SEQ ID NO 13
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 13
gatgaaaggg atgtgaatta t                                              21

<210> SEQ ID NO 14
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 14
gggagcctcc ctgatataaa t                                              21

<210> SEQ ID NO 15
<211> LENGTH: 19
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 15
ggaattcgct cagaagaaa                                                 19

<210> SEQ ID NO 16
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 16
ggaccaaact gaagctatat t                                              21

<210> SEQ ID NO 17
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 17
agaactttgg tttcctttaa t                                              21

<210> SEQ ID NO 18
<211> LENGTH: 21
<212> TYPE: DNA
<213> ORGANISM: Artificial Sequence
<220> FEATURE:
```

```
<223> OTHER INFORMATION: partial shRNA sequence, included in shRNA to
      target TIM-3 for RNA interference

<400> SEQUENCE: 18
atgaaaggga tgtgaattat t                                              21

<210> SEQ ID NO 19
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 19
tcttatcttc ggcgctttaa t                                              21

<210> SEQ ID NO 20
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 20
cttatcttcg gcgctttaat t                                              21

<210> SEQ ID NO 21
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 21
ttatcttcgg cgctttaatt t                                              21

<210> SEQ ID NO 22
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 22
gaggagccca atgagtatta t                                              21

<210> SEQ ID NO 23
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 23
aggagcccaa tgagtattat t                                              21

<210> SEQ ID NO 24
<211> LENGTH: 21
<212> TYPE: DNA
<213> ORGANISM: Artificial Sequence
<220> FEATURE:
<223> OTHER INFORMATION: partial shRNA sequence, included in shRNA to
``` target TIM-3 for RNA interference

<400> SEQUENCE: 24
atagatccaa ccaccttatt t                                              21

<210> SEQ ID NO 25
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 25
atgtcattgc ctctgtattt a                                              21

<210> SEQ ID NO 26
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 26
tgtcattgcc tctgtattta a                                              21

<210> SEQ ID NO 27
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 27
accaccatgc ccagctaatt t                                              21

<210> SEQ ID NO 28
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 28
tgttgagatt taggcttatt t                                              21

<210> SEQ ID NO 29
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 29
gaccaaactg aagctatatt t                                              21

<210> SEQ ID NO 30
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 30
aggccttcag caatctatat t                                              21

<210> SEQ ID NO 31
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 31
ggccttcagc aatctatatt a                                              21

<210> SEQ ID NO 32
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 32
gagtggtccc taaacttaaa t                                              21

<210> SEQ ID NO 33
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 33
agtggtccct aaacttaaat t                                              21

<210> SEQ ID NO 34
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 34
gtggtcccta aacttaaatt t                                              21

<210> SEQ ID NO 35
<211> LENGTH: 19
<212> TYPE: DNA
<213> ORGANISM: Artificial Sequence
<220> FEATURE:
<223> OTHER INFORMATION: partial shRNA sequence, included in shRNA to
      target TIM-3 for RNA interference

<400> SEQUENCE: 35
ctaacacaaa tatccacat                                                 19

<210> SEQ ID NO 36
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

```
<400> SEQUENCE: 36
tcagcagccc agtccaaata a                                              21

<210> SEQ ID NO 37
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

<400> SEQUENCE: 37
cagcagccca gtccaaataa a                                              21

<210> SEQ ID NO 38
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

<400> SEQUENCE: 38
tcaacgtctc catcatgtat a                                              21

<210> SEQ ID NO 39
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

<400> SEQUENCE: 39
caacgtctcc atcatgtata a                                              21

<210> SEQ ID NO 40
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

<400> SEQUENCE: 40
ctggagacaa tggcgacttt a                                              21

<210> SEQ ID NO 41
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

<400> SEQUENCE: 41
ctcagcagcc cagtccaaat a                                              21

<210> SEQ ID NO 42
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAG-3 for RNA interference

<400> SEQUENCE: 42
```
agcagcccag tccaaataaa c                                    21

<210> SEQ ID NO 43
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 43
gggatcaaag ctatctatat a                                    21

<210> SEQ ID NO 44
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 44
ggatcaaagc tatctatata a                                    21

<210> SEQ ID NO 45
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 45
ggcaacggaa cccagattta t                                    21

<210> SEQ ID NO 46
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 46
tgaagaagag agtccatatt t                                    21

<210> SEQ ID NO 47
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 47
ttggatgcgg aacccaaatt a                                    21

<210> SEQ ID NO 48
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 48
agcatcactt gggattaata t                                              21

<210> SEQ ID NO 49
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 49
tgatgtgggt caaggaatta a                                              21

<210> SEQ ID NO 50
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 50
agcgagggag aagactatat t                                              21

<210> SEQ ID NO 51
<211> LENGTH: 21
<212> TYPE: DNA
<213> ORGANISM: Artificial Sequence
<220> FEATURE:
<223> OTHER INFORMATION: partial shRNA sequence, included in shRNA to
      target CTLA-4 for RNA interference

<400> SEQUENCE: 51
tttacgtatg agacgtttat a                                              21

<210> SEQ ID NO 52
<211> LENGTH: 21
<212> TYPE: DNA
<213> ORGANISM: Artificial Sequence
<220> FEATURE:
<223> OTHER INFORMATION: partial shRNA sequence, included in shRNA to
      target BTLA for RNA interference

<400> SEQUENCE: 52
gctcctgtat agtttacttc c                                              21

<210> SEQ ID NO 53
<211> LENGTH: 21
<212> TYPE: DNA
<213> ORGANISM: Artificial Sequence
<220> FEATURE:
<223> OTHER INFORMATION: partial shRNA sequence, included in shRNA to
      target BTLA for RNA interference

<400> SEQUENCE: 53
ggaaattaac ctggttgatg c                                              21

<210> SEQ ID NO 54
<211> LENGTH: 21
<212> TYPE: DNA
<213> ORGANISM: Artificial Sequence
<220> FEATURE:
<223> OTHER INFORMATION: partial shRNA sequence, included in shRNA to
      target BTLA for RNA interference

<400> SEQUENCE: 54
gcaccaacag aatatgcatc c                                              21

<210> SEQ ID NO 55
<211> LENGTH: 21
<212> TYPE: DNA
<213> ORGANISM: Artificial Sequence
<220> FEATURE:
<223> OTHER INFORMATION: partial shRNA sequence, included in shRNA to
      target BTLA for RNA interference

<400> SEQUENCE: 55
gctcaacagg atgtcaaata a                                             21

<210> SEQ ID NO 56
<211> LENGTH: 21
<212> TYPE: DNA
<213> ORGANISM: Artificial Sequence
<220> FEATURE:
<223> OTHER INFORMATION: partial shRNA sequence, included in shRNA to
      target BTLA for RNA interference

<400> SEQUENCE: 56
gcatcttgct gttcttctta c                                             21

<210> SEQ ID NO 57
<211> LENGTH: 21
<212> TYPE: DNA
<213> ORGANISM: Artificial Sequence
<220> FEATURE:
<223> OTHER INFORMATION: partial shRNA sequence, included in shRNA to
      target BTLA for RNA interference

<400> SEQUENCE: 57
gcatttgtgg acaacttatg t                                             21

<210> SEQ ID NO 58
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD160 for RNA interference

<400> SEQUENCE: 58
ggaacgcgac taaacttaat c                                             21

<210> SEQ ID NO 59
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD160 for RNA interference

<400> SEQUENCE: 59
gatgttcacc ataagccaag t                                             21

<210> SEQ ID NO 60
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD160 for RNA interference

<400> SEQUENCE: 60
gcaagatgag tctgactatg g                                             21

<210> SEQ ID NO 61
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD160 for RNA interference

<400> SEQUENCE: 61
ggcacagaga agaatgcaac a                                              21

<210> SEQ ID NO 62
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD160 for RNA interference

<400> SEQUENCE: 62
gggaagagat gctaaatata c                                              21

<210> SEQ ID NO 63
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD160 for RNA interference

<400> SEQUENCE: 63
gcaaatcagt gtaatccttg a                                              21

<210> SEQ ID NO 64
<211> LENGTH: 21
<212> TYPE: DNA
<213> ORGANISM: Artificial Sequence
<220> FEATURE:
<223> OTHER INFORMATION: partial shRNA sequence, included in shRNA to
      target VISTA for RNA interference

<400> SEQUENCE: 64
gcaacttctc catcaccatg c                                              21

<210> SEQ ID NO 65
<211> LENGTH: 21
<212> TYPE: DNA
<213> ORGANISM: Artificial Sequence
<220> FEATURE:
<223> OTHER INFORMATION: partial shRNA sequence, included in shRNA to
      target VISTA for RNA interference

<400> SEQUENCE: 65
gcaaagatgc accatccaac t                                              21

<210> SEQ ID NO 66
<211> LENGTH: 21
<212> TYPE: DNA
<213> ORGANISM: Artificial Sequence
<220> FEATURE:
<223> OTHER INFORMATION: partial shRNA sequence, included in shRNA to
      target VISTA for RNA interference

<400> SEQUENCE: 66
gcggatggac agcaacattc a                                              21

-continued

```
<210> SEQ ID NO 67
<211> LENGTH: 21
<212> TYPE: DNA
<213> ORGANISM: Artificial Sequence
<220> FEATURE:
<223> OTHER INFORMATION: partial shRNA sequence, included in shRNA to
      target VISTA for RNA interference

<400> SEQUENCE: 67
ggacacttct gagtatgaag c                                              21

<210> SEQ ID NO 68
<211> LENGTH: 21
<212> TYPE: DNA
<213> ORGANISM: Artificial Sequence
<220> FEATURE:
<223> OTHER INFORMATION: partial shRNA sequence, included in shRNA to
      target VISTA for RNA interference

<400> SEQUENCE: 68
gggaaccaca atgcacgaaa g                                              21

<210> SEQ ID NO 69
<211> LENGTH: 21
<212> TYPE: DNA
<213> ORGANISM: Artificial Sequence
<220> FEATURE:
<223> OTHER INFORMATION: partial shRNA sequence, included in shRNA to
      target VISTA for RNA interference

<400> SEQUENCE: 69
ggtgctttcc aacacacttt c                                              21

<210> SEQ ID NO 70
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIGIT for RNA interference

<400> SEQUENCE: 70
gcttctggcc atttgtaatg c                                              21

<210> SEQ ID NO 71
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIGIT for RNA interference

<400> SEQUENCE: 71
gggagtactt ctgcatctat c                                              21

<210> SEQ ID NO 72
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIGIT for RNA interference

<400> SEQUENCE: 72
gctgcatgac tacttcaatg t                                              21

<210> SEQ ID NO 73
```

```
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIGIT for RNA interference

<400> SEQUENCE: 73
taacgtggat cttgatcata a                                              21

<210> SEQ ID NO 74
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIGIT for RNA interference

<400> SEQUENCE: 74
ggagacatac acaggccttc a                                              21

<210> SEQ ID NO 75
<211> LENGTH: 21
<212> TYPE: DNA
<213> ORGANISM: Artificial Sequence
<220> FEATURE:
<223> OTHER INFORMATION: partial shRNA sequence, included in shRNA to
      target TIGIT for RNA interference

<400> SEQUENCE: 75
gcatttgggc cttgatctac c                                              21

<210> SEQ ID NO 76
<211> LENGTH: 21
<212> TYPE: DNA
<213> ORGANISM: Artificial Sequence
<220> FEATURE:
<223> OTHER INFORMATION: partial shRNA sequence, included in shRNA to
      target 2B4 for RNA interference

<400> SEQUENCE: 76
gacaggttgc aaggcagttc t                                              21

<210> SEQ ID NO 77
<211> LENGTH: 21
<212> TYPE: DNA
<213> ORGANISM: Artificial Sequence
<220> FEATURE:
<223> OTHER INFORMATION: partial shRNA sequence, included in shRNA to
      target 2B4 for RNA interference

<400> SEQUENCE: 77
gggagtgcct cttcagttac a                                              21

<210> SEQ ID NO 78
<211> LENGTH: 21
<212> TYPE: DNA
<213> ORGANISM: Artificial Sequence
<220> FEATURE:
<223> OTHER INFORMATION: partial shRNA sequence, included in shRNA to
      target 2B4 for RNA interference

<400> SEQUENCE: 78
ggacgaggag gttgacatta a                                              21

<210> SEQ ID NO 79
<211> LENGTH: 21
```

```
<212> TYPE: DNA
<213> ORGANISM: Artificial Sequence
<220> FEATURE:
<223> OTHER INFORMATION: partial shRNA sequence, included in shRNA to
      target 2B4 for RNA interference

<400> SEQUENCE: 79
gaggagaaag aggaaggaga a                                              21

<210> SEQ ID NO 80
<211> LENGTH: 21
<212> TYPE: DNA
<213> ORGANISM: Artificial Sequence
<220> FEATURE:
<223> OTHER INFORMATION: partial shRNA sequence, included in shRNA to
      target 2B4 for RNA interference

<400> SEQUENCE: 80
gcccttcctt caatagcact a                                              21

<210> SEQ ID NO 81
<211> LENGTH: 21
<212> TYPE: DNA
<213> ORGANISM: Artificial Sequence
<220> FEATURE:
<223> OTHER INFORMATION: partial shRNA sequence, included in shRNA to
      target 2B4 for RNA interference

<400> SEQUENCE: 81
ggttgactgc atttctagac t                                              21

<210> SEQ ID NO 82
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-L1 for RNA interference

<400> SEQUENCE: 82
gcatttgctg aacgcattta c                                              21

<210> SEQ ID NO 83
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-L1 for RNA interference

<400> SEQUENCE: 83
gctgcactaa ttgtctattg g                                              21

<210> SEQ ID NO 84
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-L1 for RNA interference

<400> SEQUENCE: 84
ggatccagtc acctctgaac a                                              21

<210> SEQ ID NO 85
<211> LENGTH: 21
<212> TYPE: DNA
```

```
<213> ORGANISM: Artificial Sequence
<220> FEATURE:
<223> OTHER INFORMATION: partial shRNA sequence, included in shRNA to
      target PD-L1 for RNA interference

<400> SEQUENCE: 85
gcacatcctc caaatgaaag g                                              21

<210> SEQ ID NO 86
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-L1 for RNA interference

<400> SEQUENCE: 86
ggattctcaa cctgtggttt a                                              21

<210> SEQ ID NO 87
<211> LENGTH: 21
<212> TYPE: DNA
<213> ORGANISM: Artificial Sequence
<220> FEATURE:
<223> OTHER INFORMATION: partial shRNA sequence, included in shRNA to
      target PD-L1 for RNA interference

<400> SEQUENCE: 87
ggtgcttggt ctcctctata a                                              21

<210> SEQ ID NO 88
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-1 for RNA interference

<400> SEQUENCE: 88
gcacagtact cctggcttat c                                              21

<210> SEQ ID NO 89
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-1 for RNA interference

<400> SEQUENCE: 89
gcaacaggac cacagtcaag a                                              21

<210> SEQ ID NO 90
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-1 for RNA interference

<400> SEQUENCE: 90
gcaacaccac cctcagcata a                                              21

<210> SEQ ID NO 91
<211> LENGTH: 21
<212> TYPE: DNA
<213> ORGANISM: Artificial Sequence
```

<220> FEATURE:
<223> OTHER INFORMATION: partial shRNA sequence, included in shRNA to
       target CEACAM-1 for RNA interference

<400> SEQUENCE: 91
gcctgttcag agcactcatt c    21

<210> SEQ ID NO 92
<211> LENGTH: 21
<212> TYPE: DNA
<213> ORGANISM: Artificial Sequence
<220> FEATURE:
<223> OTHER INFORMATION: partial shRNA sequence, included in shRNA to
       target CEACAM-1 for RNA interference

<400> SEQUENCE: 92
gcagtaatgc cttctcctat t    21

<210> SEQ ID NO 93
<211> LENGTH: 21
<212> TYPE: DNA
<213> ORGANISM: Artificial Sequence
<220> FEATURE:
<223> OTHER INFORMATION: partial shRNA sequence, included in shRNA to
       target CEACAM-1 for RNA interference

<400> SEQUENCE: 93
gcaccttggt gcttagctag a    21

<210> SEQ ID NO 94
<211> LENGTH: 21
<212> TYPE: DNA
<213> ORGANISM: Artificial Sequence
<220> FEATURE:
<223> OTHER INFORMATION: partial shRNA sequence, included in shRNA to
       target CEACAM-3 for RNA interference

<400> SEQUENCE: 94
gcttccatct atgaggaatt g    21

<210> SEQ ID NO 95
<211> LENGTH: 21
<212> TYPE: DNA
<213> ORGANISM: Artificial Sequence
<220> FEATURE:
<223> OTHER INFORMATION: partial shRNA sequence, included in shRNA to
       target CEACAM-3 for RNA interference

<400> SEQUENCE: 95
gccagagaac cagctataag t    21

<210> SEQ ID NO 96
<211> LENGTH: 21
<212> TYPE: DNA
<213> ORGANISM: Artificial Sequence
<220> FEATURE:
<223> OTHER INFORMATION: partial shRNA sequence, included in shRNA to
       target CEACAM-3 for RNA interference

<400> SEQUENCE: 96
gggtccctga tgaatatctg g    21

<210> SEQ ID NO 97
<211> LENGTH: 21
<212> TYPE: DNA
<213> ORGANISM: Artificial Sequence
<220> FEATURE:

```
<223> OTHER INFORMATION: partial shRNA sequence, included in shRNA to
      target CEACAM-3 for RNA interference

<400> SEQUENCE: 97
ggcttgcagg gaaagtgaat g                                              21

<210> SEQ ID NO 98
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-3 for RNA interference

<400> SEQUENCE: 98
gcttgcaggg aaagtgaatg g                                              21

<210> SEQ ID NO 99
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-3 for RNA interference

<400> SEQUENCE: 99
agcttccatc tatgaggaat t                                              21

<210> SEQ ID NO 100
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-5 for RNA interference

<400> SEQUENCE: 100
ggaatccaga acgaattaag t                                              21

<210> SEQ ID NO 101
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-5 for RNA interference

<400> SEQUENCE: 101
ggctgattga tgggaacatc c                                              21

<210> SEQ ID NO 102
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-5 for RNA interference

<400> SEQUENCE: 102
ggactacagt caagacaatc a                                              21

<210> SEQ ID NO 103
<211> LENGTH: 21
<212> TYPE: DNA
<213> ORGANISM: Artificial Sequence
<220> FEATURE:
<223> OTHER INFORMATION: partial shRNA sequence, included in shRNA to
``` target CEACAM-5 for RNA interference

<400> SEQUENCE: 103
ggaccctcac tctattcaat g                                           21

<210> SEQ ID NO 104
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-5 for RNA interference

<400> SEQUENCE: 104
gctactggcc gcaataattc c                                           21

<210> SEQ ID NO 105
<211> LENGTH: 21
<212> TYPE: DNA
<213> ORGANISM: Artificial Sequence
<220> FEATURE:
<223> OTHER INFORMATION: partial shRNA sequence, included in shRNA to
      target CEACAM-5 for RNA interference

<400> SEQUENCE: 105
gctctttgta tgacagaata c                                           21

<210> SEQ ID NO 106
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD96 for RNA interference

<400> SEQUENCE: 106
ggtccaaggt caccaataag a                                           21

<210> SEQ ID NO 107
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD96 for RNA interference

<400> SEQUENCE: 107
gcaaccatac gatagaaata g                                           21

<210> SEQ ID NO 108
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD96 for RNA interference

<400> SEQUENCE: 108
ggttctgaaa tttcctcaac a                                           21

<210> SEQ ID NO 109
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD96 for RNA interference

<400> SEQUENCE: 109
gcaagatatc cagctacatc t                                              21

<210> SEQ ID NO 110
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD96 for RNA interference

<400> SEQUENCE: 110
gcaactcacc ctcttccatc t                                              21

<210> SEQ ID NO 111
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD96 for RNA interference

<400> SEQUENCE: 111
gctgcattcc ctaagataat t                                              21

<210> SEQ ID NO 112
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAIR1 for RNA interference

<400> SEQUENCE: 112
gggacagtag atccacatac a                                              21

<210> SEQ ID NO 113
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAIR1 for RNA interference

<400> SEQUENCE: 113
ggacaacagt cacaatgagc a                                              21

<210> SEQ ID NO 114
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAIR1 for RNA interference

<400> SEQUENCE: 114
ggctgttgat gttctagaga g                                              21

<210> SEQ ID NO 115
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAIR1 for RNA interference

```
<400> SEQUENCE: 115
gcagacaagg ccacagtcaa t                                              21

<210> SEQ ID NO 116
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAIR1 for RNA interference

<400> SEQUENCE: 116
ggaggtttct aaccagcatc c                                              21

<210> SEQ ID NO 117
<211> LENGTH: 21
<212> TYPE: DNA
<213> ORGANISM: Artificial Sequence
<220> FEATURE:
<223> OTHER INFORMATION: partial shRNA sequence, included in shRNA to
      target LAIR1 for RNA interference

<400> SEQUENCE: 117
gccttgagac tgtgctatac a                                              21

<210> SEQ ID NO 118
<211> LENGTH: 21
<212> TYPE: DNA
<213> ORGANISM: Artificial Sequence
<220> FEATURE:
<223> OTHER INFORMATION: partial shRNA sequence, included in shRNA to
      target KLRG1 for RNA interference

<400> SEQUENCE: 118
ccaagcccag aatgactatg g                                              21

<210> SEQ ID NO 119
<211> LENGTH: 21
<212> TYPE: DNA
<213> ORGANISM: Artificial Sequence
<220> FEATURE:
<223> OTHER INFORMATION: partial shRNA sequence, included in shRNA to
      target KLRG1 for RNA interference

<400> SEQUENCE: 119
gccttcttgt tcttgccttg t                                              21

<210> SEQ ID NO 120
<211> LENGTH: 21
<212> TYPE: DNA
<213> ORGANISM: Artificial Sequence
<220> FEATURE:
<223> OTHER INFORMATION: partial shRNA sequence, included in shRNA to
      target KLRG1 for RNA interference

<400> SEQUENCE: 120
gcttctgact gcagttcttc t                                              21

<210> SEQ ID NO 121
<211> LENGTH: 21
<212> TYPE: DNA
<213> ORGANISM: Artificial Sequence
<220> FEATURE:
<223> OTHER INFORMATION: partial shRNA sequence, included in shRNA to
      target KLRG1 for RNA interference

<400> SEQUENCE: 121
```
gctggatgaa atatggtaac c                                              21

<210> SEQ ID NO 122
<211> LENGTH: 21
<212> TYPE: DNA
<213> ORGANISM: Artificial Sequence
<220> FEATURE:
<223> OTHER INFORMATION: partial shRNA sequence, included in shRNA to
      target KLRG1 for RNA interference

<400> SEQUENCE: 122
ggaaatgagc ctgctccaag t                                              21

<210> SEQ ID NO 123
<211> LENGTH: 21
<212> TYPE: DNA
<213> ORGANISM: Artificial Sequence
<220> FEATURE:
<223> OTHER INFORMATION: partial shRNA sequence, included in shRNA to
      target KLRG1 for RNA interference

<400> SEQUENCE: 123
ggattggtct gaggaacaat t                                              21

<210> SEQ ID NO 124
<211> LENGTH: 21
<212> TYPE: DNA
<213> ORGANISM: Artificial Sequence
<220> FEATURE:
<223> OTHER INFORMATION: partial shRNA sequence, included in shRNA to
      target FAS for RNA interference

<400> SEQUENCE: 124
gccaagaagg gaaggagtac a                                              21

<210> SEQ ID NO 125
<211> LENGTH: 21
<212> TYPE: DNA
<213> ORGANISM: Artificial Sequence
<220> FEATURE:
<223> OTHER INFORMATION: partial shRNA sequence, included in shRNA to
      target FAS for RNA interference

<400> SEQUENCE: 125
gccaattcca ctaattgttt g                                              21

<210> SEQ ID NO 126
<211> LENGTH: 21
<212> TYPE: DNA
<213> ORGANISM: Artificial Sequence
<220> FEATURE:
<223> OTHER INFORMATION: partial shRNA sequence, included in shRNA to
      target FAS for RNA interference

<400> SEQUENCE: 126
ggttctcatg aatctccaac t                                              21

<210> SEQ ID NO 127
<211> LENGTH: 21
<212> TYPE: DNA
<213> ORGANISM: Artificial Sequence
<220> FEATURE:
<223> OTHER INFORMATION: partial shRNA sequence, included in shRNA to
      target FAS for RNA interference

<400> SEQUENCE: 127

```
gctggagtca tgacactaag t                                              21

<210> SEQ ID NO 128
<211> LENGTH: 21
<212> TYPE: DNA
<213> ORGANISM: Artificial Sequence
<220> FEATURE:
<223> OTHER INFORMATION: partial shRNA sequence, included in shRNA to
      target FAS for RNA interference

<400> SEQUENCE: 128
gcctggtttg gagatactaa c                                              21

<210> SEQ ID NO 129
<211> LENGTH: 21
<212> TYPE: DNA
<213> ORGANISM: Artificial Sequence
<220> FEATURE:
<223> OTHER INFORMATION: partial shRNA sequence, included in shRNA to
      target FAS for RNA interference

<400> SEQUENCE: 129
ggaaccacct aaagaacttc c                                              21

<210> SEQ ID NO 130
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-b for RNA interference

<400> SEQUENCE: 130
ccgcgttgat ttaaagaaag a                                              21

<210> SEQ ID NO 131
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-b for RNA interference

<400> SEQUENCE: 131
gcctgataca tatcagcatt t                                              21

<210> SEQ ID NO 132
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-b for RNA interference

<400> SEQUENCE: 132
gcggaattgg aatttcttag c                                              21

<210> SEQ ID NO 133
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-b for RNA interference

<400> SEQUENCE: 133
gcacgactac agaaatatag c                                              21
```

<210> SEQ ID NO 134
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-b for RNA interference

<400> SEQUENCE: 134
tttccggtta agttgcactc g                                              21

<210> SEQ ID NO 135
<211> LENGTH: 21
<212> TYPE: DNA
<213> ORGANISM: Artificial Sequence
<220> FEATURE:
<223> OTHER INFORMATION: partial shRNA sequence, included in shRNA to
       target Cbl-b for RNA interference

<400> SEQUENCE: 135
gcctggatct aattcagaaa g                                              21

<210> SEQ ID NO 136
<211> LENGTH: 21
<212> TYPE: DNA
<213> ORGANISM: Artificial Sequence
<220> FEATURE:
<223> OTHER INFORMATION: partial shRNA sequence, included in shRNA to
      target LRR1 for RNA interference

<400> SEQUENCE: 136
gaaagccact gttcggttaa a                                              21

<210> SEQ ID NO 137
<211> LENGTH: 21
<212> TYPE: DNA
<213> ORGANISM: Artificial Sequence
<220> FEATURE:
<223> OTHER INFORMATION: partial shRNA sequence, included in shRNA to
      target LRR1 for RNA interference

<400> SEQUENCE: 137
tcctgtggat atctgtctaa g                                              21

<210> SEQ ID NO 138
<211> LENGTH: 21
<212> TYPE: DNA
<213> ORGANISM: Artificial Sequence
<220> FEATURE:
<223> OTHER INFORMATION: partial shRNA sequence, included in shRNA to
      target LRR1 for RNA interference

<400> SEQUENCE: 138
ggctcataga ggctgtaatg t                                              21

<210> SEQ ID NO 139
<211> LENGTH: 21
<212> TYPE: DNA
<213> ORGANISM: Artificial Sequence
<220> FEATURE:
<223> OTHER INFORMATION: partial shRNA sequence, included in shRNA to
      target LRR1 for RNA interference

<400> SEQUENCE: 139
gggcttgtcc gagttgatat g                                              21

<210> SEQ ID NO 140
<211> LENGTH: 21
<212> TYPE: DNA
<213> ORGANISM: Artificial Sequence
<220> FEATURE:
<223> OTHER INFORMATION: partial shRNA sequence, included in shRNA to target LRR1 for RNA interference

<400> SEQUENCE: 140
aagatttgga taccgcaaaa a                                              21

<210> SEQ ID NO 141
<211> LENGTH: 21
<212> TYPE: DNA
<213> ORGANISM: Artificial Sequence
<220> FEATURE:
<223> OTHER INFORMATION: partial shRNA sequence, included in shRNA to target LRR1 for RNA interference

<400> SEQUENCE: 141
gtggtactga agcacctatt a                                              21

<210> SEQ ID NO 142
<211> LENGTH: 21
<212> TYPE: DNA
<213> ORGANISM: Artificial Sequence
<220> FEATURE:
<223> OTHER INFORMATION: partial shRNA sequence, included in shRNA to target TGFBR1 for RNA interference

<400> SEQUENCE: 142
gcttgttcag agaacaattg c                                              21

<210> SEQ ID NO 143
<211> LENGTH: 21
<212> TYPE: DNA
<213> ORGANISM: Artificial Sequence
<220> FEATURE:
<223> OTHER INFORMATION: partial shRNA sequence, included in shRNA to target TGFBR1 for RNA interference

<400> SEQUENCE: 143
ggagattgtt ggtacccaag g                                              21

<210> SEQ ID NO 144
<211> LENGTH: 21
<212> TYPE: DNA
<213> ORGANISM: Artificial Sequence
<220> FEATURE:
<223> OTHER INFORMATION: partial shRNA sequence, included in shRNA to target TGFBR1 for RNA interference

<400> SEQUENCE: 144
gcagctaggc ttacagcatt g                                              21

<210> SEQ ID NO 145
<211> LENGTH: 21
<212> TYPE: DNA
<213> ORGANISM: Artificial Sequence
<220> FEATURE:
<223> OTHER INFORMATION: partial shRNA sequence, included in shRNA to target TGFBR1 for RNA interference

<400> SEQUENCE: 145
ggtcctttct gtgcactatg a                                              21

-continued

```
<210> SEQ ID NO 146
<211> LENGTH: 21
<212> TYPE: DNA
<213> ORGANISM: Artificial Sequence
<220> FEATURE:
<223> OTHER INFORMATION: partial shRNA sequence, included in shRNA to
      target TGFBR1 for RNA interference

<400> SEQUENCE: 146
ggtggtagct aaagaacatt c                                              21

<210> SEQ ID NO 147
<211> LENGTH: 21
<212> TYPE: DNA
<213> ORGANISM: Artificial Sequence
<220> FEATURE:
<223> OTHER INFORMATION: partial shRNA sequence, included in shRNA to
      target TGFBR1 for RNA interference

<400> SEQUENCE: 147
ggacctgtct acaggtgatc t                                              21

<210> SEQ ID NO 148
<211> LENGTH: 21
<212> TYPE: DNA
<213> ORGANISM: Artificial Sequence
<220> FEATURE:
<223> OTHER INFORMATION: partial shRNA sequence, included in shRNA to
      target DNMT3A for RNA interference

<400> SEQUENCE: 148
gccaaggtca ttgcaggaat g                                              21

<210> SEQ ID NO 149
<211> LENGTH: 21
<212> TYPE: DNA
<213> ORGANISM: Artificial Sequence
<220> FEATURE:
<223> OTHER INFORMATION: partial shRNA sequence, included in shRNA to
      target DNMT3A for RNA interference

<400> SEQUENCE: 149
gcagaacaag cccatgattg a                                              21

<210> SEQ ID NO 150
<211> LENGTH: 21
<212> TYPE: DNA
<213> ORGANISM: Artificial Sequence
<220> FEATURE:
<223> OTHER INFORMATION: partial shRNA sequence, included in shRNA to
      target DNMT3A for RNA interference

<400> SEQUENCE: 150
cccaaggtca aggagattat t                                              21

<210> SEQ ID NO 151
<211> LENGTH: 21
<212> TYPE: DNA
<213> ORGANISM: Artificial Sequence
<220> FEATURE:
<223> OTHER INFORMATION: partial shRNA sequence, included in shRNA to
      target DNMT3A for RNA interference

<400> SEQUENCE: 151
gcagaagtgc cggaacattg a                                              21

<210> SEQ ID NO 152
```

```
<211> LENGTH: 21
<212> TYPE: DNA
<213> ORGANISM: Artificial Sequence
<220> FEATURE:
<223> OTHER INFORMATION: partial shRNA sequence, included in shRNA to
      target DNMT3A for RNA interference

<400> SEQUENCE: 152
gcgtcacaca gaagcatatc c                                              21

<210> SEQ ID NO 153
<211> LENGTH: 21
<212> TYPE: DNA
<213> ORGANISM: Artificial Sequence
<220> FEATURE:
<223> OTHER INFORMATION: partial shRNA sequence, included in shRNA to
      target DNMT3A for RNA interference

<400> SEQUENCE: 153
ccggctcttc tttgagttct a                                              21

<210> SEQ ID NO 154
<211> LENGTH: 21
<212> TYPE: DNA
<213> ORGANISM: Artificial Sequence
<220> FEATURE:
<223> OTHER INFORMATION: partial shRNA sequence, included in shRNA to
      target A2aR for RNA interference

<400> SEQUENCE: 154
cagaacgtca ccaactactt t                                              21

<210> SEQ ID NO 155
<211> LENGTH: 21
<212> TYPE: DNA
<213> ORGANISM: Artificial Sequence
<220> FEATURE:
<223> OTHER INFORMATION: partial shRNA sequence, included in shRNA to
      target A2aR for RNA interference

<400> SEQUENCE: 155
ccatgctagg ttggaacaac t                                              21

<210> SEQ ID NO 156
<211> LENGTH: 21
<212> TYPE: DNA
<213> ORGANISM: Artificial Sequence
<220> FEATURE:
<223> OTHER INFORMATION: partial shRNA sequence, included in shRNA to
      target A2aR for RNA interference

<400> SEQUENCE: 156
ccaagtggcc tgtctctttg a                                              21

<210> SEQ ID NO 157
<211> LENGTH: 21
<212> TYPE: DNA
<213> ORGANISM: Artificial Sequence
<220> FEATURE:
<223> OTHER INFORMATION: partial shRNA sequence, included in shRNA to
      target A2aR for RNA interference

<400> SEQUENCE: 157
ggtgtctatt tgcggatctt c                                              21

<210> SEQ ID NO 158
<211> LENGTH: 21
```

```
<212> TYPE: DNA
<213> ORGANISM: Artificial Sequence
<220> FEATURE:
<223> OTHER INFORMATION: partial shRNA sequence, included in shRNA to
      target A2aR for RNA interference

<400> SEQUENCE: 158
agaccttccg caagatcatt c                                              21

<210> SEQ ID NO 159
<211> LENGTH: 21
<212> TYPE: DNA
<213> ORGANISM: Artificial Sequence
<220> FEATURE:
<223> OTHER INFORMATION: partial shRNA sequence, included in shRNA to
      target A2aR for RNA interference

<400> SEQUENCE: 159
tccttagcca tgagctcaag g                                              21

<210> SEQ ID NO 160
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-c for RNA interference

<400> SEQUENCE: 160
gaaagtactg tggacacatg t                                              21

<210> SEQ ID NO 161
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-c for RNA interference

<400> SEQUENCE: 161
gcacgtgtcc atcttcgagt t                                              21

<210> SEQ ID NO 162
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-c for RNA interference

<400> SEQUENCE: 162
ggccaacact cctcaagaac t                                              21

<210> SEQ ID NO 163
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-c for RNA interference

<400> SEQUENCE: 163
ggcttctacc tctacccaga t                                              21

<210> SEQ ID NO 164
<211> LENGTH: 21
<212> TYPE: DNA
```

```
<213> ORGANISM: Artificial Sequence
<220> FEATURE:
<223> OTHER INFORMATION: partial shRNA sequence, included in shRNA to
      target Cbl-c for RNA interference

<400> SEQUENCE: 164
ggccatggac tccacatttg a                                              21

<210> SEQ ID NO 165
<211> LENGTH: 21
<212> TYPE: DNA
<213> ORGANISM: Artificial Sequence
<220> FEATURE:
<223> OTHER INFORMATION: partial shRNA sequence, included in shRNA to
      target Cbl-c for RNA interference

<400> SEQUENCE: 165
ggccgtgagt atctaccagt t                                              21

<210> SEQ ID NO 166
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK alpha for RNA interference

<400> SEQUENCE: 166
gccagaagac aagttagaat t                                              21

<210> SEQ ID NO 167
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK alpha for RNA interference

<400> SEQUENCE: 167
gctctggaag ttccagtata t                                              21

<210> SEQ ID NO 168
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK alpha for RNA interference

<400> SEQUENCE: 168
ggaaatgatc tggctcgatg c                                              21

<210> SEQ ID NO 169
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK alpha for RNA interference

<400> SEQUENCE: 169
gcaaagatcc tcaaggattt a                                              21

<210> SEQ ID NO 170
<211> LENGTH: 21
<212> TYPE: DNA
<213> ORGANISM: Artificial Sequence
```

<220> FEATURE:
<223> OTHER INFORMATION: partial shRNA sequence, included in shRNA to
      target DGK alpha for RNA interference

<400> SEQUENCE: 170
ggatgcctct attgctcatc g                                           21

<210> SEQ ID NO 171
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK alpha for RNA interference

<400> SEQUENCE: 171
gctatggtac ttcgaatttg c                                           21

<210> SEQ ID NO 172
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK zeta for RNA interference

<400> SEQUENCE: 172
ggaagggatt ccagcagaag t                                           21

<210> SEQ ID NO 173
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK zeta for RNA interference

<400> SEQUENCE: 173
gcaaggagat tgtggccatc a                                           21

<210> SEQ ID NO 174
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK zeta for RNA interference

<400> SEQUENCE: 174
gggcatcctt caagaggaag t                                           21

<210> SEQ ID NO 175
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK zeta for RNA interference

<400> SEQUENCE: 175
gcaaagatca tccagtcttt c                                           21

<210> SEQ ID NO 176
<211> LENGTH: 21
<212> TYPE: DNA
<213> ORGANISM: Artificial Sequence
<220> FEATURE:

```
<223> OTHER INFORMATION: partial shRNA sequence, included in shRNA to
      target DGK zeta for RNA interference

<400> SEQUENCE: 176
gctggagatg taccgcaaag t                                             21

<210> SEQ ID NO 177
<211> LENGTH: 21
<212> TYPE: DNA
<213> ORGANISM: Artificial Sequence
<220> FEATURE:
<223> OTHER INFORMATION: partial shRNA sequence, included in shRNA to
      target DGK zeta for RNA interference

<400> SEQUENCE: 177
gcacaggatg agatttatat c                                             21

<210> SEQ ID NO 178
<211> LENGTH: 21
<212> TYPE: DNA
<213> ORGANISM: Artificial Sequence
<220> FEATURE:
<223> OTHER INFORMATION: partial shRNA sequence, included in shRNA to
      target MerTK for RNA interference

<400> SEQUENCE: 178
ggaagaccac atacaggaaa c                                             21

<210> SEQ ID NO 179
<211> LENGTH: 21
<212> TYPE: DNA
<213> ORGANISM: Artificial Sequence
<220> FEATURE:
<223> OTHER INFORMATION: partial shRNA sequence, included in shRNA to
      target MerTK for RNA interference

<400> SEQUENCE: 179
gcattggtgt ttcctgcatg a                                             21

<210> SEQ ID NO 180
<211> LENGTH: 21
<212> TYPE: DNA
<213> ORGANISM: Artificial Sequence
<220> FEATURE:
<223> OTHER INFORMATION: partial shRNA sequence, included in shRNA to
      target MerTK for RNA interference

<400> SEQUENCE: 180
gcacacggtt gggtagatta t                                             21

<210> SEQ ID NO 181
<211> LENGTH: 21
<212> TYPE: DNA
<213> ORGANISM: Artificial Sequence
<220> FEATURE:
<223> OTHER INFORMATION: partial shRNA sequence, included in shRNA to
      target MerTK for RNA interference

<400> SEQUENCE: 181
gggtctgtaa tggaaggaaa t                                             21

<210> SEQ ID NO 182
<211> LENGTH: 21
<212> TYPE: DNA
<213> ORGANISM: Artificial Sequence
<220> FEATURE:
<223> OTHER INFORMATION: partial shRNA sequence, included in shRNA to
``` target MerTK for RNA interference

<400> SEQUENCE: 182
gcatgttgcg agatgacatg a                                              21

<210> SEQ ID NO 183
<211> LENGTH: 21
<212> TYPE: DNA
<213> ORGANISM: Artificial Sequence
<220> FEATURE:
<223> OTHER INFORMATION: partial shRNA sequence, included in shRNA to
      target MerTK for RNA interference

<400> SEQUENCE: 183
gcagaccgag tctacacaag t                                              21

<210> SEQ ID NO 184
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP1 for RNA interference

<400> SEQUENCE: 184
gcaccatcat ccacctcaag t                                              21

<210> SEQ ID NO 185
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP1 for RNA interference

<400> SEQUENCE: 185
ggtcacccac atcaaggtca t                                              21

<210> SEQ ID NO 186
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP1 for RNA interference

<400> SEQUENCE: 186
gggcaagaac cgctacaaga a                                              21

<210> SEQ ID NO 187
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP1 for RNA interference

<400> SEQUENCE: 187
ggaacaaatg cgtcccatac t                                              21

<210> SEQ ID NO 188
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP1 for RNA interference

<400> SEQUENCE: 188
gcctggactg tgacattgac a                                              21

<210> SEQ ID NO 189
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP1 for RNA interference

<400> SEQUENCE: 189
gaacctgcac actaagaaca a                                              21

<210> SEQ ID NO 190
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP2 for RNA interference

<400> SEQUENCE: 190
gcagatccta cctctgaaag g                                              21

<210> SEQ ID NO 191
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP2 for RNA interference

<400> SEQUENCE: 191
gcaatgacgg caagtctaaa g                                              21

<210> SEQ ID NO 192
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP2 for RNA interference

<400> SEQUENCE: 192
ggaactgaaa tacgacgttg g                                              21

<210> SEQ ID NO 193
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP2 for RNA interference

<400> SEQUENCE: 193
gcgtgttagg aacgtcaaag a                                              21

<210> SEQ ID NO 194
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP2 for RNA interference

```
<400> SEQUENCE: 194
gctcatgact atacgctaag a                                        21

<210> SEQ ID NO 195
<211> LENGTH: 21
<212> TYPE: DNA
<213> ORGANISM: Artificial Sequence
<220> FEATURE:
<223> OTHER INFORMATION: partial shRNA sequence, included in shRNA to
      target SHP2 for RNA interference

<400> SEQUENCE: 195
ggagagaacg gtctggcaat a                                        21

<210> SEQ ID NO 196
<211> LENGTH: 21
<212> TYPE: DNA
<213> ORGANISM: Artificial Sequence
<220> FEATURE:
<223> OTHER INFORMATION: partial shRNA sequence, included in shRNA to
      target PP2A for RNA interference

<400> SEQUENCE: 196
gcagctgaac gagaaccaag t                                        21

<210> SEQ ID NO 197
<211> LENGTH: 21
<212> TYPE: DNA
<213> ORGANISM: Artificial Sequence
<220> FEATURE:
<223> OTHER INFORMATION: partial shRNA sequence, included in shRNA to
      target PP2A for RNA interference

<400> SEQUENCE: 197
ggagactgtg actcttcttg t                                        21

<210> SEQ ID NO 198
<211> LENGTH: 21
<212> TYPE: DNA
<213> ORGANISM: Artificial Sequence
<220> FEATURE:
<223> OTHER INFORMATION: partial shRNA sequence, included in shRNA to
      target PP2A for RNA interference

<400> SEQUENCE: 198
ggaatgccaa cgtttggaaa t                                        21

<210> SEQ ID NO 199
<211> LENGTH: 21
<212> TYPE: DNA
<213> ORGANISM: Artificial Sequence
<220> FEATURE:
<223> OTHER INFORMATION: partial shRNA sequence, included in shRNA to
      target PP2A for RNA interference

<400> SEQUENCE: 199
ggatcgttta caggaagttc c                                        21

<210> SEQ ID NO 200
<211> LENGTH: 21
<212> TYPE: DNA
<213> ORGANISM: Artificial Sequence
<220> FEATURE:
<223> OTHER INFORMATION: partial shRNA sequence, included in shRNA to
      target PP2A for RNA interference

<400> SEQUENCE: 200
```
gcctttgtat gtggaagtat a                                          21

<210> SEQ ID NO 201
<211> LENGTH: 21
<212> TYPE: DNA
<213> ORGANISM: Artificial Sequence
<220> FEATURE:
<223> OTHER INFORMATION: partial shRNA sequence, included in shRNA to
      target PP2A for RNA interference

<400> SEQUENCE: 201
gcctgctgta tttatagtaa c                                          21

<210> SEQ ID NO 202
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD45 for RNA interference

<400> SEQUENCE: 202
gctgcacatc aaggagtaat t                                          21

<210> SEQ ID NO 203
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD45 for RNA interference

<400> SEQUENCE: 203
gctggaaata ctctggttag a                                          21

<210> SEQ ID NO 204
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD45 for RNA interference

<400> SEQUENCE: 204
ggagcttgtt gaaagggatg a                                          21

<210> SEQ ID NO 205
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD45 for RNA interference

<400> SEQUENCE: 205
gcagaatact ggccgtcaat g                                          21

<210> SEQ ID NO 206
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD45 for RNA interference

<400> SEQUENCE: 206
ggttatgttg tcaagctaag g                                            21

<210> SEQ ID NO 207
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD45 for RNA interference

<400> SEQUENCE: 207
gcagaaccca aggaattaat c                                            21

<210> SEQ ID NO 208
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD148 for RNA interference

<400> SEQUENCE: 208
ggtgtaacat cacaggctta c                                            21

<210> SEQ ID NO 209
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD148 for RNA interference

<400> SEQUENCE: 209
gccatagagt tcaggacaaa t                                            21

<210> SEQ ID NO 210
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD148 for RNA interference

<400> SEQUENCE: 210
gcaattctcg ggtagaaata a                                            21

<210> SEQ ID NO 211
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD148 for RNA interference

<400> SEQUENCE: 211
gctggcttca ccaacattac c                                            21

<210> SEQ ID NO 212
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD148 for RNA interference

<400> SEQUENCE: 212
gggagcaaat catctgcatt c                                            21

<210> SEQ ID NO 213
<211> LENGTH: 21
<212> TYPE: DNA
<213> ORGANISM: Artificial Sequence
<220> FEATURE:
<223> OTHER INFORMATION: partial shRNA sequence, included in shRNA to
      target CD148 for RNA interference

<400> SEQUENCE: 213
gcgactcaaa tatcaccttg a                                            21

<210> SEQ ID NO 214
<211> LENGTH: 21
<212> TYPE: DNA
<213> ORGANISM: Artificial Sequence
<220> FEATURE:
<223> OTHER INFORMATION: partial shRNA sequence, included in shRNA to
      target IL-10R alpha for RNA interference

<400> SEQUENCE: 214
gctcctgagg tatggaatag a                                            21

<210> SEQ ID NO 215
<211> LENGTH: 21
<212> TYPE: DNA
<213> ORGANISM: Artificial Sequence
<220> FEATURE:
<223> OTHER INFORMATION: partial shRNA sequence, included in shRNA to
      target IL-10R alpha for RNA interference

<400> SEQUENCE: 215
gcaaatgaca catatgaaag c                                            21

<210> SEQ ID NO 216
<211> LENGTH: 21
<212> TYPE: DNA
<213> ORGANISM: Artificial Sequence
<220> FEATURE:
<223> OTHER INFORMATION: partial shRNA sequence, included in shRNA to
      target IL-10R alpha for RNA interference

<400> SEQUENCE: 216
ggtctaaaga ggagtgcatc t                                            21

<210> SEQ ID NO 217
<211> LENGTH: 21
<212> TYPE: DNA
<213> ORGANISM: Artificial Sequence
<220> FEATURE:
<223> OTHER INFORMATION: partial shRNA sequence, included in shRNA to
      target IL-10R alpha for RNA interference

<400> SEQUENCE: 217
gggctatttg aaacaggatc c                                            21

<210> SEQ ID NO 218
<211> LENGTH: 21
<212> TYPE: DNA
<213> ORGANISM: Artificial Sequence
<220> FEATURE:
<223> OTHER INFORMATION: partial shRNA sequence, included in shRNA to
      target IL-10R alpha for RNA interference

<400> SEQUENCE: 218
gctgtaggaa tggaagcttc a                                            21

<210> SEQ ID NO 219
<211> LENGTH: 21
<212> TYPE: DNA
<213> ORGANISM: Artificial Sequence
<220> FEATURE:
<223> OTHER INFORMATION: partial shRNA sequence, included in shRNA to
      target IL-10R alpha for RNA interference

<400> SEQUENCE: 219
gcttgtgttt gctgctaatg t                                            21

<210> SEQ ID NO 220
<211> LENGTH: 726
<212> TYPE: DNA
<213> ORGANISM: Artificial Sequence
<220> FEATURE:
<223> OTHER INFORMATION: mU6-shTIM-3-><-shPD-1-hU6

<400> SEQUENCE: 220
gttaacaagg tcgggcagga agagggccta tttcccatga ttccttcata tttgcatata    60
cgatacaagg ctgttagaga gataattaga attaatttga ctgtaaacac aaagatatta   120
gtacaaaata cgtgacgtag aaagtaataa tttcttgggt agtttgcagt tttaaaatta   180
tgttttaaaa tggactatca tatgcttacc gtaacttgaa agtatttcga tttcttggct   240
ttatatatct tgtggaaagg acgaaacacc gcctgtggtt ctattatatt atttcaagag   300
aataatataa tagaaccaca ggttttttgac tagtcaaaaa ggaattcgct cagaagaaat   360
ctcttgaatt tcttctgagc gaattccaaa caaggctttt ctccaaggga tatttatagt   420
ctcaaaacac acaattactt tacagttagg gtgagtttcc ttttgtgctg ttttttaaaa   480
taataattta gtatttgtat ctcttataga aatccaagcc tatcatgtaa aatgtagcta   540
gtattaaaaa gaacagatta tctgtctttt atcgcacatt aagcctctat agttactagg   600
aaatattata tgcaaattaa ccggggcagg ggagtagccg agcttctccc acaagtctgt   660 gcgaggggc cggcgcgggc ctagagatgg cggcgtcgga tcgctagcca tatgtctaga   720
gtatac                                                             726

<210> SEQ ID NO 221
<211> LENGTH: 726
<212> TYPE: DNA
<213> ORGANISM: Artificial Sequence
<220> FEATURE:
<223> OTHER INFORMATION: shTIM-3-mU6<-->hU6-shPD-1

<400> SEQUENCE: 221
gttaaccaaa aacctgtggt tctattatat tattctcttg aaataatata atagaaccac    60
aggcggtgtt tcgtcctttc cacaagatat ataaagccaa gaaatcgaaa tactttcaag   120
ttacggtaag catatgatag tccatttttaa aacataattt taaaactgca aactacccaa   180
gaaattatta ctttctacgt cacgtatttt gtactaataat ctttgtgttt acagtcaaat   240
taattctaat tatctctcta acagccttgt atcgtatatg caaatatgaa ggaatcatgg   300
gaaataggcc ctcttcctgc ccgaccttac tagtgatccg acgccgccat ctctaggccc   360
gcgccggccc cctcgcacag acttgtggga gaagctcggc tactccctg ccccggttaa   420 tttgcatata atatttccta gtaactatag aggcttaatg tgcgataaaa gacagataat   480
ctgttctttt taatactagc tacatttac atgataggct tggatttcta taagagatac   540
aaatactaaa ttattatttt aaaaaacagc acaaaaggaa actcacccta actgtaaagt   600

| aattgtgtgt tttgagacta taaatatccc ttggagaaaa gccttgtttg gaattcgctc | 660 |
| agaagaaatt caagagattt cttctgagcg aattccttt tggctagcca tatgtctaga | 720 |
| gtatac | 726 |

<210> SEQ ID NO 222
<211> LENGTH: 385
<212> TYPE: DNA
<213> ORGANISM: Artificial Sequence
<220> FEATURE:
<223> OTHER INFORMATION: shRNA cassette base sequence
<220> FEATURE:
<221> NAME/KEY: misc_feature
<222> LOCATION: (323)..(343)
<223> OTHER INFORMATION: n is a, c, g, or t
<220> FEATURE:
<221> NAME/KEY: misc_feature
<222> LOCATION: (353)..(373)
<223> OTHER INFORMATION: n is a, c, g, or t

<400> SEQUENCE: 222

| gttaacgatc cgacgccgcc atctctaggc ccgcgccggc cccctcgcac agacttgtgg | 60 |
| gagaagctcg gctactcccc tgccccggtt aatttgcata taatatttcc tagtaactat | 120 |
| agaggcttaa tgtgcgataa aagacagata atctgttctt tttaatacta gctacatttt | 180 |
| acatgatagg cttggatttc tataagagat acaaatacta aattattatt ttaaaaaaca | 240 |
| gcacaaaagg aaactcaccc taactgtaaa gtaattgtgt gttttgagac tataaatatc | 300 |
| ccttggagaa aagccttgtt tgnnnnnnnn nnnnnnnnnn nnnttcaaga gannnnnnnn | 360 |
| nnnnnnnnnn nnnttttttgg ttaac | 385 |

<210> SEQ ID NO 223
<211> LENGTH: 409
<212> TYPE: DNA
<213> ORGANISM: Artificial Sequence
<220> FEATURE:
<223> OTHER INFORMATION: mU6-shPD-1 MCS base sequence

<400> SEQUENCE: 223

| gttaacgatc cgacgccgcc atctctaggc ccgcgccggc cccctcgcac agacttgtgg | 60 |
| gagaagctcg gctactcccc tgccccggtt aatttgcata taatatttcc tagtaactat | 120 |
| agaggcttaa tgtgcgataa aagacagata atctgttctt tttaatacta gctacatttt | 180 |
| acatgatagg cttggatttc tataagagat acaaatacta aattattatt ttaaaaaaca | 240 |
| gcacaaaagg aaactcaccc taactgtaaa gtaattgtgt gttttgagac tataaatatc | 300 |
| ccttggagaa aagccttgtt tgcctgtggt tctattatat tatttcaaga gaataatata | 360 |
| atagaaccac aggtttttga ctagtgctag ccatatgtct agagtatac | 409 |

<210> SEQ ID NO 224
<211> LENGTH: 328
<212> TYPE: DNA
<213> ORGANISM: Artificial Sequence
<220> FEATURE:
<223> OTHER INFORMATION: hU6-shPD-1 base sequence

<400> SEQUENCE: 224

| gttaacaagg tcgggcagga agagggccta tttcccatga ttccttcata tttgcatata | 60 |
| cgatacaagg ctgttagaga gataattaga attaatttga ctgtaaacac aaagatatta | 120 |
| gtacaaaata cgtgacgtag aaagtaataa tttcttgggt agtttgcagt tttaaaatta | 180 |
| tgttttaaaa tggactatca tatgcttacc gtaacttgaa agtatttcga tttcttggct | 240 |

```
ttatatatct tgtggaaagg acgaaacacc gcctgtggtt ctattatatt atttcaagag      300
aataatataa tagaaccaca ggtttttg                                        328
```

<210> SEQ ID NO 225
<211> LENGTH: 468
<212> TYPE: PRT
<213> ORGANISM: Artificial Sequence
<220> FEATURE:
<223> OTHER INFORMATION: CD22-CAR

<400> SEQUENCE: 225

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Thr Ile Trp Ser Tyr Leu Asn Trp Tyr Gln
                165                 170                 175

Gln Arg Pro Gly Lys Ala Pro Asn Leu Leu Ile Tyr Ala Ala Ser Ser
            180                 185                 190

Leu Gln Ser Gly Val Pro Ser Arg Phe Ser Gly Arg Gly Ser Gly Thr
        195                 200                 205

Asp Phe Thr Leu Thr Ile Ser Ser Leu Gln Ala Glu Asp Phe Ala Thr
    210                 215                 220

Tyr Tyr Cys Gln Gln Ser Tyr Ser Ile Pro Gln Thr Phe Gly Gln Gly
225                 230                 235                 240

Thr Lys Leu Glu Ile Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
```

```
                340                 345                 350
Gly Cys Glu Leu Arg Val Lys Phe Ser Arg Ser Ala Asp Ala Pro Ala
            355                 360                 365

Tyr Lys Gln Gly Gln Asn Gln Leu Tyr Asn Glu Leu Asn Leu Gly Arg
        370                 375                 380

Arg Glu Glu Tyr Asp Val Leu Asp Lys Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 226
<211> LENGTH: 486
<212> TYPE: PRT
<213> ORGANISM: Artificial Sequence
<220> FEATURE:
<223> OTHER INFORMATION: CD19-CAR

<400> SEQUENCE: 226

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
```

His Tyr Tyr Tyr Gly Gly Ser Tyr Ala Met Asp Tyr Trp Gly Gln Gly
225                 230                 235                 240

Thr Ser Val Thr Val Ser Ser Thr Thr Thr Pro Ala Pro Arg Pro Pro
            245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
275                 280                 285

Phe Ala Cys Asp Ile Tyr Ile Trp Ala Pro Leu Ala Gly Thr Cys Gly
290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
370                 375                 380

Gly Arg Arg Glu Glu Tyr Asp Val Leu Asp Lys Arg Gly Arg Asp
385                 390                 395                 400

Pro Glu Met Gly Gly Lys Pro Arg Arg Lys Asn Pro Gln Glu Gly Leu
        405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
435                 440                 445

Gln Gly Leu Ser Thr Ala Thr Lys Asp Thr Tyr Asp Ala Leu His Met
450                 455                 460

Gln Ala Leu Pro Pro Arg
465                 470                 475                 480

485

<210> SEQ ID NO 227
<211> LENGTH: 782
<212> TYPE: PRT
<213> ORGANISM: Artificial Sequence
<220> FEATURE:
<223> OTHER INFORMATION: Delta LNGFR_P2A_CD19-CAR

<400> SEQUENCE: 227

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly

```
                100                 105                 110
Tyr Tyr Gln Asp Glu Thr Thr Gly Arg Cys Glu Ala Cys Arg Val Cys
            115                 120                 125
Glu Ala Gly Ser Gly Leu Val Phe Ser Cys Gln Asp Lys Gln Asn Thr
            130                 135                 140
Val Cys Glu Glu Cys Pro Asp Gly Thr Tyr Ser Asp Glu Ala Asn His
145                 150                 155                 160
Val Asp Pro Cys Leu Pro Cys Thr Val Cys Glu Asp Thr Glu Arg Gln
                165                 170                 175
Leu Arg Glu Cys Thr Arg Trp Ala Asp Ala Glu Cys Glu Glu Ile Pro
            180                 185                 190
Gly Arg Trp Ile Thr Arg Ser Thr Pro Pro Glu Gly Ser Asp Ser Thr
            195                 200                 205
Ala Pro Ser Thr Gln Glu Pro Glu Ala Pro Pro Glu Gln Asp Leu Ile
210                 215                 220
Ala Ser Thr Val Ala Gly Val Val Thr Thr Val Met Gly Ser Ser Gln
225                 230                 235                 240
Pro Val Val Thr Arg Gly Thr Thr Asp Asn Leu Ile Pro Val Tyr Cys
                245                 250                 255
Ser Ile Leu Ala Ala Val Val Val Gly Leu Val Ala Tyr Ile Ala Phe
            260                 265                 270
Lys Arg Trp Gly Ser Gly Ala Thr Asn Phe Ser Leu Leu Lys Gln Ala
            275                 280                 285
Gly Asp Val Glu Glu Asn Pro Gly Pro Ala Leu Pro Val Thr Ala Leu
            290                 295                 300
Leu Leu Pro Leu Ala Leu Leu Leu His Ala Ala Arg Pro Asp Ile Gln
305                 310                 315                 320
Met Thr Gln Thr Thr Ser Ser Leu Ser Ala Ser Leu Gly Asp Arg Val
                325                 330                 335
Thr Ile Ser Cys Arg Ala Ser Gln Asp Ile Ser Lys Tyr Leu Asn Trp
                340                 345                 350
Tyr Gln Gln Lys Pro Asp Gly Thr Val Lys Leu Leu Ile Tyr His Thr
            355                 360                 365
Ser Arg Leu His Ser Gly Val Pro Ser Arg Phe Ser Gly Ser Gly Ser
            370                 375                 380
Gly Thr Asp Tyr Ser Leu Thr Ile Ser Asn Leu Glu Gln Glu Asp Ile
385                 390                 395                 400
Ala Thr Tyr Phe Cys Gln Gln Gly Asn Thr Leu Pro Tyr Thr Phe Gly
                405                 410                 415
Gly Gly Thr Lys Leu Glu Ile Thr Gly Gly Gly Ser Gly Gly Gly
            420                 425                 430
Gly Ser Gly Gly Gly Ser Glu Val Lys Leu Gln Glu Ser Gly Pro
            435                 440                 445
Gly Leu Val Ala Pro Ser Gln Ser Leu Ser Val Thr Cys Thr Val Ser
            450                 455                 460
Gly Val Ser Leu Pro Asp Tyr Gly Val Ser Trp Ile Arg Gln Pro Pro
465                 470                 475                 480
Arg Lys Gly Leu Glu Trp Leu Gly Val Ile Trp Gly Ser Glu Thr Thr
                485                 490                 495
Tyr Tyr Asn Ser Ala Leu Lys Ser Arg Leu Thr Ile Ile Lys Asp Asn
                500                 505                 510
Ser Lys Ser Gln Val Phe Leu Lys Met Asn Ser Leu Gln Thr Asp Asp
            515                 520                 525
```

Thr Ala Ile Tyr Tyr Cys Ala Lys His Tyr Tyr Gly Gly Ser Tyr
           530                 535                 540

Ala Met Asp Tyr Trp Gly Gln Gly Thr Ser Val Thr Val Ser Ser Thr
545                 550                 555                 560

Thr Thr Pro Ala Pro Arg Pro Pro Thr Pro Ala Pro Thr Ile Ala Ser
                565                 570                 575

Gln Pro Leu Ser Leu Arg Pro Glu Ala Cys Arg Pro Ala Ala Gly Gly
                580                 585                 590

Ala Val His Thr Arg Gly Leu Asp Phe Ala Cys Asp Ile Tyr Ile Trp
            595                 600                 605

Ala Pro Leu Ala Gly Thr Cys Gly Val Leu Leu Leu Ser Leu Val Ile
            610                 615                 620

Thr Leu Tyr Cys Lys Arg Gly Arg Lys Lys Leu Leu Tyr Ile Phe Lys
625                 630                 635                 640

Gln Pro Phe Met Arg Pro Val Gln Thr Thr Gln Glu Glu Asp Gly Cys
                645                 650                 655

Ser Cys Arg Phe Pro Glu Glu Glu Gly Gly Cys Glu Leu Arg Val
                660                 665                 670

Lys Phe Ser Arg Ser Ala Asp Ala Pro Ala Tyr Lys Gln Gly Gln Asn
            675                 680                 685

Gln Leu Tyr Asn Glu Leu Asn Leu Gly Arg Arg Glu Glu Tyr Asp Val
690                 695                 700

Leu Asp Lys Arg Arg Gly Arg Asp Pro Glu Met Gly Gly Lys Pro Arg
705                 710                 715                 720

Arg Lys Asn Pro Gln Glu Gly Leu Tyr Asn Glu Leu Gln Lys Asp Lys
                725                 730                 735

Met Ala Glu Ala Tyr Ser Glu Ile Gly Met Lys Gly Glu Arg Arg Arg
            740                 745                 750

Gly Lys Gly His Asp Gly Leu Tyr Gln Gly Leu Ser Thr Ala Thr Lys
            755                 760                 765

Asp Thr Tyr Asp Ala Leu His Met Gln Ala Leu Pro Pro Arg
770                 775                 780

<210> SEQ ID NO 228
<211> LENGTH: 47
<212> TYPE: DNA
<213> ORGANISM: Artificial Sequence
<220> FEATURE:
<223> OTHER INFORMATION: Forward PCR cloning primer #1

<400> SEQUENCE: 228
ggtatactct agacatatgg ctagcactag tcaaaaacct gtggttc        47

<210> SEQ ID NO 229
<211> LENGTH: 26
<212> TYPE: DNA
<213> ORGANISM: Artificial Sequence
<220> FEATURE:
<223> OTHER INFORMATION: Reverse PCR cloning primer #1

<400> SEQUENCE: 229
ttgtaccgtt aacgatccga cgccgc        26

<210> SEQ ID NO 230
<211> LENGTH: 102
<212> TYPE: DNA
<213> ORGANISM: Artificial Sequence
<220> FEATURE:

<223> OTHER INFORMATION: Forward PCR cloning primer #2

<400> SEQUENCE: 230
tgactagtca aaaacctgtg gttctattat attattctct tgaaataata taatagaacc    60
acaggcggtg tttcgtcctt tccacaagat atataaagcc aa    102

<210> SEQ ID NO 231
<211> LENGTH: 50
<212> TYPE: DNA
<213> ORGANISM: Artificial Sequence
<220> FEATURE:
<223> OTHER INFORMATION: Reverse PCR cloning primer #2

<400> SEQUENCE: 231
gtaccgttaa caaggtcggg caggaagagg gcctatttcc catgattcct    50

<210> SEQ ID NO 232
<211> LENGTH: 39
<212> TYPE: DNA
<213> ORGANISM: Artificial Sequence
<220> FEATURE:
<223> OTHER INFORMATION: Forward PCR cloning primer #3

<400> SEQUENCE: 232
aggactagtc aaaaaggaat tcgctcagaa gaaatctct    39

<210> SEQ ID NO 233
<211> LENGTH: 27
<212> TYPE: DNA
<213> ORGANISM: Artificial Sequence
<220> FEATURE:
<223> OTHER INFORMATION: Reverse PCR cloning primer #3

<400> SEQUENCE: 233
ctagctagcg atccgacgcc gccatct    27

<210> SEQ ID NO 234
<211> LENGTH: 42
<212> TYPE: DNA
<213> ORGANISM: Artificial Sequence
<220> FEATURE:
<223> OTHER INFORMATION: Forward PCR cloning primer #4

<400> SEQUENCE: 234
atgttaacca aaaacctgtg gttctattat attattctct tg    42

<210> SEQ ID NO 235
<211> LENGTH: 34
<212> TYPE: DNA
<213> ORGANISM: Artificial Sequence
<220> FEATURE:
<223> OTHER INFORMATION: Reverse PCR cloning primer #4

<400> SEQUENCE: 235
tcactagtaa ggtcgggcag gaagagggcc tatt    34

<210> SEQ ID NO 236
<211> LENGTH: 29
<212> TYPE: DNA
<213> ORGANISM: Artificial Sequence
<220> FEATURE:
<223> OTHER INFORMATION: Forward PCR cloning primer #5

<400> SEQUENCE: 236
taggccctca ctagtgatcc gacgccgcc    29

```
<210> SEQ ID NO 237
<211> LENGTH: 38
<212> TYPE: DNA
<213> ORGANISM: Artificial Sequence
<220> FEATURE:
<223> OTHER INFORMATION: Reverse PCR cloning primer #5

<400> SEQUENCE: 237
ctagctagcc aaaaaggaat tcgctcagaa gaaatctc                             38

<210> SEQ ID NO 238
<211> LENGTH: 21
<212> TYPE: DNA
<213> ORGANISM: Artificial Sequence
<220> FEATURE:
<223> OTHER INFORMATION: TIGIT-268

<400> SEQUENCE: 238
gcttctggcc atttgtaatg c                                               21

<210> SEQ ID NO 239
<211> LENGTH: 21
<212> TYPE: DNA
<213> ORGANISM: Artificial Sequence
<220> FEATURE:
<223> OTHER INFORMATION: TIGIT-2

<400> SEQUENCE: 239
gggagtactt ctgcatctat c                                               21

<210> SEQ ID NO 240
<211> LENGTH: 21
<212> TYPE: DNA
<213> ORGANISM: Artificial Sequence
<220> FEATURE:
<223> OTHER INFORMATION: TIGIT-739

<400> SEQUENCE: 240
gctgcatgac tacttcaatg t                                               21

<210> SEQ ID NO 241
<211> LENGTH: 21
<212> TYPE: DNA
<213> ORGANISM: Artificial Sequence
<220> FEATURE:
<223> OTHER INFORMATION: TIGIT-1

<400> SEQUENCE: 241
taacgtggat cttgatcata a                                               21

<210> SEQ ID NO 242
<211> LENGTH: 21
<212> TYPE: DNA
<213> ORGANISM: Artificial Sequence
<220> FEATURE:
<223> OTHER INFORMATION: TIGIT-1386

<400> SEQUENCE: 242
ggagacatac acaggccttc a                                               21

<210> SEQ ID NO 243
<211> LENGTH: 21
<212> TYPE: DNA
<213> ORGANISM: Artificial Sequence
<220> FEATURE:
```

-continued

<223> OTHER INFORMATION: TIGIT-1750

<400> SEQUENCE: 243
gcatttgggc cttgatctac c                                               21

<210> SEQ ID NO 244
<211> LENGTH: 21
<212> TYPE: DNA
<213> ORGANISM: Artificial Sequence
<220> FEATURE:
<223> OTHER INFORMATION: LAG3-138

<400> SEQUENCE: 244
ccagctttcc agctttcctc t                                               21

<210> SEQ ID NO 245
<211> LENGTH: 21
<212> TYPE: DNA
<213> ORGANISM: Artificial Sequence
<220> FEATURE:
<223> OTHER INFORMATION: LAG3-503

<400> SEQUENCE: 245
gatctcagcc ttctgcgaag a                                               21

<210> SEQ ID NO 246
<211> LENGTH: 21
<212> TYPE: DNA
<213> ORGANISM: Artificial Sequence
<220> FEATURE:
<223> OTHER INFORMATION: LAG3-1092

<400> SEQUENCE: 246
gcttcaacgt ctccatcatg t                                               21

<210> SEQ ID NO 247
<211> LENGTH: 21
<212> TYPE: DNA
<213> ORGANISM: Artificial Sequence
<220> FEATURE:
<223> OTHER INFORMATION: LAG3-1221

<400> SEQUENCE: 247
ggtctttcct cactgccaag t                                               21

<210> SEQ ID NO 248
<211> LENGTH: 21
<212> TYPE: DNA
<213> ORGANISM: Artificial Sequence
<220> FEATURE:
<223> OTHER INFORMATION: LAG3-1278

<400> SEQUENCE: 248
ctggagacaa tggcgacttt a                                               21

<210> SEQ ID NO 249
<211> LENGTH: 21
<212> TYPE: DNA
<213> ORGANISM: Artificial Sequence
<220> FEATURE:
<223> OTHER INFORMATION: LAG3-1379

<400> SEQUENCE: 249
gccactgtca cattggcaat c                                               21

```
<210> SEQ ID NO 250
<211> LENGTH: 21
<212> TYPE: DNA
<213> ORGANISM: Artificial Sequence
<220> FEATURE:
<223> OTHER INFORMATION: LAG3-1465

<400> SEQUENCE: 250
tccagtatct ggacaagaac g                                              21

<210> SEQ ID NO 251
<211> LENGTH: 21
<212> TYPE: DNA
<213> ORGANISM: Artificial Sequence
<220> FEATURE:
<223> OTHER INFORMATION: LAG3-1616

<400> SEQUENCE: 251
gcagcagtgt acttcacaga g                                              21

<210> SEQ ID NO 252
<211> LENGTH: 21
<212> TYPE: DNA
<213> ORGANISM: Artificial Sequence
<220> FEATURE:
<223> OTHER INFORMATION: LAG3-1702

<400> SEQUENCE: 252
gctgtttctc atccttggtg t                                              21

<210> SEQ ID NO 253
<211> LENGTH: 21
<212> TYPE: DNA
<213> ORGANISM: Artificial Sequence
<220> FEATURE:
<223> OTHER INFORMATION: LAG3-1751

<400> SEQUENCE: 253
gcctttggct ttcacctttg g                                              21

<210> SEQ ID NO 254
<211> LENGTH: 21
<212> TYPE: DNA
<213> ORGANISM: Artificial Sequence
<220> FEATURE:
<223> OTHER INFORMATION: LAG3-1954

<400> SEQUENCE: 254
tcagcagccc agtccaaata a                                              21

<210> SEQ ID NO 255
<211> LENGTH: 21
<212> TYPE: DNA
<213> ORGANISM: Artificial Sequence
<220> FEATURE:
<223> OTHER INFORMATION: CTLA4-3

<400> SEQUENCE: 255
ggtggagctc atgtacccac c                                              21

<210> SEQ ID NO 256
<211> LENGTH: 21
<212> TYPE: DNA
<213> ORGANISM: Artificial Sequence
<220> FEATURE:
<223> OTHER INFORMATION: CTLA4-1
```

<400> SEQUENCE: 256
cccaaattac gtgtactaca a                                              21

<210> SEQ ID NO 257
<211> LENGTH: 21
<212> TYPE: DNA
<213> ORGANISM: Artificial Sequence
<220> FEATURE:
<223> OTHER INFORMATION: CTLA4-1058

<400> SEQUENCE: 257
gcatcacttg ggattaatat g                                              21

<210> SEQ ID NO 258
<211> LENGTH: 21
<212> TYPE: DNA
<213> ORGANISM: Artificial Sequence
<220> FEATURE:
<223> OTHER INFORMATION: CTLA4-1154

<400> SEQUENCE: 258
gcgagggaga agactatatt g                                              21

<210> SEQ ID NO 259
<211> LENGTH: 21
<212> TYPE: DNA
<213> ORGANISM: Artificial Sequence
<220> FEATURE:
<223> OTHER INFORMATION: CTLA4-1309

<400> SEQUENCE: 259
gccagtgatg ctaaaggttg t                                              21

<210> SEQ ID NO 260
<211> LENGTH: 21
<212> TYPE: DNA
<213> ORGANISM: Artificial Sequence
<220> FEATURE:
<223> OTHER INFORMATION: CTLA4-1686

<400> SEQUENCE: 260
ggtggtatct gagttgactt g                                              21

<210> SEQ ID NO 261
<211> LENGTH: 21
<212> TYPE: DNA
<213> ORGANISM: Artificial Sequence
<220> FEATURE:
<223> OTHER INFORMATION: Tim3-1

<400> SEQUENCE: 261
gatgaaaggg atgtgaatta t                                              21

<210> SEQ ID NO 262
<211> LENGTH: 21
<212> TYPE: DNA
<213> ORGANISM: Artificial Sequence
<220> FEATURE:
<223> OTHER INFORMATION: Tim3-2

<400> SEQUENCE: 262
gggagcctcc ctgatataaa t                                              21

<210> SEQ ID NO 263
<211> LENGTH: 19

```
<212> TYPE: DNA
<213> ORGANISM: Artificial Sequence
<220> FEATURE:
<223> OTHER INFORMATION: Tim3-3

<400> SEQUENCE: 263
ggaattcgct cagaagaaa                                              19

<210> SEQ ID NO 264
<211> LENGTH: 21
<212> TYPE: DNA
<213> ORGANISM: Artificial Sequence
<220> FEATURE:
<223> OTHER INFORMATION: Tim3-4

<400> SEQUENCE: 264
ggaccaaact gaagctatat t                                           21

<210> SEQ ID NO 265
<211> LENGTH: 21
<212> TYPE: DNA
<213> ORGANISM: Artificial Sequence
<220> FEATURE:
<223> OTHER INFORMATION: PD1-1

<400> SEQUENCE: 265
cctgtggttc tattatatta t                                           21

<210> SEQ ID NO 266
<211> LENGTH: 21
<212> TYPE: DNA
<213> ORGANISM: Artificial Sequence
<220> FEATURE:
<223> OTHER INFORMATION: PD1-2

<400> SEQUENCE: 266
gcctagagaa gtttcaggga a                                           21

<210> SEQ ID NO 267
<211> LENGTH: 21
<212> TYPE: DNA
<213> ORGANISM: Artificial Sequence
<220> FEATURE:
<223> OTHER INFORMATION: PD1-3

<400> SEQUENCE: 267
cattgtcttt cctagcggaa t                                           21

<210> SEQ ID NO 268
<211> LENGTH: 20
<212> TYPE: DNA
<213> ORGANISM: Artificial Sequence
<220> FEATURE:
<223> OTHER INFORMATION: 18s rRNA Forward

<400> SEQUENCE: 268
gattaagtcc ctgcccttg                                              20

<210> SEQ ID NO 269
<211> LENGTH: 20
<212> TYPE: DNA
<213> ORGANISM: Artificial Sequence
<220> FEATURE:
<223> OTHER INFORMATION: 18s rRNA Reverse

<400> SEQUENCE: 269
```

```
gttcacctac ggaaaccttg                                            20
```

<210> SEQ ID NO 270
<211> LENGTH: 20
<212> TYPE: DNA
<213> ORGANISM: Artificial Sequence
<220> FEATURE:
<223> OTHER INFORMATION: PDCD1 Forward

<400> SEQUENCE: 270

```
cctccacctt tacacatgcc                                            20
```

<210> SEQ ID NO 271
<211> LENGTH: 20
<212> TYPE: DNA
<213> ORGANISM: Artificial Sequence
<220> FEATURE:
<223> OTHER INFORMATION: PDCD1 Reverse

<400> SEQUENCE: 271

```
cttactgcct cagcttccct                                            20
```

<210> SEQ ID NO 272
<211> LENGTH: 21
<212> TYPE: DNA
<213> ORGANISM: Artificial Sequence
<220> FEATURE:
<223> OTHER INFORMATION: IL2 Forward

<400> SEQUENCE: 272

```
ccaagaaggc cacagaactg a                                          21
```

<210> SEQ ID NO 273
<211> LENGTH: 26
<212> TYPE: DNA
<213> ORGANISM: Artificial Sequence
<220> FEATURE:
<223> OTHER INFORMATION: IL2 Reverse

<400> SEQUENCE: 273

```
gttgtttcag atccctttag ttccag                                     26
```

<210> SEQ ID NO 274
<211> LENGTH: 21
<212> TYPE: DNA
<213> ORGANISM: Artificial Sequence
<220> FEATURE:
<223> OTHER INFORMATION: IL4 Forward

<400> SEQUENCE: 274

```
actttgaaca gcctcacaga g                                          21
```

<210> SEQ ID NO 275
<211> LENGTH: 22
<212> TYPE: DNA
<213> ORGANISM: Artificial Sequence
<220> FEATURE:
<223> OTHER INFORMATION: IL4 Reverse

<400> SEQUENCE: 275

```
ccgagttgac cgtaacagac at                                         22
```

<210> SEQ ID NO 276
<211> LENGTH: 20
<212> TYPE: DNA
<213> ORGANISM: Artificial Sequence

```
<220> FEATURE:
<223> OTHER INFORMATION: IL17A Forward

<400> SEQUENCE: 276
caaccgatcc acctcacctt                                                   20

<210> SEQ ID NO 277
<211> LENGTH: 19
<212> TYPE: DNA
<213> ORGANISM: Artificial Sequence
<220> FEATURE:
<223> OTHER INFORMATION: IL17A Reverse

<400> SEQUENCE: 277
ggcactttgc ctcccagat                                                    19

<210> SEQ ID NO 278
<211> LENGTH: 21
<212> TYPE: DNA
<213> ORGANISM: Artificial Sequence
<220> FEATURE:
<223> OTHER INFORMATION: CD25 Forward

<400> SEQUENCE: 278
cacaagctct gccactcgga a                                                 21

<210> SEQ ID NO 279
<211> LENGTH: 20
<212> TYPE: DNA
<213> ORGANISM: Artificial Sequence
<220> FEATURE:
<223> OTHER INFORMATION: CD25 Reverse

<400> SEQUENCE: 279
tgcagtgacc tggaaggctc                                                   20

<210> SEQ ID NO 280
<211> LENGTH: 20
<212> TYPE: DNA
<213> ORGANISM: Artificial Sequence
<220> FEATURE:
<223> OTHER INFORMATION: CTLA4 Forward

<400> SEQUENCE: 280
ctacctgggc ataggcaacg                                                   20

<210> SEQ ID NO 281
<211> LENGTH: 20
<212> TYPE: DNA
<213> ORGANISM: Artificial Sequence
<220> FEATURE:
<223> OTHER INFORMATION: CTLA4 Reverse

<400> SEQUENCE: 281
ccccgaacta actgctgcaa                                                   20

<210> SEQ ID NO 282
<211> LENGTH: 23
<212> TYPE: DNA
<213> ORGANISM: Artificial Sequence
<220> FEATURE:
<223> OTHER INFORMATION: FOXP3 Forward

<400> SEQUENCE: 282
gaaacagcac attcccagag ttc                                               23
```

```
<210> SEQ ID NO 283
<211> LENGTH: 17
<212> TYPE: DNA
<213> ORGANISM: Artificial Sequence
<220> FEATURE:
<223> OTHER INFORMATION: FOXP3 Reverse

<400> SEQUENCE: 283
atggcccagc ggatgag                                                   17

<210> SEQ ID NO 284
<211> LENGTH: 19
<212> TYPE: DNA
<213> ORGANISM: Artificial Sequence
<220> FEATURE:
<223> OTHER INFORMATION: TGF-beta1 Forward

<400> SEQUENCE: 284
cccagcatct gcaaagctc                                                 19

<210> SEQ ID NO 285
<211> LENGTH: 20
<212> TYPE: DNA
<213> ORGANISM: Artificial Sequence
<220> FEATURE:
<223> OTHER INFORMATION: TGF-beta1 Reverse

<400> SEQUENCE: 285
gtccttgcgg aagtcaatgt                                                20

<210> SEQ ID NO 286
<211> LENGTH: 22
<212> TYPE: DNA
<213> ORGANISM: Artificial Sequence
<220> FEATURE:
<223> OTHER INFORMATION: TGFBR1 Forward

<400> SEQUENCE: 286
acatgattca gccacagata cc                                             22

<210> SEQ ID NO 287
<211> LENGTH: 21
<212> TYPE: DNA
<213> ORGANISM: Artificial Sequence
<220> FEATURE:
<223> OTHER INFORMATION: TGFBR1 Reverse

<400> SEQUENCE: 287
gcatagatgt cagcacgttt g                                              21

<210> SEQ ID NO 288
<211> LENGTH: 19
<212> TYPE: DNA
<213> ORGANISM: Artificial Sequence
<220> FEATURE:
<223> OTHER INFORMATION: TGFBR2 Forward

<400> SEQUENCE: 288
acgtgttgag agatcgagg                                                 19

<210> SEQ ID NO 289
<211> LENGTH: 20
<212> TYPE: DNA
<213> ORGANISM: Artificial Sequence
<220> FEATURE:
<223> OTHER INFORMATION: TGFBR2 Reverse
```

```
<400> SEQUENCE: 289
cccagcactc agtcaacgtc                                                  20
```